United States Patent
Kwon et al.

(10) Patent No.: US 12,122,730 B2
(45) Date of Patent: Oct. 22, 2024

(54) METHODS OF CARBON-CARBON BOND FRAGMENTATION

(71) Applicant: The Regents of the University of California, Oakland, CA (US)

(72) Inventors: Ohyun Kwon, Los Angeles, CA (US); Andrew Smaligo, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 461 days.

(21) Appl. No.: 17/433,518

(22) PCT Filed: Feb. 24, 2020

(86) PCT No.: PCT/US2020/019433
§ 371 (c)(1),
(2) Date: Aug. 24, 2021

(87) PCT Pub. No.: WO2020/176386
PCT Pub. Date: Sep. 3, 2020

(65) Prior Publication Data
US 2022/0169580 A1    Jun. 2, 2022

Related U.S. Application Data

(60) Provisional application No. 62/810,271, filed on Feb. 25, 2019.

(51) Int. Cl.
| | | |
|---|---|---|
| *C07B 37/00* | (2006.01) | |
| *C07B 33/00* | (2006.01) | |
| *C07B 63/04* | (2006.01) | |
| *C07C 29/00* | (2006.01) | |
| *C07C 37/00* | (2006.01) | |
| *C07C 41/03* | (2006.01) | |
| *C07C 45/28* | (2006.01) | |
| *C07C 45/40* | (2006.01) | |
| *C07C 45/64* | (2006.01) | |
| *C07C 45/67* | (2006.01) | |
| *C07C 67/00* | (2006.01) | |
| *C07C 67/333* | (2006.01) | |
| *C07C 67/39* | (2006.01) | |
| *C07C 315/02* | (2006.01) | |
| *C07C 319/14* | (2006.01) | |
| *C07F 7/18* | (2006.01) | |
| *C07F 9/53* | (2006.01) | |

(52) U.S. Cl.
CPC .............. *C07B 37/00* (2013.01); *C07B 33/00* (2013.01); *C07B 63/04* (2013.01); *C07C 29/00* (2013.01); *C07C 41/03* (2013.01); *C07C 45/28* (2013.01); *C07C 45/40* (2013.01); *C07C 45/64* (2013.01); *C07C 45/673* (2013.01); *C07C 67/00* (2013.01); *C07C 67/333* (2013.01); *C07C 67/39* (2013.01); *C07C 315/02* (2013.01); *C07C 319/14* (2013.01); *C07F 7/1892* (2013.01); *C07F 9/5325* (2013.01); *C07B 2200/07* (2013.01); *C07C 2601/02* (2017.05); *C07C 2601/04* (2017.05); *C07C 2601/10* (2017.05); *C07C 2601/14* (2017.05); *C07C 2602/08* (2017.05); *C07C 2602/26* (2017.05); *C07C 2602/28* (2017.05); *C07C 2602/46* (2017.05); *C07C 2603/74* (2017.05)

(58) Field of Classification Search
CPC ................................ C07B 37/00; C07B 63/04
See application file for complete search history.

(56) References Cited

PUBLICATIONS

Ebert et al., "Synthesis of the Insect Pheromone (2S,3S,7RS)-Diprionyl Acetate by Diastereoselective Protonation," European Journal of Organic Chemistry, 20: 3831-3835 (2001).
International Search Report and Written Opinion for International Application No. PCT/US2020/019433 dated Nov. 18, 2021.
Jansen et al., "Enantioselective Synthesis of Functionalised Decalones by Robinson Annulation of Substituted Cyclohexanones, Derived from R-(-)-Carvone," Tetrahedron, 56(14): 2075-2094 (2000).
Jansen et al., "The conversion of (-)- and (+)-dihydrocarvone into chiral intermediates for the synthesis of (-)-polygodial, (-)-warburganal and (-)-muzigadial," Tetrahedron, 45(5): 1447-1452 (1989).
Marshall et al., "Methylation of 10-methyl-1(9)-octal-2-ones by organocopper reagents," The Journal of Organic Chemistry, 33(2): 840-843 (1968).
Srikrishna et al., "An enantiospecific synthesis of (-)-2-pupukeanone via a rhodium carbenoid CH insertion reaction," Tetrahedron Letters, 42(23): 3929-3931 (2001).
Srikrishna et al., "An enantiospecific synthesis of 2-pupukeanone," Indian Journal of Chemistry—Section B Organic and Medicinal Chemistry, 45(8): 1909-1919 (2006).
Smaligo et al., "Carvone-Derived P-Stereogenic Phosphines: Design, Synthesis, and Use in Allene-Imine [3+2] Annulation," ACS Catal, 8:5188-5192 (2018).
Smaligo et al., "Supporting Information Carvone-Derived P-Stereogenic Phosphines: Design, Synthesis, and Use in Allene-Imine [3 + 2] Annulation", ACS Catalysis, pp. S1-S94 (2018).

*Primary Examiner* — Sikarl A Witherspoon
(74) *Attorney, Agent, or Firm* — Foley Hoag LLP; David P. Halstead; Alexander J. Chatterley

(57) ABSTRACT

The present disclosure relates to methods of carbon-carbon bond fragmentation.

19 Claims, 4 Drawing Sheets

FIG. 1A

A $C(sp^2)$–$C(sp^2)$ bond fragmentation

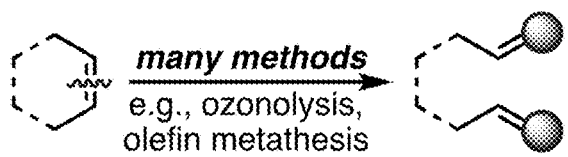

$C(sp^3)$–$C(sp^3)$ bond fragmentation

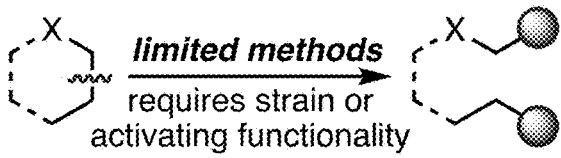

$C(sp^3)$–$C(sp^2)$ bond fragmentation

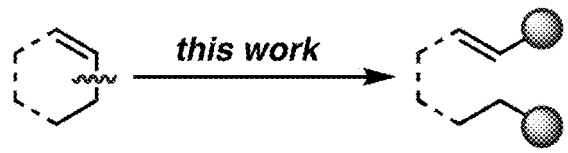

FIG. 1B

• new strategies for total synthesis

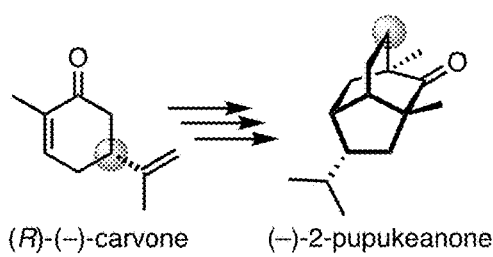

(R)-(−)-carvone → (−)-2-pupukeanone

• late-stage diversification of bioactive molecules

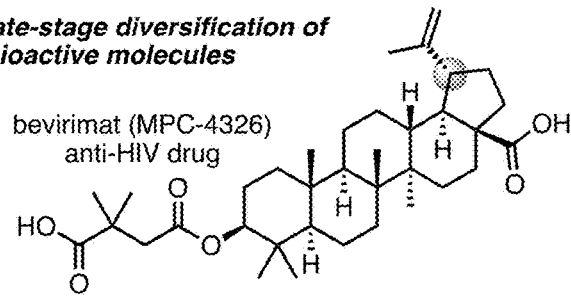

bevirimat (MPC-4326)
anti-HIV drug

• rapid generation of non-trivial compounds from readily-accessible sources

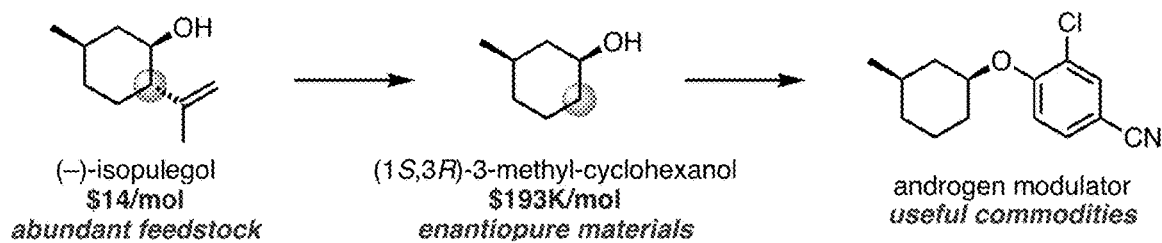

(−)-isopulegol
$14/mol
abundant feedstock (1S,3R)-3-methyl-cyclohexanol
$193K/mol
enantiopure materials androgen modulator
useful commodities FIG. 2
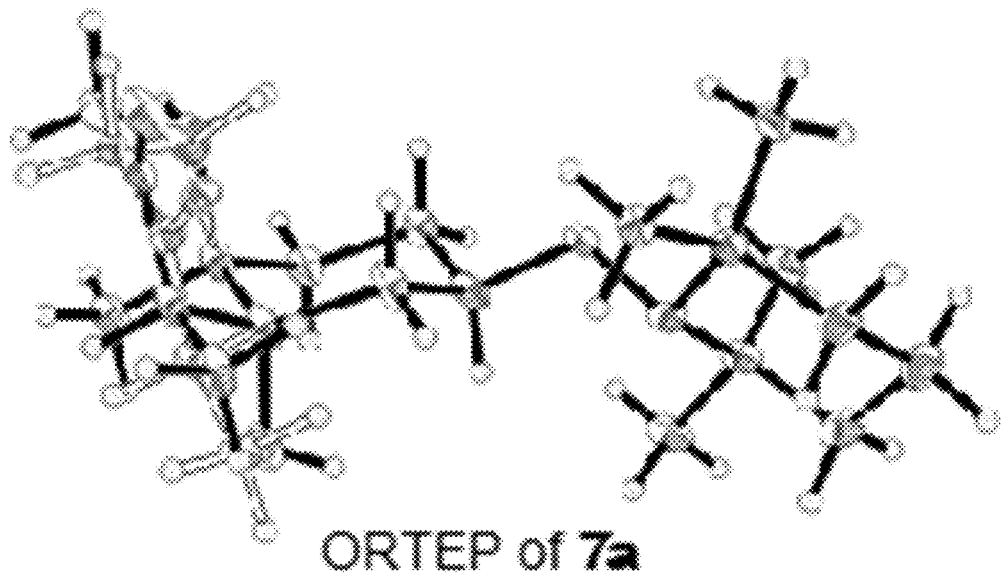
FIG. 3A
functional group occurrence in natural products
| | | | | | |
|---|---|---|---|---|---|
| = | R-C(=O)-R' | CH2=CH-C(=O)-R | R-CHO | R-Cl | R-Br |
| 39.9% | 15.9% | 6.0% | 2.4% | 1.8% | 1.5% |
| alkene | ketone | enone | aldehyde | chloride | bromide |
FIG. 3B
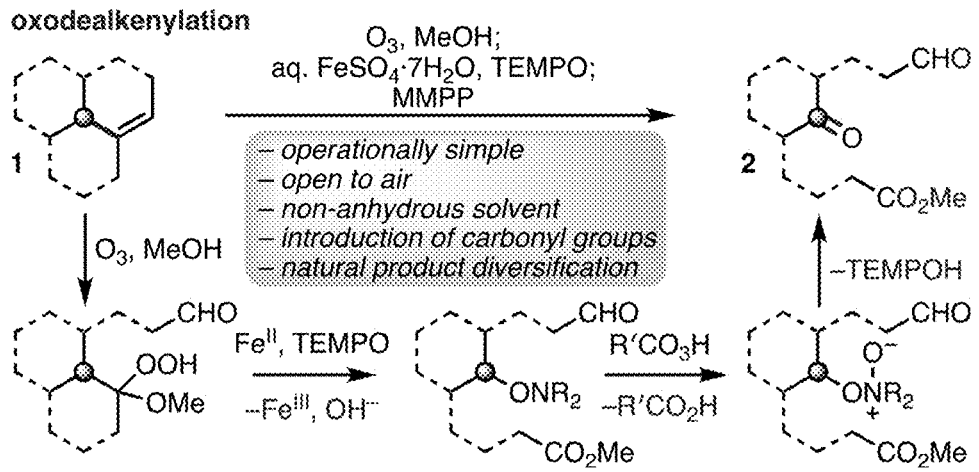

[b] The crude reaction mixture was treated with Et₃N during workup.

A thioether and sulfone units in pharmaceutical agents

METHODS OF CARBON-CARBON BOND FRAGMENTATION

RELATED APPLICATIONS

This application is the 0 371 National Stage of PCT/US2020/019433, filed Feb. 24, 2020; which claims the benefit of U.S. Provisional Application No. 62/810,271, filed Feb. 25, 2019, the contents of each of which are fully incorporated by reference herein.

STATEMENT OF GOVERNMENT SUPPORT

This invention was made with government support under GM071779 awarded by the National Institutes of Health. The government has certain rights in the invention.

BACKGROUND

A common ideal in chemical synthesis is the assembly of complex molecules from simple precursors, accompanied, more often than not, by the need to install carbon centers with precisely defined stereochemical arrangements. Despite the bevy of methods available to accomplish such goals, sometimes it can be more efficient to reorganize starting materials already containing the prerequisite complexity and/or stereochemistry into the desired molecular structures. Furthermore, deconstructive strategies can provide access to challenging, or otherwise inaccessible, molecular structures. The literature contains many examples of C—C bond fragmentations. Some well-established $C(sp^2)$-$C(sp^2)$ bond scissions are oxidative cleavage (e.g., ozonolysis) and olefin metathesis. There are also reports of $C(sp^3)$-$C(sp^3)$ bond fragmentations, albeit in much smaller numbers, but they typically require activation of the C—C bond through the effects of a heteroatom, ring strain, or a leaving group. Even with these advancements, generalized methods for the functionalization of $C(sp^3)$-$C(sp^2)$ bonds remain elusive. Given the profuse number of organic molecules containing these linkages, activation of such bonds in a controllable manner would be extremely useful.

SUMMARY OF THE INVENTION

In one aspect, the present disclosure provides methods of making compounds, comprising:
  providing a starting material comprising an $sp^3$-hybridized carbon and an $sp^2$-hybridized carbon, wherein the $sp^3$-hybridized carbon and the $sp^2$-hybridized carbon are connected by a single bond;
  placing the starting material in a reaction vessel, thereby forming a reaction mixture; and
  cleaving the single bond, wherein cleaving the single bond comprises:
    contacting the reaction mixture with an oxidant; and
    contacting the reaction mixture with a transition metal salt.

BRIEF DESCRIPTION OF THE DRAWINGS

FIG. 1A schematically depicts several concepts and applications of fragmentation of various types of C—C bonds. X represents an activating moiety.

FIG. 1B schematically depicts several exemplary applications of hydrodealkenylation reactions.

FIG. 2 depicts an ORTEP view of compound 7a.

FIG. 3A depicts the prevalence of certain functional groups in natural products.

FIG. 3B schematically depicts certain advantages of the oxodealkenylation reaction.

DETAILED DESCRIPTION OF THE INVENTION

Figure 3C:
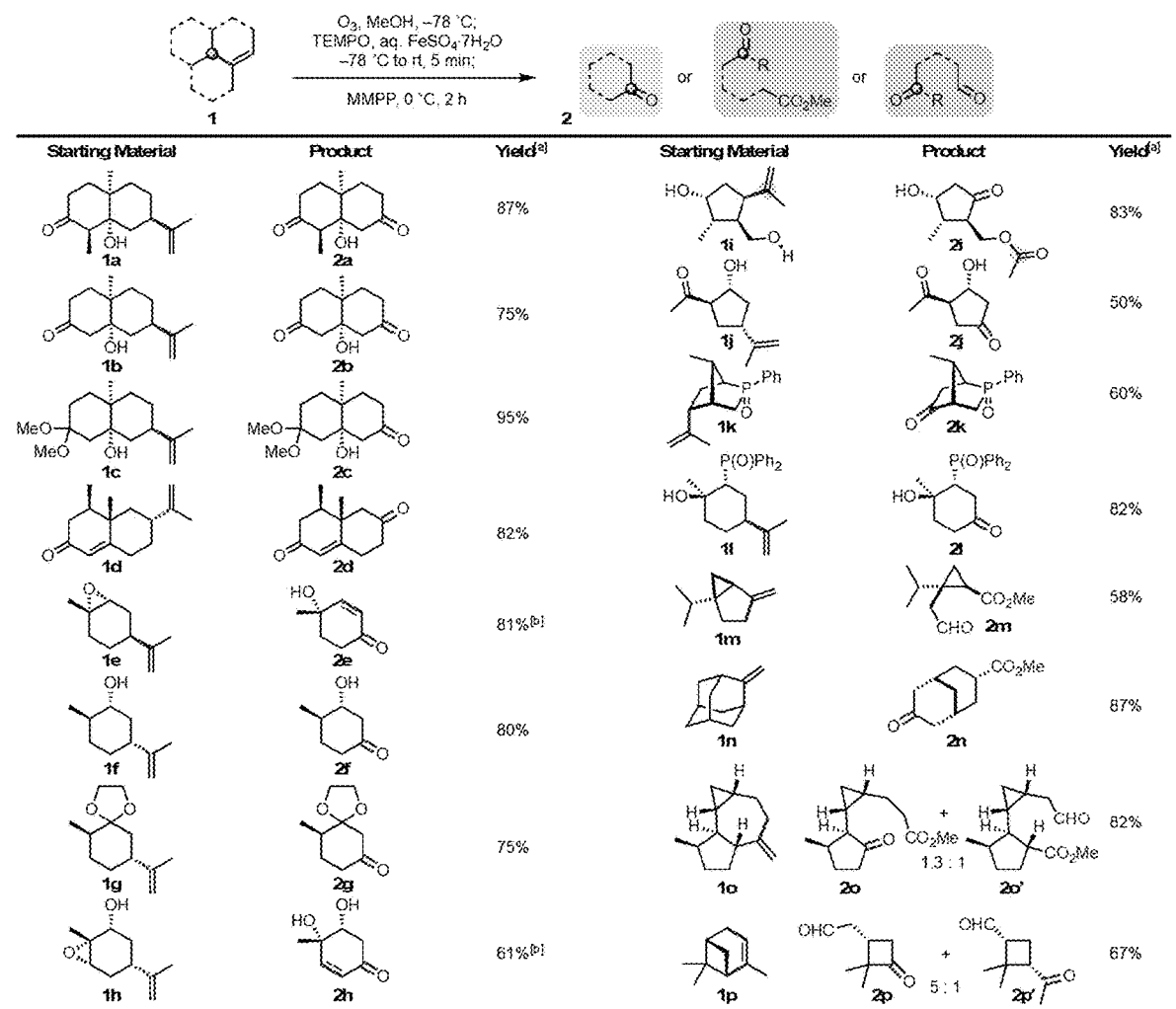
FIG. 3C depicts examples of the oxodealkenylation reaction.

In modern synthetic chemistry, emphasis is often placed on reactions that generate complexity from simple starting materials. Less common are deconstructive strategies toward complexity-particularly those involving C—C bond scission (FIG. 1A). Disclosed herein is one such transformation: the hydrodealkenylative cleavage of $C(sp^3)$-$C(sp^2)$ bonds, performed using an oxidant (e.g., ozone), a transition metal salt (e.g., an iron salt), and a hydrogen atom donor (e.g, an aryl thiol). These reactions are simple to operate (e.g., by using non-anhydrous solvent and open air) and reach completion within a few hours, delivering their products in high yields—even on decagram scales. The methods disclosed herein have been used to produce desirable synthetic intermediates, many of which are optically active, from abundantly available terpenes and terpenoid-derived precursors. It has also been applied to the total syntheses of complex molecules. With broad substrate scope and high functional group compatibility, this methodological advance opens new paths for the syntheses of organic molecules with utility in chemistry, biology, and medicine.

The reaction described herein involves cleavage of a $C(sp^3)$-$C(sp^2)$ bond, followed by formation of a new $C(sp^3)$-H bond.

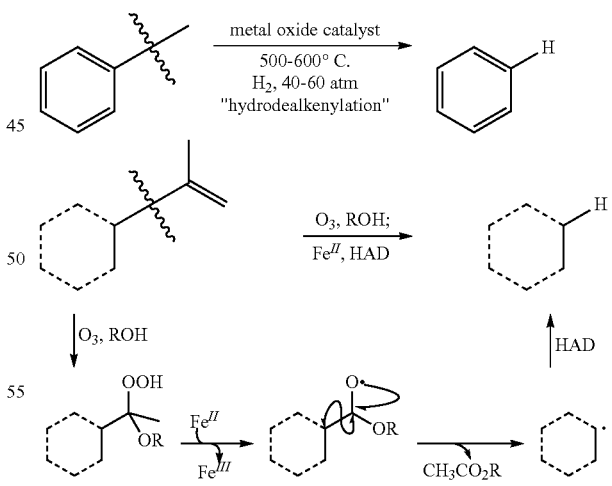

Scheme 1. Schematic depiction of several concepts and applications of hydrodealkenylative fragmentation of $C(sp3)$—$C(sp2)$ bonds.

A proposed mechanism is also illustrated.
R represents a functional group (e.g., alkyl).

The reaction disclosed herein is described as "hydrodealkenylation," coined with a nod to the hydrodealkylation process that is most commonly exemplified in the conversion of toluene to benzene in the presence of $H_2$ gas at high temperatures and pressures. The reaction design was based on previous reports of $Fe^{II}$ transferring an electron to the α-alkoxy hydroperoxides generated upon ozonolysis of alkenes in the presence of an alcohol. The resulting oxyradicals can subsequently engage in various forms of homolytic cleavage to produce alkenes, dimers, or halides. Nevertheless, these methods often occur with poor efficiencies and/or have limited use. Surprisingly, it was found that employing a readily available $Fe^{II}$ salt with a hydrogen atom donor (HAD) under Schreiber conditions promotes $C(sp^3)$-$C(sp^2)$ bond cleavage and subsequent construction of a new $C(sp^3)$-H bond. With the ubiquity of olefins in terpenes and other organic molecules, envisioned herein are several implications for this transformation: new retrosynthetic disconnections to aid total syntheses, the late-stage diversification of both small and large biologically active molecules, and the facile generation of useful "value-added" compounds from abundantly available starting materials (FIG. 1B).

The huge difference in price between (−)-isopulegol and (1S,3R)-3-methylcyclohexanol, used in the synthesis of androgen modulators, highlights one example of a disconnect between the current accessibility of these two structurally similar compounds.

After refining the reaction parameters promoting the fragmentation of the isopropenyl group in the hydroxy ketone 1a hydrodealkenylation product 2a was synthesized in 90% yield when using 1.2 equivalents of ferrous sulfate heptahydrate (as the $Fe^{II}$ salt) and 1.5 equivalents of benzenethiol (as the HAD). Applying the optimized conditions, the exemplary substrate scope of the hydrodealkenylation was investigate. Scheme 2 depicts that a number of bicyclic ketones and enones (1b-1f) underwent their fragmentations cleanly to yield their hydrodealkenylation products (2b-2f) in high yields (80-94%).

Scheme 2. Exemplary substrate scope of the hydrodealkenylation reaction.

| Starting Material | Product | Yield |
|---|---|---|
| 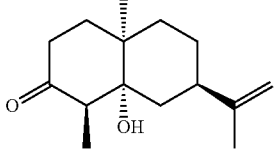 1a | 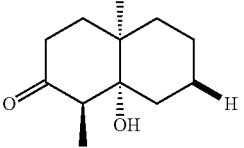 2a | 90% |
| 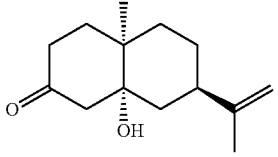 1b | 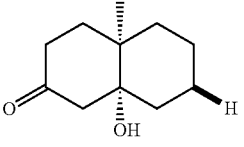 2b | 85% |
| 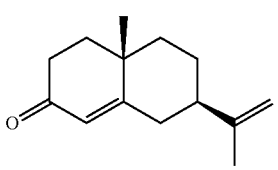 1c | 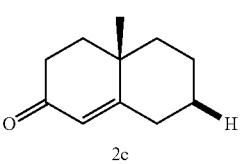 2c | 80% |
| 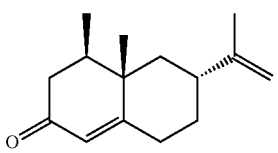 1d | 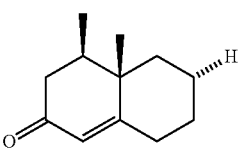 2d | 94% |
| 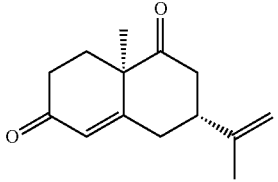 1e | 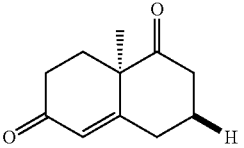 2e | 90% |

Scheme 2. Exemplary substrate scope of the hydrodealkenylation reaction.

| Starting Material | Product | Yield |
|---|---|---|
| ent-1e | ent-2e | 91% |
| 1f | 2f | 90% |
| 1g | 2g | 85% |
| 1h | 2h | 83%<br>89%[a] |
| 1i | 2i | 79% |
| 1j | 2j | 80% |
| 1k | 2k | 84% |

-continued
| Scheme 2. Exemplary substrate scope of the hydrodealkenylation reaction. | | |
|---|---|---|
| Starting Material | Product | Yield |
| 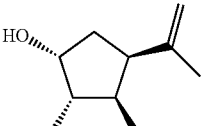<br>1l | 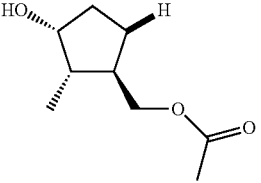<br>2l | 91% |
| 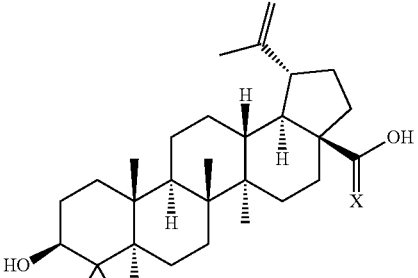<br>1m/m' | 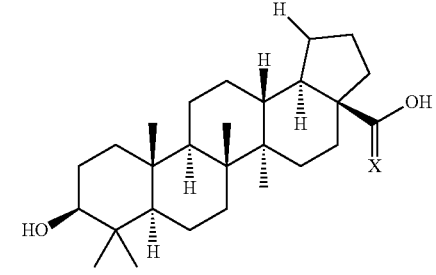<br>2m/m'<br>2m X = H$_2$<br>2m' X = O | 88%<br>83% |
| 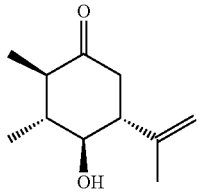<br>1n | 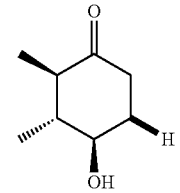<br>2n | 85% |
| 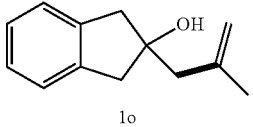<br>1o | 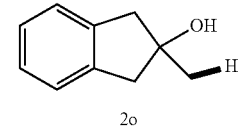<br>2o | 71% |
| 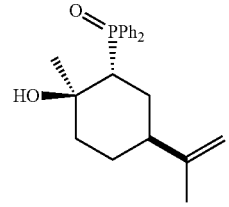<br>1p | 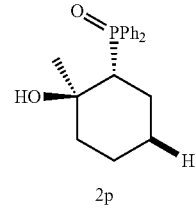<br>2p | 84% |
| 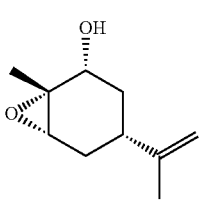<br>1q | 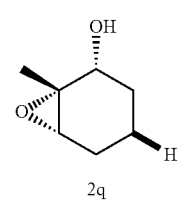<br>2q | 72% |

Scheme 2. Exemplary substrate scope of the hydrodealkenylation reaction.

| Starting Material | Product | Yield |
|---|---|---|
| 1r | 2r | 86% |
| 1s | 2s | 82% |
| 1t | 2t | 62%[b] |

| Starting Material | Product | Yield[a] |
|---|---|---|
| 1a | 2a | 87% |
| 1b | 2b | 75% |
| 1c | 2c | 95% |

-continued

Scheme 2. Exemplary substrate scope of the hydrodealkenylation reaction.

| Starting Material | Product | Yield |
|---|---|---|
| 1d | 2d | 82% |
| 1e | 2e | 81%[b] |
| 1f | 2f | 80% |
| 1g | 2g | 75% |
| 1h | 2h | 61%[b] |
| 1i | 2i | 83% |

Scheme 2. Exemplary substrate scope of the hydrodealkenylation reaction.

| Starting Material | Product | Yield |
|---|---|---|
| 1j | 2j | 50% |
| 1k | 2k | 60% |
| 1l | 2l | 82% |
| 1m | 2m | 58% |
| 1n | 2n | 87% |
| 1o | 2o + 2o' (1.3:1) | 82% |

Scheme 2. Exemplary substrate scope of the hydrodealkenylation reaction.

| Starting Material | Product | Yield |
|---|---|---|
| 1p | 2p + 2p' (5:1) | 67% |

Experiments were performed on ≥1.0 mmol scale. Yields shown refer to isolated yields after $SiO_2$ chromatography.
[a]100.0 mmol scale.
[b]After basic workup.

Notably, both enantiomers of the Wieland-Miescher ketone (2e/ent-2e), a key synthetic intermediate used in more than 50 total syntheses, were prepared from the readily accessible dienediones 1e and ent-1e. Naturally occurring terpenoids were also viable substrates, providing the hydrodealkenylation products 2g-2j, valuable building blocks in both total synthesis and the preparation of pharmaceutical agents, in good yields (79-89%). Surprisingly, the epoxide in (−)-cis-limonene oxide (1g) was opened diastereoselectively under the reaction conditions to furnish the trans-alkoxy alcohol 2g as the sole product (presumably facilitated by a Lewis-acidic $Fe^{III}$ species). The carvone-derived hydroxy ester 1k and diol 1l, both of which have been used in a number of synthetic applications, smoothly delivered their products 2k (84%) and 2l (91%), respectively. The primary hydroxyl group in the diol 1l underwent intramolecular trapping of the intermediate carbonyl oxide, producing the acetylated product 2l. Betulin (1m), a naturally occurring triterpenoid displaying wide biological activity, gave the hydrodealkenylation product 2m in high yield (88%). The hydroxy ketone 1n, containing four stereocenters, provided the fragmentation product 2n in 85% yield, while the indanol 1o furnished 2o in 71% yield. Further displaying the power of this transformation for derivatization of chiral pool-based auxiliaries, the substrates 1p-1s delivered their fragmentation products 2p-2s in good yields. It is also possible to convert the ammonium salt 1t to the amino alcohol 2t in 62% yield after performing a basic workup. As validation of the robustness of this reaction, fragmentation of (−)-isopulegol (1h) on 100-mmol scale furnished the enantiomerically pure alcohol 2h in 89% yield. Unexpectedly, and most notably, both antipodes are attainable for every chiral product in Scheme 2 (except 2d and 2m), due to the ready accessibility of the enantiopure terpenoid precursors.

To further explore the synthetic utility of this hydrodealkenylation, other types of $C(sp^3)$-$C(sp^2)$ linkages were employed as substrates. Scheme 3 demonstrates that starting materials containing exomethylene units (3) provided carboxylic ester products (4) after the loss of a one-carbon unit as formaldehyde.

Scheme 3. Generation of esters and masked aldehydes via $C(sp^3)$—$C(sp^2)$ bond fragmentation.

| Starting Material | Product | Yield |
|---|---|---|
| 3a | 4a | 80% |
| 3b | 4b | 89% |

-continued
Scheme 3. Generation of esters and masked aldehydes via C(sp³)—C(sp²) bond fragmentation.
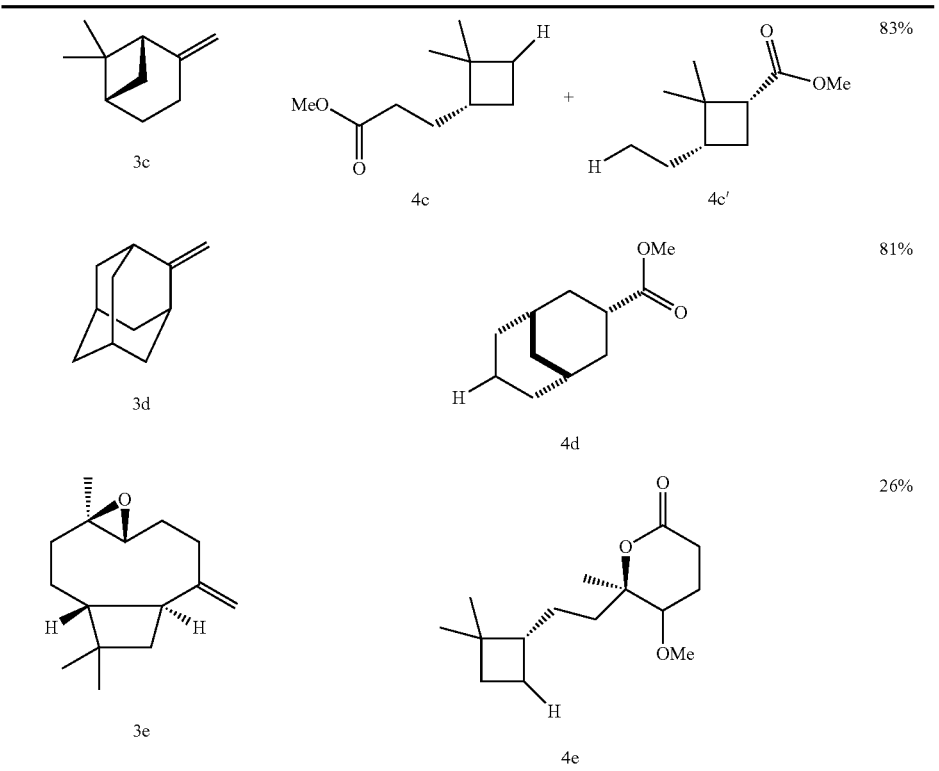
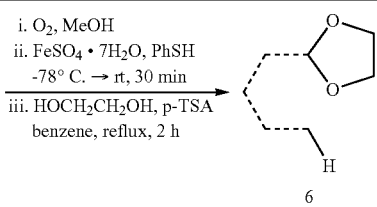
| Starting Material | Product | Yield |
|---|---|---|
| 5a | 6a | 71% |
| 5b | 6b | 60% |
| 5c | ent-6b | 65% |

Scheme 3. Generation of esters and masked aldehydes via C(sp$^3$)—C(sp$^2$) bond fragmentation.

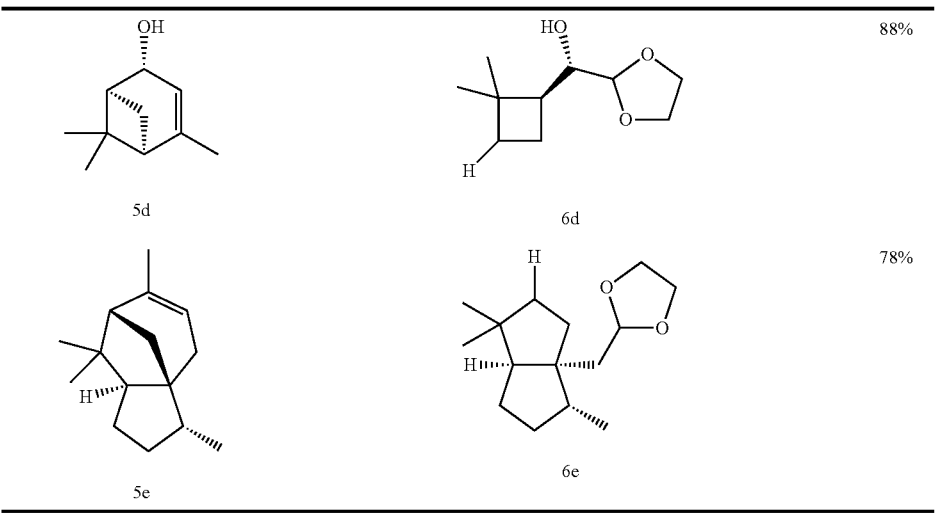

Experiments were performed on 2.0 mmol scale. Yields shown refer to isolated yields after SiO$_2$ chromatography.

Methylenecyclohexane (3a) smoothly furnished methyl hexanoate (4a) in 80% yield. The naturally occurring terpene (±)-camphene (3b) generated a single diastereoisomer of the cyclopentanecarboxylic ester 4b in 89% yield. Surprisingly, the α-alkoxy hydroperoxide intermediate fragmented to generate the tertiary carbon radical exclusively, over the alternative secondary carbon radical, prior to hydrogen atom abstraction. Contrarily, (−)-β-pinene (3c) provided a 1:1 regioisomeric mixture (83% yield) of the products 4c and 4c☐ a result of indiscriminative radical scission. Subjecting methyleneadamantane (3d) to this process furnished a single diastereoisomer of the bicyclo[3.3.1]nonane ester 4d in 81% yield. The reaction of (−)-carophyllene oxide (3e) produced the lactone 4e—the result of epoxide opening (cf. 2g) and subsequent intramolecular lactonization.

The substrate scope was further expanded by converting various cycloalkenes (5) to ethylene glycol acetals of the aldehydes (6), involving the loss of a two-carbon unit in the form of methyl acetate. Also demonstrated herein are aldehyde products that can be protected and isolated as 1,3-dioxolanes immediately after synthesis. Methylcyclohexene (5a) cleanly delivered the acetal of pentanal 6a in 71% yield. More compelling is the ability to generate optically active products from readily available and enantiomerically pure terpene and terpenoid starting materials. Although cyclobutane moieties are particularly valuable synthetic intermediates and are also present in many natural products, enantioselective preparations of these ring systems can be challenging, especially when compared with those of smaller and larger carbocycles. Cyclobutane-containing bridged terpenes are, however, prevalent; combined with hydroalkenylation they provide ready access to variants of this scaffold. (+)-α-Pinene (5b) and (−)-nopol (5c) produced opposite enantiomers of the cyclobutylacetaldehyde acetals 6b and ent-6b in yields of 60 and 65%, respectively. (S)-cis-Verbenol (5d) smoothly dispensed the corresponding aldol acetal 6d, containing two stereocenters, in 88% yield, while (−)-α-cedrene (5e) provided the cis-fused octahydropentalene 6e, with three stereocenters, in 78% yield.

The ease of operation, efficiency, and functional group compatibility of the hydrodealkenylation was further ratified through its application in the syntheses of several biologically active natural products (Scheme 4).

Scheme 4. Exemplary applications of the hydrodealkenylation reaction in total synthesis.

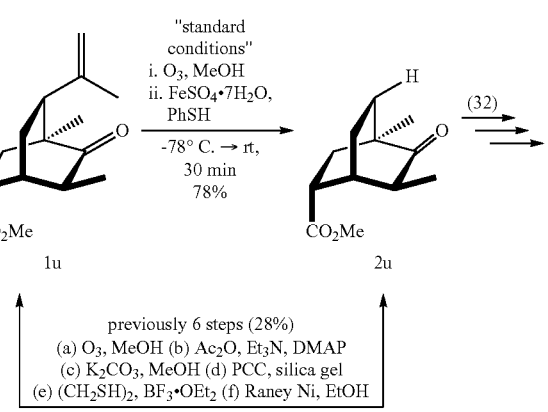

previously 6 steps (28%)
(a) O$_3$, MeOH (b) Ac$_2$O, Et$_3$N, DMAP
(c) K$_2$CO$_3$, MeOH (d) PCC, silica gel
(e) (CH$_2$SH)$_2$, BF$_3$·OEt$_2$ (f) Raney Ni, EtOH

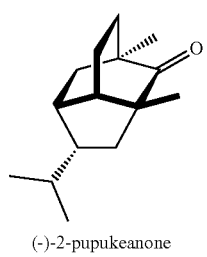

(−)-2-pupukeanone

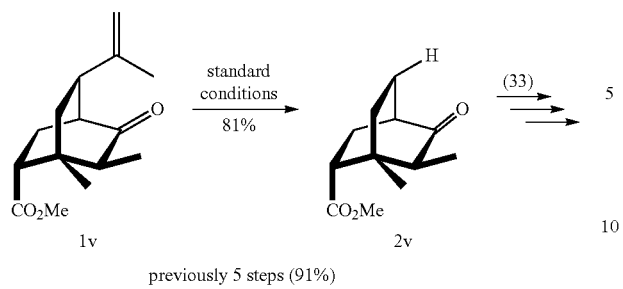

1v
previously 5 steps (91%)

1w
previously 3 steps (67%)

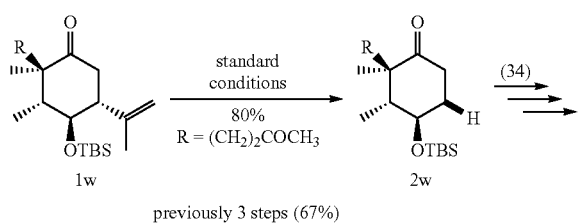

1x
previously 4 steps (47%)

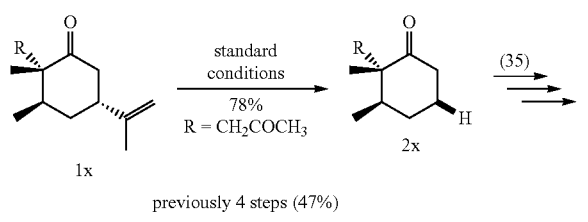

1y
previously 3 steps (49%)

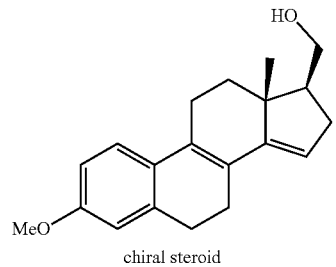

chiral steroid

In a striking and unexpected example—en route to the isotwistane sequiterpenoid (−)-2-pupukeanone—bicyclic ketoester 2u was synthesized directly from 1u in 78% yield. Previously, this conversion required six steps and gave the product in only 28% overall yield. In another example, ketoester 2v, an intermediate leading to (−)-seychellene, was obtained from its precursor 1v in 81% yield. Furthermore, the simplicity of the method described herein outshines the five purifications required by the former. The silyloxy dione 1w, an intermediate leading to the sesquiterpenoid periconianone A, provided its product 2w in 80% yield (previously prepared in three steps and 67% yield) (34). The dione 1x, an intermediate in the preparation of the spirocyclic sesquiterpenoid (−)-7-epibakkenolide-A, smoothly furnished the product 2x in 78% yield (previously four steps/47% yield) (35). Finally, the silyloxy ketone 1y delivered the chiral steroid ring D precursor 2y in 75% yield (previously three steps/49% yield). In each of these examples, direct hydrodealkenylative cleavage lowered the number of steps and purifications, while also providing an average yield increase of 22%.

Several experiments were then performed to support the notion of a free carbon radical in these hydrodealkenylations and establish the possibility of engaging the radical intermediate in other useful transformations (Scheme 5).

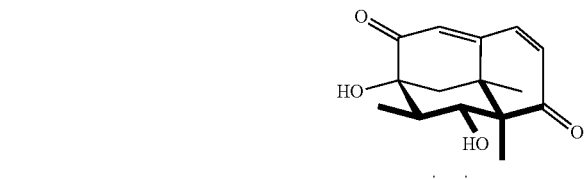

(−)-seychellene

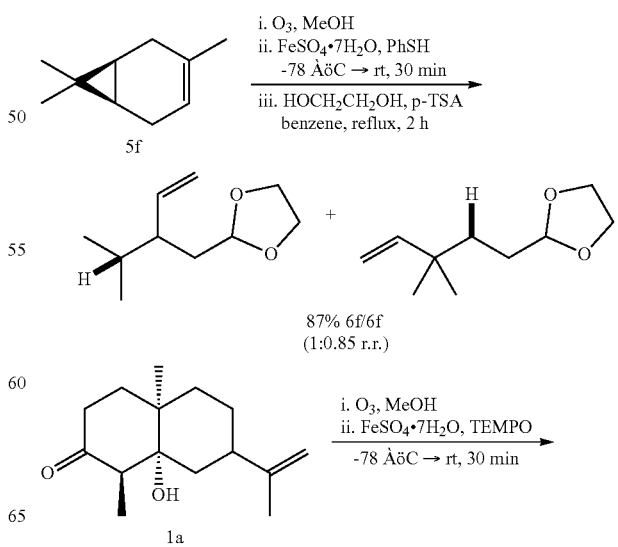

Scheme 5. Mechanistic insights of the hydrodealkenylation reaction, specifically observations that are consistent with the intermediacy of a carbon radical.

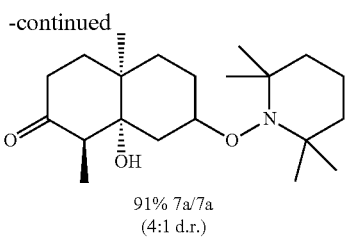

91% 7a/7a
(4:1 d.r.)

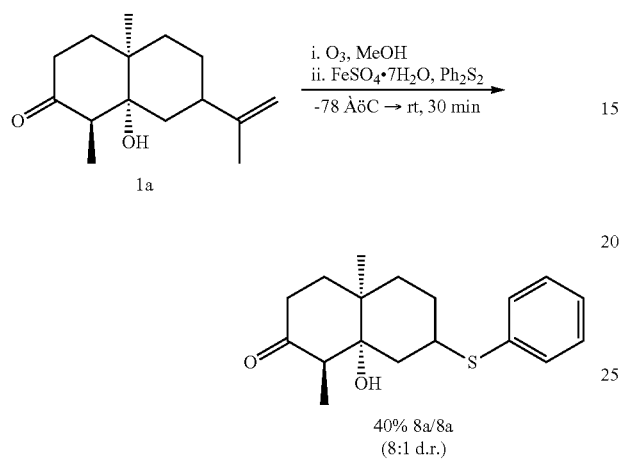

40% 8a/8a
(8:1 d.r.)

Subjecting (1S)-(+)-3-carene to the reaction conditions generated the corresponding cyclopropylcarbinyl radical, with subsequent rearrangement, hydrogen atom abstraction, and dioxolane protection supplying a 1:0.85 mixture of the products 6f and 6f☐in 87% yield. When TEMPO was substituted for the hydrogen atom donor, TEMPO adducts 7a and 7a☐were obtained in a combined isolated yield of 91%. The stereochemistry of the major product, confirmed through single-crystal X-ray diffraction of 7a, was that of the equatorial aminoxyl group. Similarly, employing diphenyldisulfide as a radical trap produced the thioethers 8a and 8a☐in a combined isolated yield of 40%. In this case, the diastereoselectivity was higher (8:1 d.r.), and the major product again displayed an equatorial—in this case, phenylthio—group.

A survey of the reaction parameters revealed advantageous conditions for the dealkenylative thiylation to be ozonolysis of the alkene at −78° C. in methanol, followed by treatment with 3.0 equivalents of the aryl disulfide and 1.2 equivalents of ferrous sulfate heptahydrate (added as a 5 wt/vol % aqueous solution) at 0° C. Under these conditions and using 4-isopropenyltetrahydropyran (1a) as the alkene substrate, the scope of the aryl disulfide reaction was examined partner. Phenyl disulfide (2a) gave the product 3aa in 80% yield, while various tolyl and xylyl disulfides also produced their thiylation products 3ab-3af in yields of 62-77%. Electron-rich and -poor aryl disulfides were competent partners, generating the expected products 3ag-3aj in yields of 50-75%, 1-Phenyltetrazol-5-yl and 2-pyridyl disulfides, notable for use of their thioether and sulfone derivatives in cross-coupling reactions, were also compatible, providing the thioethers 3ak and 3al in yields of 51 and 75%, respectively. Attempts to employ dialkyl disulfides as coupling partners were unfruitful, presumably because of side reactions resulting from the generation of reactive alkylthiyl radical intermediates.

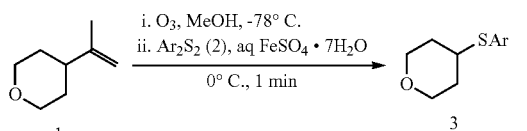

| Product | Yield |
|---|---|
| (SAr, tetrahydropyran) | Ar =<br>Ph 3aa 80%<br>o-tolyl 3ab 77%<br>m-tolyl 3ac 64%<br>p-tolyl 3ad 71%<br>2,6-xylyl 3ae 70%<br>3,4-xylyl 3af 62%<br>o-anisyl 3ag 51%<br>p-anisyl 3ah 75% |
| 3ai | 50% |
| 3aj | 70% |
| 3ak | 51% |
| 3al | 75% |

Subsequently, the substrate scope of the alkene coupling partner was investigated. The primary radical precursors 1b-1d supplied the thioethers 3ba-3da in yields of 58-80%. Secondary (1e, 1f) and tertiary (1g) radical precursors were also compatible, furnishing the desired products 3ea-3ga in yields of 74-82%. The reaction was tolerant to a range of functionalities, including alcohol, imide, amide, carboxylic ester, and carbamate groups. A powerful feature of the reaction is the ability to introduce heteroatom functionality in terpenoid [e.g., (+)-nootkatone, 1i] and terpenoid-derived starting materials. The bicyclic ketones 1h-1k gave their corresponding products in yields of 67-77% (5.9:1 to 7.5:1 d.r.). Notably, dealkenylative thiylation of the diastereoisomeric enones 1j and 1k resulted in the same distribution of product isomers. This observation is consistent with stereoselectivity trends commonly observed in reactions with cyclic radicals, in which the stereoselectivity of the addition is dictated by a combination of torsional and steric effects.

The commonly available terpenoids (−)-isopulegol (1l), trans-(+)-dihydrocarvone (1m), cis-(−)-limonene oxide (1n), (−)-dihydrocarveol (1o), and (−)-limonene-1,2-diol (1p) were also viable substrates, producing their products 3la-3pa, respectively, in yields of 60-84%. When run using 10 mmol of trans-(+)-dihydrocarvone (1m), the reaction produced the thioethers 3ma/3ma□ in 66% yield. With the exception of 3na (12:1 d.r.), the diastereoisomeric ratios of the products from the monoterpenoids were lower (in the range from 1.5:1 to 4:1) than those of the decalinone substrates 1h-1k.

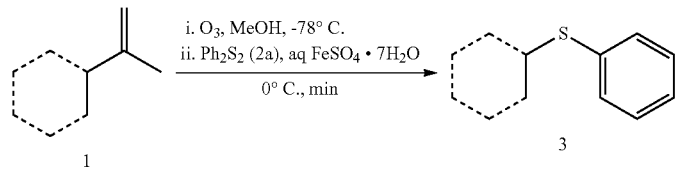

Scheme 7. Exemplary scope of the dealkenylative thiylation reaction.

Scheme 7. Exemplary scope of the dealkenylative thiylation reaction.
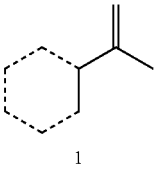
| Starting Material | Product | Yield |
|---|---|---|
| 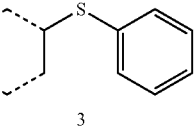<br>1i | 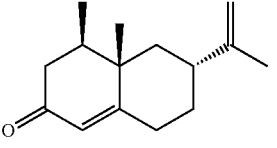 [SMILES: C=C(C)[C@@H]1CCC2=CC(=O)C[C@@H](C)[C@]2(C)C1]<br>3ia/3ia' | 67%<br>(7:1 d.r.)[a,b] |
| 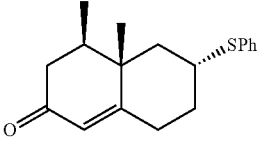<br>1j | 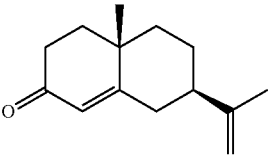<br>3ja/3ja' | 74%<br>(7.5:1 d.r.)[a] |
| 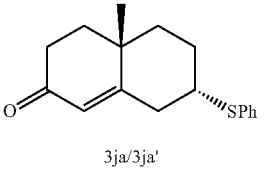<br>1k | 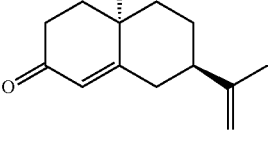<br>ent-3ja/ent-3ja' | 75%<br>(7.5:1 d.r.)[a] |
| 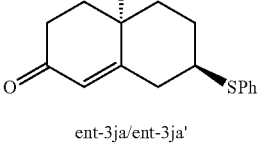<br>1l | 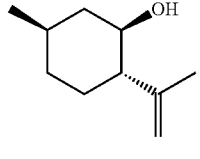<br>3la/3la' | 73%<br>(1.5:1 d.r.)[a] |
| 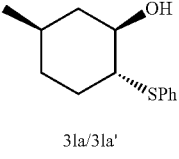<br>1m | 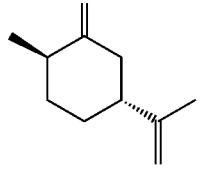<br>3ma/3ma' | 75%<br>66%[c]<br>(1.6:1 d.r.)[a] |
| 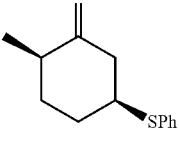<br>1n | 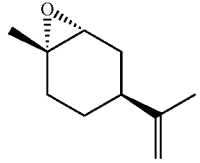<br>3na/3na' | 63%<br>(12:1 d.r.)[a,b] |

Scheme 7. Exemplary scope of the dealkenylative thiylation reaction.

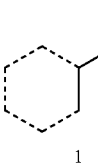

| Starting Material | Product | Yield |
|---|---|---|
| 1o | 3oa/3oa' | 79% (2:1 d.r.)$^a$ |
| 1p | 3pa/3pa' | 84% (4:1 d.r.)$^a$ |

Next, it was found that alkenes containing exo-methylene groups (4) were converted into the corresponding phenylthiyl-containing methyl carboxylates (5). The simple cycloalkenes 4a and 4b generated their products 5aa and 5ba cleanly in yields of 73 and 71%, respectively. 1-Methylene-2-methylcyclohexane (4c) provided its product 5ca in 75% yield, while the Boc-protected piperidine 4d also cleanly supplied the thioether 5da in 80% yield. 1-Methyleneindane (4e) furnished its product 5ea in 51% yield, while 2-methylenetetralin (4f) displayed the poorest efficiency, providing 5fa/5fa□(1.6:1 r.r.) in only 35% yield. The naturally occurring terpene (±)-sabinene (4g) produced a single diastereoisomer of the trisubstituted cyclopropane 5ga in 74% yield. Fragmentative coupling of methyleneadamantane (4h) also generated the exo-phenylthio ester 5ha exclusively in 51% yield.

Scheme 8. Further exemplary optimization of the dealkenylative thiylation reaction.

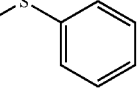

| Starting Material | Product | Yield |
|---|---|---|
| 4a | 5aa | 73% |
| 4b-d | 5ba X = CH$_2$, R = H<br>5ca X = CH$_2$, R = Me<br>5da X = NBoc, R = H | 5ba 71%<br>5ca 75%<br>5da 80% |

Scheme 8. Further exemplary optimization of the dealkenylative thiylation reaction.

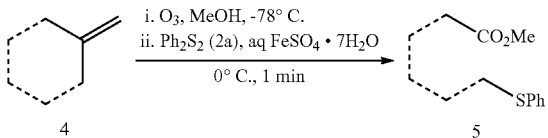

| Starting Material | Product | Yield |
|---|---|---|
| 4e | 5ea | 51% |
| 4f | 5fa + 5fa' | 35% (1.6:1 r.r.)[a] |
| 4g | 5ga | 74% |
| 4h | 5ha | 51% |

Cycloalkenes bearing endocyclic olefins (6) were also competent substrates, providing phenylthio-aldehydes (7) as products. Simple hydrocarbon substrates (6a-6c) supplied the expected products 7aa-7ca, respectively, in yields from 63 to 75%. (+)-2-Carene (6d) furnished a single diastereoisomer of the tetrasubstituted cyclopropane 7da in 65% yield. α-Terpineol (6e) gave the cyclic ketals 7ea/7ea in 42% yield (1.2:1 d.r.), the result of intramolecular trapping of the aldehyde; in contrast, the corresponding acetate 6f produced the uncyclized product 7fa in 61% yield. Upon fragmentation, norbornylene (6g) generated the products 7ga and 7ga (1.2:1 d.r.) in 50% yield. Intriguingly, attempts to extend this transformation to generate benzaldehydes resulted in cyclization of the intermediate radical, rather than trapping with the disulfide species. 6-Methyl-5,6-didehydrobenzocycloheptane (6h) provided the desired product 7ha in only 5% yield, while generating α-tetralone (7ha□) in 90% yield.

Scheme 9. Further exemplary optimization of the dealkenylative thiylation reaction.

| Starting Material | Product | Yield |
|---|---|---|
| 6a | 7aa | 67% |
| 6b-c | | 7ba X = CH$_2$ 63%<br>7ca X = CHPh 75% |
| 6d | 7da | 65% |
| 5e | 7ea/7ea' | 42%[a]<br>(1.2:1 d.r.)[b] |
| 5f | 7fa | 61% |
| 6g | 7ga/7ga' | 50%<br>(1.2:1 d.r.) |
| 6h | 7ha + 7ha' | 7ha 5%<br>7ha' 90% |

Figure 4A:
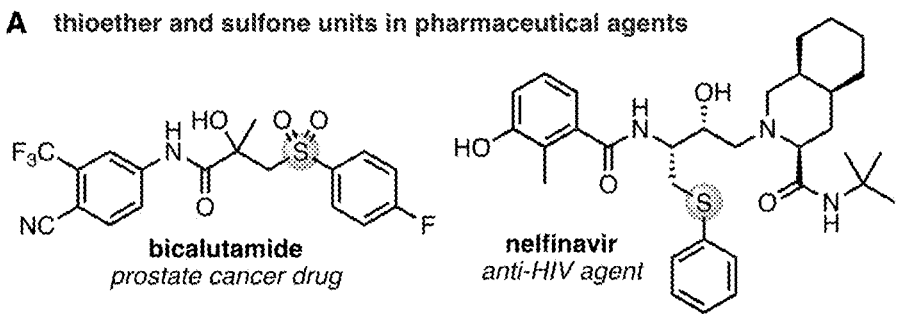
FIG. 4A depicts the prevalence of thioethers and sulfones in certain pharmaceutical agents.
Figure 4B:
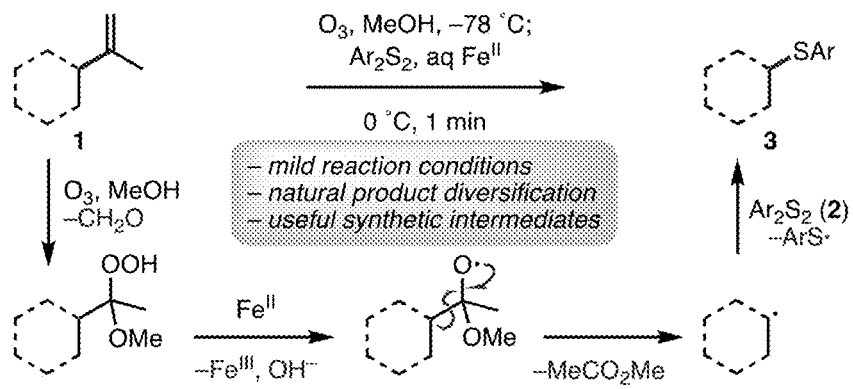
FIG. 4B schematically depicts certain advantages of the dialkenylative thiylation reaction.

The dealkenylative thiylation can be applied to a range of uses. For example, with regard to medicinal agents, this process can be a tool for the functionalization of biologically active compounds. For instance, the reaction of betulin (1q) (FIG. 4A), which has wide biological activities (in particular, anti-cancer and anti-HIV properties), yet few functional group handles on the skeleton. Notably, cleavage of the C-19 C(sp$^3$)-C(sp$^2$) bond followed by the introduction of a heteroatom at this position is rare, with most modifications occurring at the C-3 and/or C-28 positions. Dealkenylative thiylation of betulin readily furnished the thioethers 3ql and 3ql □n 78% yield (1.2:1 d.r.). Subsequent oxidation of the major diastereoisomer (3ql) gave the sulfone 8 in 43% overall yield from betulin, providing facile access to previously inaccessible derivatives of this natural product. Sulfones and sulfides are also useful functional group handles that are used widely in organic synthesis. When dealkenylative thiylation is combined with terpenoid precursors, enantiopure synthetic intermediates are generated readily. Oxidation, mesylation, and intramolecular alkylation of the dihydrocarveol-derived thioether 30a produced the enantiomerically pure bicyclo[3.1.0]hexane 9 in 85% overall yield. Vinyl sulfides and sulfones are also useful synthetic precursors. A sequence of oxidation, mesylation, and elimination generated a single enantiomer of the vinyl sulfone 10 in 96% yield from the thioether 3la. When employing the dihydrocarvone-derived thioether 3ma□ it was found that the protected sulfone underwent iron-catalyzed cross-coupling to provide the arylated products 11/11□in 47% overall yield (4.3:1 d.r.). Finally, oxidation of the thioether 3ma to the sulfone, followed by Baeyer-Villiger oxidation, gave the lactone 12 in 70% yield. Caprolactones are employed widely as monomers for polymer synthesis, and this approach establishes a route toward bio-renewable terpenoid-based caprolactones that are both diastereomerically and enantiomerically pure.

The straightforward nature of the hydrodealkenylation and dealkenylative thiylation reactions, performed with inexpensive and commercially available reagents and instruments, will engender innovations in synthesis and the use of chiral pool-based starting materials. Fundamentally, these unusual disconnection and bond formation reactions should prove extremely useful in both retrosynthetic analyses and late-stage synthetic modifications. Furthermore, the ease with which these carbon-centered radicals can be trapped opens a gateway for employing common alkenes, seldom used as radical precursors, in a plethora of known radical transformations.

In one aspect, the present disclosure provides methods of making compounds, comprising:
  providing a starting material comprising an $sp^3$-hybridized carbon and an $sp^2$-hybridized carbon, wherein the $sp^3$-hybridized carbon and the $sp^2$-hybridized carbon are connected by a single bond;
  placing the starting material in a reaction vessel, thereby forming a reaction mixture; and
  cleaving the single bond, wherein cleaving the single bond comprises:
    contacting the reaction mixture with an oxidant; and
    contacting the reaction mixture with a transition metal salt.

In some embodiments, the steps are performed in the following sequence:
  a) providing the starting material;
  b) placing the starting material in a reaction vessel; and
  c) cleaving the single bond.

In some embodiments, the steps of cleaving the single bond are performed in the following sequence:
  i) contacting the reaction mixture with the oxidant; and
  ii) contacting the reaction mixture with the transition metal salt.

In some embodiments, the methods further comprise adjusting the temperature of the reaction mixture to between −50° C. and −110° C. before contacting the reaction mixture with an oxidant.

In some embodiments, contacting the reaction mixture with the oxidant is performed at about 0° C., −5° C., −10° C., −15° C., −20° C., −25° C., −30° C., −35° C., −40° C., 45° C., −50° C., −55° C., −60° C., −65° C., −70° C., −75° C., −80° C., −85° C., −90° C., −95° C., or −100° C. In some embodiments, contacting the reaction mixture with the oxidant is performed at about −50° C., −55° C., −60° C., −65° C., −70° C., −75° C., −80° C., −85° C., −90° C., −95° C., or −100° C. In some preferred embodiments, contacting the reaction mixture with the oxidant is performed at about −70° C., −75° C., or −80° C.

In some embodiments, contacting the reaction mixture with the transition metal salt is performed at about 30° C., 25° C., 20° C., 15° C., 10° C., 5° C., 0° C., −5° C., −10° C., −15° C., −20° C., −25° C., −30° C., −35° C., −40° C., −45° C., −50° C., −55° C., −60° C., −65° C., −70° C., −75° C., −80° C., −85° C., −90° C., −95° C., or −100° C. In some preferred embodiments, contacting the reaction mixture with the transition metal salt is performed at about −70° C., −75° C., or −80° C.

In some embodiments, the starting material is no longer detectable after step i). In some embodiments, the starting material is no longer detectable after step i) but before step ii). In some embodiments, the starting material is no longer detectable by thin layer chromatography (TLC), liquid chromatography, infrared spectroscopy, or mass spectrometry.

In some embodiments, the methods further comprise quenching the reaction mixture with a radical quencher. In some embodiments, quenching the reaction mixture with a radical quencher is performed at about 30° C., 25° C., 20° C., 15° C., 10° C., 5° C., 0° C., −5° C., −10° C., −15° C., −20° C., −25° C., −30° C., −35° C., 40° C., −45° C., −50° C., −55° C., −60° C., −65° C., −70° C., −75° C., −80° C., −85° C., −90° C., −95° C., or −100° C. In some preferred embodiments, quenching the reaction mixture with a radical quencher is performed at about-70° C., −75° C., or −80° C.

In some embodiments, quenching the reaction mixture with the radical scavenger occurs after cleaving the single bond.

In some embodiments, the radical scavenger is a hydrogen atom donor.

In some preferred embodiments, the hydrogen atom donor is an aryl thiol or heteroaryl thiol. In some embodiments, the hydrogen atom donor is an aryl thiol. In some embodiments, the hydrogen atom donor is benzenethiol, methoxybenzenethiol, nitrobenzenethiol, alkylbezenethiol (e.g., trifluoromethylbenzenethiol or t-butylbenzenethiol), phenyltetrazolethiol, aminobenzenethiol, or naphthalenethiol.

In other embodiments, the hydrogen atom donor is a terpinene (e.g., γ-terpinene).

In yet other embodiments, the hydrogen atom donor is an alkyltinhydride (e.g., nBusSnH).

In certain preferred embodiments, quenching the reaction mixture with the radical scavenger results in forming an methylene or a methyl group.

In yet other embodiments, the radical scavenger is a radical. In some embodiments, the radical is an oxygen radical, a sulfur radical, a nitrogen radical, or a nitroxyl radical (e.g., (2,2,6,6-tetramethylpiperidin-1-yl)oxidanyl (TEMPO)). In some embodiments, quenching the reaction mixture with the radical scavenger results in forming a hydroxylamine (e.g., dimethylcyclohexyl hydroxylamine). In some embodiments, the radical scavenger is a disulfide (e.g., diphenyl disulfide). In certain preferred embodiments, quenching the reaction mixture with the radical scavenger results in forming an aryl sulfide (e.g., phenyl sulfide). In some embodiments, the disulfide is benzene disulfide, methoxybenzene disulfide, nitrobenzene disulfide, alkylbezene disulfide (e.g., trifluoromethylbenzene disulfide or t-butylbenzene disulfide), phenyltetrazole disulfide, aminobenzene disulfide, or naphthalene disulfide. In some embodiments, the hydrogen atom donor is benzenethiol. In some embodiments, the disulfide is alkylbenzene disulfide (e.g., methylbenzene disulfide or dimethylbenezene disulfide), alkoxybenzene disulfide (e.g., methoxybenzene disulfide), halobenzene disulfide (e.g., fluorobenzene disulfide), heteroaryl disulfide (e.g., pyridyl disulfide).

In some embodiments, the method further comprises contacting the reaction mixture with a solvent. In some embodiments, contacting the reaction mixture with a solvent occurs before cleaving the single bond. In some embodiments, the solvent is a protic solvent (e.g., methanol).

In some embodiments, the methods further comprises contacting the reaction mixture with a glycol and an acid. In some embodiments, contacting the reaction mixture with a glycol and an acid occurs after cleaving the single bond. In some embodiments, contacting the reaction mixture with a glycol and an acid occurs after quenching the reaction mixture with the radical scavenger.

In some embodiments, the glycol is ethylene glycol. In some embodiments, the acid is a Brønsted acid. In some embodiments, the acid is an organic acid. In some embodiments, the acid is a sulfonic acid (e.g., p-toluene sulfonic acid).

In some embodiments, the transition metal salt is represented by Formula I:

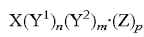

wherein
X is Fe, Fe, Cu, Ce, Ti, Mn, Cr, V, Ag, Co, or Ni;
$Y^1$ and $Y^2$ are each independently selected from $SO_4$, $NH_4$, halo, and $BF_4$;
Z is $H_2O$;
n is an integer from 1-4;
m is an integer from 0-2; and
p is an integer from 0-7.

In some embodiments, the transition metal salt is a ferrous salt, (e.g., $FeSO_4$, $FeSO_4·7H_2O$, $FeCl_2·7H_2O$, $FeCl_2·7H_2O$, $Fe(NH_4)_2(SO_4)_2·6H_2O$, $Fe(BF_4)_2·6H_2O$, $FeCl_2·4H_2O$, $TiCl_3$, $TiOSO_4$, $Cr(ClO_4)_2$, $CuOAc·H_2O$, $CuCl$, $Mn(acac)_2$, $Mn(OAc)·4H_2O$, $VO(SO_4)$, Fe(III) [tetrakis(pentafluorophenyl)] Porphyrin Chloride (F20 TPP)FeCl). In some preferred embodiments, the transition metal salt is $FeSO_4·7H_2O$.

In some preferred embodiments, the oxidant is ozone. In other preferred embodiments, the oxidant is potassium peroxymonosulfate (oxone).

In some embodiments, the starting material is represented by Formula II:

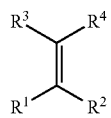

or a salt thereof, wherein
$R^1$ is alkyl, heterocyclyl, or cycloalkyl;
$R^2$ is H, alkyl, or cycloalkyl; or $R^1$ and $R^2$ combine to form a cycloalkyl or heterocyclyl;
$R^3$ is H, alkyl, or cycloalkyl; or $R^1$ and $R^3$ combine to form a cycloalkyl or heterocyclyl; and
$R^4$ is hydrogen or alkyl.

In certain embodiments, if $R^1$ is heterocyclyl, then the alkene of formula II is bonded to a carbon.

In some embodiments, the starting material is represented by Formula IIa:

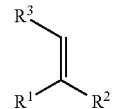

or a salt thereof, wherein
$R^1$ is alkyl, heterocyclyl, or cycloalkyl;
$R^2$ is H, alkyl, or cycloalkyl; or $R^1$ and $R^2$ combine to form a cycloalkyl; and
$R^3$ is H, alkyl, or cycloalkyl; or $R^1$ and $R^3$ combine to form a cycloalkyl.

In some embodiments, the starting material is represented by Formula IIb:

In some embodiments, $R^1$ is cycloalkyl (e.g., a cycloalkyl comprising 5-10 carbon atoms). Some embodiments, $R^1$ is a steroid. In some embodiments, $R^1$ is a cholestane, cholane, pregnane, androstane, or an estrane.

In some embodiments, the starting material is represented by Formula IIc:

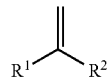

wherein,
$R^1$ and $R^2$ combine to form a cycloalkyl.

In some embodiments, contacting the reaction mixture with the radical scavenger results in forming an alkyl or cycloalkyl substituted with acyl.

In some embodiments, the starting material is represented by Formula IId:

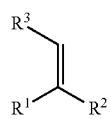

wherein,
$R^1$ and $R^3$ combine to form a cycloalkyl.
In some embodiments, $R^2$ is alkyl (e.g., methyl).
In some embodiments, contacting the reaction mixture with the radical scavenger results in forming an alkyl or cycloalkyl substituted with oxo (=O). In other embodiments, contacting the reaction mixture with the radical scavenger results in forming an alkyl or cycloalkyl substituted with dioxolanyl.

In some embodiments, $R^1$ is further substituted with oxo, alkyl (e.g., methyl), cycloalkyl (e.g., cyclobutyl), cycloalkenyl, hydroxyl, aryl (e.g., phenyl), heterocyclyl (e.g., pyrrolidinyl or pyrrolidiniumyl), epoxyl, phophoryl, acyl, or ester (e.g., methyl ester).

In some embodiments, the starting material comprises at least one stereocenter. In some embodiments, quenching the reaction mixture with the radical quencher results in a product that comprises at least one stereocenter. In some embodiments, the stereochemistry of the stereocenter of the product is retained as compared to the stereochemistry of the stereocenter of the starting material. In some embodiments, the stereochemistry of the stereocenter of the product is inverted as compared to the stereochemistry of the stereocenter of the starting material.

In certain embodiments, the method comprises:
providing a starting material comprising an sp3-hybridized carbon and an sp2-hybridized carbon, wherein the sp3-hybridized carbon and the sp2-hybridized carbon are connected by a single bond;
placing the starting material in a reaction vessel, thereby forming a reaction mixture; and
cleaving the single bond, wherein cleaving the single bond comprises:
  contacting the reaction mixture with an oxidant;
  contacting the reaction mixture with a transition metal salt; and
  quenching the reaction mixture with a hydrogen atom donor.

In certain embodiments, the quenching the reaction mixture with the hydrogen atom donor in forming an methylene or a methyl group.

In other embodiments, the method comprises:
providing a starting material comprising an sp3-hybridized carbon and an sp2-hybridized carbon, wherein the sp3-hybridized carbon and the sp2-hybridized carbon are connected by a single bond;
placing the starting material in a reaction vessel, thereby forming a reaction mixture; and
cleaving the single bond, wherein cleaving the single bond comprises:
  contacting the reaction mixture with an oxidant;
  contacting the reaction mixture with a transition metal salt; and
  quenching the reaction mixture with a disulphide.

In certain embodiments, the quenching the reaction mixture with the disulphide results in forming a thioether.

In yet other embodiments, the method comprises:
providing a starting material comprising an sp3-hybridized carbon and an sp2-hybridized carbon, wherein the sp3-hybridized carbon and the sp2-hybridized carbon are connected by a single bond;
placing the starting material in a reaction vessel, thereby forming a reaction mixture; and
cleaving the single bond, wherein cleaving the single bond comprises:
  contacting the reaction mixture with an oxidant;
  contacting the reaction mixture with a transition metal salt; and
  quenching the reaction mixture with a oxygen radical.

In certain embodiments, the quenching the reaction mixture with the oxygen radical results in forming hydroxylamine.

In some embodiments, the starting material is

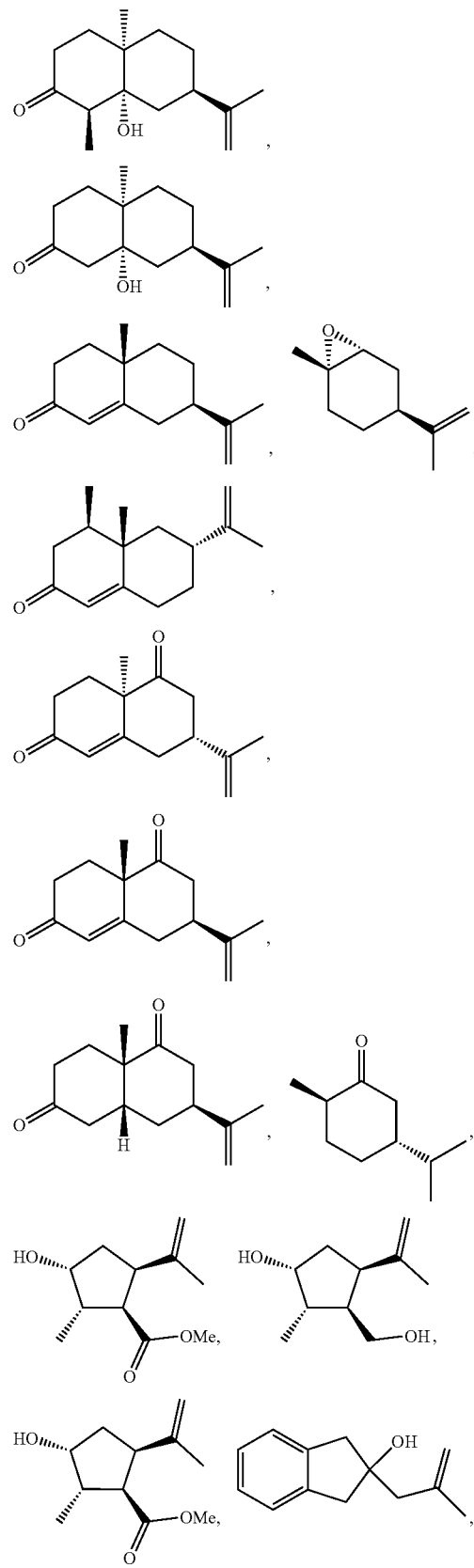

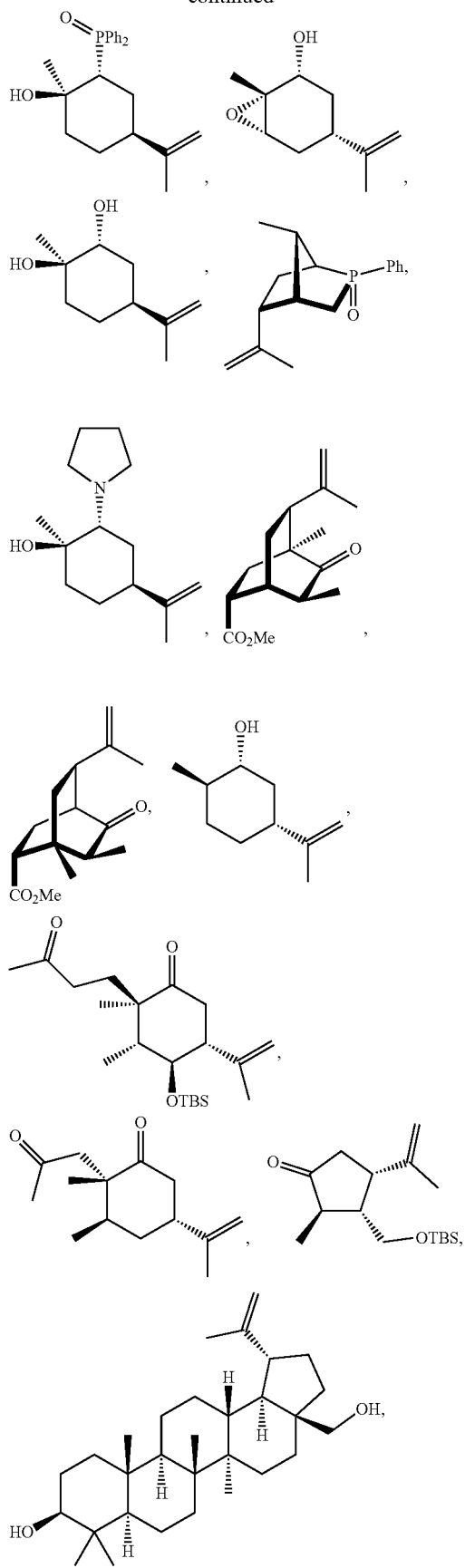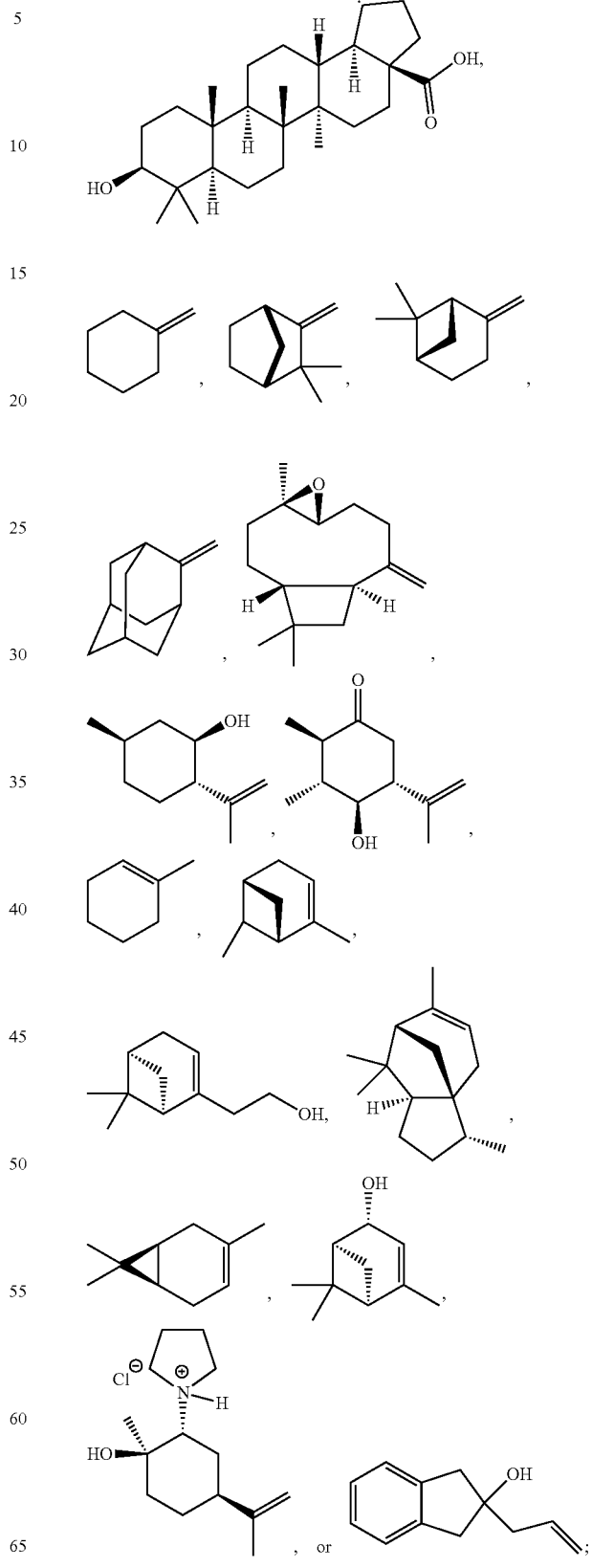

or a salt thereof. In some embodiments, the starting material is

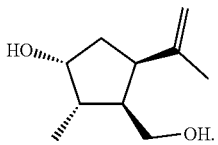

In some embodiments, the starting material is

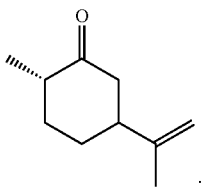

In some embodiments, the starting material is

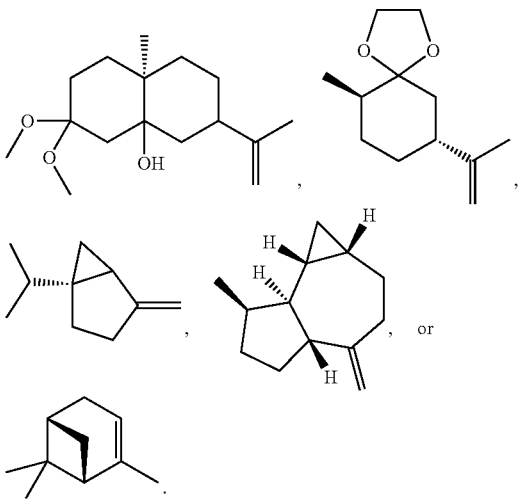

In some embodiments, the starting material is not

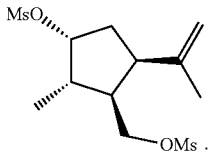 [SMILES: C=C(C)[C@@H]1C[C@@H](OS(C)(=O)=O)[C@@H](C)[C@@H]1COS(C)(=O)=O]

In some embodiments, the method further comprises performing one or more additional reactions on the product of the quenching step.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

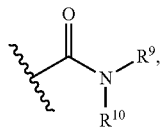

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

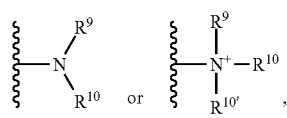

wherein $R^9$, $R^{10}$, and $R^{10\prime}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

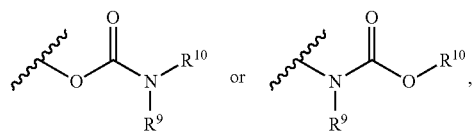

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —OCO$_2$—.

The term "carboxy", as used herein, refers to a group represented by the formula —CO$_2$H.

The term "ester", as used herein, refers to a group —C(O)OR$^9$ wherein R$^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

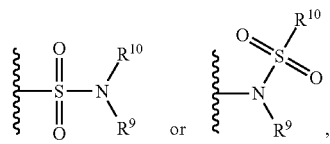

wherein R$^9$ and R$^{10}$ independently represents hydrogen or hydrocarbyl.

The term "sulfoxide" is art-recognized and refers to the group —S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

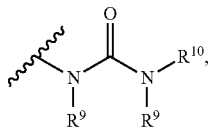

wherein R$^9$ and R$^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Salt" is used herein to refer to an acid addition salt or a basic addition salt.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

The term "steroid" as used herein refers to naturally occurring and synthetic compounds, based on the cyclopenta[a]phenanthrene carbon skeleton, that may be partially or completely saturated. It will be understood by those skilled in the art that the carbon skeleton can be substituted, if appropriate. Examples of steroids include, but are not limited to, alclometasone, prednisone, dexamethasone, triamcinolone, cortisone, fludrocortisone, dihydrotachysterol, oxandrolone, oxabolone, testosterone, nandrolone, diethylstilbestrol, estradiol, norethisterone, medroxyprogesterone acetate, hydroxyprogesterone caproate.

EXAMPLES

The invention now being generally described, it will be more readily understood by reference to the following examples which are included merely for purposes of illustration of certain aspects and embodiments of the present invention, and are not intended to limit the invention.

Example 1: Exemplary Materials and Methods

Unless otherwise stated, reactions were performed in flame-dried glassware fitted with rubber septa under an argon atmosphere and were stirred with Teflon-coated magnetic stirring bars. Liquid reagents and solvents were transferred via syringe using standard Schlenk techniques. Methanol was distilled over magnesium under an argon atmosphere. Dichloromethane and triethylamine were distilled over calcium hydride under an argon atmosphere. Tetrahydrofuran, benzene, toluene, and diethyl ether were distilled over sodium/benzophenone ketyl under an argon atmosphere. All other solvents and reagents were used as received from commercial sources, unless otherwise noted. Reaction temperatures above 23° C. refer to oil bath temperatures. Thin layer chromatography (TLC) was performed using SiliCycle silica gel 60 F-254 precoated plates (0.25 mm) and visualized under UV irradiation, with a cerium ammonium molybdate (CAM) stain or a potassium permanganate (KMnO$_4$) stain. SiliCycle Silica-P silica gel (particle size 40-63 µm) was used for flash column chromatography. $^1$H and $^{13}$C NMR spectra were recorded using Bruker AV-500, DRX-500, and AV-400 MHz spectrometers, with $^{13}$C NMR spectroscopic operating frequencies of 125, 125, and 100 MHZ, respectively. Chemical shifts (δ) are reported in parts per million (ppm) relative to the residual protonated solvent: CDCl$_3$ signal (δ=7.26 for $^1$H NMR; δ=77.2 for $^{13}$C NMR), C$_6$D$_6$ signal (δ=7.16 for $^1$H NMR; δ=128.1 for $^{13}$C NMR), DMSO-d$_6$ (δ=2.50 for $^1$H NMR; δ=39.5 for $^{13}$C NMR). Data for $^1$H NMR spectra are reported as follows: chemical shift, multiplicity, coupling constants (Hz), and number of hydrogen atoms. Data for $^{13}$C NMR spectra are reported in terms of chemical shift. The following abbreviations are used to describe the multiplicities: s=singlet; d=doublet; t=triplet; q=quartet; quint=quintet; m=multiplet; br=broad. Melting points (MP) are uncorrected and were recorded using an Electrothermal® capillary melting point apparatus. IR spectra were recorded on a Jasco FTIR-4100 spectrometer with an ATR attachment; the selected signals are reported in cm$^{-1}$. Optical rotations were recorded using an Autopol IV polarimeter and a 100-mm cell, at concentrations close to 1 g/100 mL. HRMS (ESI) was performed using a Waters LCT Premier spectrometer equipped with ACQUITY UPLC system and autosampler. HRMS (DART) was performed using a Thermo Fisher Scientific Exactive Plus spectrometer equipped with an IonSense ID-CUBE DART source. X-ray crystallographic data were collected using a Bruker SMART CCD-based diffractometer equipped with a low-temperature apparatus operated at 100 K. Ozonolysis experiments were performed using a Pacific Ozone LAB21 (18 g/h) ozone generator and a Globalozone GO-D3G (3 g/h) ozone generator. Abbreviations: Ac, acetyl; Bu, butyl; DMSO, dimethyl sulfoxide; Et, ethyl; EtOAc, ethyl acetate; Et$_2$O, diethyl ether; HAD, hydrogen atom donor; Me, methyl; MeOH, methanol; Ph, phenyl; PhSH, benzenethiol; TBS, tert-butyldimethylsilyl; TEMPO, (2,2,6,6-tetramethylpiperidin-1-yl)oxyl; p-TSA, para-toluenesulfonic acid.

Example 2: Preparation of Exemplary Substrates
Substrate Preparation
The following compounds were either synthesized according to procedures analogous to those described in the literature or purchased from commercial sources.
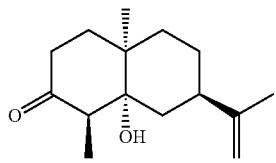
1a
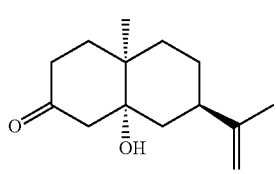
1b
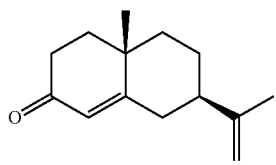
1c
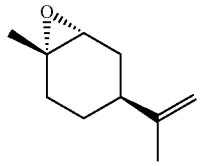
1g
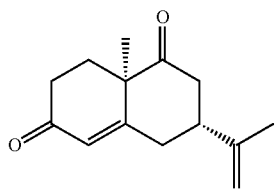
1e
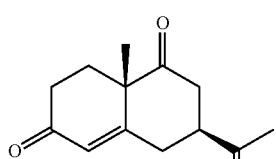
ent-1e
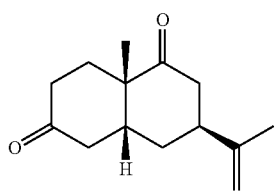
1f
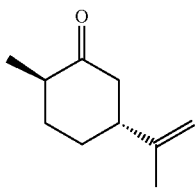
1i
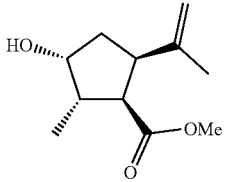
1k
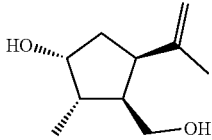
1l
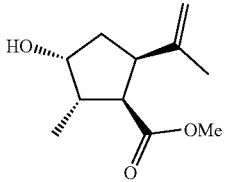
1k
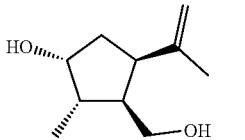
1l
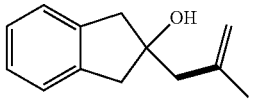
1o
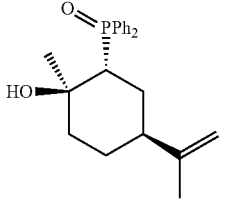
1p
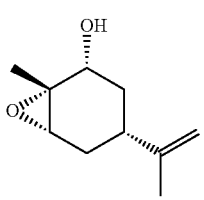
1q
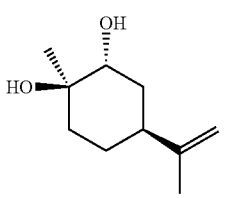
1r -continued

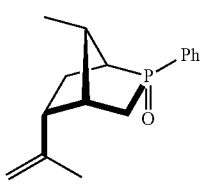

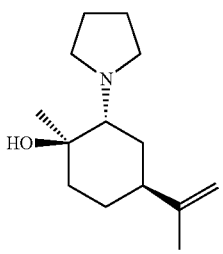

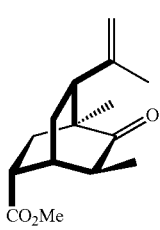

CO₂Me

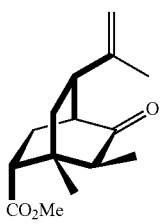

CO₂Me

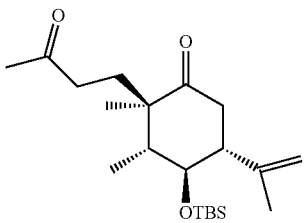

OTBS

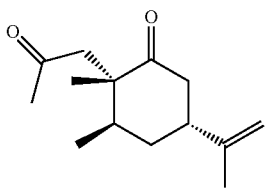

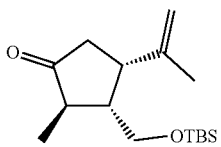

OTBS

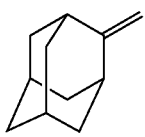

1s

1u

1v

1w

1x

1y

SI-III

-continued

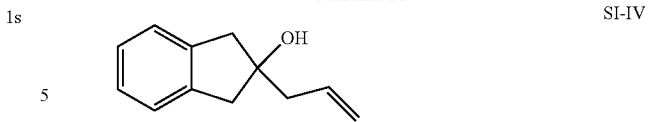

SI-IV

During the synthesis of 1e and ent-1e, something not mentioned previously in the literature was observed. The silica-mediated isomerization shown below has been reported (38) to arise as a result of contact with the silica gel during column chromatography. If the desired ratio of SI-I to SI-II was not achieved, it has also been reported that stirring the compounds with silica gel will further increase the amount of SI-II.

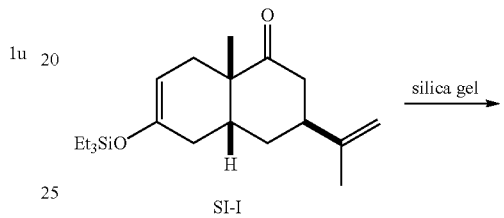

SI-I

SI-II

It was found this isomerization was actually due to trace amounts of HCl present in the deuterated chloroform used to take the NMR spectrum. Five NMR spectra of the same sample recorded sequentially in deuterated chloroform revealed that the isomerization of SI-I into SI-II occurred within minutes. For an accurate assessment of the isomerization, NMR spectra should be recorded using deuterated benzene as the solvent.

The isomerization was performed by heating a solution of SI-I under reflux in toluene in the presence of silica gel for 20 h, obtaining SI-II and SI-I in a 14:1 regioisomeric ratio. It was critical to wash the silica gel filter cake with EtOAc to ensure full recovery of all the isomerized product (washing with dichloromethane led to less than 50% recovery of material).

SI-I

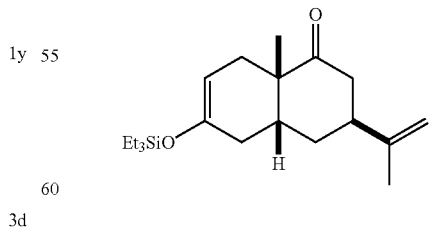

3d

Physical State: colorless oil. $^1$H NMR (500 MHZ, $C_6D_6$): δ 4.78-4.74 (m, 3H), 2.50-2.29 (m, 4H), 2.16-2.08 (m, 1H), 1.83-1.71 (m, 2H), 1.63-1.53 (m, 2H), 1.53-1.43 (m, 1H), 1.46 (s, 3H), 1.12 (s, 3H), 1.00 (t, J=7.9 Hz, 9H), 0.65 (q, J=7.9 Hz, 6H). $^{13}$C NMR (125 MHz, $C_6D_6$): δ 211.6, 147.8, 146.8, 111.3, 99.4, 46.6, 40.6, 40.5, 37.2, 32.5, 30.8, 30.0, 21.5, 21.1, 6.6, 5.0. R$_f$=0.41 (5% EtOAc/hexanes). Purification: (SiO$_2$, 0→5% EtOAc/hexanes).

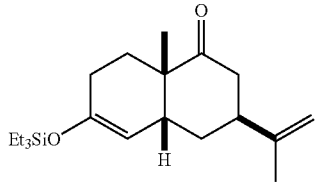

SI-II

Physical State: colorless oil. $^1$H NMR (500 MHZ, C$_6$D$_6$): δ 4.71 (s, 1H), 4.67 (s, 1H), 4.60 (s, 1H), 2.61-2.51 (m, 1H), 2.51-2.43 (m, 1H), 2.37-2.24 (m, 3H), 2.20 (dd, J=14.6, 13.1 Hz, 1H), 1.96 (dd, J=17.5, 6.1 Hz, 1H), 1.74 (ddd, J=12.8, 12.8, 4.0 Hz, 1H), 1.52 (s, 3H), 1.47-1.40 (m, 1H), 1.12 (ddd, J=12.8, 11.4, 6.4 Hz, 1H), 0.96 (t, J=8.0 Hz, 9H), 0.88 (s, 3H), 0.61 (q, J=8.0 Hz, 6H). $^{13}$C NMR (125 MHz, C$_6$D$_6$): δ 211.5, 152.3, 147.5, 109.3, 107.0, 45.5, 43.2, 41.7, 41.0, 32.9, 31.7, 27.3, 24.7, 20.1, 6.5, 5.1. R$_f$=0.39 (5% EtOAc/hexanes). Purification: (SiO$_2$, 0→5% EtOAc/hexanes).

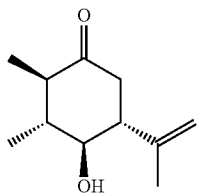

1n

Compound 1n was obtained during preparation of compound 1v, the result of bisdesilylation of the silyl enol ether precursor. Physical State: white solid. $^1$H NMR (500 MHZ, CDCl$_3$): δ 4.96-4.92 (m, 1H), 4.88 (s, 1H), 3.46 (dd, J=9.3, 9.3 Hz, 1H), 2.47-2.29 (m, 3H), 2.11 (dq, J=12.9, 6.5 Hz, 1H), 2.04 (br s, 1H), 1.71 (s, 3H), 1.42 (ddq, J=12.7, 9.8, 6.5 Hz, 1H), 1.17 (d, J=6.3 Hz, 3H), 1.02 (d, J=6.4 Hz, 3H). $^{13}$C NMR (125 MHz, CDCl$_3$): δ 210.1, 144.0, 114.7, 73.7, 53.0, 48.5, 45.6, 43.7, 18.3, 16.8, 11.6. MP: 95° C. IR (neat, ATR): ν$_{max}$ 3390, 2969, 2925, 2897, 1707, 1443 cm$^{-1}$. Optical Rotation: [α]$^{23}$$_D$ 9.5 (c 1.00, CHCl$_3$). HRMS (DART): calc'd for C$_{11}$H$_{20}$O$_2$ [M+H]$^+$183.1380, found 183.1380. R$_f$=0.24 (20% EtOAc/hexanes). Purification: (SiO$_2$, 10→20% EtOAc/hexanes).

A solution of 2-indanone (3.03 g, 22.9 mmol, 1.0 equiv) in tetrahydrofuran (10 mL, 2.3 M) was added dropwise to a well-stirred mixture of zinc powder (2.99 g, 45.7 mmol, 2.0 equiv), saturated aqueous ammonium chloride (100 mL), and tetrahydrofuran (20 mL). A solution of 3-Bromo-2-methylpropene (4.60 mL, 45.7 mmol, 1.0 equiv) in tetrahydrofuran (10 mL, 4.6 M) was added dropwise to the reaction mixture. The reaction was mildly exothermic and began to reflux spontaneously. After the refluxing had ceased, the mixture was stirred for an additional 24 h at room temperature. The mixture was subjected to extraction with Et$_2$O; the combined organic phases were dried (anhydrous sodium sulfate), filtered, and concentrated under reduced pressure. The residue was purified by flash column chromatography (SiO$_2$) to give pure 1o. Yield: 63% (2.71 g). Physical State: white solid. $^1$H NMR (500 MHZ, CDCl$_3$): δ 7.25-7.15 (m, 4H), 4.99 (s, 1H), 4.87 (s, 1H), 3.12 (d, J=16.2 Hz, 2H), 2.96 (d, J=16.1 Hz, 2H), 2.52 (s, 2H), 2.04 (br s, 1H), 1.92 (s, 3H). $^{13}$C NMR (125 MHZ, CDCl$_3$): δ 142.6, 141.2, 126.5, 124.8, 114.9, 81.3, 48.1, 47.2, 24.4. MP: 48° C. IR (neat, ATR): ν$_{max}$ 3467, 3067, 3021, 2894, 2832, 1078, 1061, 883, 742 cm$^{-1}$. HRMS (DART): calc'd for C$_{13}$H$_{15}$ [M-OH]$^+$ 171.1168, found 171.1171. R$_f$=0.51 (10% EtOAc/hexanes). Purification: (SiO$_2$, 5→10% EtOAc/hexanes).

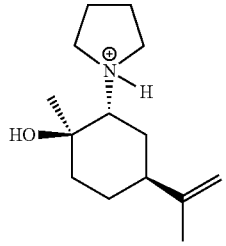

1t

Compound 1t was synthesized from the amino alcohol SI-III in the following manner. Anhydrous HCl in dioxane (4.0 M, 1.0 ml., 4.0 mmol, 1.0 equiv) was added dropwise to a solution of SI-III (894 mg, 4.00 mmol, 1.0 equiv) in anhydrous Et$_2$O (10 mL, 0.4 M) at 0° C. under argon with vigorous stirring. The mixture was warmed to room temperature and then stirred for 30 min. A small amount of acetone was added to the mixture, which was then sonicated, prompting precipitation of a white solid. The solvent was decanted off. The solids were rinsed with anhydrous Et$_2$O (3×) and then dried under vacuum to yield the ammonium salt 1t as a white solid, which was used without any further purification. Yield: 90% (935 mg). Physical State: white solid. $^1$H NMR (500 MHZ, CDCl$_3$): δ 11.42 (br s, 1H), 5.01 (s, 1H), 4.77 (s, 1H), 3.89-3.80 (m, 1H), 3.76-3.68 (m, 1H), 3.32 (d, J=13.0 Hz, 1H), 3.09-2.96 (m, 2H), 2.55 (br s, 1H), 2.40-2.31 (m, 1H), 2.30-2.19 (m, 1H), 2.14 (dd, J=13.1, 2.0 Hz, 1H), 2.06-1.89 (m, 4H), 1.83 (ddd, J=13.2, 13.2, 5.2 Hz, 1H), 1.74 (s, 3H), 1.71-1.53 (m, 3H), 1.51 (s, 3H). $^{13}$C NMR (125 MHZ, CDCl$_3$): δ 143.9, 112.1, 72.3, 69.7, 55.9, 49.8, 38.0, 36.9, 26.4, 24.5, 24.1, 23.2, 22.3, 21.6. MP: 99-100° C. IR (neat, ATR): ν$_{max}$ 3351, 2969, 2946, 2599, 2476, 1461, 1451 cm$^{-1}$. Optical Rotation: [α]$^{20}$$_D$ −6.8 (c 1.00, CHCl$_3$). HRMS (DART): calc'd for C$_{14}$H$_{26}$NO [M+H]$^+$ 224.2009, found 224.2008. Purification: (trituration with acetone/Et$_2$O).

Example 3: Exemplary General Procedure for Hydrodealkenylation

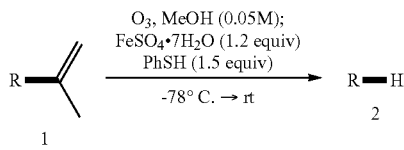

A round-bottom flask equipped with a magnetic stirrer bar was charged with 1 (1.0 equiv) and MeOH (0.05 M). The flask was then placed in a dry ice/acetone bath and cooled to −78° C. while open to the air. Ozone was bubbled through the solution until complete consumption of the starting material had occurred (as indicated by TLC and/or a blue color in the reaction mixture). The solution was then sparged with argon for 15 minutes to expel excess ozone. Benzenethiol (1.5 equiv) was then added as a 1.0 M stock solution[a] in MeOH, followed by ferrous sulfate heptahydrate (1.2 equiv). The mixture was stirred at −78° C. for 15 minutes before the cooling bath was removed. After warming to room temperature, the reaction mixture was transferred to a separatory funnel and water was added. The MeOH/water mixture was extracted with dichloromethane[b] (3×). The combined organic fractions were washed with brine, dried (anhydrous sodium sulfate), filtered, and concentrated under reduced pressure. Purification by flash column chromatography ($SiO_2$) provided the hydrodealkenylation product 2. Any modification of the above procedure is described below with the specific entry. [a]Benzenethiol stock solutions were prepared with anhydrous MeOH; they were stored under argon and discarded after three days to avoid formation of diphenyldisulfide. [b]Several of the compounds required additional extractions because of their solubility in the MeOH/water layer.

Preparation of the Alcohol 2h (100.0 mmol scale)

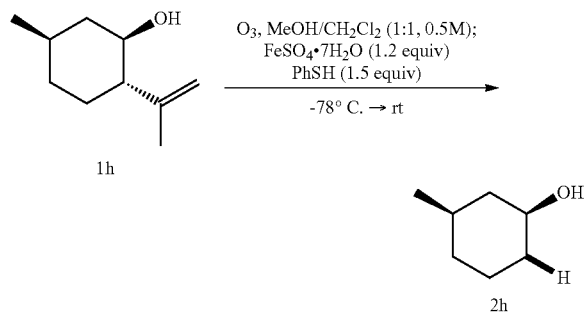

A round-bottom flask equipped with a magnetic stirrer bar was charged with (−)-isopulegol (1h, 17.3 mL, 100 mmol, 1.0 equiv) and MeOH/dichloromethane (1:1, 200 mL, 0.5 M). The flask was then placed in a dry ice/acetone bath and cooled to −78° C. while open to the air. Ozone was bubbled through the solution until complete consumption of the starting material had occurred (as indicated by TLC with CAM stain and a blue color in the reaction mixture). The solution was then sparged with argon for 30 minutes to expel excess ozone. Ferrous sulfate heptahydrate (33.4 g, 120 mmol, 1.2 equiv) was then added to the reaction mixture, followed by the slow addition of benzenethiol (15.4 mL, 150 mmol, 1.5 equiv) while maintaining an internal temperature of less than or equal to −65° C. The mixture was stirred at −78° C. for 15 minutes before the cooling bath was removed. After warming to room temperature, the mixture was stirred for an additional 12 h. Water (200 mL) was then slowly added to the solution (accompanied by a slight increase in temperature by ca. 8-10° C.). The mixture was transferred to a separatory funnel and extracted with dichloromethane (3×250 mL). The combined organic fractions were washed with brine (100 mL), dried (anhydrous sodium sulfate), filtered, and concentrated under reduced pressure to provide a viscous yellow oil. The residue was passed through a large silica plug, eluting with a gradient from 5% EtOAc in hexanes to 75% EtOAc in hexanes, while taking 500-mL fractions. This process provided 9.29 g of pure 2h in addition to a small amount of impure material. The fractions containing the impure material were concentrated and subjected to flash column chromatography ($SiO_2$), eluting with a gradient of 20% EtOAc in hexanes to 30% EtOAc in hexanes to provide an additional 840 mg of pure 2h. Combined, 10.1 g of 2h were obtained, giving an isolated yield of 89%.

Characterization Data

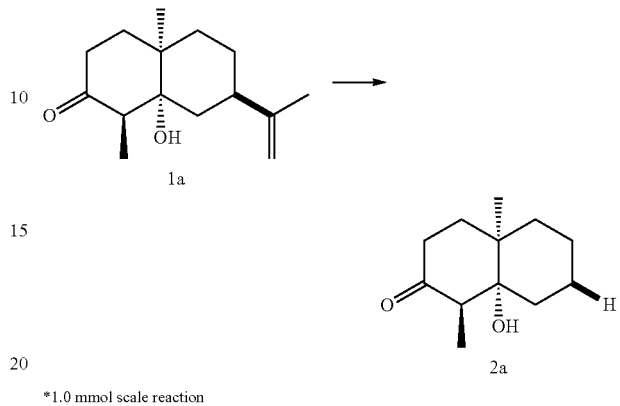

*1.0 mmol scale reaction

Yield: 90% (177 mg). Physical State: white solid. $^1$H NMR (500 MHZ, $CDCl_3$): δ 2.86 (q, J=6.6 Hz, 1H), 2.56 (dddd, J=14.2, 14.2, 7.1, 1.0 Hz, 1H), 2.31 (ddd, J=14.2, 5.0, 1.8 Hz, 1H), 2.10 (ddd, J=14.0, 14.0, 4.9 Hz, 1H), 1.80-1.72 (m, 1H), 1.62 (s, 1H), 1.58-1.43 (m, 5H), 1.39 (ddd, J=13.9, 7.1, 1.9 Hz, 1H), 1.33-1.27 (m, 1H), 1.21 (s, 3H), 1.15-1.07 (m, 1H), 1.00 (d, J=6.7 Hz, 3H). $^{13}$C NMR (125 MHZ, $CDCl_3$): δ 210.9, 77.2, 51.5, 37.8, 37.6, 35.2, 31.4, 28.2, 21.9, 20.9, 20.3, 6.4. MP: 76-78° C. IR (neat, ATR): $v_{max}$ 3507, 2928, 2866, 1690, 1001 $cm^{-1}$. Optical Rotation: $[\alpha]^{23}_D$ 50.4 (c 1.00, $CHCl_3$). HRMS (ESI-TOF): calc'd for $C_{12}H_{19}O$ $[M-OH]^+$ 179.1430, found 179.1444. $R_f$=0.44 (30% EtOAc/hexanes). Purification: ($SiO_2$, 10→20% EtOAc/hexanes).

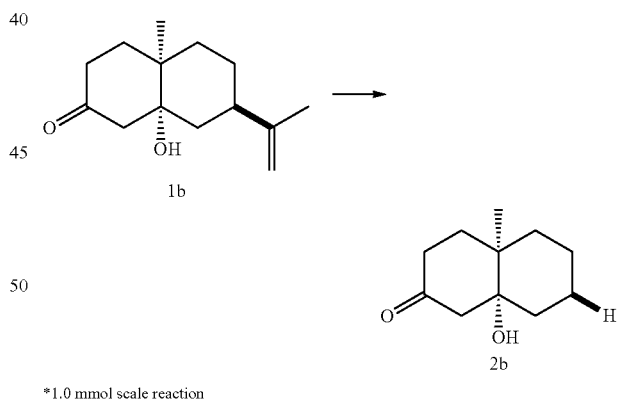

*1.0 mmol scale reaction

Yield: 85% (155 mg). Physical State: white solid. $^1$H NMR (500 MHZ, DMSO-$d_6$, 70° C.): δ 4.16 (s, 1H), 2.55-2.48 (m, 1H), 2.32-2.13 (m, 3H), 1.74-1.53 (m, 4H), 1.49-1.22 (m, 6H), 1.00 (s, 3H). $^{13}$C NMR (125 MHZ, DMSO-$d_6$, 70° C.): δ 210.2, 75.4, 51.2, 37.6, 37.1, 35.6, 34.2, 33.8, 22.7, 21.7, 21.0. MP: 124-125° C. IR (neat, ATR): $v_{max}$ 3419, 2923, 1702, 1130, 1042 $cm^{-1}$. Optical Rotation: $[\alpha]^{23}_D$ −23.3 (c 1.00, $CHCl_3$). HRMS (ESI-TOF): calc'd for $C_{11}H_{17}O$ $[M-OH]^+$ 165.1274, found 165.1286. $R_f$=0.50 (50% EtOAc/hexanes). Purification: ($SiO_2$, 10→20% EtOAc/hexanes). Note: The hydroxy ketone 2b exists as a mixture of conformational isomers. Thus, its NMR spectra were recorded at elevated temperature.

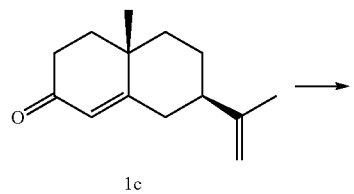

1c

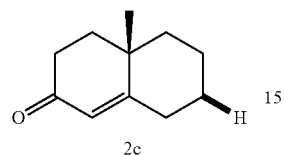

2c

*1.0 mmol scale reaction

Yield: 80% (131 mg). Physical State: colorless oil. $^1$H NMR (500 MHZ, CDCl$_3$): δ 5.70 (s, 1H), 2.48 (ddd, J=17.0, 14.3, 5.5 Hz, 1H), 2.38-2.29 (m, 2H), 2.26-2.20 (m, 1H), 1.92-1.84 (m, 1H), 1.81 (dd, J=14.0, 4.5 Hz, 1H), 1.75 (ddd, J=13.5, 5.5, 3.1 Hz, 1H), 1.70-1.61 (m, 3H), 1.43-1.30 (m, 2H), 1.22 (s, 3H). $^{13}$C NMR (125 MHz, CDCl$_3$): δ 199.7, 170.6, 124.1, 41.5, 38.0, 35.9, 33.9, 32.7, 27.1, 22.0, 21.7. Optical Rotation: [α]$^{23}_D$ 199.6 (c 1.00, CHCl$_3$). R$_f$=0.43 (20% EtOAc/hexanes). Purification: (SiO$_2$, 10→20% EtOAc/hexanes).

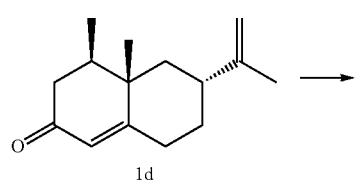

1d

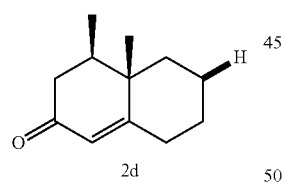

2d

*1.0 mmol scale reaction

Yield: 94% (168 mg). Physical State: colorless oil. $^1$H NMR (500 MHZ, CDCl$_3$): δ 5.73 (s, 1H), 2.40 (dddd, J=15.0, 13.7, 5.3, 1.9 Hz, 1H), 2.31-2.25 (m, 1H), 2.26 (d, J=13.8 Hz, 1H), 2.20 (ddd, J=17.0, 4.4, 1.0 Hz, 1H), 2.03-1.91 (m, 2H), 1.91-1.84 (m, 1H), 1.73-1.65 (m, 1H), 1.62 (dddd, J=26.5, 13.2, 3.5, 3.5 Hz, 1H), 1.33 (dddd, J=26.4, 13.0, 4.2, 4.2 Hz, 1H), 1.17 (ddd, J=13.2, 13.2, 4.4 Hz, 1H), 1.07 (s, 3H), 0.94 (d, J=6.9 Hz, 3H). $^{13}$C NMR (125 MHZ, CDCl$_3$): δ 200.0, 171.5, 124.5, 42.1, 40.2, 39.0, 38.6, 33.0, 26.7, 21.8, 16.2, 14.8. Optical Rotation: [α]$^{23}_D$ 197.1 (c 1.00, CHCl$_3$). R$_f$=0.50 (30% EtOAc/hexanes). Purification: (SiO$_2$, 5→10% EtOAc/hexanes).

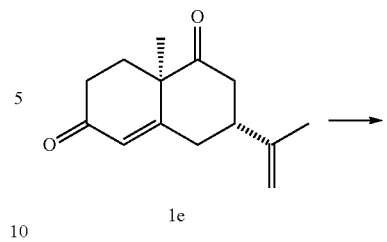

1e

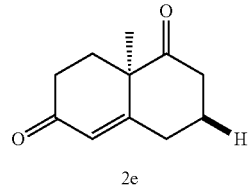

2e

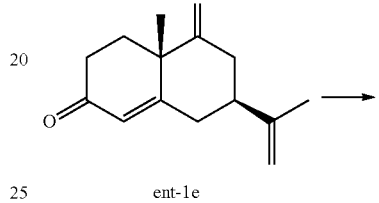

ent-1e

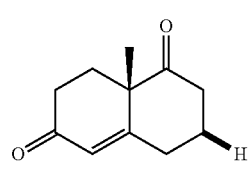

ent-2e

*1.0 mmol scale reaction

Yield: 2e 90% (160 mg); ent-2e 91% (161 mg). Physical State: pale yellow solid. $^1$H NMR (500 MHZ, CDCl$_3$): δ 5.85 (d, J=1.8 Hz, 1H), 2.76-2.67 (m, 2H), 2.54-2.42 (m, 4H), 2.18-2.08 (m, 3H), 1.76-1.67 (m, 1H), 1.44 (s, 3H). $^{13}$C NMR (125 MHZ, CDCl$_3$): δ 210.9, 198.2, 165.7, 125.7, 50.5, 37.6, 33.5, 31.6, 29.6, 23.2, 22.8. Optical Rotation: 2e [α]$^{23}_D$ −102.9 (c 1.00, CHCl$_3$); 2e' [α]$^{23}_D$ 108.0 (c 1.00, CHCl$_3$). R$_f$=0.22 (30% EtOAc/hexanes). Purification: (SiO$_2$, 20→30% EtOAc/hexanes).

1f

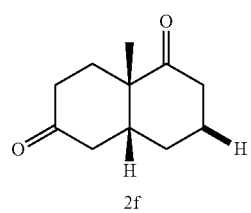

2f

*1.0 mmol scale reaction

Yield: 90% (162 mg). Physical State: white solid. $^1$H NMR (500 MHz, CDCl$_3$): δ 2.61-2.45 (m, 3H), 2.40 (dddd, J=15.1, 5.6, 5.6, 0.8 Hz, 1H), 2.35-2.23 (m, 4H), 2.10 (dddd, J=14.2, 10.2, 4.0, 4.0 Hz, 1H), 2.04-1.86 (m, 2H), 1.53 (ddd, J=14.0, 9.4, 4.5 Hz, 1H), 1.47-1.38 (m, 1H), 1.34 (s, 3H). $^{13}$C NMR (125 MHZ, CDCl$_3$): δ 214.0, 211.1, 48.4, 45.9, 43.6, 38.3, 37.4, 33.6, 26.5, 23.8, 22.8. Optical Rotation: [α]$^{23}_D$ 2.3 (c 1.00, CHCl$_3$). R$_f$=0.20 (20% EtOAc/hexanes). Purification: (SiO$_2$, 20% EtOAc/hexanes). When the reaction mixture of 1f to 2f was stirred for a prolonged period of time (for ca. 24 h after warming to rt), the complete conversion into the dimethyl ketal SI-VI was observed.

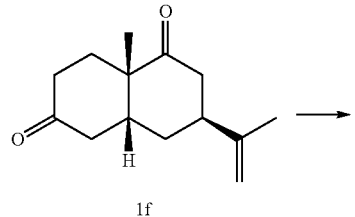

1f

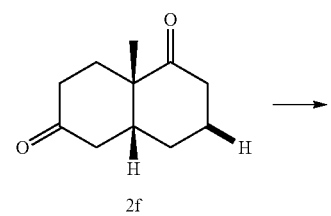

2f

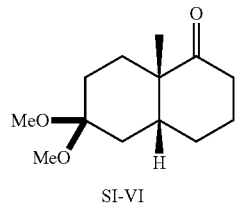

SI-VI

*0.5 mmol scale reaction

Yield: 88% (99 mg). Physical State: white solid. $^1$H NMR (500 MHz, CDCl$_3$): δ 3.14 (s, 3H), 3.10 (s, 3H), 2.57-2.48 (m, 1H), 2.22-2.14 (m, 2H), 2.11 (ddd, J=13.6, 3.7, 3.7 Hz, 1H), 1.98 (ddd, J=13.2, 6.9, 3.9 Hz, 1H), 1.90-1.84 (m, 2H), 1.80 (ddd, J=13.7, 7.3, 3.3 Hz, 1H), 1.70 (ddd, J=13.7, 3.4, 3.4 Hz, 1H), 1.44 (ddd, J=13.7, 13.7, 4.1 Hz, 2H), 1.31 (dd, J=13.5, 13.5 Hz, 1H), 1.20 (s, 3H), 1.07 (ddd, J=13.6, 13.6, 4.2 Hz, 1H). $^{13}$C NMR (125 MHZ, CDCl$_3$): δ 215.0, 100.3, 48.6, 47.4, 47.4, 41.3, 37.6, 34.8, 30.6, 29.1, 26.2, 25.8, 22.2. MP: 79-80° C. IR (neat, ATR): $v_{max}$ 2945, 2828, 1707, 1093, 1056 cm$^{-1}$. Optical Rotation: [α]$^{20}_D$ 78.4 (c 1.00, CHCl$_3$). HRMS (DART): calc'd for C$_{12}$H$_{19}$O$_2$ [M-OCH$_3$]$^+$195.1380, found 195.1378. R$_f$=0.42 (20% EtOAc/hexanes). Purification: (SiO$_2$, 10→20% EtOAc/hexanes). Note: 2D NMR spectra are consistent with the proposed structure of SI-VI.

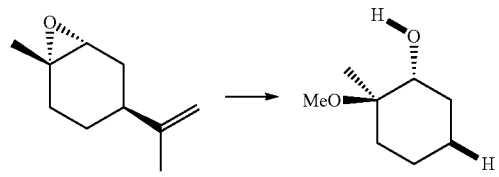

1g → 2g

*2.0 mmol scale reaction

Yield: 85% (245 mg). Physical State: colorless oil. $^1$H NMR (500 MHZ, CDCl$_3$): δ 3.55 (dd, J=10.2, 4.3 Hz, 1H), 3.21 (s, 3H), 2.28 (br s, 1H), 1.89-1.82 (m, 1H), 1.81-1.75 (m, 1H), 1.70-1.63 (m, 1H), 1.62-1.56 (m, 1H), 1.42-1.22 (m, 4H), 1.13 (s, 3H). $^{13}$C NMR (125 MHZ, CDCl$_3$): δ 77.7, 74.8, 48.3, 32.8, 29.8, 23.3, 22.7, 15.2. Optical Rotation: [α]$^{21}_D$ −1.6 (c 1.00, CHCl$_3$). R$_f$=0.39 (30% EtOAc/hexanes). Purification: (SiO$_2$, 10→30% Et$_2$O/pentane).

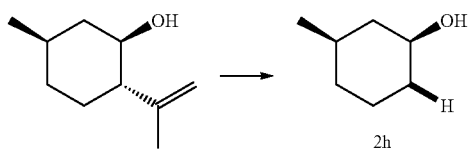

1h → 2h

*2.0 mmol scale reaction

Yield: 83% (189 mg). Physical State: colorless oil. $^1$H NMR (500 MHZ, CDCl$_3$): δ 3.56 (dddd, J=10.9, 10.9, 4.3, 4.3 Hz, 1H), 1.98-1.90 (m, 2H), 1.74 (dddd, J=13.5, 6.7, 3.4, 3.4 Hz, 1H), 1.60 (br s, 1H), 1.62-1.55 (m, 1H), 1.47-1.36 (m, 1H), 1.26 (dddd, J=26.6, 13.3, 3.5, 3.5 Hz, 1H), 1.15-1.05 (m, 1H), 0.91 (d, J=6.6 Hz, 3H), 0.87 (dd, J=23.2, 11.8 Hz, 1H), 0.77 (ddd, J=24.8, 13.0, 3.8 Hz, 1H). $^{13}$C NMR (125 MHz, CDCl$_3$): δ 70.7, 44.5, 35.3, 34.0, 31.3, 24.1, 22.2. Optical Rotation: [α]$^{20}_D$ −1.4 (c 1.00, CHCl$_3$). R$_f$=0.41 (30% EtOAc/hexanes). Purification: (SiO$_2$, 10→20% EtOAc/hexanes).

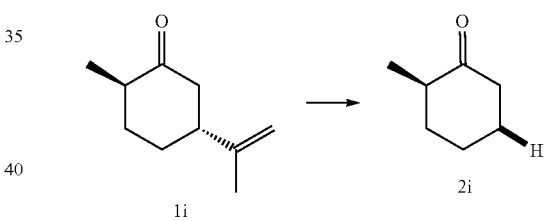

1i → 2i

*2.0 mmol scale reaction

Yield: 79% (178 mg). Physical State: colorless oil. $^1$H NMR (500 MHZ, CDCl$_3$): δ 2.43-2.34 (m, 2H), 2.33-2.24 (m, 1H), 2.12-2.01 (m, 2H), 1.88-1.80 (m, 1H), 1.74-1.59 (m, 2H), 1.38 (ddd, J=25.3, 12.4, 3.6 Hz, 1H), 1.02 (d, J=6.6 Hz, 3H). $^{13}$C NMR (125 MHZ, CDCl$_3$): δ 213.5, 45.3, 41.7, 36.0, 27.8, 25.1, 14.6. Optical Rotation: [α]$^{20}_D$ −13.5 (c 1.00, CHCl$_3$). R$_f$=0.34 (5% EtOAc/hexanes). Purification: (SiO$_2$, 0→10% Et$_2$O/pentane). Note: Extraction with Et$_2$O/Pentane (1:1).

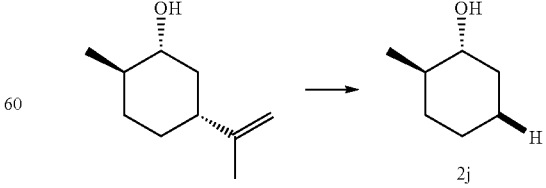

1j → 2j

*2.0 mmol scale reaction

Yield: 80% (183 mg). Physical State: colorless oil. $^1$H NMR (500 MHZ, CDCl$_3$): δ 3.11 (ddd, J=9.7, 9.7, 4.1 Hz, 1H), 1.97-1.90 (m, 1H), 1.78-1.66 (m, 2H), 1.64-1.51 (m, 2H), 1.34-1.13 (m, 4H), 1.00 (d, J=6.5 Hz, 3H), 0.96 (ddd, J=12.4, 12.4, 2.4 Hz, 1H). $^{13}$C NMR (125 MHz, CDCl$_3$): δ 76.4, 40.1, 35.4, 33.5, 25.6, 25.1, 18.4. Optical Rotation: $[α]^{23}_D$ −4.0 (c 1.00, CHCl$_3$). R$_f$=0.55 (30% EtOAc/hexanes). Purification: (SiO$_2$, 10→30% Et$_2$O/pentane). Note: The starting material was a 1:0.15:0.07:0.03 (n-/neoiso-/iso-/neo-) mixture of (−)-dihydrocarveol isomers. Only the trans product was isolated.

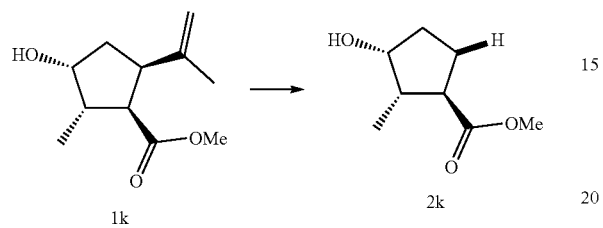

*1.0 mmol scale reaction

Yield: 84% (133 mg). Physical State: colorless oil. $^1$H NMR (500 MHZ, CDCl$_3$): δ 4.12 (ddd, J=4.4, 4.4, 1.2 Hz, 1H), 3.66 (s, 3H), 2.57 (ddd, J=10.0, 10.0, 7.7 Hz, 1H), 2.15-2.03 (m, 2H), 1.99-1.91 (m, 1H), 1.87-1.78 (m, 1H), 1.74 (br s, 1H), 1.68 (dddd, J=13.5, 8.9, 4.5, 1.6 Hz, 1H), 1.05 (d, J=6.9 Hz, 3H). $^{13}$C NMR (125 MHZ, CDCl$_3$): δ 176.9, 76.1, 51.5, 48.0, 44.3, 33.8, 27.0, 12.7. IR (neat, ATR): ν$_{max}$ 3438, 2955, 1734, 1197, 1168 cm$^{-1}$. Optical Rotation: $[α]^{23}_D$ −54.4 (c 1.00, CHCl$_3$). HRMS (ESI-TOF): calc'd for C$_8$H$_{15}$O$_3$ [M+H]$^+$ 159.1016, found 159.1023. R$_f$=0.20 (20% EtOAc/hexanes). Purification: (SiO$_2$, 10→20% EtOAc/hexanes).

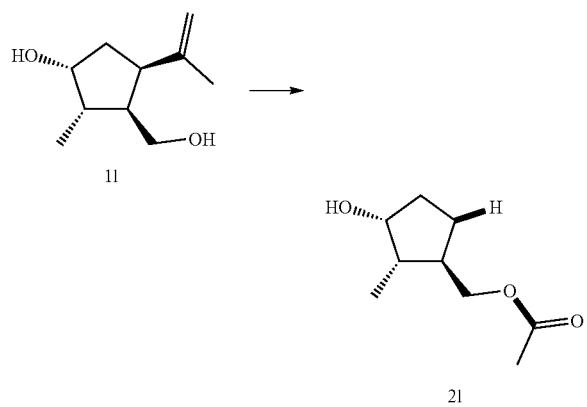

*2.0 mmol scale reaction

Yield: 91% (311 mg). Physical State: colorless oil. $^1$H NMR (500 MHZ, CDCl$_3$): δ 4.10 (ddd, J=4.6, 4.6, 1.9 Hz, 1H), 4.06 (dd, J=10.8, 4.9 Hz, 1H), 3.95 (dd, J=10.8, 6.1 Hz, 1H), 2.02 (s, 3H), 2.01-1.93 (m, 2H), 1.88-1.79 (m, 1H), 1.74-1.67 (m, 1H), 1.67-1.54 (m, 2H), 1.41-1.29 (m, 1H), 1.02 (d, J=6.9 Hz, 3H). $^{13}$C NMR (125 MHZ, CDCl$_3$): δ 171.3, 76.4, 67.4, 42.4, 42.2, 33.3, 26.5, 20.8, 12.7. IR (neat, ATR): ν$_{max}$ 3456, 2963, 2837, 1738, 1236 cm$^{-1}$. Optical Rotation: $[α]^{22}_D$ −69.7 (c 1.00, CHCl$_3$). HRMS (ESI-TOF): calc'd for C$_9$H$_{17}$O$_3$ [M+H]$^+$ 173.1172, found 173.1166. R$_f$=0.34 (30% EtOAc/hexanes). Purification: (SiO$_2$, 10→30% EtOAc/hexanes).

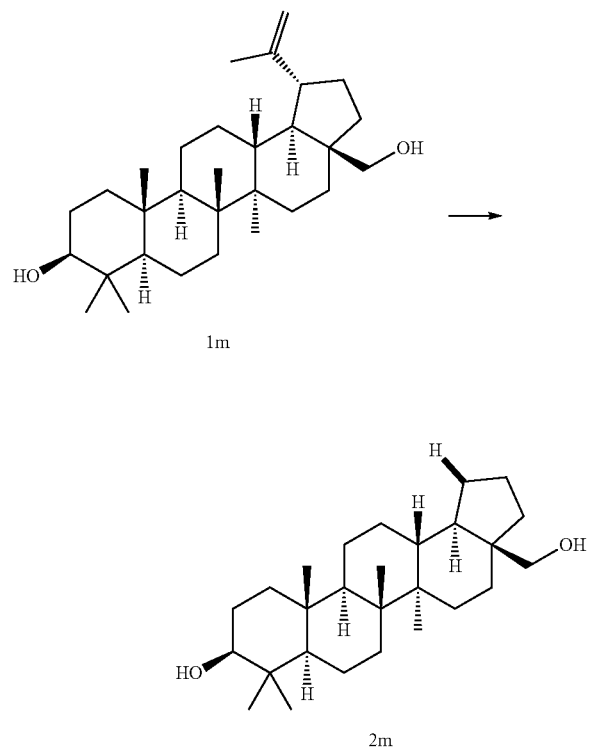

*1.0 mmol scale reaction

Yield: 88% (355 mg). Physical State: white solid. $^1$H NMR (500 MHZ, CDCl$_3$): δ 3.71 (dd, J=10.8, 2.0 Hz, 1H), 3.22 (d, J=10.9 Hz, 1H), 3.19 (dd, J=11.5, 4.8 Hz, 1H), 1.92 (ddd, J=13.5, 4.4, 2.7 Hz, 1H), 1.87 (ddd, J=12.3, 5.4, 4.3 Hz, 1H), 1.74-0.86 (m, 25H), 1.02 (s, 3H), 0.97 (s, 3H), 0.94 (s, 3H), 0.83 (s, 3H), 0.76 (s, 3H), 0.70 (d, J=9.4 Hz, 1H). $^{13}$C NMR (125 MHz, CDCl$_3$): δ 79.0, 60.1, 55.4, 50.4, 47.7, 46.2, 42.2, 40.8, 38.9, 38.8, 37.2, 36.2, 34.4, 34.1, 28.7, 28.0, 27.4, 27.1, 26.3, 25.5, 20.8, 20.5, 18.3, 16.1, 15.9, 15.4, 14.6. MP: 235-236° C. (decomp). IR (neat, ATR): ν$_{max}$ 3409, 3396, 2941, 1037, 1018 cm$^{-1}$. Optical Rotation: $[α]^{23}_D$ 1.4 (c 0.10, CHCl$_3$). HRMS (ESI-TOF): calc'd for C$_{27}$H$_{45}$O [M-OH]$^+$ 385.3465, found 385.3470. R$_f$=0.20 (CHCl$_3$). Purification: (SiO$_2$, CHCl$_3$). Note: The reaction was performed in CH$_2$Cl$_2$/MeOH (1:1, 0.05 M) because of the insolubility of betulin (1m) in MeOH.

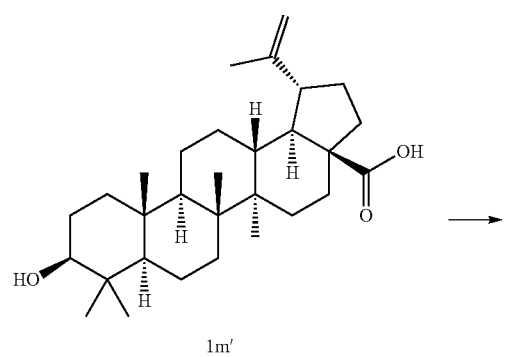

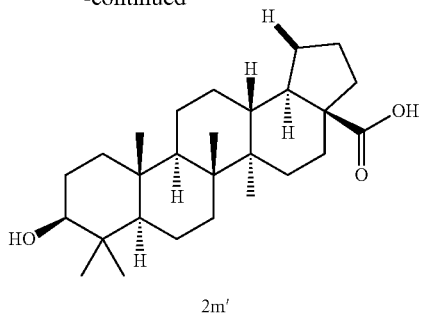

2m'

*0.2 mmol scale reaction

Yield: 83% (69 mg). Physical State: white solid. $^1$H NMR (500 MHz, CDCl$_3$): δ 3.19 (dd, J=11.5, 4.9 Hz, 1H), 2.24 (ddd, J=13.1, 3.3, 3.3 Hz, 1H), 2.08 (ddd, J=12.4, 12.4, 3.5 Hz, 1H), 2.06-1.99 (m, 1H), 1.76-1.28 (m, 20H), 1.17 (ddd, J=13.7, 3.2, 3.2 Hz, 1H), 1.13-1.05 (m, 1H), 0.99-0.90 (m, 1H), 0.96 (s, 3H), 0.94 (s, 3H), 0.93 (s, 3H), 0.83 (s, 3H), 0.76 (s, 3H), 0.72-0.67 (m, 1H). $^{13}$C NMR (125 MHZ, CDCl$_3$): δ 180.1, 79.0, 55.4, 54.4, 50.6, 48.4, 42.0, 40.6, 38.9, 38.8, 37.7, 37.3, 37.2, 34.2, 31.9, 29.7, 28.0, 27.4, 26.2, 25.4, 21.4, 20.8, 18.3, 16.1, 15.9, 15.3, 14.5. MP: 280° C. IR (neat, ATR): ν$_{max}$ 2969, 2935, 2872, 1686 cm$^{-1}$. Optical Rotation: [α]$^{24}_D$ 1.82 (c 0.20, CHCl$_3$). HRMS (ESI-TOF): calc'd for C$_{27}$H$_{43}$O$_2$ [M—OH]$^+$ 399.3258, found 399.3283. R$_f$=0.40 (5% THF/CHCl$_3$). Purification: (SiO$_2$, 0→5% THF/CHCl$_3$). Note: The reaction was performed in MeOH (0.01 M) because of the insolubility of betulinic acid at higher concentrations.

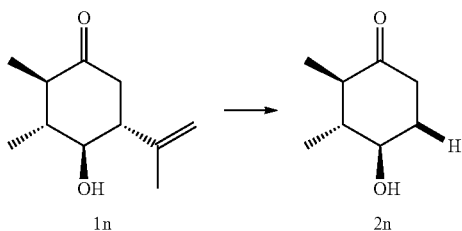

1n    2n

*1.0 mmol scale reaction

Yield: 85% (121 mg). Physical State: white solid. $^1$H NMR (500 MHz, CDCl$_3$): δ 3.67 (ddd, J=10.1, 10.1, 4.2 Hz, 1H), 2.47-2.37 (m, 2H), 2.30-2.23 (m, 1H), 2.08 (dq, J=12.9, 6.1 Hz, 1H), 1.76-1.68 (m, 1H), 1.64 (br s, 1H), 1.44 (ddq, J=12.8, 9.5, 6.0 Hz, 1H), 1.16 (d, J=6.5 Hz, 3H), 1.06 (d, J=6.6 Hz, 3H). $^{13}$C NMR (125 MHZ, CDCl$_3$): δ 211.2, 73.5, 48.0, 46.7, 38.6, 34.1, 16.6, 11.7. MP: 43° C. IR (neat, ATR): ν$_{max}$ 3366, 2970, 2838, 1713, 1200 cm$^{-1}$. Optical Rotation: [α]$^{24}_D$ −16.2 (c 1.00, CHCl$_3$). HRMS (DART): calc'd for C$_8$H$_{15}$O$_2$ [M+H]$^+$ 143.1067, found 143.1065. R$_f$=0.32 (50% EtOAc/hexanes). Purification: (SiO$_2$, 30→50% EtOAc/hexanes).

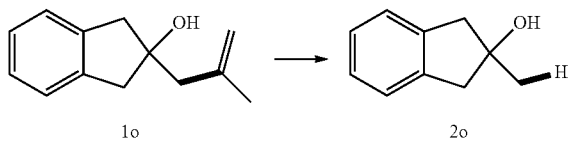

1o    2o

*1.0 mmol scale reaction

Yield: 71% (104 mg); Physical State: white solid. $^1$H NMR (400 MHZ, CDCl$_3$): δ 7.24-7.13 (m, 4H), 3.08-2.96 (m, 4H), 1.82 (br s, 1H), 1.52 (s, 3H). $^{13}$C NMR (100 MHz, CDCl$_3$): δ 141.6, 126.6, 125.0, 80.2, 48.4, 27.4. MP: 43° C. IR (neat, ATR): ν$_{max}$ 3319, 2969, 2938, 2902, 1480, 1460 cm$^{-1}$. HRMS (DART): calc'd for C$_{10}$H$_{11}$ [M-OH]$^+$ 131.0855, found 131.0853. R$_f$=0.50 (20% EtOAc/hexanes). Purification: (SiO$_2$, 10→15% EtOAc/hexanes).

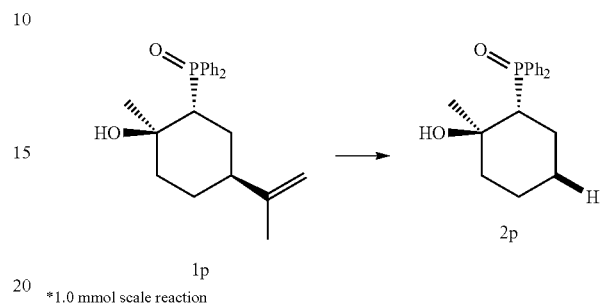

1p    2p

*1.0 mmol scale reaction

Yield: 84% (268 mg). Physical State: white solid. $^1$H NMR (500 MHZ, CDCl$_3$): δ 7.80-7.70 (m, 4H), 7.56-7.50 (m, 2H), 7.50-7.43 (m, 4H), 5.58 (br s, 1H), 2.82 (ddd, J=13.1, 13.1, 2.3 Hz, 1H), 1.86-1.79 (m, 1H), 1.79-1.64 (m, 3H), 1.60 (ddd, J=13.0, 13.0, 3.1 Hz, 1H), 1.36-1.18 (m, 3H), 1.30 (s, 3H). $^{13}$C NMR (125 MHZ, CDCl$_3$): δ 133.4 (d, J$_{CP}$=96.1 Hz), 132.6 (d, J$_{CP}$=8.9 Hz), 132.0 (d, J$_{CP}$=2.6 Hz), 131.7 (d, J$_{CP}$=2.7 Hz), 130.6 (d, J$_{CP}$=9.1 Hz), 130.4 (d, J$_{CP}$=93.2 Hz), 128.7 (d, J$_{CP}$=11.3 Hz), 128.1 (d, J$_{CP}$=11.4 Hz), 72.9 (d, J$_{CP}$=4.9 Hz), 47.8 (d, J$_{CP}$=68.3 Hz), 42.5 (d, J$_{CP}$=10.1 Hz), 26.5, 26.3 (d, J$_{CP}$=13.6 Hz), 23.7 (d, J$_{CP}$=2.5 Hz), 22.9. $^{31}$P NMR (202 MHZ, CDCl$_3$): δ 37.9. MP: 189-190° C. IR (neat, ATR): ν$_{max}$ 3329, 2925, 2853, 1457, 1436, 1159 cm$^{-1}$. Optical Rotation: [α]$^{23}_D$ −2.6 (c 1.00, CHCl$_3$). HRMS (ESI-TOF): calc'd for C$_{19}$H$_{24}$O$_2$P [M+H]$^+$ 315.1508, found 315.1514. R$_f$=0.36 (50% EtOAc/hexanes). Purification: (SiO$_2$, 30→100% EtOAc/hexanes).

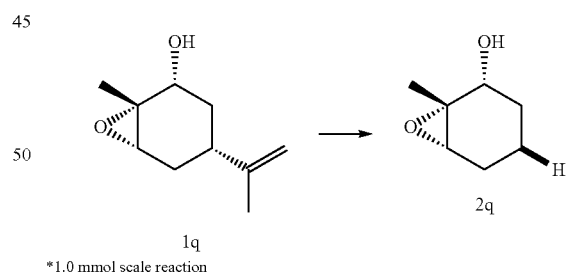

1q    2q

*1.0 mmol scale reaction

Yield: 72% (93 mg). Physical State: colorless oil. $^1$H NMR (500 MHz, CDCl$_3$): δ 3.81 (dd, J=5.6, 5.6 Hz, 1H), 3.16 (dd, J=3.4, 0.8 Hz, 1H), 1.93-1.85 (m, 1H), 1.81-1.74 (m, 1H), 1.70 (br s, 1H), 1.56-1.44 (m, 3H), 1.42 (s, 3H), 1.29-1.20 (m, 1H). $^{13}$C NMR (125 MHz, CDCl$_3$): δ 69.9, 62.6, 60.1, 29.8, 23.9, 20.5, 16.9. Optical Rotation: [α]$^{24}_D$ 9.4 (c 1.00, CHCl$_3$). R$_f$=0.20 (30% EtOAc/hexanes). Purification: (SiO$_2$, 15→30% EtOAc/hexanes).

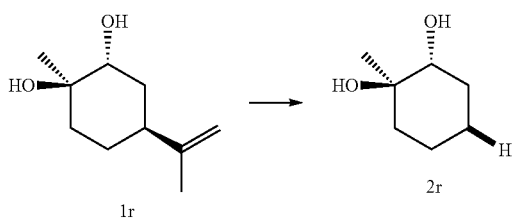

*2.0 mmol scale reaction

Yield: 86% (224 mg). Physical State: white solid. $^1$H NMR (500 MHZ, CDCl$_3$): δ 3.48 (dd, J=10.5, 4.5 Hz, 1H), 2.16 (br s, 2H), 1.90-1.82 (m, 1H), 1.77-1.66 (m, 2H), 1.65-1.56 (m, 1H), 1.43-1.27 (m, 4H), 1.19 (s, 3H). $^{13}$C NMR (125 MHZ, CDCl$_3$): δ 77.1, 73.9, 38.5, 30.9, 23.9, 23.2, 19.5. Optical Rotation: $[\alpha]^{24}_D$ −1.5 (c 1.00, CHCl$_3$). R$_f$=0.16 (50% EtOAc/hexanes). Purification: (SiO$_2$, 50→75% EtOAc/hexanes).

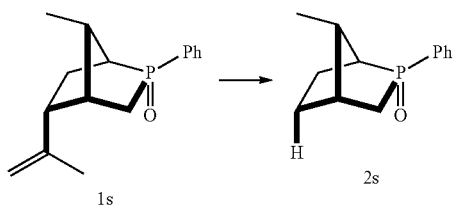

*4.0 mmol scale reaction

Yield: 82% (696 mg). Physical State: white solid. $^1$H NMR (500 MHz, CDCl$_3$): δ 7.79-7.74 (m, 2H), 7.54-7.45 (m, 3H), 2.53-2.43 (m, 1H), 2.40-2.27 (m, 3H), 2.12-1.95 (m, 3H), 1.72-1.58 (m, 2H), 0.95 (d, J=6.7 Hz, 3H). $^{13}$C NMR (125 MHZ, CDCl$_3$): δ 133.6 (d, J$_{CP}$=89.2 Hz), 131.5 (d, J$_{CP}$=2.8 Hz), 130.3 (d, J$_{CP}$=9.3 Hz), 128.6 (d, J$_{CP}$=11.3 Hz), 42.2 (d, J$_{CP}$=46.3 Hz), 41.9 (d, J$_{CP}$=4.6 Hz), 41.9 (d, J$_{CP}$=4.0 Hz), 34.4 (d, J$_{CP}$=60.7 Hz), 26.7 (d, J$_{CP}$=1.5 Hz), 17.7 (d, J$_{CP}$=7.1 Hz), 13.7 (d, J$_{CP}$=15.6 Hz). Optical Rotation: $[\alpha]^{23}_D$ 7.1 (c 1.00, CHCl$_3$). R$_f$=0.32 (5% MeOH/EtOAc). Purification: (SiO$_2$, 0→5% MeOH/EtOAc).

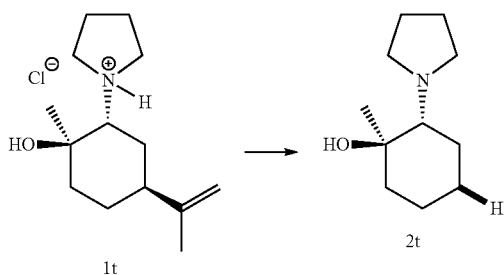

*1.0 mmol scale reaction

Yield: 62% (114 mg). Physical State: yellow oil. $^1$H NMR (500 MHz, CDCl$_3$): δ 2.75-2.64 (m, 4H), 2.51 (dd, J=11.8, 3.5 Hz, 1H), 1.85-1.79 (m, 1H), 1.78-1.67 (m, 6H), 1.67-1.60 (m, 1H), 1.39 (ddd, J=12.6, 12.6, 3.9 Hz, 1H), 1.34-1.23 (m, 3H), 1.18 (s, 3H). $^{13}$C NMR (125 MHz, CDCl$_3$): δ 72.4, 68.5, 51.2, 40.2, 26.2, 23.8, 23.4, 22.6, 22.3. IR (neat, ATR): $\nu_{max}$ 3491, 2969, 2933, 2863, 1463, 1367 cm$^{-1}$. Optical Rotation: $[\alpha]^{20}_D$ −43.2 (c 1.00, CHCl$_3$). HRMS (ESI-TOF): calc'd for C$_{11}$H$_{22}$NO [M+H]$^+$ 184.1696, found 184.1694. R$_f$=0.14 (10% MeOH/CH$_2$Cl$_2$ with 1% NH$_4$OH). Purification: (SiO$_2$, 10% MeOH/CH$_2$Cl$_2$ with 1% NH$_4$OH). Note: After quenching, the reaction was basified with 1.0 M aqueous NaOH until pH≥10.

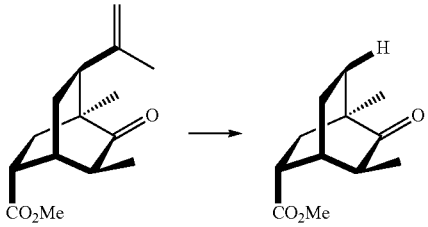

*1.0 mmol scale reaction

Yield: 78% (165 mg). Physical State: colorless oil. $^1$H NMR (500 MHZ, CDCl$_3$): δ 3.68 (s, 3H), 2.83 (ddd, J=10.7, 7.2, 1.9 Hz, 1H), 2.39-2.33 (m, 1H), 2.26-2.23 (m, 1H), 2.07 (ddd, J=14.1, 7.0, 3.0 Hz, 1H), 1.85-1.74 (m, 2H), 1.67-1.59 (m, 2H), 1.56-1.49 (m, 1H), 1.09 (d, J=7.3 Hz, 3H), 0.95 (s, 3H). $^{13}$C NMR (125 MHz, CDCl$_3$): δ 218.6, 175.1, 51.9, 42.5, 42.4, 41.8, 37.3, 32.5, 31.2, 21.3, 19.7, 12.8. Optical Rotation: $[\alpha]^{24}_D$ −52.5 (c 1.00, CHCl$_3$). R$_f$=0.40 (10% EtOAc/hexanes). Purification: (SiO$_2$, 5→10% EtOAc/hexanes).

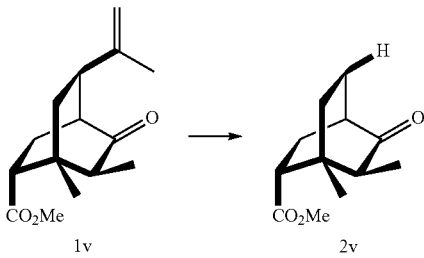

*1.0 mmol scale reaction

Yield: 81% (170 mg). Physical State: colorless oil. $^1$H NMR (500 MHZ, CDCl$_3$): δ 3.68 (s, 3H), 2.74 (ddd, J=14.5, 7.2, 1.6 Hz, 1H), 2.65 (dd, J=10.5, 7.4 Hz, 1H), 2.37-2.31 (m, 1H), 2.13-2.05 (m, 1H), 2.01 (ddd, J=13.9, 10.6, 3.4 Hz, 1H), 1.84-1.75 (m, 2H), 1.70-1.61 (m, 1H), 1.37-1.28 (m, 1H), 1.03 (d, J=7.4 Hz, 3H), 0.93 (s, 3H). $^{13}$C NMR (125 MHz, CDCl$_3$): δ 218.4, 175.4, 51.5, 47.0, 45.4, 41.4, 38.0, 28.6, 26.7, 24.0, 22.3, 9.1. Optical Rotation: $[\alpha]^{24}_D$ −85.9 (c 1.00, CHCl$_3$). R$_f$=0.20 (10% EtOAc/hexanes). Purification: (SiO$_2$, 5-10% EtOAc/hexanes).

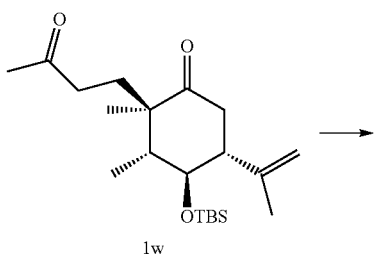

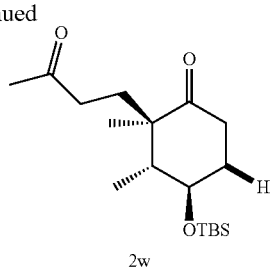

2w

*1.0 mmol scale reaction

Yield: 80% (262 mg). Physical State: colorless oil. $^1$H NMR (500 MHZ, CDCl$_3$): δ 3.78 (ddd, J=8.9, 8.9, 4.1 Hz, 1H), 2.48 (ddd, J=14.8, 12.4, 5.9 Hz, 1H), 2.45-2.35 (m, 2H), 2.26 (ddd, J=16.8, 11.5, 5.1 Hz, 1H), 2.12 (s, 3H), 2.11-2.05 (m, 1H), 1.95 (ddd, J=14.2, 11.3, 4.6 Hz, 1H), 1.76-1.61 (m, 3H), 1.00 (s, 3H), 0.92 (d, J=6.8 Hz, 3H), 0.89 (s, 9H), 0.08 (s, 3H), 0.07 (s, 3H). $^{13}$C NMR (125 MHz, CDCl$_3$): δ 214.1, 208.6, 71.4, 50.3, 44.4, 38.7, 35.6, 33.5, 29.8, 29.3, 25.7, 20.2, 17.9, 12.3, -4.4, -4.9. Optical Rotation: [α]$^{24}_D$ -1.9 (c 1.00, CHCl$_3$). R$_f$=0.36 (20% EtOAc/hexanes). Purification: (SiO$_2$, 5→10% EtOAc/hexanes).

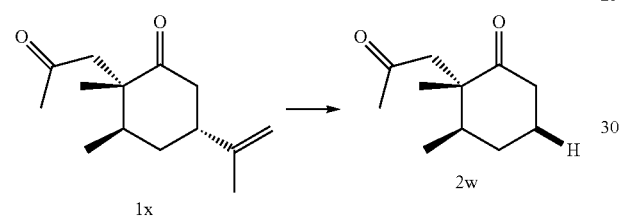

1x → 2w

*1.0 mmol scale reaction

Yield: 78% (143 mg). Physical State: colorless oil. $^1$H NMR (500 MHZ, CDCl$_3$): δ 2.84 (d, J=17.4 Hz, 1H), 2.52 (d, J=17.3 Hz, 1H), 2.47-2.32 (m, 2H), 2.31-2.21 (m, 1H), 2.15 (s, 3H), 1.97-1.88 (m, 1H), 1.84-1.73 (m, 1H), 1.68-1.62 (m, 1H), 1.60-1.50 (m, 1H), 1.04 (s, 3H), 0.89 (d, J=6.9 Hz, 3H). $^{13}$C NMR (125 MHz, CDCl$_3$): δ 214.8, 207.3, 51.2, 48.3, 37.9, 37.5, 31.0, 29.3, 24.1, 18.5, 15.8. Optical Rotation: [α]$^{24}_D$ -89.7 (c 1.00, CHCl$_3$). R$_f$=0.43 (30% EtOAc/hexanes). Purification: (SiO$_2$, 5→10% EtOAc/hexanes).

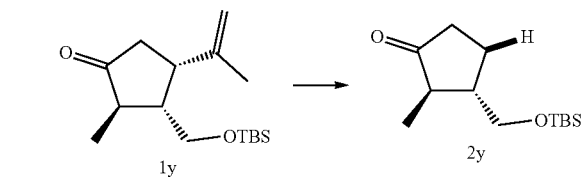

1y → 2y

*1.0 mmol scale reaction

Yield: 75% (183 mg). Physical State: pale yellow oil. $^1$H NMR (400 MHZ, CDCl$_3$): δ 3.72 (dd, J=10.2, 4.1 Hz, 1H), 3.66 (dd, J=10.2, 5.0 Hz, 1H), 2.39-2.30 (m, 1H), 2.17-2.05 (m, 1H), 2.03-1.93 (m, 2H), 1.89-1.78 (m, 1H), 1.71-1.59 (m, 1H), 1.06 (d, J=7.0 Hz, 3H), 0.87 (s, 9H), 0.04 (d, J=2.0 Hz, 6H). $^{13}$C NMR (100 MHZ, CDCl$_3$): δ 221.2, 64.4, 47.0, 46.2, 37.2, 25.9, 24.0, 18.3, 13.0, -5.5. Optical Rotation: [α]$^{24}_D$ -39.3 (c 1.00, CHCl$_3$). R$_f$=0.20 (5% EtOAc/hexanes). Purification: (SiO$_2$, 2→5% EtOAc/hexanes).

Example 4: Exemplary Optimization of the Hydrodealkenylation Reaction

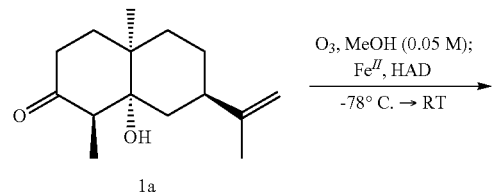

1a → 2a

O$_3$, MeOH (0.05 M); Fe$^{II}$, HAD
-78° C. → RT

A round-bottom flask equipped with a magnetic stirrer bar was charged with the hydroxy ketone 1a (118 mg, 0.500 mmol, 1.0 equiv) and MeOH (0.05 M), then placed in a dry ice/acetone bath and cooled to -78° C. while open to the air. Ozone was bubbled through the solution until complete consumption of the starting material had occurred (as indicated by TLC with CAM stain). The solution was then sparged with argon for 15 minutes to expel excess ozone. The HAD was then added at the specified temperature, followed by immediate addition of the Fe$^{II}$ salt. The mixture was stirred at the specified temperature for 15 minutes before the cooling bath was removed. After warming to room temperature, the reaction mixture was stirred for an additional 30 minutes. 1,3,5-Trimethoxybenzene (84 mg, 0.50 mmol, 1.0 equiv) was added to the flask. An aliquot (1.0 mL) was removed and placed in a vial under high-vacuum until the solvent had evaporated. Deuterated chloroform was added to the vial, and then the mixture was filtered through a short Celite plug directly into an NMR tube.

TABLE S1

Optimization of Reaction Parameters

| Entry | Fe$^{II}$ (equiv) | HAD (equiv) | % yield$^a$ |
|---|---|---|---|
| 1 | FeSO$_4$•7H$_2$O (1.2) | benzenethiol (1.5) | 98 |
| 2 | FeSO$_4$•7H$_2$O (1.2) | 4-methoxybenzenethiol (1.5) | 93 |
| 3 | FeSO$_4$•7H$_2$O (1.2) | 4-trifluoromethylbenzenethiol (1.5) | 90 |
| 4 | FeSO$_4$•7H$_2$O (1.2) | 4-bromobenzenethiol (1.5) | 92 |
| 5 | FeSO$_4$•7H$_2$O (1.2) | 4-nitrobenzenethiol (1.5) | 90 |
| 6 | FeSO$_4$•7H$_2$O (1.2) | 4-t-butylbenzenethiol (1.5) | 92 |

TABLE S1-continued

Optimization of Reaction Parameters

| Entry | $Fe^{II}$ (equiv) | HAD (equiv) | % yield[a] |
|---|---|---|---|
| 7 | $FeSO_4 \cdot 7H_2O$ (1.2) | 1-phenyl-1H-tetrazole-5-thiol (1.5) | 60 |
| 8 | $FeSO_4 \cdot 7H_2O$ (1.2) | 4-mercaptobenzonitrile (1.5) | 94 |
| 9 | $FeSO_4 \cdot 7H_2O$ (1.2) | 2-aminobenzenethiol (1.5) | 89 |
| 10 | $FeSO_4 \cdot 7H_2O$ (1.2) | 2-naphthalenethiol (1.5) | 88 |
| 11 | $FeSO_4 \cdot 7H_2O$ (1.2) | 2-methylbenzenethiol (1.5) | 93 |
| 12 | $FeSO_4 \cdot 7H_2O$ (1.2) | $nBu_3SnH$ (1.5) | 62 |
| 13 | $FeSO_4 \cdot 7H_2O$ (1.2) | γ-terpinene (1.5) | 65 |
| 14 | $FeSO_4 \cdot 7H_2O$ (1.2) | none | trace |
| 15 | $FeSO_4 \cdot 7H_2O$ (1.2) | benzenethiol (0.5) | 65 |
| 16 | $FeSO_4 \cdot 7H_2O$ (1.2) | benzenethiol (1.0) | 83 |
| 17 | $FeSO_4 \cdot 7H_2O$ (1.2) | benzenethiol (2.0) | 98 |
| 18 | $FeCl_2 \cdot 7H_2O$ (1.2) | benzenethiol (1.5) | 74 |
| 19 | $Fe(NH_4)_2(SO_4)_2 \cdot 6H_2O$ (1.2) | benzenethiol (1.5) | 81 |
| 20 | $Fe(BF_4)_2 \cdot 6H_2O$ (1.2) | benzenethiol (1.5) | 25 |
| 21 | none | benzenethiol (1.5) | 0 |
| 22 | $FeSO_4 \cdot 7H_2O$ (0.5) | benzenethiol (1.5) | 71 |
| 23 | $FeSO_4 \cdot 7H_2O$ (1.5) | benzenethiol (1.5) | 98 |
| 24 | $FeSO_4 \cdot 7H_2O$ (2.0) | benzenethiol (1.5) | 97 |
| 25 | $FeSO_4 \cdot 7H_2O$ (1.2) | benzenethiol (1.5) | 98[b] |
| 26 | $FeSO_4 \cdot 7H_2O$ (1.2) | benzenethiol (1.5) | 97[c] |

Example 5: General Procedure for Carboxylic Ester Synthesis

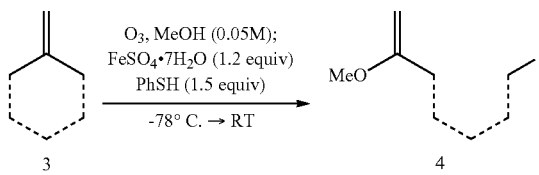

A round-bottom flask equipped with a magnetic stirrer bar was charged with 3 (1.0 equiv) and MeOH (0.05 M). The flask was then placed in a dry ice/acetone bath and cooled to −78° C. while open to the air. Ozone was bubbled through the solution until complete consumption of the starting material had occurred (as indicated by TLC and/or a blue color in the reaction mixture). The solution was then sparged with argon for 15 minutes to expel excess ozone. Benzenethiol (1.5 equiv) was then added as a 1.0 M stock solution[a] in MeOH, followed by ferrous sulfate heptahydrate (1.2 equiv). The mixture was stirred at −78° C. for 15 minutes before the cooling bath was removed. After warming to room temperature, the reaction mixture was transferred to a separatory funnel and water was added. The MeOH/water mixture was extracted with 1:1 $Et_2O$/pentane (3×). The combined organic fractions were washed with brine, dried (anhydrous sodium sulfate), filtered, and concentrated under reduced pressure. Purification by flash column chromatography ($SiO_2$) provided the carboxylic ester 4.
[a]Benzenethiol stock solutions were prepared with anhydrous MeOH; they were stored under argon and discarded after three days to avoid formation of diphenyldisulfide.

Characterization Data

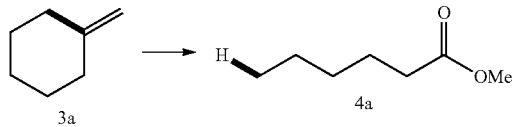

*1.0 mmol scale reaction

*2.0 mmol scale reaction Yield: 80% (208 mg). Physical State: pale yellow oil. $^1$H NMR (500 MHZ, $CDCl_3$): δ 3.66 (s, 3H), 2.29 (t, J=7.6 Hz, 2H), 1.66-1.58 (m, 2H), 1.36-1.24 (m, 4H), 0.88 (t, J=7.0 Hz, 3H). $^{13}$C NMR (125 MHZ, $CDCl_3$): δ 174.2, 51.3, 33.9, 31.2, 24.5, 22.2, 13.8. $R_f$=0.30 (5% EtOAc/hexanes). Purification: ($SiO_2$, 0→1% $Et_2O$/pentane).

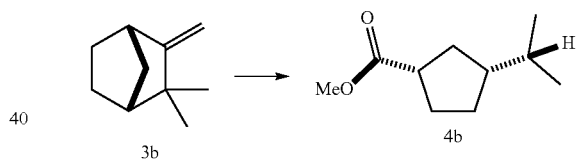

*2.0 mmol scale reaction

Yield: 89% (302 mg). Physical State: colorless oil. $^1$H NMR (500 MHZ, $CDCl_3$): δ 3.66 (s, 3H), 2.74 (ddd, J=17.2, 9.2, 7.6 Hz, 1H), 2.05 (dt, J=13.1, 6.6 Hz, 1H), 1.89-1.73 (m, 3H), 1.58-1.48 (m, 1H), 1.47-1.36 (m, 2H), 1.30 (ddd, J=17.6, 11.9, 9.5 Hz, 1H), 0.88 (d, J=6.6 Hz, 3H), 0.88 (d, J=6.6 Hz, 3H). $^{13}$C NMR (125 MHZ, $CDCl_3$): δ 177.0, 51.4, 48.2, 43.5, 35.2, 33.2, 29.8, 28.8, 21.5, 21.4 IR (neat, ATR): $v_{max}$ 2954, 2871, 1735, 1197, 1160 $cm^{-1}$. HRMS (ESI-TOF): calc'd for $C_{10}H_{19}O_2$ $[M+H]^+$ 171.1380, found 171.1384. $R_f$=0.33 (5% EtOAc/hexanes). Purification: ($SiO_2$, 0→1% $Et_2O$/pentane). Note: 2D NMR experiments are consistent with the proposed structure of 4b.

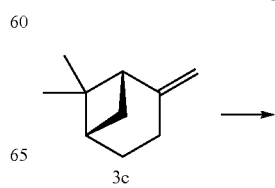

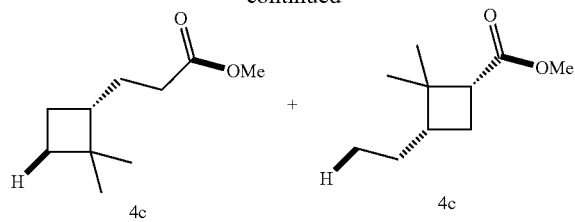

4c

4c'

*2.0 mmol scale reaction

Yield: 83% (280 mg, 1:1 4c/4c', inseparable mixture). Physical State: colorless oil. $^1$H NMR (500 MHZ, CDCl$_3$) 4c: δ 3.65 (s, 3H), 2.22 (ddd, J=15.6, 9.1, 6.6 Hz, 1H), 2.17 (ddd, J=15.5, 9.0, 6.5 Hz, 1H), 1.92-1.85 (m, 2H), 1.69 (dddd, J=13.5, 9.1, 6.3, 6.3 Hz, 1H), 1.64-1.45 (m, 4H), 1.04 (s, 3H), 1.00 (s, 3H). $^1$H NMR (500 MHZ, CDCl$_3$) 4c': δ 3.64 (s, 3H), 2.65 (dd, J=10.1, 7.8 Hz, 1H), 2.05-1.96 (m, 1H), 1.83-1.77 (m, 2H), 1.36 (dddd, J=13.7, 13.7, 7.2, 7.2 Hz, 1H), 1.24 (ddd, J=13.5, 7.5, 7.5 Hz, 1H), 1.19 (s, 3H), 0.90 (s, 3H), 0.80 (dd, J=7.4, 7.4 Hz, 3H). $^{13}$C NMR (125 MHz, CDCl$_3$) 4c: δ 174.2, 51.3, 43.9, 37.5, 32.3, 32.1, 30.3, 26.2, 22.0, 21.9. $^{13}$C NMR (125 MHZ, CDCl$_3$) 4c': δ 173.6, 50.9, 45.7, 44.2, 42.5, 30.4, 24.2, 23.1, 17.2, 11.7. IR (neat, ATR): ν$_{max}$ 2952, 2873, 2864, 1737, 1175 cm$^{-1}$. HRMS (DART): calc'd for C$_{10}$H$_{19}$O$_2$ [M+H]$^+$ 171.1380, found 171.1376 and 171.1379. R$_f$=0.33 (5% EtOAc/hexanes). Purification: (SiO$_2$, 0→1% Et$_2$O/pentane). Note: 2D NMR experiments are consistent with the proposed structures of 4c and 4c'.

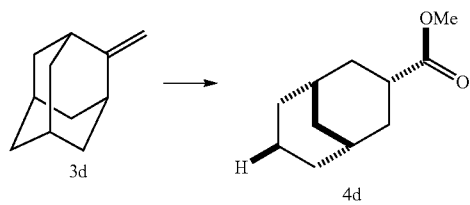

3d

4d

*2.0 mmol scale reaction

Yield: 81% (297 mg). Physical State: colorless oil. $^1$H NMR (500 MHZ, CDCl$_3$): δ 3.66 (s, 3H), 2.57-2.47 (m, 1H), 2.12-2.01 (m, 4H), 1.78-1.67 (m, 1H), 1.64-1.58 (m, 1H), 1.49-1.33 (m, 7H), 1.17-1.11 (m, 1H). $^{13}$C NMR (125 MHZ, CDCl$_3$): δ 177.4, 51.4, 35.9, 32.8, 29.0, 28.9, 24.8, 15.8. IR (neat, ATR): ν$_{max}$ 2921, 2866, 2849, 1739, 1172 cm$^{-1}$. HRMS (ESI-TOF): calc'd for C$_{11}$H$_{19}$O$_2$ [M+H]$^+$ 183.1380, found 183.1389. R$_f$=0.36 (5% EtOAc/hexanes). Purification: (SiO$_2$, 0→1% Et$_2$O/pentane).

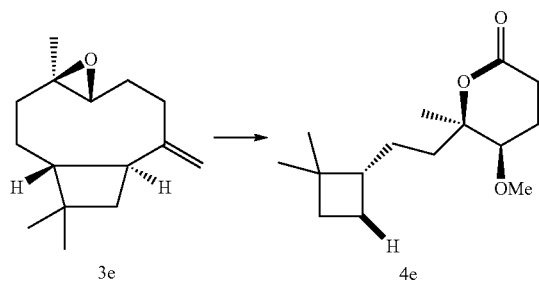

3e

4e

*2.0 mmol scale reaction

Yield: 26% (131 mg). Physical State: colorless oil. $^1$H NMR (500 MHZ, CDCl$_3$): δ 3.68 (s, 3H), 3.38 (dd, J=10.7, 2.1 Hz, 1H), 2.60-2.44 (m, 2H), 1.93-1.78 (m, 4H), 1.71-1.57 (m, 2H), 1.55-1.44 (m, 2H), 1.44-1.27 (m, 2H), 1.25-1.18 (m, 1H), 1.17 (s, 3H), 1.03 (s, 3H), 0.99 (s, 3H). $^{13}$C NMR (125 MHZ, CDCl$_3$): δ 174.7, 77.6, 74.4, 51.6, 44.9, 37.5, 33.8, 32.4, 31.2, 30.5, 26.1, 24.4, 23.3, 22.3, 22.1. IR (neat, ATR): ν$_{max}$ 3506, 2951, 2863, 1739, 1366 cm$^{-1}$. Optical Rotation: [α]$^{20}_D$ −1.8 (c 1.00, CHCl$_3$). HRMS (ESI-TOF): calc'd for C$_{15}$H$_{27}$O$_3$ [M+H]$^+$ 255.1955, found 255.1966. R$_f$=0.46 (50% EtOAc/hexanes). Purification: (SiO$_2$, 15→20% EtOAc/hexanes). Note: The 1H and $^{13}$C NMR spectra of the δ-lactone 4e are consistent with those reported for (R)-5-methoxy-6,6-dimethyltetrahydro-2H-pyran-2-one: 1H NMR (400 MHZ, CDCl$_3$) δ 3.41 (s, 3H), 3.25 (dd, J=6.2, 3.4 Hz, 1H), 2.67-2.61 (m, 1H), 2.52-2.49 (m, 1H), 2.08-2.01 (m, 2H), 1.41 (s, 6H); $^{13}$C NMR (400 MHz, CDCl$_3$) δ 170.0, 83.3, 77.8, 56.8, 27.3, 25.2, 23.5, 19.5.

Example 6: General Procedure for 1.3-Dioxolane Synthesis

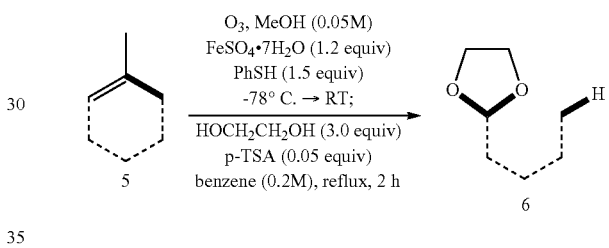

5

6

A round-bottom flask equipped with a magnetic stirrer bar was charged with 3 (1.0 equiv) and MeOH (0.05 M). The flask was then placed in a dry ice/acetone bath and cooled to −78° C. while open to the air. Ozone was bubbled through the solution until complete consumption of the starting material had occurred (as indicated by TLC and/or a blue color in the reaction mixture). The solution was then sparged with argon for 15 minutes to expel excess ozone. Benzenethiol (1.5 equiv) was then added as a 1.0 M stock solution$^a$ in MeOH, followed by ferrous sulfate heptahydrate (1.2 equiv). The mixture was stirred at −78° C. for 15 minutes before the cooling bath was removed. After warming to room temperature, the reaction mixture was transferred to a separatory funnel and water was added. The MeOH/water mixture was extracted with 1:1 Et$_2$O/pentane (3×). The combined organic fractions were washed with brine, dried over anhydrous sodium sulfate, filtered, and carefully concentrated under reduced pressure. The residue was dissolved in dry benzene (0.2 M) and placed in a round-bottom flask equipped with a magnetic stirrer bar. p-TSA (0.05 equiv) and ethylene glycol (3.0 equiv) were added, and then the mixture was heated under reflux in a Dean-Stark apparatus until complete consumption of the aldehyde starting material had occurred (as indicated by TLC). The mixture was cooled, washed with saturated aqueous sodium bicarbonate, and extracted with 1:1 Et$_2$O/pentane (3×). The combined organic fractions were dried (anhydrous sodium sulfate), filtered, and concentrated under reduced pressure. Purification by flash column chromatography (SiO$_2$) provided the dioxolane 6. "Benzenethiol stock solutions were prepared with anhydrous MeOH; they were stored under argon and discarded after three days to avoid formation of diphenyldisulfide.

Characterization Data

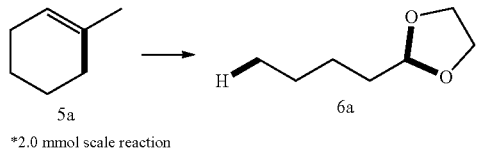

*2.0 mmol scale reaction

Yield: 71% (185 mg). Physical State: colorless oil. $^1$H NMR (500 MHZ, CDCl$_3$): δ 4.84 (t, J=4.9 Hz, 1H), 4.00-3.92 (m, 2H), 3.88-3.80 (m, 2H), 1.69-1.62 (m, 2H), 1.45-1.29 (m, 4H), 0.90 (t, J=7.0 Hz, 3H). $^{13}$C NMR (125 MHZ, CDCl$_3$): δ 104.6, 64.7, 33.5, 26.1, 22.5, 13.9. R$_f$=0.35 (5% EtOAc/hexanes). Purification: (SiO$_2$, 0→5% Et$_2$O/pentane).

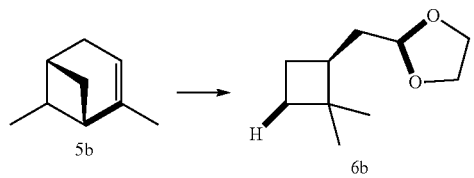

*2.0 mmol scale reaction

Yield: 60% (203 mg). Physical State: colorless oil. $^1$H NMR (500 MHz, CDCl$_3$): δ 4.77 (dd, J=5.0, 5.0 Hz, 1H), 3.98-3.92 (m, 2H), 3.86-3.80 (m, 2H), 2.12 (ddd, J=16.9, 8.4, 6.2 Hz, 1H), 1.97-1.90 (m, 1H), 1.74-1.52 (m, 5H), 1.04 (s, 3H), 1.00 (s, 3H). $^{13}$C NMR (125 MHZ, CDCl$_3$): δ 103.7, 64.7, 64.5, 39.8, 37.7, 35.1, 32.9, 30.0, 22.5, 22.3. IR (neat, ATR): ν$_{max}$ 2949, 2860, 1217, 1136, 1042 cm$^{-1}$. Optical Rotation: [α]$^{24}_D$ −6.4 (c 1.00, CHCl$_3$). HRMS (DART): calc'd for C$_{10}$H$_{19}$O$_2$ [M+H]$^+$ 171.1380, found 171.1376. R$_f$=0.28 (5% EtOAc/hexanes). Purification: (SiO$_2$, 0→5% Et$_2$O/pentane). Note: 2D NMR experiments are consistent with the proposed structure of 6b.

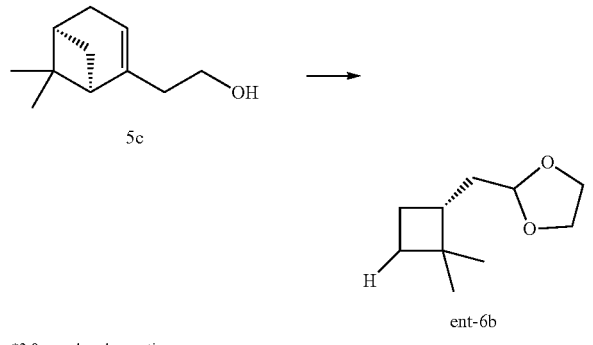

*2.0 mmol scale reaction

Yield: 65% (222 mg). Physical State: colorless oil. $^1$H NMR (500 MHZ, CDCl$_3$): δ 4.77 (dd, J=5.0, 5.0 Hz, 1H), 3.98-3.92 (m, 2H), 3.86-3.80 (m, 2H), 2.12 (ddd, J=16.9, 8.4, 6.2 Hz, 1H), 1.97-1.90 (m, 1H), 1.74-1.52 (m, 5H), 1.04 (s, 3H), 1.00 (s, 3H). $^{13}$C NMR (125 MHz, CDCl$_3$): δ 103.7, 64.7, 64.5, 39.8, 37.7, 35.1, 32.9, 30.0, 22.5, 22.3. IR (neat, ATR): ν$_{max}$ 2949, 2860, 1217, 1136, 1042 cm$^{-1}$. Optical Rotation: [α]$^{24}_D$ 6.3 (c 1.00, CHCl$_3$). HRMS (DART): calc'd for C$_{10}$H$_{19}$O$_2$ [M+H]$^+$ 171.1380, found 171.1380. R$_f$=0.28 (5% EtOAc/hexanes). Purification: (SiO$_2$, 0→5% Et$_2$O/pentane).

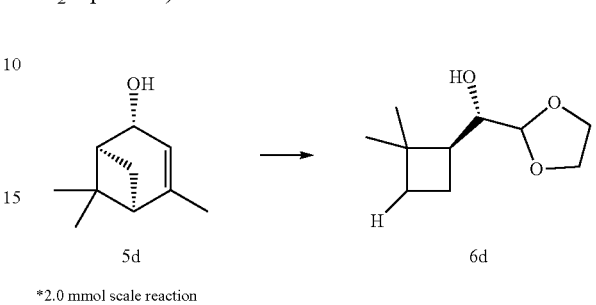

*2.0 mmol scale reaction

Yield: 88% (327 mg). Physical State: colorless oil. $^1$H NMR (500 MHZ, CDCl$_3$): δ 4.71 (d, J=2.7 Hz, 1H), 4.05-3.96 (m, 2H), 3.95-3.86 (m, 2H), 3.67 (dd, J=8.5, 2.7 Hz, 1H), 2.15 (ddd, J=18.0, 8.5, 0.8 Hz, 1H), 1.95-1.86 (m, 2H), 1.77 (br s, 1H), 1.68 (ddd, J=10.6, 9.1, 9.1 Hz, 1H), 1.57 (dddd, J=10.8, 8.1, 3.8, 0.9 Hz, 1H), 1.09 (s, 3H), 1.07 (s, 3H). $^{13}$C NMR (125 MHZ, CDCl$_3$): δ 104.4, 71.9, 65.4, 65.4, 45.1, 37.5, 32.9, 30.6, 23.1, 18.7. IR (neat, ATR): ν$_{max}$ 3460, 2949, 2890, 1461, 1366, 1151, 946 cm$^{-1}$. Optical Rotation: [α]$^{24}_D$ 13.6 (c 1.00, CHCl$_3$). HRMS (ESI-TOF): calc'd for C$_{10}$H$_{17}$O$_2$ [M-OH]$^+$ 169.1223, found 169.1227. R$_f$=0.35 (30% EtOAc/hexanes). Purification: (SiO$_2$, 10→30% EtOAc/hexanes). Note: 2D NMR experiments are consistent with the proposed structure of 6d.

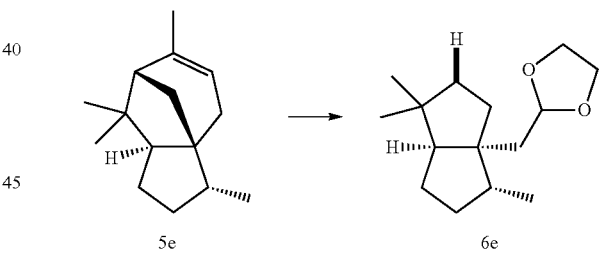

*2.0 mmol scale reaction

Yield: 78% (372 mg). Physical State: colorless oil. $^1$H NMR (500 MHZ, CDCl$_3$): δ 4.91 (dd, J=4.5, 4.5 Hz, 1H), 4.00-3.92 (m, 2H), 3.83-3.77 (m, 2H), 1.91 (dd, J=8.7, 8.7 Hz, 1H), 1.77 (ddd, J=12.9, 11.3, 6.9 Hz, 1H), 1.73-1.70 (m, 2H), 1.65-1.45 (m, 4H), 1.35-1.27 (m, 3H), 1.18 (ddd, J=23.3, 11.6, 6.6 Hz, 1H), 0.96 (s, 3H), 0.92 (d, J=6.9 Hz, 3H), 0.92 (s, 3H). $^{13}$C NMR (125 MHZ, CDCl$_3$): δ 104.0, 64.6, 64.3, 58.0, 53.3, 45.5, 41.0, 40.2, 39.2, 34.3, 34.2, 29.6, 27.6, 25.3, 14.0. IR (neat, ATR): ν$_{max}$ 2947, 2874, 1464, 1365, 1057 cm$^{-1}$. Optical Rotation: [α]$^{20}_D$ −7.4 (c 1.00, CHCl$_3$). HRMS (DART): calc'd for C$_{15}$H$_{27}$O$_2$ [M+H]$^+$ 239.2006, found 239.2004. R$_f$=0.36 (5% EtOAc/hexanes). Purification: (SiO$_2$, 0→5% Et$_2$O/pentane).

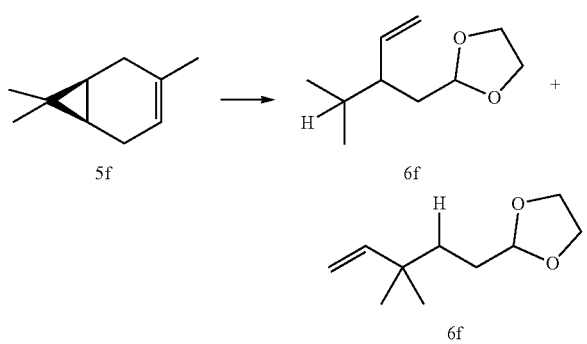

*2.0 mmol scale reaction

Yield: 87% (220 mg, 1:0.85 6f/6f', inseparable mixture). Physical State: yellow oil. $^1$H NMR (500 MHZ, CDCl$_3$) 6f: δ 5.60 (ddd, J=17.1, 10.2, 9.3 Hz, 1H), 5.05 (dd, J=10.3, 2.0 Hz, 1H), 5.01 (ddd, J=17.1, 2.1, 0.8 Hz, 1H), 4.83 (dd, J=6.3, 3.9 Hz, 1H), 3.99-3.91 (m, 2H), 3.88-3.78 (m, 2H), 2.08 (ddd, J=14.3, 9.4, 5.1 Hz, 1H), 1.72-1.61 (m, 3H), 0.88 (d, J=6.8 Hz, 3H), 0.84 (d, J=6.8 Hz, 3H). $^1$H NMR (500 MHZ, CDCl$_3$) 6f': 5.74 (dd, J=17.3, 10.9 Hz, 1H), 4.93 (dd, J=3.5, 1.3 Hz, 1H), 4.90 (dd, J=10.0, 1.4 Hz, 1H), 4.81 (t, J=4.7 Hz, 1H), 3.99-3.91 (m, 2H), 3.88-3.78 (m, 2H), 1.61-1.56 (m, 2H), 1.43-1.37 (m, 2H), 0.99 (s, 6H). $^{13}$C NMR (125 MHZ, CDCl$_3$) 6f: δ 139.6, 115.8, 104.9, 64.6, 64.6, 46.1, 31.7, 29.1, 20.2, 18.4. $^{13}$C NMR (125 MHz, CDCl$_3$) 6f': δ 147.8, 110.7, 103.7, 64.7, 36.2, 36.1, 36.0, 26.5. IR (neat, ATR): $v_{max}$ 3081, 2958, 2875, 1134, 914, 735 cm$^{-1}$. HRMS (DART): calc'd for C$_{10}$H$_{19}$O$_2$ [M+H]$^+$ 171.1380, found 171.1379 and 171.1380. R$_f$=0.39 (30% EtOAc/hexanes). Purification: (SiO$_2$, 10→20% EtOAc/hexanes). Note: 2D NMR experiments are consistent with the proposed structures of 6f and 6f'.

Example 7: Preparation of Further Exemplary Compounds

Preparation of the TEMPO Adducts 7a and 7a'

A round-bottom flask equipped with a magnetic stirrer bar was charged with the hydroxy ketone 1a (118 mg, 0.500 mmol, 1.0 equiv) and MeOH (10 mL, 0.05 M). The flask was then placed in a dry ice/acetone bath and cooled to −78° C. while open to the air. Ozone was bubbled through the solution until complete consumption of the starting material (as indicated by TLC with CAM stain). The solution was then sparged with argon for 15 minutes to expel excess ozone. TEMPO (117 mg, 0.750 mmol, 1.5 equiv) was then added, followed by ferrous sulfate heptahydrate (167 mg, 0.600 mmol, 1.2 equiv). The mixture was stirred at −78° C. for 15 minutes before the cooling bath was removed. After warming to room temperature, the reaction mixture was transferred to a separatory funnel and water was added. The MeOH/water mixture was extracted with dichloromethane (3×). The combined organic fractions were washed with brine, dried (anhydrous sodium sulfate), filtered, and concentrated under reduced pressure. Purification by flash column chromatography (SiO$_2$) provided the TEMPO adducts 7a and 7a' (4:1) in a combined isolated yield of 91%. To verify the stereochemistry of the new C—O bond, 5 mg of 7a was placed in a small crystallization tube and dissolved in a minimal amount of dichloromethane. This vial was placed within a larger 4-mL vial containing approximately 1 mL of pentane. The vial was capped and sealed with Teflon and parafilm. After 3 days, single crystals suitable for X-ray diffraction had formed.

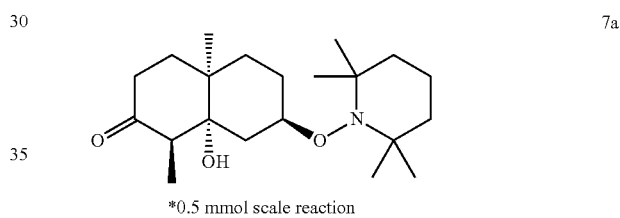

*0.5 mmol scale reaction

Yield: 74% (130 mg). Physical State: white solid. $^1$H NMR (500 MHZ, CDCl$_3$): δ 3.85 (ddd, J=16.0, 11.4, 4.5 Hz, 1H), 2.77 (q, J=6.6 Hz, 1H), 2.53 (ddd, J=14.1, 14.1, 7.0 Hz,

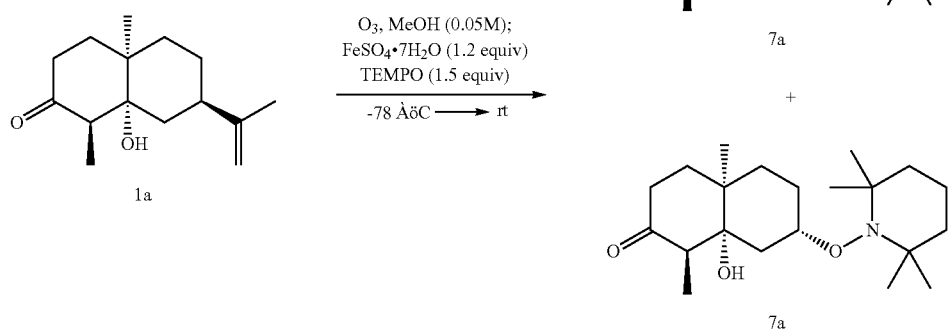

1H), 2.31 (ddd, J=14.1, 4.9, 1.5 Hz, 1H), 2.12 (ddd, J=14.1, 14.1, 4.9 Hz, 1H), 2.04-1.94 (m, 2H), 1.84-1.75 (m, 1H), 1.47-1.21 (m, 9H), 1.18 (s, 3H), 1.14-0.98 (m, 13H), 1.04 (d, J=6.7 Hz, 3H). $^{13}$C NMR (125 MHz, CDCl$_3$): δ 210.4, 79.3, 78.4, 59.5, 51.9, 40.1, 37.5, 37.3, 34.8, 34.3, 34.2, 31.5, 27.2, 21.1, 20.1, 17.1, 6.6. MP: 143-144° C. IR (neat, ATR): $\nu_{max}$ 3557, 2931, 2868, 1780, 1696 cm$^{-1}$. Optical Rotation: $[\alpha]^{24}_D$ 30.9 (c 1.00, CHCl$_3$). HRMS (ESI-TOF): calc'd for C$_{21}$H$_{38}$NO$_3$ [M+H]$^+$ 352.2835, found 352.2844. R$_f$=0.42 (30% EtOAc/hexanes). Purification: (SiO$_2$, 10→30% EtOAc/hexanes).

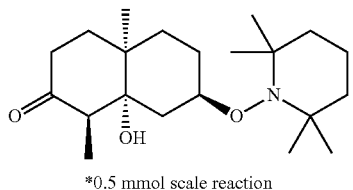

7a

*0.5 mmol scale reaction

Yield: 17% (30 mg). Physical State: white solid. $^1$H NMR (500 MHz, CDCl$_3$): δ 4.23 (s, 1H), 4.10-4.06 (m, 1H), 2.84 (q, J=6.6 Hz, 1H), 2.59 (ddd, J=14.1, 14.1, 7.2 Hz, 1H), 2.30 (dd, J=14.2, 3.0 Hz, 1H), 2.15-2.06 (m, 2H), 2.01 (ddd, J=14.2, 14.2, 3.6 Hz, 1H), 1.90 (ddd, J=14.0, 14.0, 4.9 Hz, 1H), 1.55-1.30 (m, 8H), 1.26 (s, 3H), 1.24-1.11 (m, 14H), 1.08 (d, J=6.6 Hz, 3H). $^{13}$C NMR (125 MHZ, CDCl$_3$): δ 211.4, 80.6, 77.9, 61.0, 59.2, 50.7, 40.5, 38.4, 37.9, 34.5, 33.9, 31.8, 31.4, 30.3, 24.5, 21.8, 20.7, 20.2, 17.0, 6.7. MP: 155-157° C. IR (neat, ATR): $\nu_{max}$ 3469, 2928, 2910, 2871, 1711 cm$^{-1}$. Optical Rotation: $[\alpha]^{24}_D$ 40.2 (c 1.00, CHCl$_3$). HRMS (ESI-TOF): calc'd for C$_{21}$H$_{38}$NO$_3$ [M+H]$^+$ 352.2835, found 352.2854. R$_f$=0.62 (30% EtOAc/hexanes). Purification: (SiO$_2$, 10→30% EtOAc/hexanes).

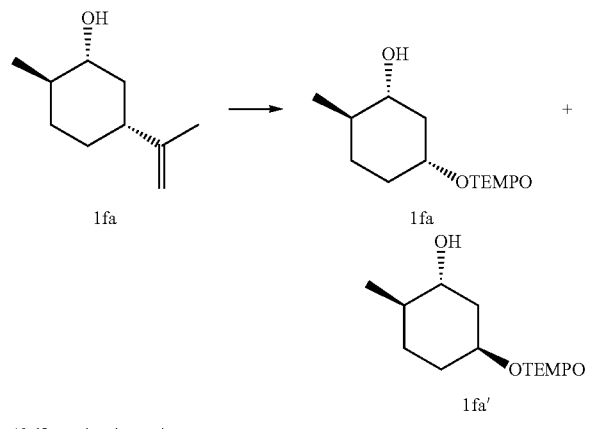

*0.65 mmol scale reaction

The O-alkyl TEMPO adducts 1fa/1fa' were synthesized by following the General Procedure found in Section 4.1. After the addition of TEMPO and aqueous ferrous sulfate, the mixture was allowed to warm until its reaction temperature reached 0° C. The reaction was quenched through the addition of 10% saturated aqueous sodium thiosulfate and saturated aqueous sodium bicarbonate. After warming to room temperature, the MeOH/water layer was extracted with dichloromethane (3×), washed with brine, dried (anhydrous sodium sulfate), filtered, and concentrated under reduced pressure. Purification of the residue by flash column chromatography (SiO$_2$) provided the pure products 1fa and 1fa' (1.8:1 d.r.). Combined Yield: 92% (161 mg). Regioisomeric Ratio: 1.8:1 (1fa/1fa', determined from crude $^1$H NMR spectrum).

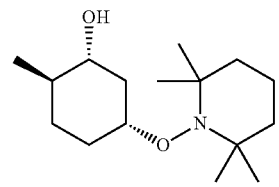

1fa

Yield: 59% (103 mg). Physical State: colorless oil. $^1$H NMR (500 MHZ, CDCl$_3$): δ 3.65 (dddd, J=11.0, 11.0, 4.0, 4.0 Hz, 1H), 3.10 (ddd, J=10.4, 9.9, 3.9 Hz, 1H), 2.48-2.40 (m, 1H), 2.11-2.02 (m, 1H), 1.76 (br s, 1H), 1.71 (dddd, J=13.8, 3.8, 3.8, 3.8 Hz, 1H), 1.65-0.82 (m, 22H), 0.98 (d, J=6.5 Hz, 3H). $^{13}$C NMR (125 MHZ, CDCl$_3$): δ 80.3, 74.7, 59.6, 41.4, 40.1, 39.3, 34.3, 31.8, 29.9, 20.2, 17.8, 17.2. IR (neat, ATR): $\nu_{max}$ 3367, 2974, 2931, 2875, 1457, 1375, 1354, 1135, 1004, 989 cm$^{-1}$. Optical Rotation: $[\alpha]_D^{21.2}$ −3.5 (c 1.00, CHCl$_3$). HRMS (ESI-TOF): calc'd for C$_{16}$H$_{32}$NO$_2$ [M+H]$^+$ m/z 270.2428, found 270.2393. R$_f$=0.54 (20% EtOAc/hexanes). Purification: (SiO$_2$, 5→10% EtOAc/hexanes). Note: 2D NMR experimental data were consistent with the proposed structural assignment of the product.

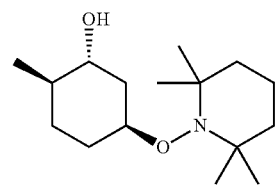

1fa'

Yield: 33% (58 mg). Physical State: white solid. $^1$H NMR (500 MHZ, CDCl$_3$): δ 4.09-4.01 (m, 1H), 3.59-3.49 (m, 1H), 2.34-2.24 (m, 1H), 2.02-1.94 (m, 1H), 1.67-1.02 (m, 24H), 1.04 (d, J=5.7 Hz, 3H). $^{13}$C NMR (125 MHZ, CDCl$_3$): δ 79.6, 72.9, 59.6, 40.2, 39.4, 39.3, 34.1, 29.6, 28.1, 20.1, 18.2, 17.0. MP: 74-75° C. IR (neat, ATR): $\nu_{max}$ 3374, 3003, 2978, 2931, 2872, 1457, 1375, 1358, 1131, 1064, 1032, 986, 756 cm$^{-1}$. Optical Rotation: $[\alpha]_D^{21.8}$ −0.4 (c 0.50, CHCl$_3$). HRMS (ESI-TOF): calc'd for C$_{16}$H$_{32}$NO$_2$ [M+H]$^+$ m/z 270.2428, found 270.2398. R$_f$=0.47 (20% EtOAc/hexanes). Purification: (SiO$_2$, 5→10% EtOAc/hexanes). Note: 2D NMR experimental data were consistent with the proposed structural assignment of the product.

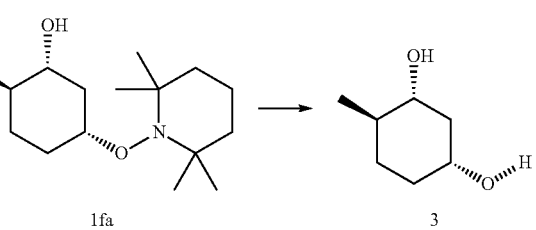

A vial equipped with a magnetic stirrer bar was charged with O-alkyl TEMPO adduct 1fa (54 mg, 0.2 mmol, 1.0 equiv) and acetic acid/THF (1.2:1, 0.1 M). Activated zinc dust (512 mg, 8.0 mmol, 40.0 equiv) was added and the mixture was heated to 50° C. Upon completion of the reaction (as indicated by TLC, 3 h), the mixture was cooled to room temperature and diluted with diethyl ether. The solution was filtered through a plug of silica, which was subsequently washed with EtOAc. The combined organic fractions were concentrated under reduced pressure. Purification by flash column chromatography (SiO$_2$) provided the pure product 3.

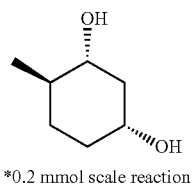

*0.2 mmol scale reaction

Yield: 92% (24 mg). Physical State: colorless oil. $^1$H NMR (500 MHZ, CDCl$_3$): δ 3.68 (dddd, J=10.4, 10.4, 4.2, 4.2 Hz, 1H), 3.21 (ddd, J=9.8, 9.8, 3.9 Hz, 1H), 2.28-2.20 (m, 1H), 1.95-1.87 (m, 1H), 1.76 (dddd, J=13.8, 4.0, 4.0, 4.0 Hz, 1H), 1.41-1.24 (m, 3H), 1.06-0.95 (m, 1H), 1.01 (d, J=6.5 Hz, 3H). $^{13}$C NMR (125 MHZ, CDCl$_3$): δ 74.1, 69.1, 43.5, 38.9, 34.4, 29.0, 17.7. IR (neat, ATR): $\nu_{max}$ 3357, 2935, 2907, 2868, 1457, 1364, 1014 cm$^{-1}$. Optical Rotation: $[\alpha]_D^{22.0}$ −15.5 (c 0.20, CHCl$_3$). HRMS (DART): calc'd for C$_7$H$_{14}$O$_2$Na [M+H]$^+$ m/z 153.0886, found 153.0907. R$_f$=0.21 (75% EtOAc/hexanes). Purification: (SiO$_2$, 50→75% EtOAc/hexanes).

Preparation of the Thioethers 8a and 8a'

A round-bottom flask equipped with a magnetic stirrer bar was charged with the hydroxy ketone 1a (118 mg, 0.500 mmol, 1.0 equiv) and MeOH (10 mL, 0.05 M). The flask was then placed in a dry ice/acetone bath and cooled to −78° C. while open to the air. Ozone was bubbled through the solution until complete consumption of the starting material had occurred (as indicated by TLC with CAM stain). The solution was then sparged with argon for 15 minutes to expel excess ozone. Diphenyldisulfide (131 mg, 0.600 mmol, 1.2 equiv) was then added followed by ferrous sulfate heptahydrate (167 mg, 0.600 mmol, 1.2 equiv). The mixture was stirred at −78° C. for 15 minutes before the cooling bath was removed. After warming to room temperature, the reaction mixture was transferred to a separatory funnel and water was added. The methanol/water mixture was extracted with dichloromethane (3×). The combined organic fractions were washed with brine, dried over anhydrous sodium sulfate, filtered, and concentrated under reduced pressure. Purification by flash column chromatography (SiO$_2$) provided the thioethers 8a and 8a' (8:1) in a combined isolated yield of 40%.

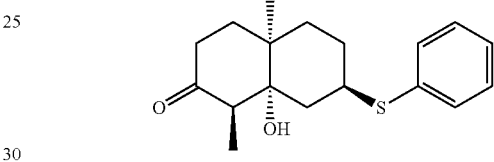

*0.5 mmol scale reaction

Yield: 36% (55 mg). Physical State: pale yellow oil. $^1$H NMR (500 MHz, CDCl$_3$): δ 7.42-7.36 (m, 2H), 7.32-7.20 (m, 3H), 3.35 (dddd, J=16.6, 8.4, 4.1, 4.1 Hz, 1H), 2.81 (q, J=6.6 Hz, 1H), 2.55 (ddd, J=14.1, 14.1, 7.1 Hz, 1H), 2.33 (dd, J=14.2, 3.7 Hz, 1H), 2.06 (ddd, J=13.9, 13.9, 5.0 Hz, 1H), 1.95-1.79 (m, 3H), 1.59-1.48 (m, 2H), 1.46-1.36 (m, 2H), 1.24-1.26 (m, 1H), 1.22 (s, 3H), 1.00 (d, J=6.7 Hz, 3H). $^{13}$C NMR (125 MHZ, CDCl$_3$): δ 209.7, 134.0, 132.1, 128.8, 127.0, 78.3, 51.6, 42.0, 37.4, 37.3, 35.2, 35.2, 31.3, 27.9, 21.3, 6.3. IR (neat, ATR): $\nu_{max}$ 2986, 2938, 1700, 1048, 986 cm$^{-1}$. Optical Rotation: $[\alpha]_D^{24}$ 56.0 (c 1.00, CHCl$_3$). HRMS

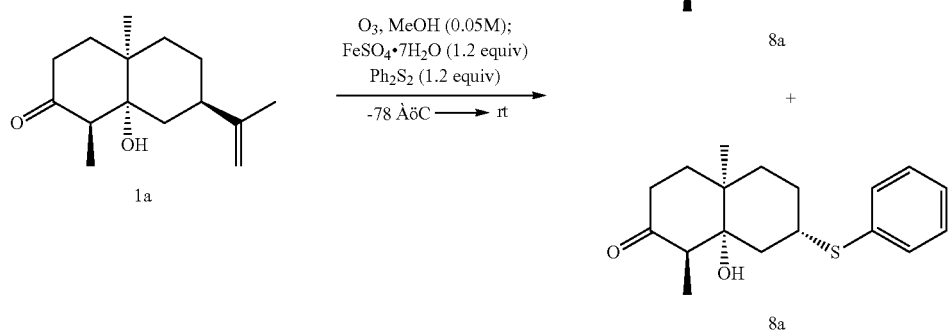

(ESI-TOF): calc'd for $KC_{18}H_{24}O_2S$ [M+K]$^+$ 343.1129, found 343.1143. $R_f$=0.32 (20% EtOAc/hexanes). Purification: (SiO$_2$, 10→20% EtOAc/hexanes).

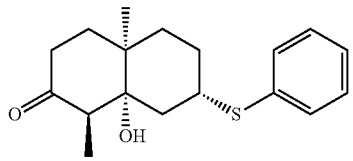

*0.5 mmol scale reaction

8a

Yield: 4% (6 mg). Physical State: white solid. $^1$H NMR (500 MHz, CDCl$_3$): δ 7.47-7.43 (m, 2H), 7.36-7.29 (m, 3H), 4.19 (br s, 1H), 3.61-3.57 (m, 1H), 2.81 (q, J=6.5 Hz, 1H), 2.60 (dddd, J=21.3, 7.1, 7.1, 1.1 Hz, 1H), 2.30 (ddd, J=14.1, 4.9, 1.9 Hz, 1H), 2.16-1.95 (m, 3H), 1.85-1.78 (m, 2H), 1.47 (ddd, J=13.9, 6.9, 2.0 Hz, 1H), 1.37 (dd, J=15.7, 4.8 Hz, 1H), 1.34-1.29 (m, 1H), 1.28 (s, 3H), 0.97 (d, J=6.7 Hz, 3H). $^{13}$C NMR (125 MHz, CDCl$_3$): δ 211.0, 133.5, 133.0, 129.2, 128.0, 78.5, 51.3, 44.2, 38.1, 37.7, 31.4, 30.7, 29.7, 24.9, 22.1, 6.6. MP: 112° C. IR (neat, ATR): $v_{max}$ 3414, 3050, 2971, 2921, 1698 cm$^{-1}$. Optical Rotation: [α]$^{24}_D$ 3.5 (c 0.20, CHCl$_3$). HRMS (ESI-TOF): calc'd for $KC_{18}H_{24}O_2S$ [M+K]$^+$ 343.1129, found 343.1128. $R_f$=0.49 (20% EtOAc/hexanes). Purification: (SiO$_2$, 10→20% EtOAc/hexanes).

Byproduct Formation with 1p byproduct formation

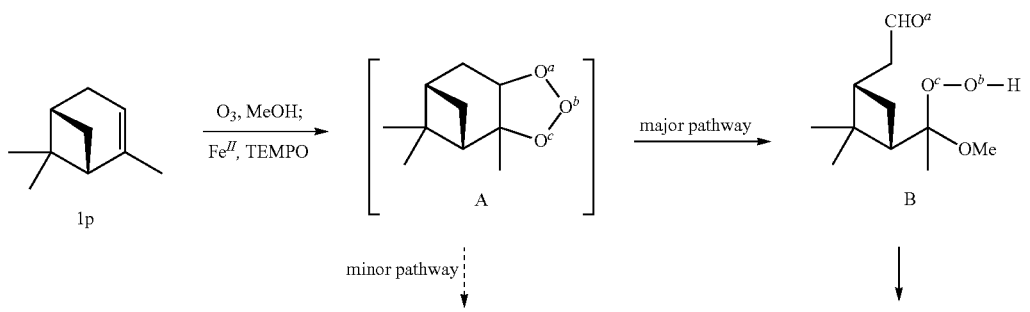

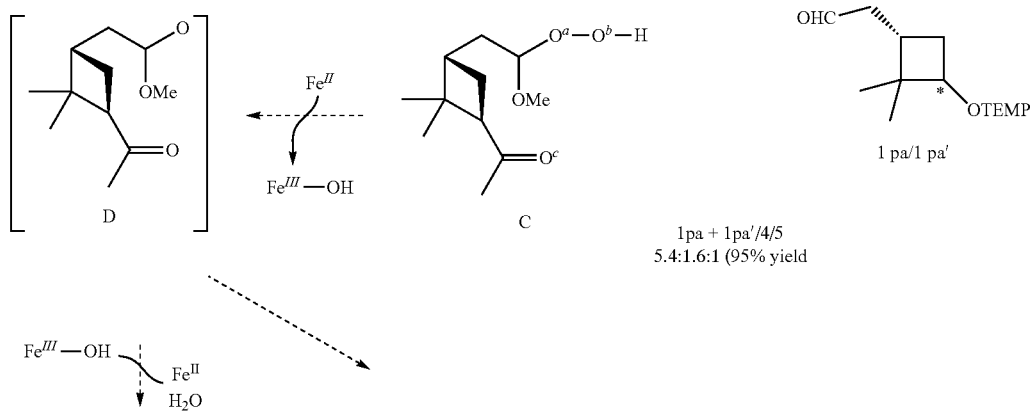

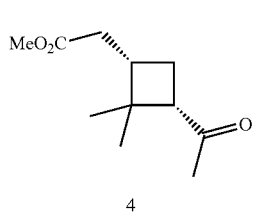

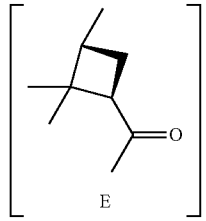

Typically, it was found that the combination of Criegee ozonolysis and SET-based fragmentation reactions and subsequent trapping of the alkyl radical intermediate converted the terpenoid starting materials cleanly to their desired products. Nevertheless, in some cases (primarily when employing cycloalkenes) side products were also observed. To investigate the pathways leading to these side products, all of the detectable products were isolated from the reaction of (+)-α-pinene (1p). Based on NMR spectroscopic and mass spectrometric analyses, the products produced were determined to be the O-alkyl TEMPO adducts 1pa and 1pa', the ketoester 4, and the O-alkyl TEMPO adduct 5 (1pa+1pa'/4/5, 5.4:1.6:1). These products arose through two possible molozonide (A) fragmentation pathways.[22] In the major pathway, the tertiary α-alkoxy hydroperoxide B is generated. When treated with a ferrous species, the resulting alkoxy radical can undergo β-scission smoothly to give the desired O-alkyl TEMPO adducts 1pa and 1pa' (which upon oxidation provides the carbonyl product 2p). In the minor pathway, the secondary α-alkoxy hydroperoxide C is generated. SET-based reduction of the O—O bond provides the alkoxy radical D. Subsequent Fe(III)-catalyzed dehydration converts this reactive intermediate to the ketoester 4.[23] Alternatively, β-fragmentation of the alkoxy radical D and subsequent trapping of the alkyl radical E gives the O-alkyl TEMPO adduct 5 (which, upon oxidation, gives the product 2p').

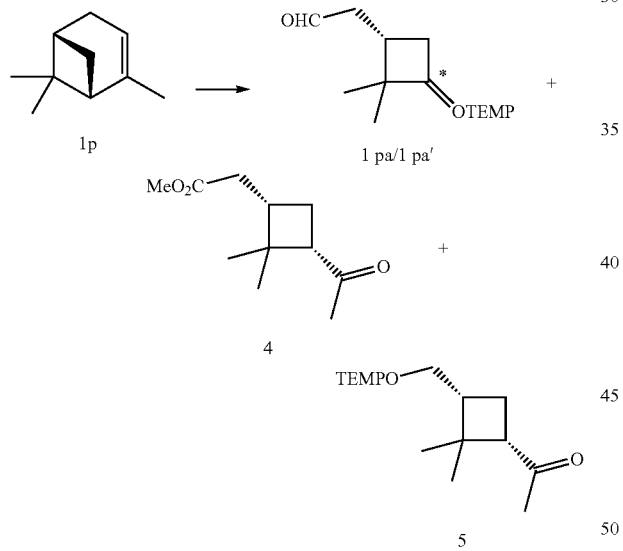

*1.0 mmol scale reaction

Combined Yield: 95% (252 mg). Regioisomeric Ratio: 5.4:1.6:1.0 (1pa+1pa'/4/5, determined from crude $^1$H NMR spectrum).

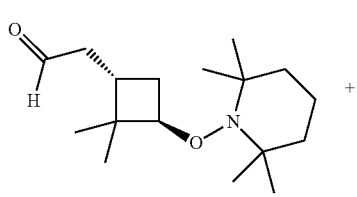

1pa

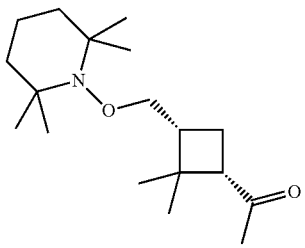

5

Physical State: colorless oil. $^1$H NMR (500 MHZ, CDCl$_3$) 1pa: δ 9.72 (dd, J=1.9, 1.9 Hz, 1H), 4.06-3.99 (m, 1H), 2.57 (ddd, J=16.4, 6.0, 1.5 Hz, 1H), 2.35 (ddd, J=16.7, 9.5, 2.1 Hz, 1H), 2.32-2.24 (m, 1H), 2.06-1.92 (m, 2H), 1.58-1.00 (m, 18H), 1.22 (s, 3H), 1.04 (s, 3H). $^1$H NMR (500 MHZ, CDCl$_3$) 5: δ 3.74 (dd, J=9.0, 9.0 Hz, 1H), 3.61 (dd, J=9.3, 5.9 Hz, 1H), 2.84 (dd, J=10.3, 7.4 Hz, 1H), 2.24 (dddd, J=8.4, 8.4, 2.5, 2.5 Hz, 1H), 2.04 (s, 3H), 1.77 (ddd, J=11.4, 7.8, 7.8 Hz, 1H), 1.58-1.00 (m, 19H) 1.34 (s, 3H), 0.94 (s, 3H). $^{13}$C NMR (125 MHZ, CDCl$_3$) 1pa: δ 202.6, 85.1, 60.1, 58.5, 46.2, 44.2, 39.9, 34.5, 34.0, 33.2, 30.9, 24.0, 23.2, 20.2, 17.3. $^{13}$C NMR (125 MHZ, CDCl$_3$) 5: δ 208.1, 77.4, 59.7, 59.5, 54.1, 43.1, 40.7, 39.6, 39.5, 33.4, 32.8, 31.0, 30.1, 20.0, 19.9, 19.8, 17.4, 17.1. IR (neat, ATR): $v_{max}$ 2967, 2935, 2872, 2716, 1725, 1708, 1468, 1372, 1358, 1138, 1089, 1036 cm$^{-1}$. Optical Rotation: $[α]_D^{21.9}$ −20.6 (c 0.50, CHCl$_3$). HRMS (ESI-TOF): calc'd for C$_{17}$H$_{32}$NO$_2$ [M+H]$^+$ m/z 282.2428, found 282.2408; calc'd for C$_{18}$H$_{34}$NO$_2$ [M+H]$^+$ 296.2584, found 296.2562. R$_f$=0.41 (10% EtOAc/hexanes). Purification: (SiO$_2$, 5% EtOAc/hexanes). Note: It was not possible to fully separate the products 1pa and 5. The NMR spectra are provided for a mixture of 1pa/5 (3.4:1). All characterization data were collected from this mixture. 2D NMR spectroscopic experiments were consistent with the proposed structural assignments of the products.

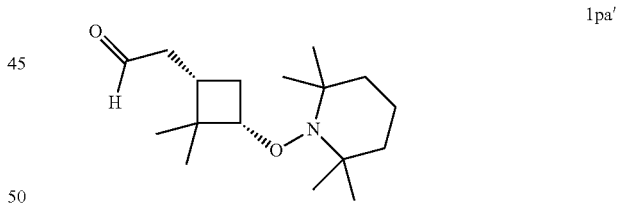

1pa'

Physical State: colorless oil. $^1$H NMR (500 MHZ, CDCl$_3$): δ 9.72 (dd, J=2.1, 2.1 Hz, 1H), 3.89 (dd, J=8.8, 7.1 Hz, 1H), 2.54-2.43 (m, 2H), 2.36 (ddd, J=16.5, 8.0, 1.8 Hz, 1H), 1.77 (dddd, J=10.6, 7.4, 7.4, 7.4 Hz, 1H), 1.65 (ddd, J=10.6, 10.6, 9.0 Hz, 1H), 1.58-1.23 (m, 6H), 1.20-0.98 (m, 12H), 1.17 (s, 3H), 1.02 (s, 3H). $^{13}$C NMR (125 MHZ, CDCl$_3$): δ 202.2, 85.2, 60.1, 58.5, 45.9, 44.9, 39.9, 35.6, 34.0, 33.2, 30.5, 28.8, 20.1, 17.3, 16.4. IR (neat, ATR): $v_{max}$ 2999, 2967, 2935, 2875, 2719, 1729, 1471, 1379, 1362, 1135, 1039 cm$^{-1}$. Optical Rotation: $[α]_D^{22.1}$ 9.0 (c 0.20, CHCl$_3$). HRMS (ESI-TOF): calc'd for C$_{17}$H$_{32}$NO$_2$ [M+H]$^+$ m/z 282.2428, found 282.2433. R$_f$=0.50 (10% EtOAc/hexanes). Purification: (SiO$_2$, 5% EtOAc/hexanes). Note: 2D NMR spectroscopic data were consistent with the proposed structural assignment of the product.

4

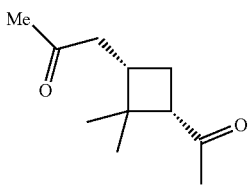

Physical State: colorless oil. $^1$H NMR (500 MHZ, CDCl$_3$): δ 3.65 (s, 3H), 2.88 (dd, J=10.2, 7.6 Hz, 1H), 2.41-2.22 (m, 3H), 2.04 (s, 3H), 2.02-1.93 (m, 1H), 1.91 (ddd, J=11.4, 7.8, 7.8 Hz, 1H), 1.32 (s, 3H), 0.86 (s, 3H). $^{13}$C NMR (125 MHz, CDCl$_3$): δ 207.6, 173.2, 54.2, 51.5, 43.3, 38.0, 34.9, 30.2, 30.2, 23.0, 17.3. IR (neat, ATR): ν$_{max}$ 2999, 2960, 2950, 2907, 2878, 1743, 1704, 1174 cm$^{-1}$. Optical Rotation: [α]$_D^{22.1}$ 14.0 (c 0.20, CHCl$_3$). HRMS (DART): calc'd for C$_{11}$H$_{19}$ NO$_3$ [M+H]$^+$ m/z 199.1329, found 199.1325. R$_f$=0.21 (10% EtOAc/hexanes). Purification: (SiO$_2$, 5% EtOAc/hexanes). Note: 2D NMR spectroscopic data were consistent with the proposed structural assignment of the product.

Example 8: Exemplary Mechanistic Discussion

When the indanol SI-IV was subjected to the hydrodealkenylation conditions, hydrodealkenylation product 2o was obtained (38% yield) along with the methyl ester SI-V (31% yield).

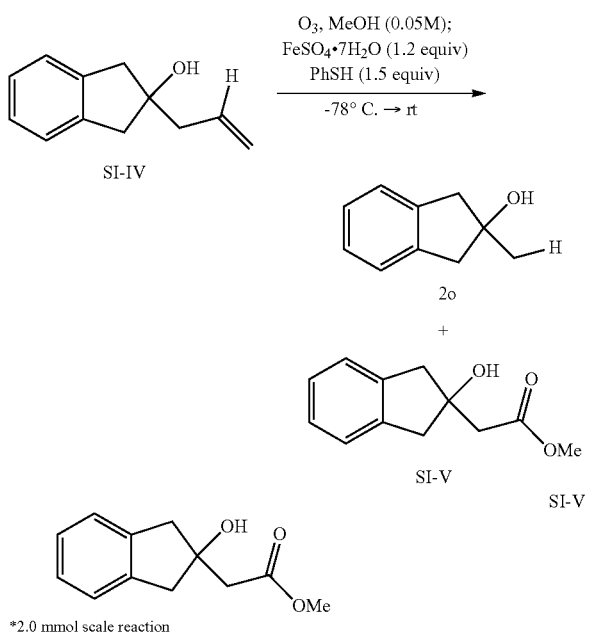

*2.0 mmol scale reaction

Yield: 31% (100 mg)+38% (110 mg) of 2o. Physical State: white solid. $^1$H NMR (500 MHZ, CDCl$_3$): δ 7.24-7.14 (m, 4H), 3.76 (s, 3H), 3.64 (br s, 1H), 3.16 (d, J=16.1 Hz, 2H), 3.03 (d, J=16.1 Hz, 2H), 2.78 (s, 2H). $^{13}$C NMR (125 MHZ, CDCl$_3$): δ 173.2, 140.6, 126.6, 124.7, 79.4, 51.7, 46.5, 43.7. R$_f$=0.50 (30% EtOAc/hexanes). Purification: (SiO$_2$, 15→20% EtOAc/hexanes).

Example 9: Exemplary Optimization of the Oxodealkenylation Reaction

Initially, hydroxy ketone 1a was used to examine the conditions necessary for the conversion of an alkene to a ketone (Tables S1 and S2). The optimal temperature for ferrous sulfate addition (added as a 5% w/v aqueous solution) was −78° C., followed by warming to room temperature (Table S2, entries 1-4). The reaction itself was extremely rapid and typically complete within a minute of the addition of the iron salt. Using 1.0 equivalent of TEMPO gave a slightly lower yield (versus 1.5 equiv, entry 5), while no benefit gained when using 2.0 equivalents (Table S2, entry 6). Under these reaction conditions, it was also found that MMPP performed better than mCPBA and other commonly used oxidizing agents such as hydrogen peroxide, urea hydrogen peroxide (UHP), and potassium peroxymonosulfate (Table S2, entries 7-11). Furthermore, the water-solubility of MMPP allowed simple work-up conditions and facile removal of by-products. The highest yield of 2a was achieved when employing 2.5 equivalents of MMPP (Table S2, entries 12-15). One reason for the use of excess MMPP was to ensure the oxidation of TEMPO hydroxyl to TEMPO free radical, a process supported by the observation that MMPP-mediated oxidation of pure 1aa to give 2a was accompanied by the regeneration of TEMPO. An attempt to convert the intermediate α-alkoxy hydroperoxide directly to oxygenated products by trapping the alkyl radical with O$_2$ in the presence of PhSiH$_3$ produced the ketone 2a in 24% yield (Table S2, entry 16). [13f,14]

TABLE S2

Further Optimization of Reaction Parameters

| entry | TEMPO (equiv) | Oxidant (equiv) | Temp (° C.) | Yield[b] 1aa + 1aa' | Yield[c] 2a |
|---|---|---|---|---|---|
| 1 | 1.5 | — | −78 to rt | 91 | — |
| 2[d] | 1.5 | — | −78 to rt | 94 | — |
| 3[d] | 1.5 | — | 0 | 85 | — |
| 4[d] | 1.5 | — | rt | 92 | — |
| 5[d] | 1.0 | — | −78 to rt | 79 | — |
| 6[d] | 2.0 | — | −78 to rt | 93 | — |
| 7[d] | 1.5 | mCPBA (1.2) | −78 to rt | — | 33 |
| 8[d] | 1.5 | H$_2$O$_2$ (1.2) | −78 to rt | — | Trace |
| 9[d] | 1.5 | UHP (1.2) | −78 to rt | — | 0 |
| 10[d] | 1.5 | MMPP (1.2) | −78 to rt | — | 53 |
| 11[d] | 1.5 | Oxone ™ (1.2) | −78 to rt | — | Trace |
| 12[d] | 1.5 | MMPP (1.5) | −78 to rt | — | 62 |
| 13[d] | 1.5 | MMPP (2.0) | −78 to rt | — | 78 |
| 14[d] | 1.5 | MMPP (2.5) | −78 to rt | — | 84 |
| 15[d] | 1.5 | MMPP (3.0) | −78 to rt | — | 81 |
| 16[e] | — | O$_2$ | 0 to rt | — | 24 |

[b]Yield based on NMR spectral analysis, using 1-chloro-2,4-dinitrobenzene as the internal standard.
[c]Isolated yield.
[d]aq. FeSO$_4$•7H$_2$O (5% w/v)
[e]2.5 equiv FeSO$_4$•7H$_2$O and 2.5 equiv PhSiH$_3$.

Entries 1-6: Upon complete consumption of the intermediate α-alkoxy hydroperoxides (as indicated by TLC), 1-chloro-2,4-dinitrobenzene (20.3 mg, 0.100 mmol, 1.0 equiv) was added to the reaction mixture. The mixture was then cooled to 0° C. in an ice-water bath, and 10% saturated aqueous sodium thiosulfate (4.0 mL) was added. After warming to room temperature and stirring for 15 minutes, the MeOH/water layer was extracted with dichloromethane (3×3.0 mL). The combined organic fractions were transferred to a vial, and the 10% saturated aqueous sodium thiosulfate (4.0 mL) was added, followed by 1.0 M HCl (0.50 mL). After vigorously stirring for 10 min, the organic layer was separated, washed with brine (5.0 mL), dried, and concentrated. The crude product was dissolved in deuterated chloroform, then filtered directly into an NMR tube for analysis.

Entries 7-15: Upon complete consumption of the intermediate α-alkoxy hydroperoxide (as indicated by TLC), the reaction mixture was cooled to 0° C. in an ice-water bath and the oxidant was added in a single portion. After stirring for 30 minutes at 0° C., 10% saturated aqueous sodium thiosulfate (2.00 mL) was added, followed by saturated aqueous sodium bicarbonate (2.00 mL). The mixture was warmed to room temperature, then extracted with dichloromethane (3×3.00 mL). The combined organic fractions were washed with brine, dried over anhydrous sodium sulfate, filtered, and concentrated. The residue was purified by flash column chromatography (SiO$_2$; 30→40% EtOAc/hexanes).

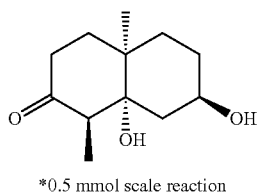

*0.5 mmol scale reaction

Yield: 34% (36 mg). Physical State: white solid. $^1$H NMR (500 MHZ, CDCl$_3$): δ 3.92 (dddd, J=11.3, 11.3, 4.8, 4.8 Hz, 1H), 2.77 (q, J=6.6 Hz, 1H), 2.56 (dddd, J=14.2, 14.2, 7.0, 1.0 Hz, 1H), 2.34 (ddd, J=14.2, 5.0, 1.8 Hz, 1H), 2.13 (ddd, J=14.1, 14.1, 5.1 Hz, 1H), 1.95-1.79 (m, 3H), 1.54-1.38 (m, 5H), 1.22 (s, 3H), 1.08 (dd, J=13.6, 11.4 Hz, 1H), 1.05 (d, J=6.7 Hz, 3H). $^{13}$C NMR (125 MHZ, CDCl$_3$): δ 209.9, 79.3, 67.4, 51.9, 37.7, 37.6, 37.4, 33.9, 31.6, 30.2, 21.2, 6.6. MP: 188° C. (decomp). IR (neat, ATR): ν$_{max}$ 3391, 2967, 2925, 2882, 1704, 1258, 1061, 976 cm$^{-1}$. Optical Rotation: [α]$_D^{21.1}$ 26.5 (c 0.20, CHCl$_3$). HRMS (ESI-TOF): calc'd for C$_{12}$H$_{19}$O$_2$ [M-OH]$^+$ m/z 195.1380, found 195.1384. R$_f$=0.09 (50% EtOAc/hexanes). Purification: (SiO$_2$, 20→100% EtOAc/hexanes).

SI-I'

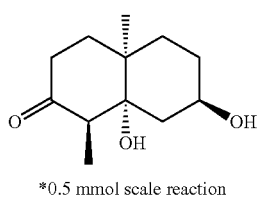

*0.5 mmol scale reaction

Yield: 4% (4 mg). Physical State: colorless oil. $^1$H NMR (500 MHZ, CDCl$_3$): δ 4.22-4.15 (m, 1H), 3.98 (br s, 1H), 2.81 (d, J=6.6 Hz, 1H), 2.59 (dddd, J=14.2, 14.2, 7.1, 1.1 Hz, 1H), 2.32 (ddd, J=14.2, 5.0, 1.8 Hz, 1H), 2.14 (br s, 1H), 2.13 (ddd, J=14.2, 14.2, 4.6 Hz, 1H), 1.92 (ddd, J=14.1, 14.1, 5.1 Hz, 1H), 1.86 (ddd, J=15.1, 2.7, 2.7 Hz, 1H), 1.77 (dddd, J=14.4, 14.4, 4.4, 2.9 Hz, 1H), 1.71-1.63 (m, 1H), 1.47 (ddd, J=13.9, 7.1, 1.9 Hz, 1H), 1.27 (s, 3H), 1.25-1.19 (m, 2H), 1.06 (d, J=6.7 Hz, 3H). $^{13}$C NMR (125 MHZ, CDCl$_3$): δ 211.0, 78.3, 67.6, 51.1, 38.4, 37.8, 32.5, 31.2, 29.3, 28.0, 21.9, 6.8. IR (neat, ATR): ν$_{max}$ 3377, 2951, 2932, 2861, 1707, 1263 cm$^{-1}$. Optical Rotation: [α]$_D^{21.0}$ 17.0 (c 0.10, CHCl$_3$). HRMS (ESI-TOF): calc'd for C$_{12}$H$_{19}$O$_2$ [M-OH]$^+$ m/z 195.1380, found 195.1388. R$_f$=0.48 (50% EtOAc/hexanes). Purification: (SiO$_2$, 20→100% EtOAc/hexanes).

Example 10: Exemplary General Procedure for Hydrodealkenylation

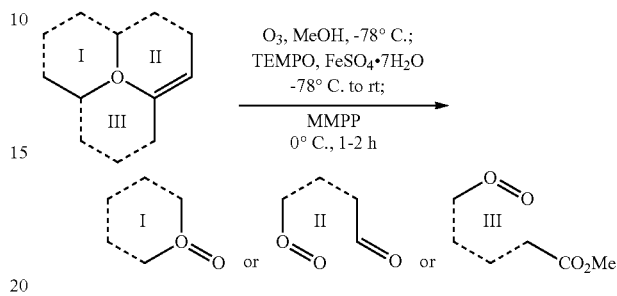

For example, a round-bottom flask equipped with a magnetic stirrer bar was charged with alkene 1a (1.0 equiv) and MeOH (0.025 M), then cooled to −78° C. in a dry-ice/acetone bath while open to the air. Ozone was bubbled through the solution until complete consumption of the starting material had occurred (as indicated by TLC and/or a blue color in the reaction solution). The solution was then sparged with argon for 5 min to expel excess ozone. TEMPO (1.5 equiv; dissolved in a minimal amount of MeOH) was added, followed by freshly prepared aqueous (5% wt/vol) ferrous sulfate heptahydrate (1.2 equiv). The flask was removed from the cooling bath and warmed to room temperature.$^a$ Upon complete conversion of the α-alkoxy hydroperoxides to the intermediate TEMPO-adducts (as indicated by TLC), the flask was cooled to 0° C. with an ice-water bath. MMPP (2.5 equiv) was added portionwise over 10 min (generally resulting in an orange suspension).$^b$ Upon its completion (as indicated by TLC, generally between 1-2 h), the reaction was quenched by the addition of 10% saturated aqueous sodium thiosulfate and saturated aqueous sodium bicarbonate. The mixture was then warmed to room temperature and transferred to a separatory funnel. The MeOH/water suspension was extracted with EtOAc (3×) and the combined organic fractions washed with brine, dried (anhydrous sodium sulfate), filtered, and concentrated under reduced pressure. Purification of the residue through flash column chromatography (SiO$_2$) provided the carbonyl product 2a. $^a$Conversion of the α-alkoxy hydroperoxide to the intermediate TEMPO adduct was often complete before the mixture reached room temperature. In these cases, the 0° C. cooling bath was applied (because prolonged stirring facilitated acetalization/ketalization of the ketone/aldehyde intermediates). $^b$In some cases (noted with each entry), an additional 0.5 equiv of MMPP was added after stirring for 1 h.

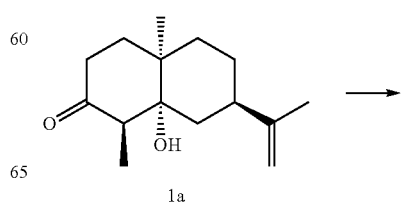

1a

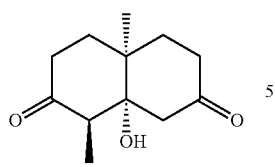

2a

*1.0 mmol scale reaction

Yield: 87% (183 mg). Physical State: white solid. $^1$H NMR (500 MHZ, CDCl$_3$): δ 2.83 (q, J=6.7 Hz, 1H), 2.67 (dddd, J=14.2, 14.2, 7.2, 0.7 Hz, 1H), 2.53-2.43 (m, 2H), 2.34-2.29 (m, 2H), 2.29-2.18 (m, 2H), 2.17-2.12 (m, 1H), 1.70 (dddd, J=13.8, 11.8, 7.0, 1.6 Hz, 1H), 1.33 (s, 3H), 1.02 (d, J=6.7 Hz, 3H). $^{13}$C NMR (125 MHZ, CDCl$_3$): δ 209.4, 209.2, 81.5, 51.7, 45.2, 37.7, 37.4, 37.2, 35.0, 31.0, 20.7, 6.3. MP: 153-155° C. IR (neat, ATR): $v_{max}$ 3459, 2971, 2921, 2850, 1708, 1053 cm$^{-1}$. Optical Rotation: $[α]_D^{21.4}$ 31.6 (c 0.50, CHCl$_3$). HRMS (DART): calc'd for C$_{12}$H$_{17}$O$_2$ [M-OH]$^+$ m/z 193.1223, found 193.1221. R$_f$=0.41 (50% EtOAc/hexanes). Purification: (SiO$_2$, 30→50% EtOAc/hexanes).

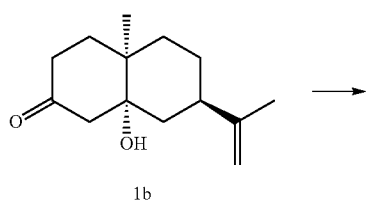

1b

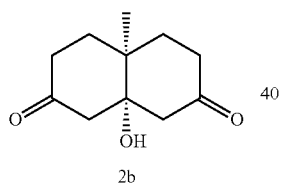

2b 1.0 mmol scale reaction

Yield: 75% (147 mg). Physical State: white solid. $^1$H NMR (500 MHz, CDCl$_3$): δ 2.55-2.36 (m, 8H), 1.98 (dd, J=7.1, 7.1 Hz, 4H), 1.93 (br s, 1H), 1.30 (s, 3H). $^{13}$C NMR (125 MHZ, CDCl$_3$): δ 208.1, 79.0, 51.8, 37.5, 37.0, 32.9, 20.5. MP: 182° C. (decomposition). IR (neat, ATR): $v_{max}$ 3378, 2956, 2939, 2921, 1708, 1432, 1276 cm$^{-1}$. HRMS (DART): calc'd for C$_{11}$H$_{15}$O$_2$ [M+H]$^+$ m/z 179.1067, found 179.1062. R$_f$=0.35 (50% EtOAc/hexanes). Purification: (trituration, pentane).

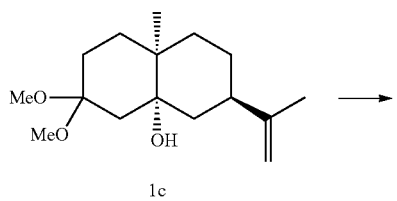

1c

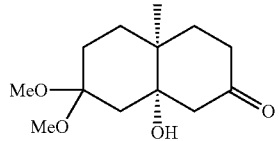

2c

*0.5 mmol scale reaction

Yield: 95% (115 mg). Physical State: white solid. $^1$H NMR (500 MHZ, CDCl$_3$): δ 4.41 (br s, 1H), 3.21 (s, 3H), 3.18 (s, 3H), 2.78-2.67 (m, 1H), 2.53 (ddd, J=14.2, 14.2, 7.0 Hz, 1H), 2.37-2.12 (m, 2H), 2.01-1.80 (m, 3H), 1.79-1.67 (m, 1H), 1.62-1.42 (m, 3H), 1.39-1.29 (m, 1H), 1.20 (s, 3H). $^{13}$C NMR (125 MHz, CDCl$_3$): δ 209.7, 100.8, 75.0, 51.9, 47.9, 47.4, 39.6, 37.5, 37.4, 31.4, 31.2, 26.5, 21.2. MP: 109-110° C. IR (neat, ATR): $v_{max}$ 3473, 2956, 2931, 1714, 1177, 1110, 1078, 1046, 849 cm$^{-1}$. Optical Rotation: $[α]_D^{20.6}$ −21.1 (c 1.00, CHCl$_3$). HRMS (DART): calc'd for C$_{13}$H$_{21}$O$_3$ [M-OH]$^+$ m/z 225.1485, found 225.1477. R$_f$=0.36 (30% EtOAc/hexanes). Purification: (SiO$_2$, 20→30% EtOAc/hexanes).

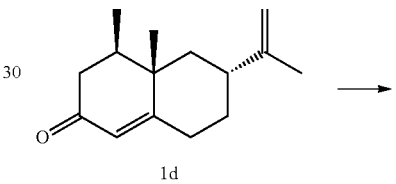

1d

2d 1.0 mmol scale reaction

Yield: 82% (157 mg). Physical State: white solid. $^1$H NMR (500 MHZ, CDCl$_3$): δ 5.89 (s, 1H), 2.83 (dddd, J=15.9, 10.9, 7.6, 2.0 Hz, 1H), 2.72 (ddd, J=15.9, 6.1, 4.2 Hz, 1H), 2.58-2.47 (m, 3H), 2.31-2.11 (m, 4H), 1.06 (s, 3H), 0.94 (d, J=6.5 Hz, 3H). $^{13}$C NMR (125 MHZ, CDCl$_3$): δ 208.6, 198.4, 165.3, 125.7, 51.3, 42.2, 41.5, 39.8, 39.4, 31.4, 17.9, 14.8. MP: 102-104° C. IR (neat, ATR): $v_{max}$ 3045, 2963, 2918, 1712, 1661, 1301, 1184 cm$^{-1}$. Optical Rotation: $[α]_D^{20.7}$ 104.2 (c 1.00, CHCl$_3$). HRMS (DART): calc'd for C$_{12}$H$_{17}$O$_2$ [M+H]$^+$ m/z 193.1223, found 193.1219. R$_f$=0.52 (50% EtOAc/hexanes). Purification: (SiO$_2$, 30→50% EtOAc/hexanes).

1e

-continued

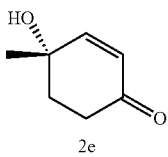

2e

*1.0 mmol scale reaction

Yield: 81% (102 mg). Physical State: pale yellow oil. $^1$H NMR (500 MHZ, CDCl$_3$): δ 6.77 (d, J=10.0 Hz, 1H), 5.89 (d, J=10.1 Hz, 1H), 2.63 (ddd, J=17.2, 5.5, 5.5 Hz, 1H), 2.43 (ddd, J=17.2, 9.0, 5.8 Hz, 1H), 2.21-2.08 (m, 2H), 1.96 (br s, 1H), 1.47 (s, 3H). $^{13}$C NMR (125 MHz, CDCl$_3$): δ 199.2, 155.0, 127.8, 68.3, 37.2, 34.8, 27.1. Optical Rotation: $[\alpha]_D^{20.7}$ −8.7 (c 1.00, CHCl$_3$). R$_f$=0.28 (50% EtOAc/hexanes). Purification: (SiO$_2$, 10→50% EtOAc/hexanes). Note: Extraction performed with CH$_2$Cl$_2$. The presumed product formed during the reaction was the corresponding epoxy ketone (R$_f$=0.38; 30% EtOAc/hexanes). After extraction, triethylamine (0.15 mL, 1.1 mmol, 1.1 equiv) was added to the organic layer. The mixture was stirred for approximately 5 min and concentrated. The residue was subjected to purification by flash column chromatography to give the enone 2e.

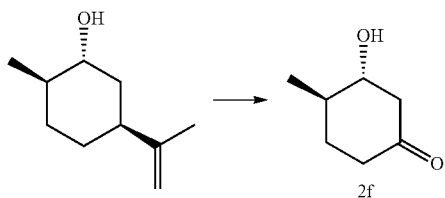

*1.0 mmol scale reaction

Yield: 80% (102 mg). Physical State: colorless oil. $^1$H NMR (500 MHZ, CDCl$_3$): δ 3.54 (ddd, J=9.5, 9.5, 4.5 Hz, 1H), 2.72 (ddd, J=13.9, 4.5, 1.5 Hz, 1H), 2.44-2.26 (m, 3H), 2.07-1.94 (m, 2H), 1.83-1.73 (m, 1H), 1.40-1.28 (m, 1H), 1.13 (d, J=6.6 Hz, 3H). $^{13}$C NMR (125 MHZ, CDCl$_3$): δ 209.5, 74.8, 49.7, 40.3, 38.2, 29.2, 17.3. IR (neat, ATR): ν$_{max}$ 3416, 2960, 2925, 2878, 1712, 1460, 1057 cm$^{-1}$. Optical Rotation: $[\alpha]_D^{20.8}$ −12.9 (c 1.00, CHCl$_3$). HRMS (DART): calc'd for C$_7$H$_{13}$O$_2$ [M+H]$^+$ m/z 129.0910, found 129.0906. R$_f$=0.25 (30% EtOAc/hexanes). Purification: (SiO$_2$, 20→50% EtOAc/hexanes). Note: Extraction performed with CH$_2$Cl$_2$.

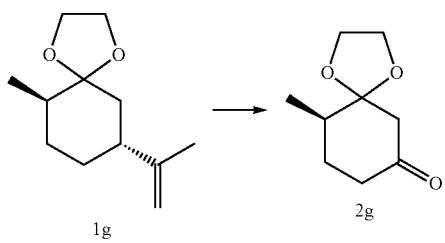

*1.0 mmol scale reaction

Yield: 75% (128 mg). *5.6 mmol scale reaction Yield: 75% (714 mg). Physical State: colorless oil. $^1$H NMR (400 MHZ, CDCl$_3$): δ 4.02-3.90 (m, 4H), 2.61 (dd, J=14.1, 1.9 Hz, 1H), 2.48 (d, J=14.1 Hz, 1H), 2.39 (dddd, J=14.7, 5.2, 4.7, 1.9 Hz, 1H), 2.31 (dddd, J=14.7, 11.2, 6.2, 1.1 Hz, 1H), 2.10 (dddd, J=17.5, 6.6, 6.6, 4.3, 1H), 1.89 (dddd, J=13.5, 6.2, 4.4, 4.4 Hz, 1H), 1.62 (dddd, J=13.5, 11.0, 11.0, 5.4 Hz, 1H), 1.01 (d, J=6.7 Hz, 3H). $^{13}$C NMR (100 MHZ, CDCl$_3$): δ 207.8, 111.2, 65.4, 65.3, 50.8, 39.8, 38.5, 28.2, 13.4. IR (neat, ATR): ν$_{max}$ 2974, 2942, 2921, 2893, 1718, 1148, 1095, 1018 cm$^{-1}$. Optical Rotation: $[\alpha]_D^{20.9}$ 8.4 (c 1.00, CHCl$_3$). HRMS (DART): calc'd for C$_9$H$_{15}$O$_3$ [M+H]$^+$ m/z 171.1016, found 171.1012. R$_f$=0.42 (20% EtOAc/hexanes). Purification: (SiO$_2$, 5→20% EtOAc/hexanes). Note: When the reaction was performed on 5.6 mmol scale, a reaction time of approximately 5 h was required.

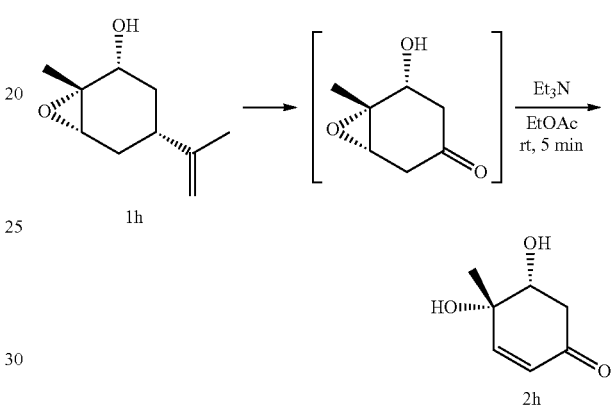

*1.0 mmol scale reaction

Yield: 61% (87 mg). Physical State: pale yellow oil. $^1$H NMR (500 MHZ, CDCl$_3$): δ 6.68 (dd, J=10.2, 1.2 Hz, 1H), 5.95 (d, J=10.2 Hz, 1H), 4.08-4.01 (m, 1H), 3.06 (br s, 2H), 2.76-2.63 (m, 2H), 1.46 (s, 3H). $^{13}$C NMR (125 MHz, CDCl$_3$): δ 197.1, 152.3, 128.2, 73.7, 70.2, 42.8, 25.0. IR (neat, ATR): ν$_{max}$ 3410, 2974, 2918, 2846, 1676, 1545, 1383, 1053 cm$^{-1}$. Optical Rotation: $[\alpha]_D^{21.7}$ 14.8 (c 0.50, CHCl$_3$). HRMS (DART): calc'd for C$_7$H$_{11}$O$_3$ [M+H]$^+$ m/z 143.0703, found 143.0700. R$_f$=0.39 (EtOAc). Purification: (SiO$_2$, 80→100% EtOAc/hexanes). Note: The presumed product formed during the reaction was the corresponding epoxy ketone (R$_f$=0.21; 50% EtOAc/hexanes). After extraction, triethylamine (0.15 mL, 1.1 mmol, 1.1 equiv) was added to the organic layer. The mixture was stirred for approximately 5 min and concentrated. The residue was subjected to purification by flash column chromatography to give the enone 2h.

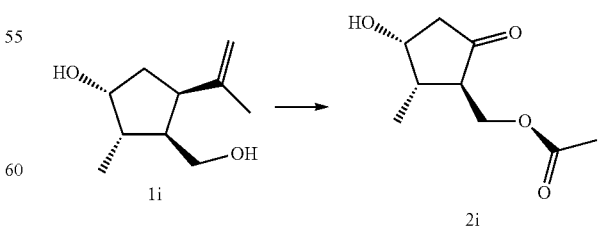

*1.0 mmol scale reaction

Yield: 83% (154 mg). Physical State: colorless oil. $^1$H NMR (500 MHZ, CDCl$_3$): δ 4.39 (dd, J=3.5, 3.5 Hz, 1H), 4.31 (qd, J=10.8, 3.7 Hz, 2H), 2.47-2.34 (m, 2H), 2.30 (ddd, J=12.0, 3.7, 3.7 Hz, 1H), 2.21-2.11 (m, 1H), 2.01 (s, 3H), 1.89 (br s, 1H), 1.21 (d, J=6.8 Hz, 3H), $^{13}$C NMR (125 MHz, CDCl$_3$): δ 215.5, 170.8, 70.3, 60.6, 50.6, 48.0, 38.8, 20.7, 13.0. IR (neat, ATR): $\nu_{max}$ 3473, 2963, 2921, 2850, 1743, 1390, 1248, 993 cm$^{-1}$. Optical Rotation: $[\alpha]_D^{21.4}$ 103.2 (c 0.50, CHCl$_3$). HRMS (DART): calc'd for C$_9$H$_{13}$O$_3$ [M-OH]$^+$ m/z 169.0859, found 169.0857. R$_f$=0.33 (50% EtOAc/hexanes). Purification: (SiO$_2$, 30→40% EtOAc/hexanes). Note: After stirring for 1 h, another portion of MMPP (0.5 equiv) was added and the mixture stirred for an additional 1 h (3.0 equiv MMPP total, 2 h total reaction time).

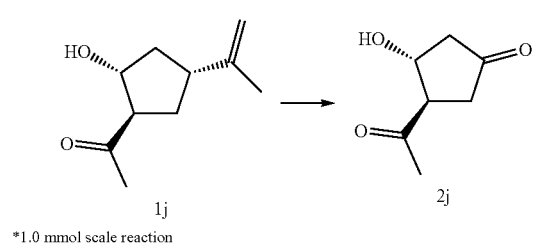

1j → 2j

*1.0 mmol scale reaction

Yield: 50% (71 mg). Physical State: colorless oil. $^1$H NMR (500 MHZ, CDCl$_3$): δ 4.60 (ddd, J=6.5, 6.5, 6.5 Hz, 1H), 3.25 (ddd, J=8.6, 8.6, 6.2 Hz, 1H), 2.74-2.58 (m, 2H), 2.56 (br s, 1H), 2.44 (dd, J=18.8, 8.7 Hz, 1H), 2.37-2.27 (m, 1H), 2.31 (s, 3H). $^{13}$C NMR (125 MHZ, CDCl$_3$): δ 212.4, 208.1, 70.8, 56.4, 46.6, 39.3, 30.0. IR (neat, ATR): $\nu_{max}$ 3423, 2918, 2854, 1743, 1704, 1542, 1368 cm$^{-1}$. Optical Rotation: $[\alpha]_D^{21.5}$ −58.4 (c 0.50, CHCl$_3$). HRMS (DART): calc'd for C$_7$H$_9$O$_2$ [M-OH]$^+$ m/z 125.0597, found 125.0594. R$_f$=0.58 (EtOAc). Purification: (SiO$_2$, 30→60% EtOAc/hexanes).

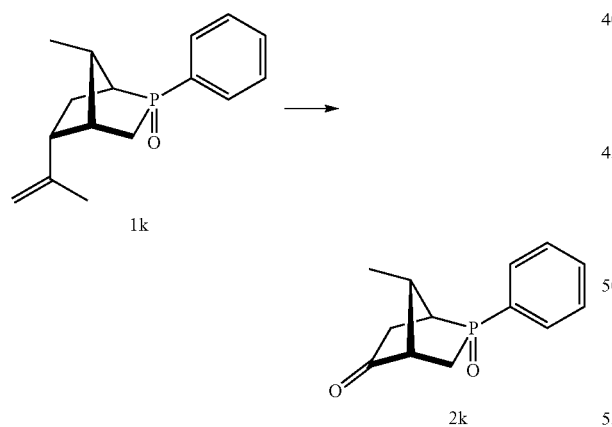

1k → 2k

*1.0 mmol scale reaction

Yield: 60% (140 mg). Physical State: colorless oil. $^1$H NMR (500 MHZ, CDCl$_3$): δ 7.88-7.79 (m, 2H), 7.65-7.51 (m, 3H), 3.05 (dd, J=17.6, 17.6 Hz, 1H), 2.79-2.56 (m, 4H), 2.36 (pent, J=7.1 Hz, 1H), 1.89 (dd, J=15.4, 11.9 Hz, 1H), 1.07 (d, J=6.9 Hz, 3H). $^{13}$C NMR (125 MHZ, CDCl$_3$): δ 213.4 (d, J$_{CP}$=3.0 Hz), 132.5 (d, J$_{CP}$=2.7 Hz), 131.9 (d, J$_{CP}$=94.7 Hz), 130.5 (d, J$_{CP}$=9.4 Hz), 129.1 (d, J$_{CP}$=11.7 Hz), 55.2, 40.8 (d, J$_{CP}$=66.3 Hz), 39.8 (d, J$_{CP}$=12.2 Hz), 32.2 (d, J$_{CP}$=6.5 Hz), 28.3 (d, J$_{CP}$=63.9 Hz), 14.1 (d, J$_{CP}$=13.7 Hz). 31P NMR (202 MHZ, CDCl$_3$): δ 51.9. IR (neat, ATR): $\nu_{max}$ 3434, 2967, 2931, 1750, 1188, 1170, 1120 cm$^{-1}$. Optical Rotation: $[\alpha]_D^{21.0}$ −7.4 (c 1.00, CHCl$_3$). HRMS (ESI-TOF): calc'd for C$_{13}$H$_{16}$O$_2$P [M+H]$^+$ m/z 235.0882, found 235.0874. R$_f$=0.40 (10% methanol/EtOAc). Purification: (SiO$_2$, 1→5% methanol/EtOAc).

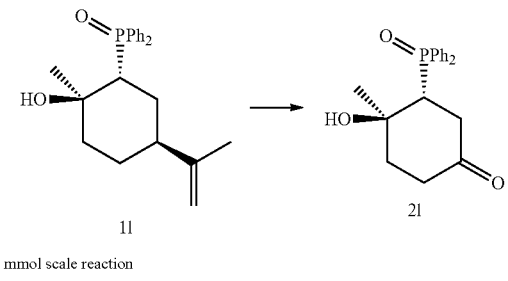

1l → 2l

*0.5 mmol scale reaction

Yield: 82% (134 mg). Physical State: white solid. $^1$H NMR (500 MHZ, CDCl$_3$): δ 7.80-7.67 (m, 4H), 7.62-7.44 (m, 6H), 5.41 (s, 1H), 3.23 (ddd, J=13.4, 13.4, 3.9 Hz, 1H), 2.52-2.40 (m, 2H), 2.39-2.20 (m, 2H), 2.10-1.99 (m, 2H), 1.53 (s, 3H). $^{13}$C NMR (125 MHZ, CDCl$_3$): δ 207.5 (d, J$_{CP}$=14.4 Hz), 132.6 (d, J$_{CP}$=2.8 Hz), 132.5 (d, J$_{CP}$=9.1 Hz), 132.4 (d, J$_{CP}$=2.8 Hz), 132.3 (d, J$_{CP}$=98.2 Hz), 130.7 (d, J$_{CP}$=9.2 Hz), 129.2 (d, J$_{CP}$=95.6 Hz), 129.1 (d, J$_{CP}$=11.7 Hz), 128.7 (d, J$_{CP}$=11.6 Hz), 71.9 (d, J$_{CP}$=4.4 Hz), 45.6 (d, J$_{CP}$=67.5 Hz), 41.3 (d, J$_{CP}$=11.8 Hz), 40.3, 38.0, 23.5 (d, J$_{CP}$=2.1 Hz). 31P NMR (202 MHZ, CDCl$_3$): δ 35.5. MP: 232-233° C. IR (neat, ATR): $\nu_{max}$ 3342, 2995, 2971, 2918, 1712, 1443, 1163 cm$^{-1}$. Optical Rotation: $[\alpha]_D^{21.1}$ −42.9 (c 1.00, CHCl$_3$). HRMS (ESI-TOF): calc'd for C$_{19}$H$_{22}$O$_3$P [M+H]$^+$ m/z 329.1301, found 329.1297. R$_f$=0.40 (EtOAc). Purification: trituration (Et$_2$O).

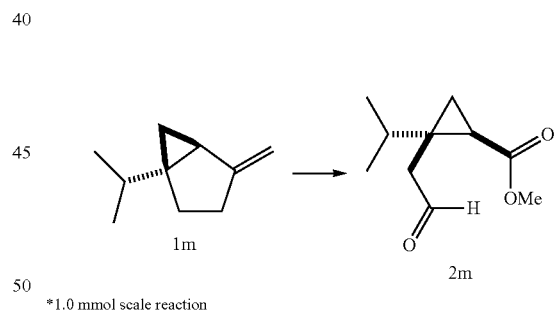

1m → 2m

*1.0 mmol scale reaction

Yield: 58% (107 mg). Physical State: colorless oil. $^1$H NMR (500 MHZ, CDCl$_3$): δ 9.64 (dd, J=2.1, 2.1 Hz, 1H), 3.66 (s, 3H), 2.73 (dd, J=17.6, 2.0 Hz, 1H), 2.58 (dd, J=17.6, 1.9 Hz, 1H), 1.68 (dd, J=8.4, 5.6 Hz, 1H), 1.23-1.12 (m, 2H), 1.07 (dd, J=8.3, 4.8 Hz, 1H), 0.92 (d, J=3.9 Hz, 3H), 0.90 (d, J=3.9 Hz, 3H). $^{13}$C NMR (125 MHZ, CDCl$_3$): δ 202.4, 173.2, 51.9, 41.6, 36.6, 31.3, 24.3, 20.3, 19.6, 19.5. IR (neat, ATR): $\nu_{max}$ 2963, 2882, 1725, 1712, 1446, 1393, 1199, 1174 cm$^{-1}$. HRMS (DART): calc'd for C$_{10}$H$_{17}$O$_3$ [M+H]$^+$ m/z 185.1172, found 185.1169. R$_f$=0.42 (10% EtOAc/hexanes). Purification: (SiO$_2$, 2→5% EtOAc/hexanes).

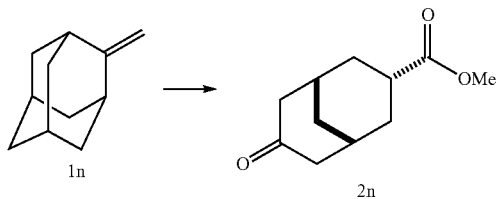

*1.0 mmol scale reaction

Yield: 87% (171 mg). Physical State: white solid. ¹H NMR (500 MHZ, CDCl₃): δ 3.65 (s, 3H), 2.62 (t, J=7.3 Hz, 1H), 2.54-2.32 (m, 8H), 1.95-1.73 (m, 4H). ¹³C NMR (125 MHZ, CDCl₃): δ 212.2, 175.2, 52.5, 46.8, 35.0, 32.2, 31.0, 29.0. $R_f$=0.36 (30% EtOAc/hexanes). Purification: (SiO₂, 10→20% EtOAc/hexanes).

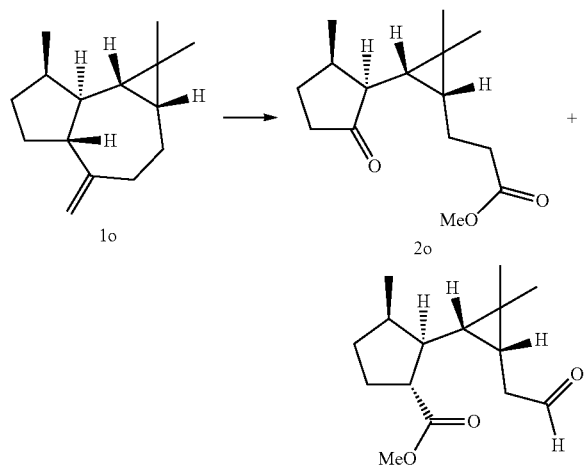

*1.0 mmol scale reaction

Combined Yield: 82% (206 mg). Regioisomeric Ratio: 1.3:1 (2o/2o', determined from crude ¹H NMR spectrum). Note: After stirring for 1 h, another portion of MMPP (0.5 equiv) was added and the mixture stirred for an additional 1 h (3.0 equiv MMPP total, 2 h total reaction time).

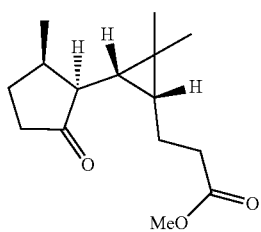

Yield: 45% (114 mg).
Physical State: colorless oil. ¹H NMR (500 MHZ, CDCl₃): δ 3.65 (s, 3H), 2.51 (ddd, J=15.7, 9.9, 5.8 Hz, 1H), 2.50-2.42 (m, 1H), 2.38 (ddd, J=15.9, 9.7, 6.3 Hz, 1H), 2.26-2.18 (m, 2H), 2.06-1.98 (m, 1H), 1.96 (dd, J=10.9, 7.6 Hz, 1H), 1.78-1.65 (m, 2H), 1.58 (dddd, J=14.1, 9.7, 7.5, 6.6 Hz, 1H), 1.06 (s, 3H), 0.96 (s, 3H), 0.96 (d, J=6.4 Hz, 3H), 0.68 (ddd, J=8.8, 7.3, 7.3 Hz, 1H), 0.46 (dd, J=10.8, 9.2 Hz, 1H). ¹³C NMR (125 MHZ, CDCl₃): δ 221.1, 174.3, 51.5, 50.9, 34.7, 34.1, 33.7, 28.9, 28.0, 26.3, 23.9, 21.0, 17.1, 16.0, 15.8. IR (neat, ATR): ν_max 2963, 2928, 2875, 1733, 1460, 1174, 1146 cm⁻¹. Optical Rotation: $[α]_D^{21.9}$ −36.5 (c 0.20, CHCl₃). HRMS (ESI-TOF): calc'd for C₁₅H₂₄O₃Na [M+Na]⁺ m/z 275.1618, found 275.1672. $R_f$=0.26 (10% EtOAc/hexanes). Purification: (SiO₂, 2→5% EtOAc/hexanes).

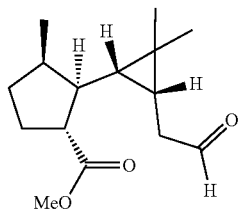

Yield: 37% (92 mg). Physical State: colorless oil. ¹H NMR (500 MHZ, CDCl₃): δ 9.77 (dd, J=1.4, 1.4 Hz, 1H), 3.64 (s, 3H), 2.61 (ddd, J=9.1, 7.1, 7.1 Hz, 1H), 2.45 (ddd, J=18.5, 6.5, 1.4 Hz, 1H), 2.31 (ddd, J=18.5, 7.8, 1.4 Hz, 1H), 2.18 (sept, J=7.0 Hz, 1H), 2.02 (dddd, J=12.8, 8.9, 8.9, 5.0 Hz, 1H), 1.93-1.84 (m, 2H), 1.76 (J=13.0, 8.9, 7.3, 7.3 Hz, 1H), 1.37 (dddd, J=12.6, 8.2, 7.0, 7.0 Hz, 1H), 1.10 (s, 3H), 0.94 (s, 3H), 0.92 (d, J=7.1 Hz, 3H), 0.92-0.87 (m, 1H), 0.56 (dd, J=11.4, 9.0 Hz, 1H). ¹³C NMR (125 MHZ, CDCl₃): δ 202.4, 177.4, 51.7, 49.7, 44.0, 40.3, 36.7, 33.2, 28.7, 28.7, 28.6, 19.7, 18.2, 16.2, 16.1. IR (neat, ATR): ν_max 2956, 2931, 2872, 1733, 1712, 1457, 1432, 1372, 1205, 1163 cm⁻¹. Optical Rotation: $[α]_D^{21.7}$ −16.4 (c 0.50, CHCl₃). HRMS (ESI-TOF): calc'd for C₁₅H₂₄O₃Na [M+Na]⁺ m/z 275.1618, found 275.1660. $R_f$=0.37 (10% EtOAc/hexanes). Purification: (SiO₂, 2→5% EtOAc/hexanes).

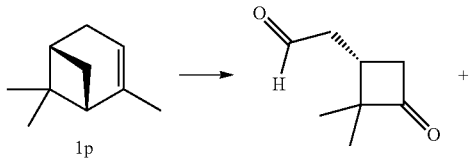

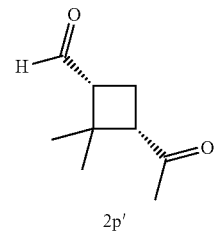

*2.0 mmol scale reaction

Yield: 67% (190 mg). Regioisomeric Ratio: 5:1 (2p/2p', inseparable mixture). Physical State: colorless oil. ¹H NMR (500 MHZ, CDCl₃) 2p: δ 9.84 (s, 1H), 3.27 (dd, J=17.7, 9.2 Hz, 1H), 2.83-2.65 (m, 3H), 2.59-2.50 (m, 1H), 1.25 (s, 3H), 1.05 (s, 3H). ¹H NMR (500 MHz, CDCl₃) 2p': δ 9.70 (d, J=1.9 Hz, 1H), 2.99-2.94 (m, 1H), 2.81-2.64 (m, 2H), 2.06 (s, 3H), 1.90-1.84 (m, 1H), 1.49 (s, 3H), 0.99 (s, 3H). ¹³C NMR (125 MHz, CDCl₃) 2p: δ 213.7, 200.6, 61.3, 48.4, 45.5, 30.2, 23.3, 17.5. ¹³C NMR (125 MHZ, CDCl₃) 2p': δ 206.9, 203.1, 53.3, 51.7, 31.2, 30.2, 18.7, 16.9. IR (neat, ATR): $v_{max}$ 2967, 2935, 2872, 1775, 1722, 1464, 1383, 1071 cm$^{-1}$. Optical Rotation: $[\alpha]_D^{20.0}$ 3.8 (c 1.00, CHCl$_3$). HRMS (DART): calc'd for C$_8$H$_{13}$O$_2$ [M+H]$^+$ m/z 141.0910, found 141.0907; calc'd for C$_8$H$_{15}$O$_2$ [M+H]$^+$ m/z 155.1067, found 155.1063. R$_f$=0.34 (20% EtOAc/hexanes). Purification: (SiO$_2$, 5→20% EtOAc/hexanes). Note: Extraction performed with CH$_2$Cl$_2$. Approximately 50 mg of the ester 4 (characterization data are provided in Section 7) was also obtained from the reaction.

Example 11: Exemplary Cyclopropylcarbinyl Ring-Opening

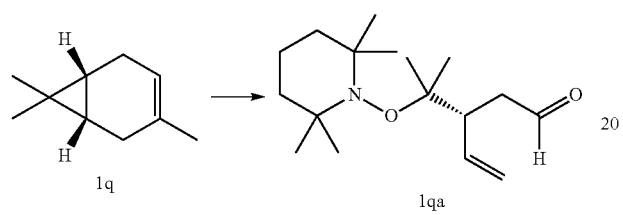

The O-alkyl TEMPO adduct 1qa was synthesized as described above. After the addition of TEMPO and aqueous ferrous sulfate, the mixture was allowed to warm until the reaction temperature reached 0° C. The reaction was quenched through the addition of 10% saturated aqueous sodium thiosulfate and saturated aqueous sodium bicarbonate. After warming to room temperature, the MeOH/water layer was extracted with EtOAc (3×), washed with brine, dried (anhydrous sodium sulfate), filtered, and concentrated under reduced pressure. Purification of the residue by flash column chromatography (SiO$_2$) provided the pure product 1qa.

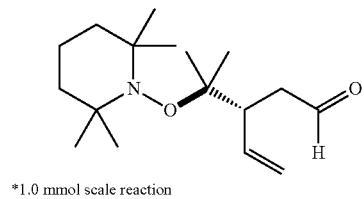

*1.0 mmol scale reaction

Yield: 50% (140 mg). Physical State: colorless oil. $^1$H NMR (500 MHZ, CDCl$_3$): δ 9.72 (dd, J=3.3, 1.4 Hz, 1H), 5.70 (ddd, J=17.1, 10.3, 8.2 Hz, 1H), 5.13-5.02 (m, 2H), 3.12 (ddd, J=10.8, 8.1, 2.9 Hz, 1H), 2.97 (ddd, J=16.2, 3.1, 1.3 Hz, 1H), 2.41 (ddd, J=16.2, 10.7, 3.4 Hz, 1H), 1.59-1.42 (m, 4H), 1.32-1.24 (m, 2H), 1.26 (s, 3H), 1.18 (s, 3H), 1.14 (s, 3H), 1.14 (s, 3H), 1.07 (s, 3H), 1.06 (s, 3H). $^{13}$C NMR (125 MHZ, CDCl$_3$): δ 202.9, 138.4, 117.3, 79.6, 59.4, 59.3, 49.1, 43.2, 40.9, 40.8, 35.1, 34.9, 24.1, 23.7, 21.2, 20.6, 17.0. IR (neat, ATR): $v_{max}$ 3081, 3006, 2978, 2935, 2875, 2712, 1729, 1468, 1379, 1368, 1127, 919 cm$^{-1}$. Optical Rotation: $[\alpha]_D^{22.3}$ 14.3 (c 2.00, CHCl$_3$). HRMS (DART): calc'd for C$_{17}$H$_{32}$NO$_2$ [M+H]$^+$ m/z 282.2428, found 282.2425. R$_f$=0.39 (5% EtOAc/hexanes). Purification: (SiO$_2$, 3→5% EtOAc/hexanes). Note: An additional product (R$_f$=0.30, 5% EtOAc/hexanes) was also formed in this reaction. It was presume it was 1qa', based on LCMS analysis of the mixture (1.5:1 1qa/1qa'). Nevertheless, this compound was extremely unstable and decomposed upon attempts at purification.

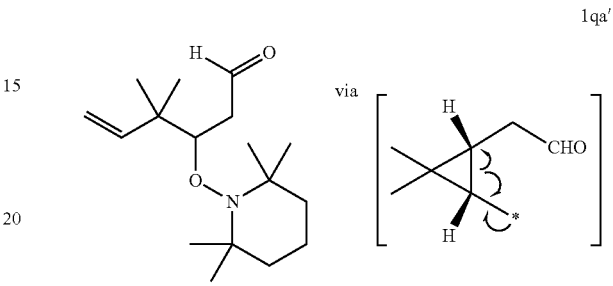

Example 12: Exemplary Optimization of the Thiylation Reaction

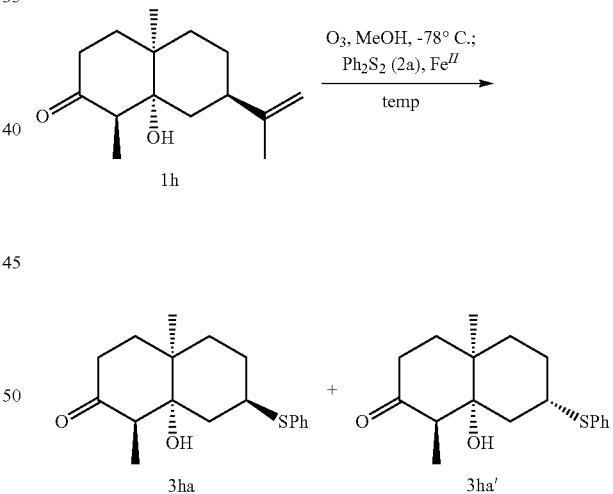

A 10-mL vial equipped with a magnetic stirrer bar was charged with the hydroxy ketone 1h (47.3 mg, 0.200 mmol, 1.0 equiv) and MeOH (0.05 M), then placed in a dry-ice/acetone bath and cooled to −78° C. while open to air. Ozone was bubbled through the solution until complete consumption of the starting material (TLC, with CAM stain). The solution was then sparged with argon for 5 min to expel excess ozone. Diphenyl disulfide (2a) was added at the specified temperature, the mixture was stirred for 10 min, and then the Fe$^{II}$ salt was added. Upon complete conversion of the intermediate α-alkoxy hydroperoxides (TLC), 1-chloro-2,4-dinitrobenzene (40.5 mg, 0.200 mmol, 1.0 equiv) was added to the reaction mixture. A 1.0-mL aliquot was removed and placed under high vacuum until the solvent had evaporated. Deuterated chloroform was added to the vial, and then the mixture was filtered through a short Celite plug directly into an NMR tube

TABLE 3

Optimization of reaction conditions

| entry | Ph$_2$S$_2$ (equiv) | Fe$^{II}$ (equiv) | temp (° C.) | yield$^a$ | d.r.$^b$ |
|---|---|---|---|---|---|
| 1 | 1.2 | FeSO$_4$ · 7H$_2$O (1.2) | −78 | 46 | 8:1 |
| 2 | 1.2 | FeSO$_4$ · 7H$_2$O (1.2) | 0° C. | 62 | 5.8:1 |
| 3 | 1.2 | FeSO$_4$ · 7H$_2$O (1.2) | rt | 63 | 5.6:1 |
| 4 | 1.2 | FeSO$_4$ · 7H$_2$O (1.2) | 30° C. | 61 | 5.1:1 |
| 5 | 1.2 | FeSO$_4$ · 7H$_2$O (1.2) | 40° C. | 59 | 4.9:1 |
| 6 | 1.2 | FeSO$_4$ · 7H$_2$O (1.2) | 50° C. | 53 | 4.9:1 |
| 7 | 1.2 | FeSO$_4$ · 7H$_2$O (1.2) | 60° C. | 46 | 4.1:1 |
| 8 | 1.5 | FeSO$_4$ · 7H$_2$O (1.2) | rt | 62 | 5.8:1 |
| 9 | 2.0 | FeSO$_4$ · 7H$_2$O (1.2) | rt | 66 | 5.6:1 |
| 10 | 2.5 | FeSO$_4$ · 7H$_2$O (1.2) | rt | 67 | 5.7:1 |
| 11 | 3.0 | FeSO$_4$ · 7H$_2$O (1.2) | rt | 70 | 5.9:1 |
| 12 | 4.0 | FeSO$_4$ · 7H$_2$O (1.2) | rt | 68 | 6:1 |
| 13 | 5.0 | FeSO$_4$ · 7H$_2$O (1.2) | rt | 70 | 5.9:1 |
| 14 | 3.0 | FeSO$_4$ · 7H$_2$O (0.5) | rt | 28 | 6:1 |
| 15 | 3.0 | FeSO$_4$ · 7H$_2$O (1.0) | rt | 63 | 6:1 |
| 16 | 3.0 | FeSO$_4$ · 7H$_2$O (1.5) | rt | 70 | 5.9:1 |
| 17 | 3.0 | FeSO$_4$ · 7H$_2$O (2.0) | rt | 65 | 6.2:1 |
| 18 | 3.0 | FeCl$_2$ · 4H$_2$O (1.2) | rt | trace | ND |
| 19 | 3.0 | Fe(NH$_4$)$_2$(SO$_4$)$_2$ · 6H$_2$O (1.2) | rt | 11 | 10:1 |
| 20 | 3.0 | Fe(BF$_4$)$_2$ · 6H$_2$O (1.2) | rt | 50 | 2.6:1 |
| 21 | 3.0 | Fe(ClO$_4$)$_2$ · 6H$_2$O (1.2) | rt | 28 | 10:1 |
| 22 | 3.0 | FeC$_2$O$_4$ · 2H$_2$O (1.2) | rt | 14 | 6:1 |
| 23 | 3.0 | ferrous gluconate · 2H$_2$O (1.2) | rt | 14 | 6:1 |
| 24 | 3.0 | ferrous phthalocyanine (1.2) | rt | 25 | 5:1 |
| 25 | 3.0 | Fe(OTf)$_2$ (1.2) | rt | 21 | 6:1 |
| 26 | 3.0 | FeSO$_4$ · 7H$_2$O (1.2) | rt | 41$^c$ | 2.2:1 |
| 27 | 3.0 | FeSO$_4$ · 7H$_2$O (1.2) | rt | 68$^d$ | 6.2:1 |
| 28 | 3.0 | FeSO$_4$ · 7H$_2$O (1.2) | rt | 60$^e$ | 6:1 |
| 29 | 3.0 | FeSO$_4$ · 7H$_2$O (1.2) | rt | 52$^f$ | 3:1 |
| 30 | 3.0 | FeSO$_4$ · 7H$_2$O (1.2) | rt | 20$^g$ | 3:1 |
| 31 | 3.0 | FeSO$_4$ · 7H$_2$O (1.2) | rt | 13$^h$ | 5.5:1 |
| 32 | 3.0 | FeSO$_4$ · 7H$_2$O (1.2) | rt | 11$^i$ | 4.5:1 |
| 33 | 3.0 | FeSO$_4$ · 7H$_2$O (1.2) | rt | 8$^j$ | 7:1 |
| 34 | 3.0 | FeSO$_4$ · 7H$_2$O (1.2) | rt | 23$^k$ | 2.8:1 |
| 35 | 3.0 | FeSO$_4$ · 7H$_2$O (1.2) | rt | 16$^l$ | 1.8:1 |
| 36 | 3.0 | FeSO$_4$ · 7H$_2$O (1.2) | rt | 21$^m$ | 3.2:1 |
| 37 | 3.0 | FeSO$_4$ · 7H$_2$O (1.2) | rt | 36$^n$ | 2.3:1 |
| 38 | 3.0 | FeSO$_4$ · 7H$_2$O (1.2) | rt | 32$^o$ | 3.6:1 |
| 39 | 3.0 | FeSO$_4$ · 7H$_2$O (1.2) | rt | 70$^p$ | 5.4:1 |
| 40 | 3.0 | FeSO$_4$ · 7H$_2$O (1.2) | rt | 65$^q$ | 5.5:1 |
| 41 | 3.0 | FeSO$_4$ · 7H$_2$O (1.2) | rt | 70$^r$ | 6:1 |
| 42 | 3.0 | FeSO$_4$ · 7H$_2$O (1.2) | rt | 68$^s$ | 5.8:1 |
| 43 | 3.0 | FeSO$_4$ · 7H$_2$O (1.2)$^t$ | rt | 68 | 6.6:1 |
| 44 | 3.0 | FeSO$_4$ · 7H$_2$O (1.2)$^t$ | 0° C. | 83 | 5.9:1 |

$^a$Combined yield of 3ha + 3ha', determined by $^1$H-NMR using 1-chloro-2,4-dinitrobenzene as an internal standard.
$^b$Diastereomeric ratio determined by $^1$H-NMR.
$^c$0.01 M.
$^d$0.025 M.
$^e$0.1 M.
$^f$CH$_2$Cl$_2$/MeOH (1:1).
$^g$EtOH/MeOH (1:1).
$^h$2-PrOH/MeOH (1:1).
$^i$MeCN/MeOH (1:1).
$^j$acetone/MeOH (1:1).
$^k$benzene/MeOH (1:1).
$^l$THF/MeOH (1:1).
$^m$toluene/MeOH (1:1).
$^n$DCE/MeOH (1:1).
$^o$water/MeOH (1:1).
$^p$NaHCO$_3$ additive (2.0 equiv).
$^q$pyridine additive (2.0 equiv).
$^r$Ar atmosphere.
$^s$oxygen atmosphere.
$^t$FeSO$_4$ · 7H$_2$O added as 5 wt/vol% aqueous solution.

Note:

The major byproduct formed during the dealkenylative thiylation was the hydrodealkenylation product SI-III along with small amounts of the elimination product SI-IV. Under some conditions (especially with the use of co-solvents and other iron salts), appreciable formation of the ozonolysis product SI-V was observed as well. The use of an aqueous solution of ferrous sulfate heptahydrate and an addition temperature of 0° C. minimized the formation of these byproducts (ca. 15% SI-III/SI-IV and trace amounts of SI-V). On larger scales (≥1.0 mmol), a concentration of 0.025 M provided results consistent with the optimized conditions.

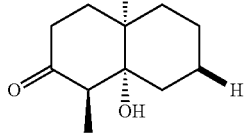

SI-III

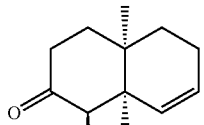

SI-IV

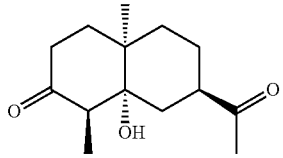

SI-V

A proposed mechanism for the formation of the major byproduct (SI-III) is provided below.

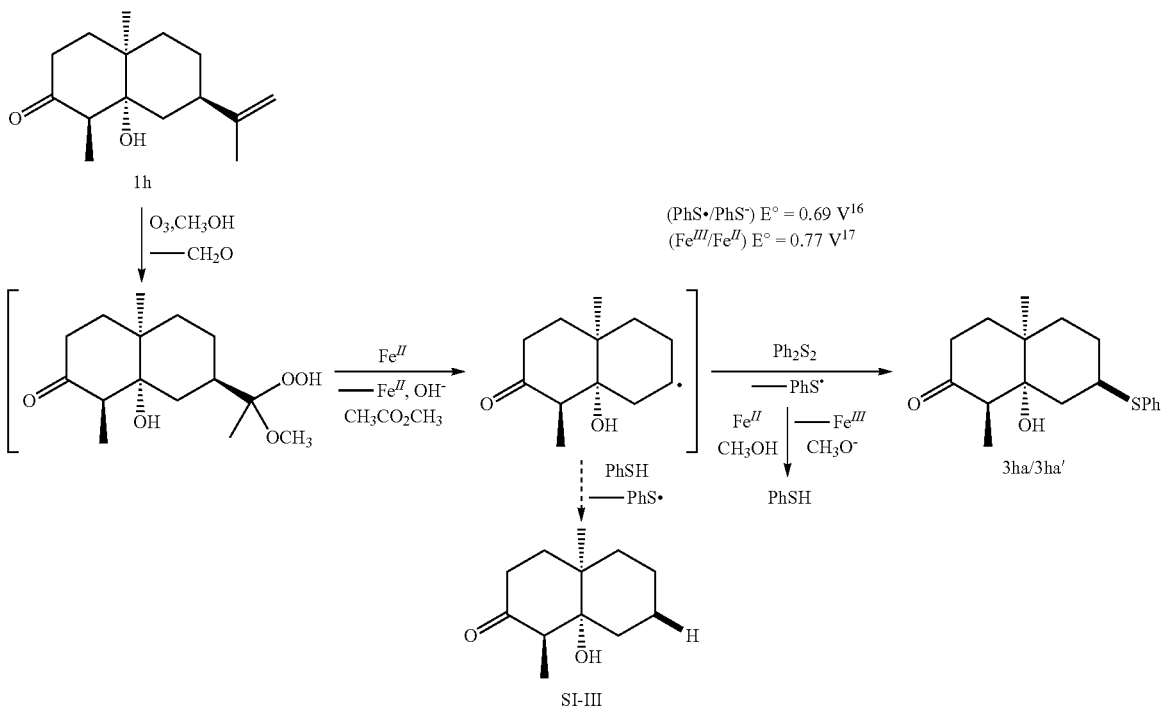

Example 13: Exemplary General Procedure for Dealkenylative Thiylation

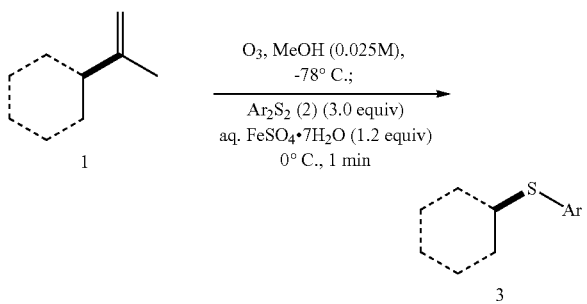

For example, a round-bottom flask equipped with a magnetic stirrer bar was charged with 1a (1.0 equiv) and MeOH (0.025 M), then cooled to −78° C. with a dry-ice/acetone bath while open to the air. Ozone was bubbled through the solution until complete consumption of the starting material (as indicated by TLC and/or a blue color in the reaction mixture). The solution was then sparged with argon for 5 min to expel excess ozone. The aryl disulfide (2, 3.0 equiv) was added and then the reaction mixture was warmed to 0° C. in an ice-water bath and stirred for 10 min. An aqueous solution (5%, wt/vol) of ferrous sulfate heptahydrate (1.2 equiv) was added over a period of approximately 1 min. Upon completion of the reaction (TLC), the mixture was diluted with water and transferred to a separatory funnel. The MeOH/water layer was extracted with dichloromethane (3×). The combined organic fractions were washed with brine, dried (anhydrous sodium sulfate), filtered, and concentrated under reduced pressure. Purification through flash column chromatography ($SiO_2$) provided the thiylated product 3aa. Any modification of the above procedure is described below with the specific entry. Note: All solid aryl disulfides were ground to a fine powder prior to use. Additionally, For products that generated a stereocenter at the newly formed C—S bond, structural assignments were based on a combination of 1D and 2D NMR spectroscopy experiments. It is known that tertiary and secondary axial/equatorial protons in cyclohexane derivatives typically appear at different fields (an axial proton resonance shift is upfield relative to the resonance shift of an equatorial proton). Additionally, the coupling constant between neighboring axial protons is generally 2-3 times as large as the coupling constant between two neighboring equatorial protons. As a result, the signal for an axial α-proton is much broader relative to that of an equatorial α-proton. All structural assignments are consistent with these observations, which were further supported by single-crystal X-ray diffraction of the thioether 31a ☐ and the sulfone 8.

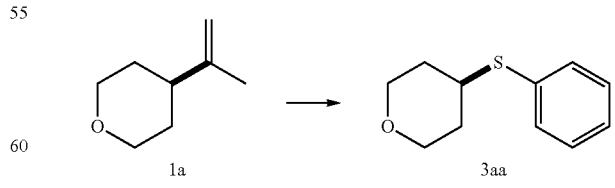

*1.0 mmol scale reaction

Yield: 80% (155 mg). Physical State: colorless oil. $^1$H NMR (500 MHZ, $CDCl_3$): δ 7.45-7.40 (m, 2H), 7.24-7.28 (m, 2H), 7.28-7.23 (m, 1H), 3.97 (ddd, J=11.7, 3.7, 3.7 Hz,

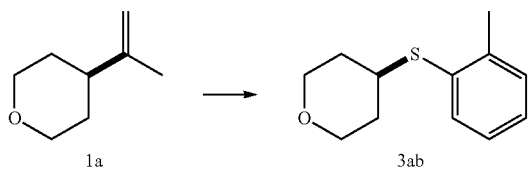

*1.0 mmol scale reaction

Yield: 77% (160 mg). Physical State: colorless oil. $^1$H NMR (500 MHZ, CDCl$_3$): δ 7.42-7.37 (m, 1H), 7.24-7.19 (m, 1H), 7.19-7.12 (m, 2H), 3.98 (ddd, J=11.7, 3.8, 3.8 Hz, 2H), 3.44 (ddd, J=11.2, 11.2, 2.3 Hz, 2H), 3.27 (dddd, J=10.5, 10.5, 4.0, 4.0 Hz, 1H), 2.44 (s, 3H), 1.96-1.87 (m, 2H), 1.76-1.65 (m, 2H). $^{13}$C NMR (125 MHZ, CDCl$_3$): δ 140.0, 133.1, 132.3, 130.3, 127.0, 126.2, 67.2, 42.7, 33.1, 20.8. IR (neat, ATR): ν$_{max}$ 3059, 2944, 2921, 2843, 1468, 1085, 743, 691 cm$^{-1}$. HRMS (DART): calc'd for C$_{12}$H$_{17}$OS [M+H]$^+$ 209.0995, found 209.0955. R$_f$=0.42 (10% EtOAc/hexanes). Purification: (SiO$_2$, 2→5% EtOAc/hexanes).

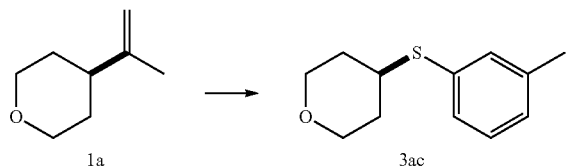

*1.0 mmol scale reaction

Yield: 64% (133 mg). Physical State: colorless oil. $^1$H NMR (500 MHZ, CDCl$_3$): δ 7.26-7.16 (m, 3H), 7.09-7.05 (m, 1H), 3.97 (ddd, J=11.7, 3.7, 3.7 Hz, 2H), 3.43 (ddd, J=11.2, 11.2, 2.5 Hz, 2H), 3.26 (dddd, J=10.6, 10.6, 4.0, 4.0 Hz, 1H), 2.34 (s, 3H), 1.94-1.87 (m, 2H), 1.72-1.62 (m, 2H). $^{13}$C NMR (125 MHz, CDCl$_3$): δ 138.6, 133.3, 133.2, 129.6, 128.6, 128.0, 67.2, 43.3, 33.1, 21.2. IR (neat, ATR): ν$_{max}$ 3058, 2945, 2843, 1591, 1131, 1085, 778 cm$^{-1}$. HRMS (DART): calc'd for C$_{12}$H$_{17}$OS [M+H]$^+$ 209.0995, found 209.0985. R$_f$=0.45 (10% EtOAc/hexanes). Purification: (SiO$_2$, 2→5% EtOAc/hexanes).

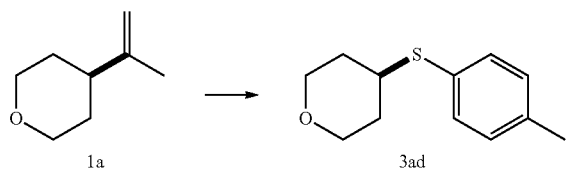

*1.0 mmol scale reaction

Yield: 71% (148 mg). Physical State: colorless oil. $^1$H NMR (500 MHZ, CDCl$_3$): δ 7.34 (d, J=8.1 Hz, 2H), 7.12 (d, J=7.9 Hz, 2H), 3.96 (ddd, J=11.6, 3.7, 3.7 Hz, 2H), 3.41 (ddd, J=11.3, 11.3, 2.1 Hz, 2H), 3.18 (dddd, J=10.7, 10.7, 4.0, 4.0 Hz, 1H), 2.34 (s, 3H), 1.92-1.84 (m, 2H), 1.65 (dddd, J=13.7, 10.7, 10.7, 4.1 Hz, 2H). $^{13}$C NMR (125 MHZ, CDCl$_3$): δ 137.5, 133.4, 129.7, 129.6, 67.3, 43.8, 33.1, 21.0. R$_f$=0.48 (10% EtOAc/hexanes). Purification: (SiO$_2$, 2→5% EtOAc/hexanes).

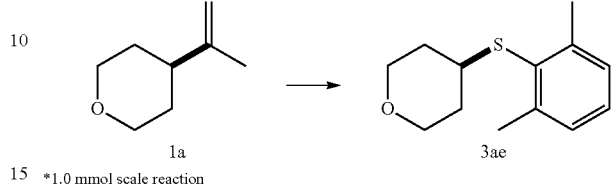

*1.0 mmol scale reaction

Yield: 70% (156 mg). Physical State: white solid. $^1$H NMR (500 MHZ, CDCl$_3$): δ 7.16-7.08 (m, 3H), 3.95 (ddd, J=11.6, 3.7, 3.7 Hz, 2H), 3.36 (ddd, J=11.2, 11.2, 2.6 Hz, 2H), 3.02 (dddd, J=10.5, 10.5, 4.3, 4.3 Hz, 1H), 2.55 (s, 6H), 1.81-1.74 (m, 2H), 1.74-1.65 (m, 2H). $^{13}$C NMR (125 MHZ, CDCl$_3$): δ 143.4, 131.8, 128.2, 128.0, 67.4, 43.7, 33.4, 22.2. MP: 40° C. IR (neat, ATR): ν$_{max}$ 3056, 2996, 2842, 1459, 1085, 830, 770 cm$^{-1}$. HRMS (DART): calc'd for C$_{13}$H$_{19}$OS [M+H]$^+$ 223.1151, found 223.1178. R$_f$=0.57 (10% EtOAc/hexanes). Purification: (SiO$_2$, 2→5% EtOAc/hexanes).

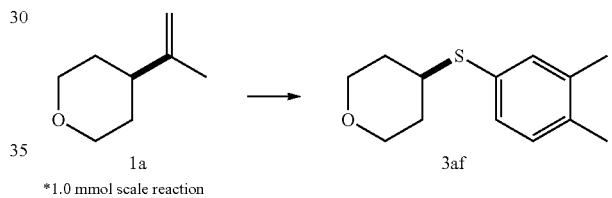

*1.0 mmol scale reaction

Yield: 62% (138 mg). Physical State: colorless oil. $^1$H NMR (500 MHZ, CDCl$_3$): δ 7.23 (d, J=1.2 Hz, 1H), 7.18 (dd, J=7.7, 1.8 Hz, 1H), 7.07 (d, J=7.8 Hz, 1H), 3.96 (ddd, J=11.6, 3.7, 3.7 Hz, 2H), 3.41 (ddd, J=11.3, 11.3, 2.2 Hz, 2H), 3.18 (dddd, J=10.7, 10.7, 4.0, 4.0 Hz, 1H), 2.24 (s, 6H), 1.92-1.85 (m, 2H), 1.70-1.61 (m, 2H). $^{13}$C NMR (125 MHZ, CDCl$_3$): δ 137.2, 136.2, 134.6, 130.8, 130.0, 129.9, 67.3, 43.7, 33.1, 19.6, 19.3. IR (neat, ATR): ν$_{max}$ 3014, 2942, 2920, 2843, 1130, 1085, 884, 815 cm$^{-1}$. HRMS (DART): calc'd for C$_{13}$H$_{19}$OS [M+H]$^+$ 223.1151, found 223.1162. R$_f$=0.48 (10% EtOAc/hexanes). Purification: (SiO$_2$, 2→5% EtOAc/hexanes).

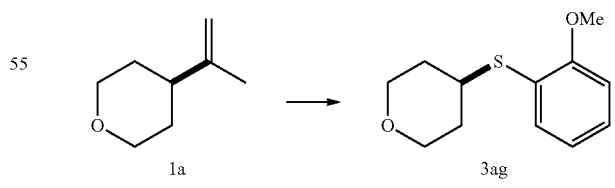

*1.0 mmol scale reaction

Yield: 51% (114 mg). Physical State: colorless oil. $^1$H NMR (500 MHZ, CDCl$_3$): δ 7.38 (dd, J=7.6, 1.6 Hz, 1H), 7.25 (ddd, J=8.1, 7.5, 1.6 Hz, 1H), 6.96-6.85 (m, 2H), 3.97 (ddd, J=11.7, 3.8, 3.8 Hz, 2H), 3.89 (s, 3H), 3.44 (ddd, J=11.2, 11.2, 2.4 Hz, 2H), 3.41-3.35 (m, 1H), 1.93-1.84 (m, 2H), 1.73-1.60 (m, 2H). $^{13}$C NMR (125 MHz, CDCl$_3$): δ 158.7, 133.5, 128.6, 121.5, 120.8, 110.7, 67.2, 55.7, 41.2, 32.9. IR (neat, ATR): $ν_{max}$ 3059, 2944, 2838, 1473, 1239, 1020, 746 cm$^{-1}$. HRMS (DART): calc'd for C$_{12}$H$_{17}$O$_2$S [M+H]$^+$ 225.0944, found 225.0954. R$_f$=0.27 (10% EtOAc/hexanes). Purification: (SiO$_2$, 5→10% EtOAc/hexanes).

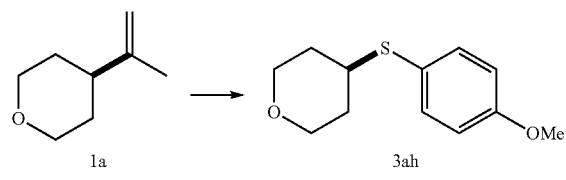

*1.0 mmol scale reaction

Yield: 75% (167 mg). Physical State: colorless oil. $^1$H NMR (500 MHZ, CDCl$_3$): δ 7.44-7.37 (m, 2H), 6.88-6.82 (m, 2H), 3.95 (ddd, J=11.6, 3.6, 3.6 Hz, 2H), 3.80 (s, 3H), 3.38 (ddd, J=11.3, 11.3, 2.1 Hz, 2H), 3.07 (dddd, J=10.8, 10.8, 4.0, 4.0 Hz, 1H), 1.88-1.81 (m, 2H), 1.68-1.57 (m, 2H). $^{13}$C NMR (125 MHz, CDCl$_3$): δ 159.6, 136.0, 123.5, 114.3, 67.3, 55.2, 44.4, 33.1. R$_f$=0.27 (10% EtOAc/hexanes). Purification: (SiO$_2$, 5→10% EtOAc/hexanes).

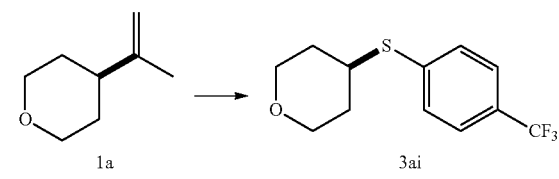

*1.0 mmol scale reaction

Yield: 50% (132 mg). Physical State: white solid. $^1$H NMR (500 MHZ, CDCl$_3$): δ 7.53 (dd, J=8.6, 0.6 Hz, 2H), 7.45 (dd, J=8.6, 0.6 Hz, 2H), 3.98 (ddd, J=11.8, 3.8, 3.8 Hz, 2H), 3.47 (ddd, J=11.6, 10.8, 2.3 Hz, 2H), 3.42 (dddd, J=10.5, 10.5, 4.1, 4.1 Hz, 1H), 1.98-1.91 (m, 2H), 1.70 (dddd, J=13.8, 10.5, 10.5, 4.1 Hz, 2H). $^{13}$C NMR (125 MHZ, CDCl$_3$): δ 139.5 (q, $J_{C-F}$=1.3 Hz), 130.5, 128.5 (q, $J_{C-F}$=32.7 Hz), 125.6 (q, $J_{C-F}$=3.8 Hz), 123.9 (q, $J_{C-F}$=271.9 Hz), 67.1, 42.4, 32.8. $^{19}$F NMR (282 MHz, CDCl$_3$): δ −62.6. MP: 55° C. IR (neat, ATR): $ν_{max}$ 2953, 2846, 1606, 1322, 1120, 1094, 1063, 1012, 829 cm$^{-1}$. HRMS (ESI-TOF): calc'd for C$_{12}$H$_{13}$F$_3$OSNa [M+Na]$^+$ 285.0471, found 285.0458. R$_f$=0.24 (10% EtOAc/hexanes). Purification: (SiO$_2$, 2→5% EtOAc/hexanes).

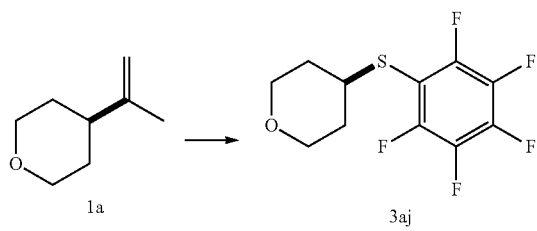

*1.0 mmol scale reaction

Yield: 70% (199 mg). Physical State: white solid. $^1$H NMR (500 MHZ, CDCl$_3$): δ 3.96 (ddd, J=11.8, 3.7, 3.7 Hz, 2H), 3.40 (ddd, J=11.3, 11.3, 2.3 Hz, 2H), 3.29 (dddd, J=10.7, 10.7, 4.1, 4.1 Hz, 1H), 1.89-1.81 (m, 2H), 1.72-1.61 (m, 2H). $^{13}$C NMR (125 MHz, CDCl$_3$): δ 147.8 (ddddd, $J_{C-F}$=245.6, 10.5, 4.0, 4.0, 4.0 Hz), 141.5 (ddddd, $J_{C-F}$=256.5, 13.6, 13.6, 5.1, 5.1 Hz), 137.5 (ddddd, $J_{C-F}$=253.7, 18.2, 12.8, 5.5, 2.1 Hz), 106.9 (ddd, $J_{C-F}$=21.5, 21.5, 4.1 Hz), 66.9, 43.9, 33.1. $^{19}$F NMR (282 MHZ, CDCl$_3$): δ −131.0, −131.0, −131.0, −131.1, −131.1, −131.1. MP: 57° C. IR (neat, ATR): $ν_{max}$ 2988, 2970, 2956, 2846, 1514, 1478, 970 cm$^{-1}$. HRMS (ESI-TOF): calc'd for C$_{11}$H$_{10}$F$_5$OS [M+H]$^+$ 285.0367, found 285.0390. R$_f$=0.40 (10% EtOAc/hexanes). Purification: (SiO$_2$, 2→5% EtOAc/hexanes).

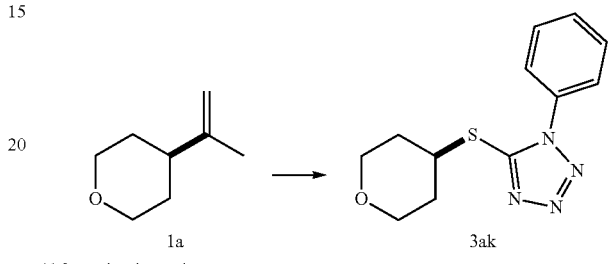

*1.0 mmol scale reaction

Yield: 51% (134 mg). Physical State: white solid. $^1$H NMR (500 MHZ, CDCl$_3$): δ 7.62-7.51 (m, 5H), 4.19 (dddd, J=10.9, 10.9, 4.1, 4.1 Hz, 1H), 3.99 (ddd, J=11.9, 3.7, 3.7 Hz, 2H), 3.58 (ddd, J=11.8, 10.9, 2.2 Hz, 2H), 2.26-2.19 (m, 2H), 1.82 (dddd, J=13.5, 10.8, 10.8, 4.2 Hz, 2H). $^{13}$C NMR (125 MHZ, CDCl$_3$): δ 153.3, 133.6, 130.2, 129.8, 124.0, 67.2, 43.8, 33.0. R$_f$=0.20 (20% EtOAc/hexanes). Purification: (SiO$_2$, 15→25% EtOAc/hexanes).

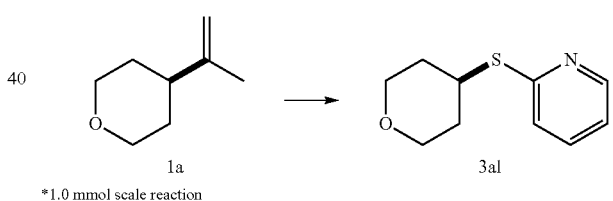

*1.0 mmol scale reaction

Yield: 75% (148 mg). Physical State: colorless oil. $^1$H NMR (500 MHz, CDCl$_3$): δ 8.41 (dd, J=4.8, 0.8 Hz, 1H), 7.47 (ddd, J=7.7, 7.7, 1.9 Hz, 1H), 7.16 (d, J=8.1 Hz, 1H), 6.97 (ddd, J=7.3, 5.0, 0.8 Hz, 1H), 4.06 (dddd, J=10.5, 10.5, 4.1, 4.1 Hz, 1H), 3.97 (ddd, J=11.7, 3.8, 3.8 Hz, 2H), 3.58 (ddd, J=11.6, 10.5, 2.3 Hz, 2H), 2.11-2.02 (m, 2H), 1.84-1.71 (m, 2H). $^{13}$C NMR (125 MHZ, CDCl$_3$): δ 158.1, 149.4, 135.9, 122.9, 119.5, 67.4, 39.3, 33.0. IR (neat, ATR): $ν_{max}$ 3045, 2952, 2843, 1577, 1556, 1452, 1414, 1122, 1084, 755, 722 cm$^{-1}$. HRMS (DART): calc'd for C$_{10}$H$_{14}$NOS [M+H]$^+$ 196.0791, found 196.0780. R$_f$=0.27 (10% EtOAc/hexanes). Purification: (SiO$_2$, 5→15% EtOAc/hexanes).

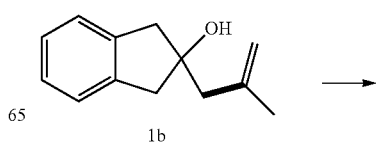

-continued

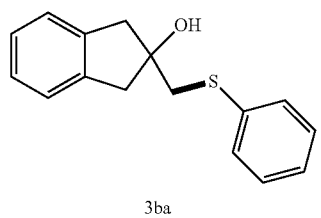

3ba

*1.0 mmol scale reaction

Yield: 71% (184 mg). Physical State: white solid. $^1$H NMR (500 MHZ, CDCl$_3$): δ 7.48-7.43 (m, 2H), 7.35-7.28 (m, 2H), 7.25-7.16 (m, 5H), 3.38 (s, 2H), 3.15-3.03 (m, 4H), 2.62 (s, 1H). $^{13}$C NMR (125 MHz, CDCl$_3$): δ 140.6, 136.4, 129.7, 129.0, 126.7, 126.4, 124.8, 81.8, 46.2, 45.7. MP: 72-74° C. IR (neat, ATR): ν$_{max}$ 3418, 3069, 3058, 2937, 2922, 1480, 1023, 738 cm$^{-1}$. HRMS (DART): calc'd for C$_{16}$H$_{15}$S [M-OH]$^+$ 239.0889, found 239.0876. R$_f$=0.50 (20% EtOAc/hexanes). Purification: (SiO$_2$, 5→10% EtOAc/hexanes).

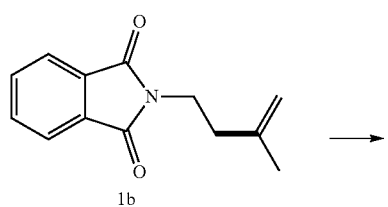

1b

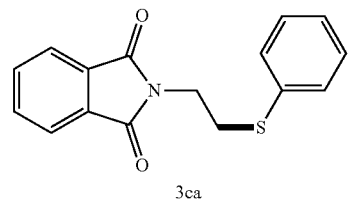

3ca

*1.0 mmol scale reaction

Yield: 80% (227 mg). Physical State: colorless oil. $^1$H NMR (500 MHz, CDCl$_3$): δ 7.86-7.78 (m, 2H), 7.76-7.67 (m, 2H), 7.45-7.39 (m, 2H), 7.28-7.22 (m, 2H), 7.16-7.10 (m, 1H), 3.93 (dd, J=7.0, 7.0 Hz, 2H), 3.23 (dd, J=7.4, 6.7 Hz, 2H). $^{13}$C NMR (125 MHZ, CDCl$_3$): δ 168.0, 134.7, 133.9, 131.9, 129.6, 128.9, 126.3, 123.2, 37.4, 31.5. R$_f$=0.43 (20% EtOAc/hexanes). Purification: (SiO$_2$, 5→15% EtOAc/hexanes).

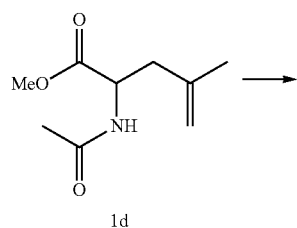

1d

-continued

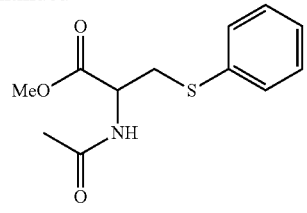

3da

*1.0 mmol scale reaction

Yield: 58% (147 mg). Physical State: colorless oil. $^1$H NMR (500 MHz, CDCl$_3$): δ 7.44-7.39 (m, 2H), 7.32-7.27 (m, 2H), 7.24-7.19 (m, 1H), 6.21 (d, J=6.1 Hz, 1H), 4.87 (dt, J=4.4, 7.6 Hz, 1H), 3.56 (s, 3H), 3.48 (dd, J=14.3, 4.5 Hz, 1H), 3.36 (dd, J=14.3, 4.5 Hz, 1H), 1.87 (s, 3H). $^{13}$C NMR (125 MHz, CDCl$_3$): δ 170.6, 169.6, 134.6, 130.9, 129.0, 127.0, 52.4, 52.3, 36.4, 22.8. IR (neat, ATR): ν$_{max}$ 3281, 3063, 2951, 1743, 1657, 1536, 1439, 1216 cm$^{-1}$. HRMS (DART): calc'd for C$_{12}$H$_{16}$NO$_3$S [M+H]$^+$ 254.0845, found 254.0830. R$_f$=0.43 (50% EtOAc/hexanes). Purification: (SiO$_2$, 30→60% EtOAc/hexanes).

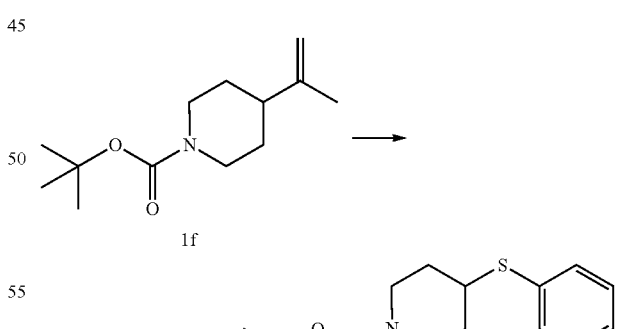

*1.0 mmol scale reaction

Yield: 82% (157 mg). Physical State: colorless oil. $^1$H NMR (500 MHZ, CDCl$_3$): δ 7.43-7.38 (m, 2H), 7.32-7.27 (m, 2H), 7.24-7.19 (m, 1H), 3.11 (dddd, J=10.4, 10.4, 3.6, 3.6 Hz, 1H), 2.06-1.95 (m, 2H), 1.84-1.74 (m, 2H), 1.67-1.58 (m, 1H), 1.45-1.20 (m, 5H). $^{13}$C NMR (125 MHz, CDCl$_3$): δ 135.1, 131.8, 128.6, 126.5, 46.5, 33.2, 26.0, 25.7. R$_f$=0.41 (pentane). Purification: (SiO$_2$, pentane).

*1.0 mmol scale reaction

Yield: 79% (231 mg). Physical State: colorless oil. $^1$H NMR (500 MHZ, CDCl$_3$): δ 7.45-7.39 (m, 2H), 7.33-7.28 (m, 2H), 7.27-7.23 (m, 1H), 3.96 (br s, 2H), 3.21 (dddd, J=10.2, 10.2, 3.9, 3.9 Hz, 1H), 2.91 (dd, J=11.2, 11.2 Hz, 2H), 1.97-1.87 (m, 2H), 1.58-1.47 (m, 2H), 1.44 (s, 9H). $^{13}$C NMR (125 MHZ, CDCl$_3$): δ 154.6, 133.7, 132.6, 128.8, 127.2, 79.5, 44.4, 32.0, 28.3, 28.2. R$_f$=0.38 (10% EtOAc/hexanes). Purification: (SiO$_2$, 2→7% EtOAc/hexanes).

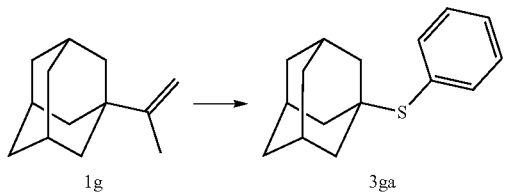

*1.0 mmol scale reaction

Yield: 74% (181 mg). Physical State: white solid. $^1$H NMR (500 MHZ, CDCl$_3$): δ 7.53-7.48 (m, 2H), 7.39-7.29 (m, 3H), 2.04-1.99 (m, 3H), 1.82 (d, J=2.5 Hz, 6H), 1.68-1.57 (m, 6H). $^{13}$C NMR (125 MHZ, CDCl$_3$): δ 137.6, 130.4, 128.4, 128.2, 47.7, 43.5, 36.1, 29.9. R$_f$=0.31 (hexanes). Purification: (SiO$_2$, 0→2% EtOAc/hexanes).

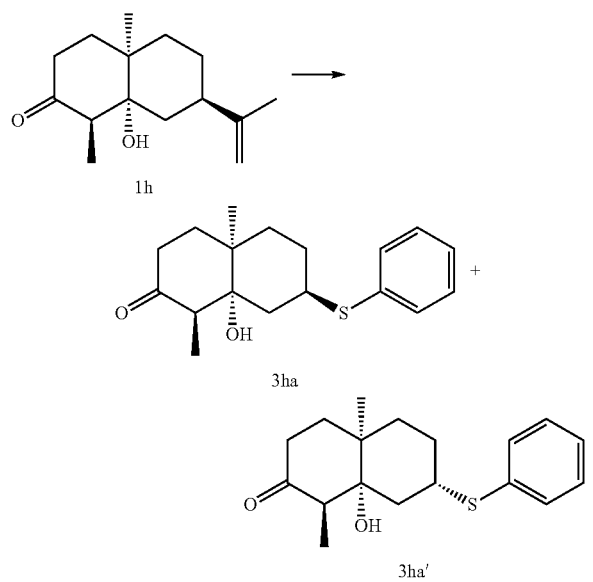

*1.0 mmol scale reaction

Combined Yield: 77% (234 mg). Diastereomeric Ratio: 5.9:1 (determined from $^1$H NMR spectrum of the crude products).

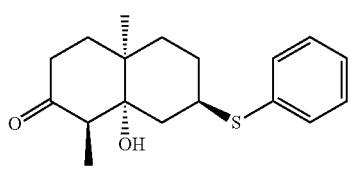

3ha

Yield: 67% (205 mg). Physical State: yellow oil. $^1$H NMR (500 MHZ, CDCl$_3$): δ 7.42-7.36 (m, 2H), 7.32-7.20 (m, 3H), 3.35 (dddd, J=16.6, 8.4, 4.1, 4.1 Hz, 1H), 2.81 (q, J=6.6 Hz, 1H), 2.55 (ddd, J=14.1, 14.1, 7.1 Hz, 1H), 2.33 (dd, J=14.2, 3.7 Hz, 1H), 2.06 (ddd, J=13.9, 13.9, 5.0 Hz, 1H), 1.95-1.79 (m, 3H), 1.59-1.48 (m, 2H), 1.46-1.36 (m, 2H), 1.24-1.26 (m, 1H), 1.22 (s, 3H), 1.00 (d, J=6.7 Hz, 3H). $^{13}$C NMR (125 MHZ, CDCl$_3$): δ 209.7, 134.0, 132.1, 128.8, 127.0, 78.3, 51.6, 42.0, 37.4, 37.3, 35.2, 35.2, 31.3, 27.9, 21.3, 6.3. R$_f$=0.32 (20% EtOAc/hexanes). Purification: (SiO$_2$, 5→20% EtOAc/hexanes).

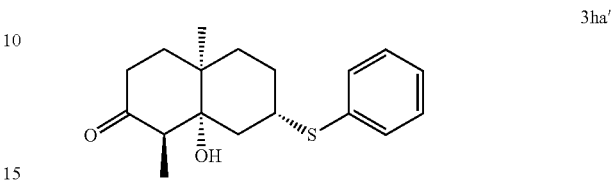

3ha'

Yield: 10% (29 mg). Physical State: white solid. $^1$H NMR (500 MHz, CDCl$_3$): δ 7.47-7.43 (m, 2H), 7.36-7.29 (m, 3H), 4.19 (br s, 1H), 3.61-3.57 (m, 1H), 2.81 (q, J=6.5 Hz, 1H), 2.60 (dddd, J=21.3, 7.1, 7.1, 1.1 Hz, 1H), 2.30 (ddd, J=14.1, 4.9, 1.9 Hz, 1H), 2.16-1.95 (m, 3H), 1.85-1.78 (m, 2H), 1.47 (ddd, J=13.9, 6.9, 2.0 Hz, 1H), 1.37 (dd, J=15.7, 4.8 Hz, 1H), 1.34-1.29 (m, 1H), 1.28 (s, 3H), 0.97 (d, J=6.7 Hz, 3H). $^{13}$C NMR (125 MHZ, CDCl$_3$): δ 210.8, 133.4, 132.9, 129.1, 127.9, 78.4, 51.2, 44.0, 38.0, 37.6, 31.3, 30.6, 29.6, 24.7, 22.0, 6.5. R$_f$=0.49 (20% EtOAc/hexanes). Purification: (SiO$_2$, 5→20% EtOAc/hexanes).

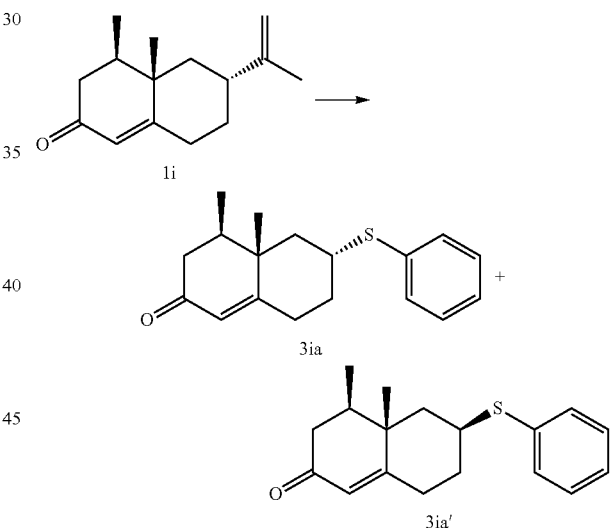

*1.0 mmol scale reaction

Combined Yield: 67% (192 mg, inseparable mixture). Diastereomeric Ratio: 7:1 (determined from $^1$H NMR spectrum of the crude products). Physical State: yellow oil. $^1$H NMR (500 MHZ, CDCl$_3$) major: δ 7.44-7.39 (m, 2H), 7.34-7.29 (m, 2H), 7.28-7.25 (m, 1H), 5.75 (d, J=1.1 Hz, 1H), 3.37 (dddd, J=12.5, 12.5, 3.5, 3.5 Hz, 1H), 2.54-2.44 (m, 1H), 2.35 (ddd, J=15.3, 4.1, 2.6 Hz, 1H), 2.28-2.21 (m, 3H), 2.19-2.12 (m, 1H), 2.04-1.94 (m, 1H), 1.41 (ddd, J=26.3, 12.8, 4.2 Hz, 1H), 1.30-1.21 (m, 1H), 1.10 (s, 3H), 0.93 (d, J=6.8 Hz, 3H). $^1$H NMR (500 MHz, CDCl$_3$) minor: δ 7.46-7.21 (m, 5H), 5.79 (s, 1H), 3.64-3.58 (m, 1H), 2.93 (dddd, J=14.5, 12.7, 6.1, 1.7 Hz, 1H), 2.30-1.93 (m, 6H), 1.91-1.79 (m, 2H), 1.10 (s, 3H), 0.90 (d, J=6.8 Hz, 3H). $^{13}$C NMR (125 MHz, CDCl$_3$) major: δ 199.0, 168.2, 133.7, 132.3, 128.9, 127.2, 125.0, 44.9, 42.1, 41.7, 40.1, 40.0, 33.3, 32.7, 16.7, 14.8. $^{13}$C NMR (125 MHz, CDCl$_3$) minor: δ 199.0, 170.8, 135.6, 131.3, 129.0, 126.9, 124.9, 43.1, 42.3, 41.8, 39.8, 39.3, 30.5, 28.3, 18.8, 14.8. IR (neat, ATR): $v_{max}$ 3052, 2969, 2939, 2887, 1664, 911, 731, 693 cm$^{-1}$. Optical Rotation: [α]$_D^{21.0}$ 93.8 (c 1.00, CHCl$_3$). HRMS (DART): calc'd for C$_{18}$H$_{23}$OS [M+H]$^+$ 287.1464, found 287.1446. R$_f$=0.35 (20% EtOAc/hexanes). Purification: (SiO$_2$, 10→20% EtOAc/hexanes). Note: 2D NMR spectra are consistent with the proposed structures of 3ia/3ia'.

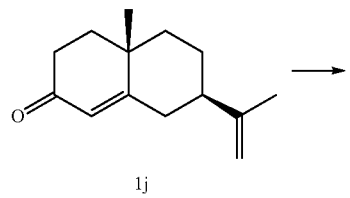

1j

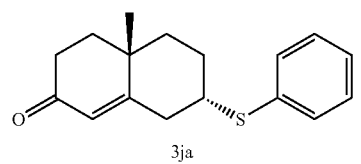

3ja

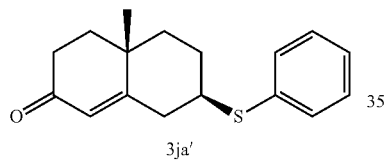

3ja'

*1.0 mmol scale reaction

Combined Yield: 74% (202 mg). Diastereomeric Ratio: 7.5:1 (determined from $^1$H NMR spectrum of the crude products). Note: 2D NMR spectra are consistent with the proposed structures of 3ja/3ja'.

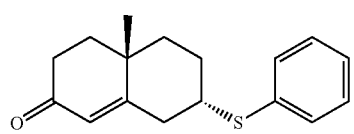

3ja

Yield: 65% (178 mg). Physical State: colorless oil. $^1$H NMR (500 MHz, CDCl$_3$): δ 7.43-7.37 (m, 2H), 7.33-7.28 (m, 2H), 7.26-7.23 (m, 1H), 5.73 (d, J=1.3 Hz, 1H), 3.79-3.73 (m, 1H), 2.77 (ddd, J=15.3, 4.9, 2.0 Hz, 1H), 2.51 (ddd, J=17.1, 14.7, 5.1 Hz, 1H), 2.45-2.35 (m, 2H), 2.11 (dddd, J=14.0, 14.0, 3.8, 3.8 Hz, 1H), 2.06-1.91 (m, 2H), 1.89-1.76 (m, 2H), 1.49 (ddd, J=13.6, 3.1, 3.1 Hz, 1H), 1.25 (s, 3H). $^{13}$C NMR (125 MHZ, CDCl$_3$): δ 199.0, 166.1, 134.4, 132.3, 129.0, 127.2, 126.8, 45.8, 37.5, 36.7, 35.6, 35.5, 34.0, 25.7, 22.1. IR (neat, ATR): $v_{max}$ 3060, 2928, 2860, 1664, 1261, 908, 731, 689 cm$^{-1}$. Optical Rotation: [α]$_D^{20.9}$ 34.2 (c 0.50, CHCl$_3$). HRMS (DART): calc'd for C$_{17}$H$_{21}$OS [M+H]$^+$ 273.1308, found 273.1291. R$_f$=0.37 (20% EtOAc/hexanes). Purification: (SiO$_2$, 5→20% EtOAc/hexanes).

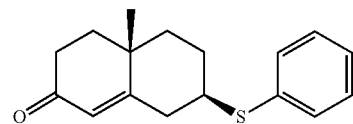

3ja'

Yield: 9% (24 mg). Physical State: colorless oil. $^1$H NMR (500 MHZ, CDCl$_3$): δ 7.46-7.40 (m, 2H), 7.35-7.26 (m, 3H), 5.71 (s, 1H), 3.12 (dddd, J=12.4, 12.4, 4.0, 4.0 Hz, 1H), 2.59-2.38 (m, 3H), 2.35 (ddd, J=17.1, 3.6, 3.6 Hz, 1H), 2.03-1.95 (m, 1H), 1.84-1.79 (m, 2H), 1.79-1.71 (m, 2H), 1.43 (ddd, J=14.0, 14.0, 3.9 Hz, 1H), 1.22 (s, 3H). $^{13}$C NMR (125 MHZ, CDCl$_3$): δ 199.2, 167.1, 133.3, 132.5, 128.9, 127.4, 125.0, 46.5, 40.8, 39.2, 37.5, 35.2, 33.9, 28.8, 21.9. IR (neat, ATR): $v_{max}$ 3060, 2928, 2860, 1668, 908, 727, 689 cm$^{-1}$. Optical Rotation: [α]$_D^{20.8}$ 43.4 (c 0.50, CHCl$_3$). HRMS (DART): calc'd for C$_{17}$H$_{21}$OS [M+H]$^+$ 273.1308, found 273.1290. R$_f$=0.43 (20% EtOAc/hexanes). Purification: (SiO$_2$, 5→20% EtOAc/hexanes).

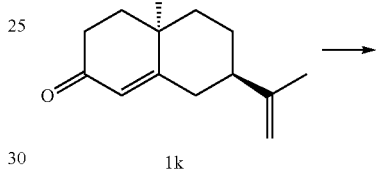

1k

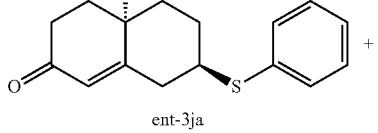

ent-3ja

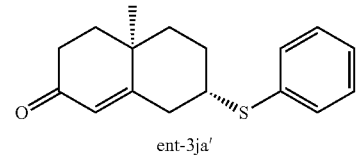

ent-3ja'

*1.0 mmol scale reaction

Combined Yield: 75% (204 mg). Diastereomeric Ratio: 7.5:1 (determined from $^1$H NMR spectrum of the crude products). Note: 2D NMR spectra are consistent with the proposed structures of ent-3ja/ent-3ja'.

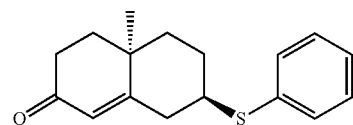

ent-3ja

Yield: 66% (180 mg). Physical State: colorless oil. $^1$H NMR (500 MHz, CDCl$_3$): δ 7.43-7.37 (m, 2H), 7.33-7.28 (m, 2H), 7.26-7.23 (m, 1H), 5.73 (d, J=1.3 Hz, 1H), 3.79-3.73 (m, 1H), 2.77 (ddd, J=15.3, 4.9, 2.0 Hz, 1H), 2.51 (ddd, J=17.1, 14.7, 5.1 Hz, 1H), 2.45-2.35 (m, 2H), 2.11 (dddd, J=14.0, 14.0, 3.8, 3.8 Hz, 1H), 2.06-1.91 (m, 2H), 1.89-1.76 (m, 2H), 1.49 (ddd, J=13.6, 3.1, 3.1 Hz, 1H), 1.25 (s, 3H). $^{13}$C NMR (125 MHZ, CDCl$_3$): δ 199.0, 166.1, 134.4, 132.3, 129.0, 127.2, 126.8, 45.8, 37.5, 36.7, 35.6, 35.5, 34.0, 25.7, 22.1. IR (neat, ATR): $v_{max}$ 3060, 2928, 2860, 1664, 1261, 908, 731, 689 cm$^{-1}$. Optical Rotation: $[\alpha]_D^{21.1}$ −34.2 (c 0.50, CHCl$_3$). HRMS (DART): calc'd for C$_{17}$H$_{21}$OS [M+H]$^+$ 273.1308, found 273.1292. R$_f$=0.37 (20% EtOAc/hexanes). Purification: (SiO$_2$, 5→20% EtOAc/hexanes).

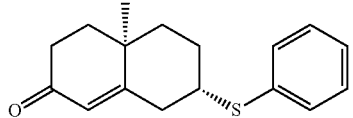

ent-3ja'

Yield: 9% (24 mg). Physical State: colorless oil. $^1$H NMR (500 MHZ, CDCl$_3$): δ 7.46-7.40 (m, 2H), 7.35-7.26 (m, 3H), 5.71 (s, 1H), 3.12 (dddd, J=12.4, 12.4, 4.0, 4.0 Hz, 1H), 2.59-2.38 (m, 3H), 2.35 (ddd, J=17.1, 3.6, 3.6 Hz, 1H), 2.03-1.95 (m, 1H), 1.84-1.79 (m, 2H), 1.79-1.71 (m, 2H), 1.43 (ddd, J=14.0, 14.0, 3.9 Hz, 1H), 1.22 (s, 3H). $^{13}$C NMR (125 MHZ, CDCl$_3$): δ 199.2, 167.1, 133.3, 132.5, 128.9, 127.4, 125.0, 46.5, 40.8, 39.2, 37.5, 35.2, 33.9, 28.8, 21.9. IR (neat, ATR): $v_{max}$ 3060, 2928, 2860, 1668, 908, 727, 689 cm$^{-1}$. Optical Rotation: $[\alpha]_D^{21.3}$ −41.6 (c 0.50, CHCl$_3$). HRMS (DART): calc'd for C$_{17}$H$_{21}$OS [M+H]$^+$ 273.1308, found 273.1291. R$_f$=0.43 (20% EtOAc/hexanes). Purification: (SiO$_2$, 5→20% EtOAc/hexanes).

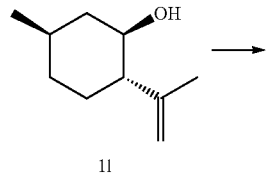

11

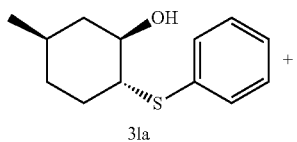

3la

+

3la'

*1.0 mmol scale reaction

Combined Yield: 73% (162 mg). Diastereomeric Ratio: 1.5:1 (determined from $^1$H NMR spectrum of the crude products). Note: To verify the stereochemistry of the newly formed C—S bond, approximately 5 mg of 3la' was placed in a small crystallization tube and dissolved in a minimal amount of ethyl acetate. This vial was placed within a larger 4-mL vial containing approximately 1 mL of hexanes. The vial was capped and sealed with Teflon and Parafilm. After 2 days, single crystals suitable for X-ray diffraction had formed. 2D NMR spectra are also consistent with the proposed structures of 3la/3la'.

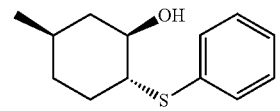

3la

Yield: 44% (97 mg). Physical State: white solid. $^1$H NMR (500 MHZ, CDCl$_3$): δ 7.52-7.44 (m, 2H), 7.35-7.27 (m, 3H), 3.35 (ddd, J=10.5, 10.5, 4.4 Hz, 1H), 2.95 (br s, 1H), 2.72 (ddd, J=12.5, 10.1, 4.0 Hz, 1H), 2.13-2.04 (m, 2H), 1.69-1.62 (m, 1H), 1.50-1.41 (m, 1H), 1.36 (ddd, J=26.0, 13.3, 3.8 Hz, 1H), 1.06 (dd, J=23.4, 12.3 Hz, 1H), 0.96 (ddd, J=25.1, 13.2, 3.6 Hz, 1H), 0.91 (d, J=6.6 Hz, 3H). $^{13}$C NMR (125 MHZ, CDCl$_3$): δ 133.7, 132.4, 128.8, 127.7, 71.6, 56.3, 42.3, 34.7, 32.2, 31.0, 21.8. MP: 68-69° C. IR (neat, ATR): $v_{max}$ 3421, 3063, 2947, 2925, 2852, 1449, 1047, 743, 689 cm$^{-1}$. Optical Rotation: $[\alpha]_D^{21.8}$ −36.4 (c 1.00, CHCl$_3$). HRMS (DART): calc'd for C$_{13}$H$_{17}$S [M-OH]$^+$ 205.1045, found 205.1033. R$_f$=0.26 (10% EtOAc/hexanes). Purification: (SiO$_2$, 5→10% EtOAc/hexanes).

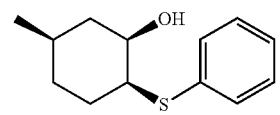

3la'

Yield: 29% (65 mg). Physical State: white solid. $^1$H NMR (500 MHZ, CDCl$_3$): δ 7.51-7.45 (m, 2H), 7.32-7.19 (m, 3H), 3.80 (ddd, J=11.5, 4.2, 4.2 Hz, 1H), 3.64-3.59 (m, 1H), 2.31 (br s, 1H), 2.10 (ddd, J=14.1, 6.5, 3.3 Hz, 1H), 1.86-1.78 (m, 1H), 1.73 (dddd, J=13.6, 13.6, 3.5, 3.5 Hz, 1H), 1.55-1.41 (m, 2H), 1.35-1.24 (m, 1H), 1.13 (dd, J=24.1, 11.6 Hz, 1H), 0.96 (d, J=6.4 Hz, 3H). $^{13}$C NMR (125 MHZ, CDCl$_3$): δ 136.2, 131.3, 128.9, 126.7, 71.0, 56.3, 40.4, 31.1, 30.9, 28.9, 21.9. MP: 98-99° C. IR (neat, ATR): $v_{max}$ 3327, 3048, 2947, 2925, 2856, 1439, 1028, 735 cm$^{-1}$. Optical Rotation: $[\alpha]_D^{22.0}$ 33.2 (c 1.00, CHCl$_3$). HRMS (DART): calc'd for C$_{13}$H$_{17}$S [M-OH]$^+$ 205.1045, found 205.1036. R$_f$=0.20 (10% EtOAc/hexanes). Purification: (SiO$_2$, 5→10% EtOAc/hexanes).

1m

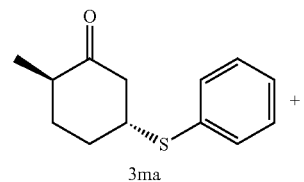

3ma

+

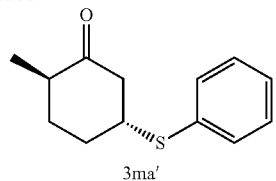

3ma'

Combined Yield: 75% (1.0 mmol scale, 165 mg); 66% (10.0 mmol scale, 1.46 g). Diastereomeric Ratio: 1.6:1 (determined from ¹H NMR spectrum of the crude products). Note: 2D NMR spectra are consistent with the proposed structures of 3ma/3ma'.

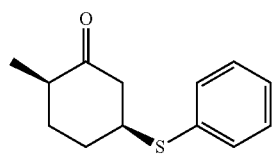

3ma

Yield: 47% (1.0 mmol scale, 104 mg); 41% (10.0 mmol scale, 900 mg). Physical State: white solid. ¹H NMR (500 MHZ, CDCl$_3$): δ 7.44-7.39 (m, 2H), 7.34-7.24 (m, 3H), 3.86-3.80 (m, 1H), 2.67 (ddd, J=14.5, 5.0, 1.1 Hz, 1H), 2.53 (ddd, J=14.5, 4.7, 1.7 Hz, 1H), 2.45-2.36 (m, 1H), 2.14-2.05 (m, 1H), 1.98 (ddd, J=8.8, 4.5, 1.7 Hz, 1H), 1.96-1.89 (m, 2H), 1.10 (d, J=6.7 Hz, 3H). ¹³C NMR (125 MHz, CDCl$_3$): δ 210.3, 133.6, 132.8, 129.0, 127.5, 47.0, 45.3, 44.7, 30.5, 28.7, 14.8. MP: 55° C. IR (neat, ATR): ν$_{max}$ 3060, 2969, 2931, 2860, 1713, 746, 693 cm$^{-1}$. Optical Rotation: [α]$_D^{22.1}$ −32.7 (c 1.00, CHCl$_3$). HRMS (DART): calc'd for C$_{13}$H$_{17}$OS [M+H]$^+$ 221.0995, found 221.0984. R$_f$=0.39 (10% EtOAc/hexanes). Purification: (SiO$_2$, 5→10% EtOAc/hexanes).

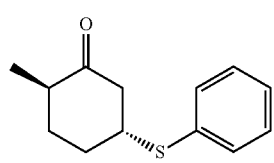

3ma'

Yield: 28% (1.0 mmol scale, 61 mg); 26% (10.0 mmol scale, 563 mg). Physical State: white solid. ¹H NMR (500 MHZ, CDCl$_3$): δ 7.45-7.39 (m, 2H), 7.35-7.27 (m, 3H), 3.28 (dddd, J=12.5, 12.5, 4.0, 4.0 Hz, 1H), 2.70 (ddd, J=13.5, 4.3, 2.2 Hz, 1H), 2.41-2.30 (m, 2H), 2.24-2.16 (m, 1H), 2.16-2.09 (m, 1H), 1.76 (ddd, J=25.3, 13.1, 3.7 Hz, 1H), 1.36 (ddd, J=26.4, 13.1, 3.5 Hz, 1H), 1.01 (d, J=6.5 Hz, 3H). ¹³C NMR (125 MHz, CDCl$_3$): δ 209.9, 133.1, 132.8, 128.9, 127.7, 48.2, 46.7, 44.4, 33.8, 32.3, 14.1. MP: 39-40° C. IR (neat, ATR): ν$_{max}$ 3063, 2968, 2932, 2861, 1710, 745, 693 cm$^{-1}$. Optical Rotation: [α]$_D^{22.3}$ 102.7 (c 1.00, CHCl$_3$). HRMS (DART): calc'd for C$_{13}$H$_{17}$OS [M+H]$^+$ 221.0995, found 221.0982. R$_f$=0.57 (10% EtOAc/hexanes). Purification: (SiO$_2$, 5→10% EtOAc/hexanes).

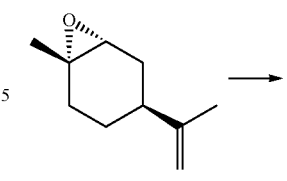

1n

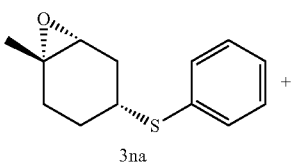

3na

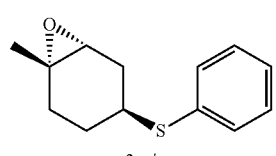

3na'

*1.0 mmol scale reaction

Combined Yield: 60% (132 mg, inseparable mixture). Diastereomeric Ratio: 10:1 (determined from ¹H NMR spectrum of the crude products). Physical State: colorless oil. ¹H NMR (500 MHZ, CDCl$_3$) major: δ 7.41-7.36 (m, 2H), 7.32-7.27 (m, 2H), 7.25-7.20 (m, 1H), 3.33-3.25 (m, 1H), 3.04-3.00 (m, 1H), 2.37 (dd, J=15.2, 5.1 Hz, 1H), 1.98 (ddd, J=15.2, 6.1, 6.1 Hz, 1H), 1.92-1.85 (m, 2H), 1.82-1.75 (m, 1H), 1.40 (dddd, J=13.6, 8.5, 8.5, 6.0 Hz, 1H), 1.33 (s, 3H). ¹³C NMR (125 MHz, CDCl$_3$) major: δ 134.4, 131.8, 128.8, 126.8, 59.1, 57.0, 39.5, 31.4, 27.5, 26.2, 23.7. IR (neat, ATR): ν$_{max}$ 3067, 2980, 2928, 1435, 905, 727, 693 cm$^{-1}$. Optical Rotation: [α]$_D^{22.4}$ −11.8 (c 1.00, CHCl$_3$). HRMS (DART): calc'd for C$_{13}$H$_{17}$OS [M+H]$^+$ 221.0995, found 221.0983. R$_f$=0.24 (5% EtOAc/hexanes). Purification: (SiO$_2$, 2→5% EtOAc/hexanes). Note: 2D NMR spectra are consistent with the proposed structures of 3na/3na'. Note: When solid ferrous sulfate heptahydrate was added at room temperature for the reaction with 1n, formation of the products SI-VI and SI-VI' was observed.

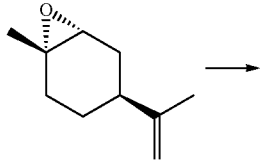

1n

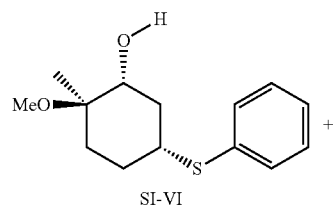

SI-VI

-continued

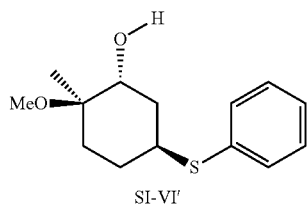

SI-VI'

*1.0 mmol scale reaction

Combined Yield: 57% (143 mg). Diastereomeric Ratio: 10:1 (determined from $^1$H NMR spectrum of the crude products). Note: Solid ferrous sulfate heptahydrate was added at room temperature.

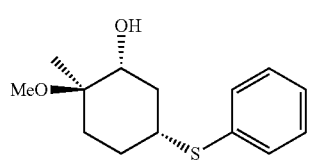

SI-VI

Yield: 53% (132 mg). Physical State: colorless oil. $^1$H NMR (500 MHZ, CDCl$_3$): δ 7.43-7.38 (m, 2H), 7.31-7.26 (m, 2H), 7.24-7.19 (m, 1H), 3.79 (br s, 1H), 3.48 (ddd, J=13.4, 9.3, 4.2 Hz, 1H), 3.19 (s, 3H), 2.04 (ddd, J=13.4, 9.8, 3.4 Hz, 1H), 1.92-1.83 (m, 2H), 1.80-1.71 (m, 2H), 1.66-1.59 (m, 2H), 1.15 (s, 3H). $^{13}$C NMR (125 MHz, CDCl$_3$): δ 134.9, 131.6, 128.8, 126.6, 75.6, 72.0, 48.4, 41.3, 35.1, 28.7, 27.8, 18.5. IR (neat, ATR): $v_{max}$ 3428, 3071, 2931, 1435, 1077, 743, 693 cm$^{-1}$. Optical Rotation: $[\alpha]_D^{22.6}$ −17.8 (c 1.00, CHCl$_3$). HRMS (ESI-TOF): calc'd for C$_{14}$H$_{20}$O$_2$SNa [M+Na]$^+$ 291.0816, found 291.0811. R$_f$=0.33 (20% EtOAc/hexanes). Purification: (SiO$_2$, 10→30% EtOAc/hexanes).

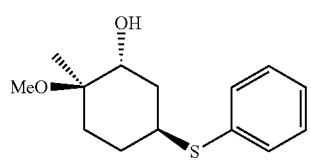

SI-VI'

Yield: 4% (11 mg). Physical State: colorless oil. $^1$H NMR (500 MHZ, CDCl$_3$): δ 7.45-7.38 (m, 2H), 7.34-7.25 (m, 3H), 3.62-3.53 (m, 1H), 3.21 (s, 3H), 3.15-3.05 (m, 1H), 2.36 (br s, 1H), 2.21-2.12 (m, 1H), 2.00-1.85 (m, 2H), 1.55-1.47 (m, 1H), 1.43-1.33 (m, 2H), 1.14 (s, 3H). $^{13}$C NMR (125 MHZ, CDCl$_3$): δ 133.9, 132.8, 129.0, 127.4, 77.4, 74.7, 48.8, 43.8, 36.1, 32.2, 29.7, 14.7. IR (neat, ATR): $v_{max}$ 3436, 3048, 2943, 2868, 1126, 1073, 746 cm$^{-1}$. Optical Rotation: $[\alpha]_D^{22.5}$ −6.4 (c 0.10, CHCl$_3$). HRMS (ESI-TOF): calc'd for C$_{14}$H$_{20}$O$_2$SNa [M+Na]$^+$ 291.0816, found 291.0822. R$_f$=0.19 (20% EtOAc/hexanes). Purification: (SiO$_2$, 10→30% EtOAc/hexanes).

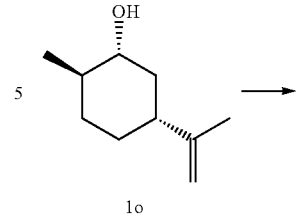

1o

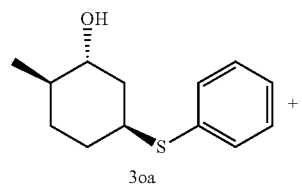

3oa

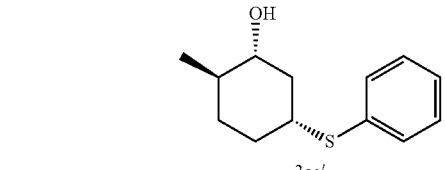

3oa'

*1.0 mmol scale reaction

Combined Yield: 79% (175 mg). Diastereomeric Ratio: 2:1 (determined from $^1$H NMR spectrum of the crude products). Note: 2D NMR spectra are consistent with the proposed structures of 3oa/3oa'.

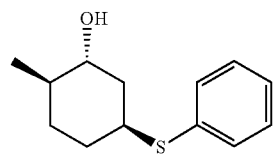

3oa

Yield: 55% (121 mg). Physical State: white solid. $^1$H NMR (500 MHZ, CDCl$_3$): δ 7.42-7.37 (m, 2H), 7.33-7.27 (m, 2H), 7.25-7.19 (m, 1H), 3.73-3.68 (m, 1H), 3.67 (ddd, J=8.7, 8.7, 3.7 Hz, 1H), 2.09 (dddd, J=13.4, 4.3, 4.3, 1.3 Hz, 1H), 1.83-1.40 (m, 7H), 1.05 (d, J=6.5 Hz, 3H). $^{13}$C NMR (125 MHZ, CDCl$_3$): δ 135.4, 131.3, 128.8, 126.6, 72.0, 44.7, 39.0, 38.3, 29.3, 28.1, 17.8. MP: 48-49° C. IR (neat, ATR): $v_{max}$ 3346, 3067, 2925, 2872, 1439, 1055, 1028, 746, 693 cm$^{-1}$. Optical Rotation: $[\alpha]_D^{22.6}$ −0.8 (c 1.00, CHCl$_3$). HRMS (DART): calc'd for C$_{13}$H$_{19}$OS [M+H]$^+$ 223.1151, found 223.1141. R$_f$=0.38 (20% EtOAc/hexanes). Purification: (SiO$_2$, 5→10% EtOAc/hexanes).

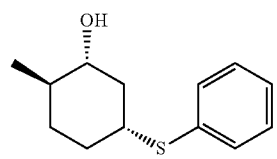

3oa'

Yield: 24% (54 mg). Physical State: white solid. $^1$H NMR (500 MHZ, CDCl$_3$): δ 7.44-7.39 (m, 2H), 7.32-7.27 (m, 2H), 7.26-7.22 (m, 1H), 3.15 (ddd, J=10.3, 10.3, 4.1 Hz, 1H), 3.03 (dddd, J=12.2, 12.2, 3.7, 3.7 Hz, 1H), 2.27 (dddd, J=12.3, 3.8, 3.8, 2.2 Hz, 1H), 2.00-1.93 (m, 1H), 1.77 (dq, J=13.7, 3.5 Hz, 1H), 1.54 (br s, 1H), 1.40-1.24 (m, 3H), 1.10-1.01 (m, 1H), 1.00 (d, J=6.5 Hz, 3H). 3C NMR (125 MHZ, CDCl$_3$): δ 134.1, 132.5, 128.7, 127.0, 75.5, 44.5, 42.0, 39.4, 32.7, 32.6, 17.9. MP: 94-95° C. IR (neat, ATR): $v_{max}$ 3364, 3063, 2925, 2864, 1439, 1043, 743, 689 cm$^{-1}$. Optical Rotation: $[α]_D^{22.7}$ 2.0 (c 0.50, CHCl$_3$). HRMS (DART): calc'd for C$_{13}$H$_{19}$OS [M+H]$^+$ 223.1151, found 223.1143. R$_f$=0.42 (20% EtOAc/hexanes). Purification: (SiO$_2$, 5→10% EtOAc/hexanes).

3.5 Hz, 1H), 1.84 (ddd, J=13.6, 7.6, 4.3 Hz, 1H), 1.81-1.67 (m, 5H), 1.23 (s, 3H). $^{13}$C NMR (125 MHZ, CDCl$_3$): δ 134.8, 131.7, 128.8, 126.8, 73.5, 72.3, 42.2, 35.6, 33.8, 28.0, 23.0. MP: 66-68° C. IR (neat, ATR): $v_{max}$ 3368, 3063, 2935, 2864, 1439, 1051, 1028, 746, 689 cm$^{-1}$. Optical Rotation: $[α]_D^{22.8}$ −7.2 (c 1.00, CHCl$_3$). HRMS (ESI-TOF): calc'd for C$_{13}$H$_{18}$O$_2$SK [M+K]$^+$ 277.0659, found 277.0663. R$_f$=0.45 (50% EtOAc/hexanes). Purification: (SiO$_2$, 30→50% EtOAc/hexanes).

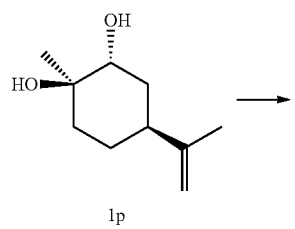

1p

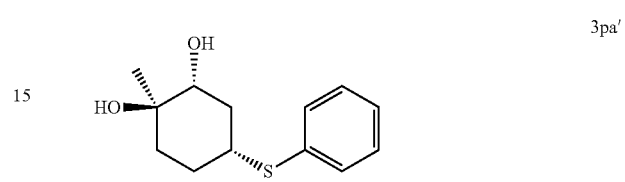

3pa'

Yield: 17% (41 mg). Physical State: white solid. $^1$H NMR (500 MHZ, CDCl$_3$): δ 7.46-7.40 (m, 2H), 7.33-7.24 (m, 3H), 3.52 (dd, J=11.4, 4.3 Hz, 1H), 3.14-3.06 (m, 1H), 2.16 (dddd, J=12.9, 4.3, 4.3, 2.1 Hz, 1H), 1.98-1.92 (m, 1H), 1.85 (br s, 2H), 1.82-1.77 (m, 1H), 1.50-1.38 (m, 3H), 1.20 (s, 3H). $^{13}$C NMR (125 MHZ, CDCl$_3$): δ 133.9, 132.9, 129.0, 127.5, 76.3, 73.5, 44.1, 37.7, 37.5, 30.3, 19.3. MP: 80-82° C. IR (neat, ATR): $v_{max}$ 3384, 3056, 2992, 2935, 1134, 1069, 746, 693 cm$^{-1}$. Optical Rotation: $[α]_D^{22.8}$ 6.4 (c 0.50, CHCl$_3$). HRMS (ESI-TOF): calc'd for C$_{13}$H$_{19}$O$_2$S [M+H]$^+$ 239.1100, found 239.1109. R$_f$=0.32 (50% EtOAc/hexanes). Purification: (SiO$_2$, 30→50% EtOAc/hexanes).

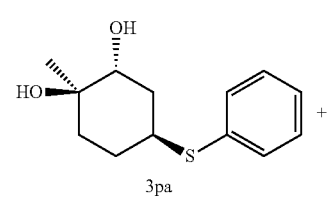

3pa

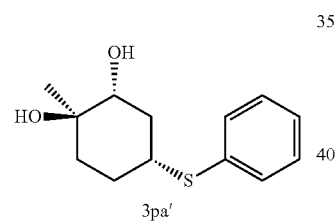

3pa'

*1.0 mmol scale reaction

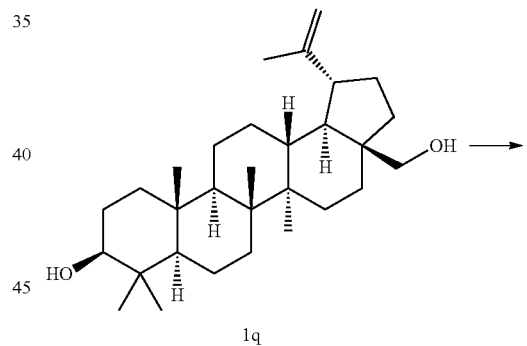

1q

Combined Yield: 84% (200 mg). Diastereomeric Ratio: 4:1 (determined from $^1$H NMR spectrum of the crude products). Note: 2D NMR spectra are consistent with the proposed structures of 3pa/3pa'.

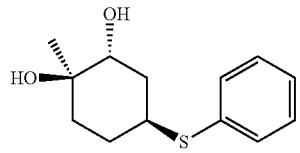

3pa

Yield: 67% (159 mg). Physical State: white solid. $^1$H NMR (500 MHZ, CDCl$_3$): δ 7.43-7.38 (m, 2H), 7.32-7.27 (m, 2H), 7.25-7.20 (m, 1H), 3.81 (dd, J=7.1, 3.2 Hz, 1H), 3.59-3.50 (m, 1H), 2.12 (br s, 1H), 2.05 (ddd, J=13.7, 7.7,

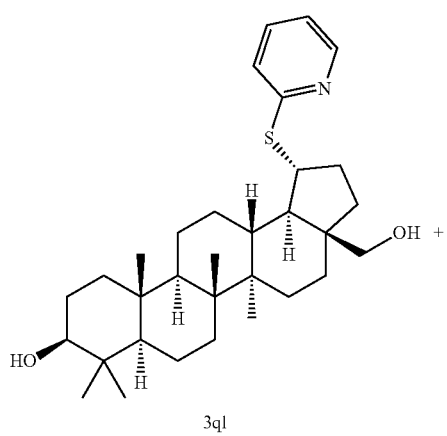

3ql

-continued

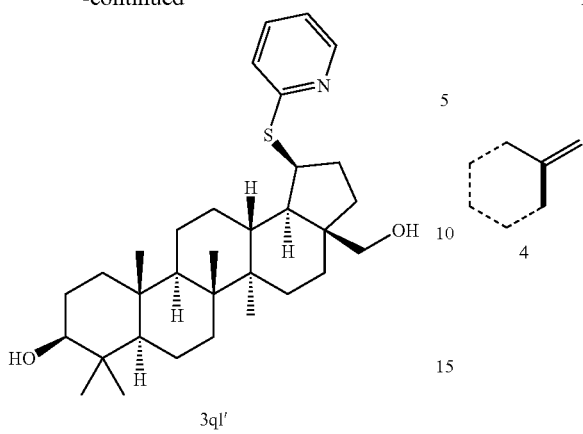

3ql'

*0.5 mmol scale reaction

Combined Yield: approximately 78% (see Note). Diastereomeric Ratio: 1.2:1 (determined from $^1$H NMR spectrum of the crude products). Note: The thioether 3ql was inseparable from an unidentified byproduct (2.2:1 desired/undesired). Subsequent oxidation to the sulfone 8 (section 5.3.) enabled separation from this impurity. The combined yield is based on the yield of 3ql'+the yield of the sulfone 8.

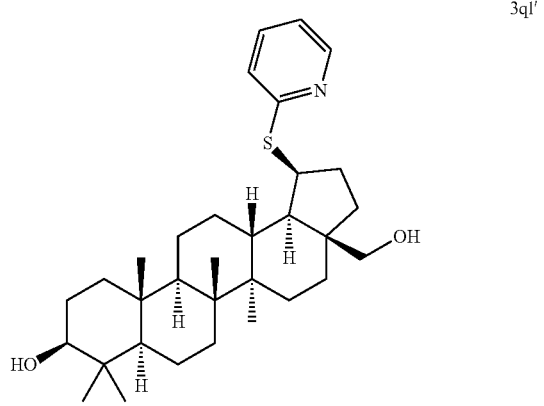

3ql'

Yield: 35% (91 mg). Physical State: white solid. $^1$H NMR (500 MHZ, CDCl$_3$): δ 8.39 (dd, J=4.9, 0.8 Hz, 1H), 7.44 (ddd, J=7.7, 7.7, 1.8 Hz, 1H), 7.11 (d, J=8.1 Hz, 1H), 6.94 (ddd, J=7.2, 5.1, 0.8 Hz, 1H), 4.35 (ddd, J=8.5, 7.8, 2.9 Hz, 1H), 3.83-3.72 (m, 2H), 3.18 (dd, J=11.4, 4.8 Hz, 1H), 2.61 (ddd, J=15.0, 9.0, 9.0 Hz, 1H), 2.08-1.98 (m, 2H), 1.96-0.86 (m, 22H), 1.05 (s, 3H), 0.98 (s, 3H), 0.96 (s, 3H), 0.82 (s, 3H), 0.75 (s, 3H), 0.72-0.67 (m, 1H). $^{13}$C NMR (125 MHZ, CDCl$_3$): δ 159.7, 149.3, 135.9, 122.4, 119.1, 79.0, 61.3, 55.4, 50.9, 50.7, 47.3, 43.3, 42.6, 41.0, 38.9, 38.7, 37.2, 35.4, 34.5, 34.5, 34.1, 29.1, 28.0, 27.4, 27.1, 25.4, 20.7, 18.3, 16.1, 16.0, 15.3, 15.2. MP: 130-132° C. IR (neat, ATR): ν$_{max}$ 3380, 3048, 2939, 2872, 1578, 1453, 1412, 1126, 1032, 761, 735 cm$^{-1}$. Optical Rotation: [α]$_D^{23.1}$ 35.8 (c 1.00, CHCl$_3$). HRMS (ESI-TOF): calc'd for C$_{32}$H$_{50}$NO$_2$S [M+H]$^+$ 512.3557, found 512.3563. R$_f$=0.32 (30% EtOAc/hexanes). Purification: (SiO$_2$, 10→30% EtOAc/hexanes). Note: The reaction was run at a concentration of 0.01 M because of the low solubility of 1q in MeOH.

Example 14: Exemplary General Procedure for Carboxylic Ester Synthesis

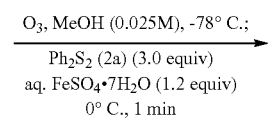

$O_3$, MeOH (0.025M), -78° C.;
Ph$_2$S$_2$ (2a) (3.0 equiv)
aq. FeSO$_4$·7H$_2$O (1.2 equiv)
0° C., 1 min

4

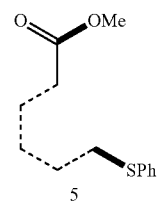

5

For example, a round-bottom flask equipped with a magnetic stirrer bar was charged with 4a (1.0 equiv) and MeOH (0.025 M), then cooled to -78° C. in a dry-ice/acetone bath while open to the air. Ozone was bubbled through the solution until complete consumption of the starting material (as indicated by TLC and/or a blue color in the reaction mixture). The solution was then sparged with argon for 5 min to expel excess ozone. Diphenyl disulfide (2a, 3.0 equiv) was added, and then the reaction mixture was warmed to 0° C. in an ice-water bath and stirred for 10 min. An aqueous solution (5%, wt/vol) of ferrous sulfate heptahydrate (1.2 equiv) was added over a period of approximately 1 min. Upon completion of the reaction (TLC), the mixture was diluted with water and transferred to a separatory funnel. The MeOH/water layer was extracted with dichloromethane (3×). The combined organic fractions were washed with brine, dried (anhydrous sodium sulfate), filtered, and concentrated under reduced pressure. Purification through flash column chromatography (SiO$_2$) provided the thiylated carboxylic ester product 5aa. Any modification of the above procedure is described below with the specific entry. Note: Solid phenyl disulfide was ground to a fine powder prior to use.

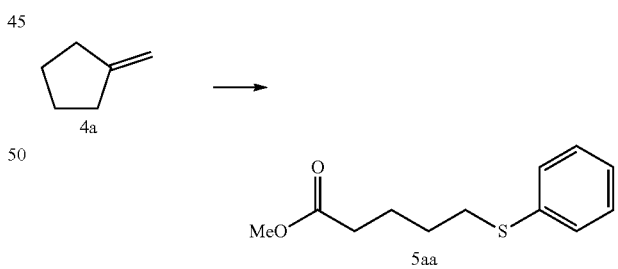

*1.0 mmol scale reaction

Yield: 73% (164 mg). Physical State: colorless oil. $^1$H NMR (500 MHZ, CDCl$_3$): δ 7.35-7.30 (m, 2H), 7.30-7.25 (m, 2H), 7.20-7.14 (m, 1H), 3.66 (s, 3H), 2.93 (t, J=7.2 Hz, 2H), 2.33 (t, J=7.4 Hz, 2H), 1.82-1.73 (m, 2H), 1.71-1.63 (m, 2H). $^{13}$C NMR (125 MHZ, CDCl$_3$): δ 173.6, 136.4, 129.0, 128.8, 125.8, 51.4, 33.4, 33.1, 28.4, 23.9. IR (neat, ATR): ν$_{max}$ 3060, 2943, 2860, 1736, 1439, 1205, 1172, 743, 686 cm$^{-1}$. HRMS (ESI-TOF): calc'd for C$_{12}$H$_{16}$O$_2$SK [M+K]$^+$ 263.0503, found 263.0503. R$_f$=0.44 (10% EtOAc/hexanes). Purification: (SiO$_2$, 0→10% Et$_2$O/pentane).

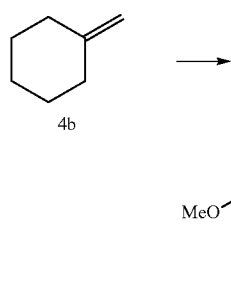

4b

→

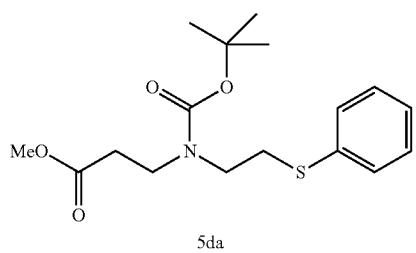

5ba

*1.0 mmol scale reaction

Yield: 71% (168 mg). Physical State: colorless oil. $^1$H NMR (500 MHZ, CDCl$_3$): δ 7.34-7.30 (m, 2H), 7.30-7.25 (m, 2H), 7.19-7.14 (m, 1H), 3.66 (s, 3H), 2.91 (t, J=7.3 Hz, 2H), 2.31 (t, J=7.5 Hz, 2H), 1.71-1.59 (m, 4H), 1.52-1.41 (m, 2H). $^{13}$C NMR (125 MHz, CDCl$_3$): δ 173.9, 136.6, 128.9, 128.7, 125.7, 51.4, 33.8, 33.3, 28.7, 28.1, 24.4. IR (neat, ATR): ν$_{max}$ 3063, 2939, 2856, 1736, 1435, 1257, 1201, 1168, 739, 689 cm$^{-1}$. HRMS (ESI-TOF): calc'd for C$_{13}$H$_{18}$O$_2$SK [M+K]$^+$ 277.0659, found 277.0669. R$_f$=0.44 (10% EtOAc/hexanes). Purification: (SiO$_2$, 0→10% Et$_2$O/pentane).

Yield: 80% (273 mg). Physical State: colorless oil. $^1$H NMR (500 MHz, CDCl$_3$): δ 7.39-7.33 (m, 2H), 7.30-7.26 (m, 2H), 7.21-7.14 (m, 1H), 3.68-3.62 (m, 3H), 3.52-3.37 (m, 4H), 3.14-2.98 (m, 2H), 2.60-2.49 (m, 2H), 1.47-1.40 (m, 9H). $^{13}$C NMR (125 MHZ, CDCl$_3$): δ 172.4, 172.1, 155.0, 135.9, 135.6, 129.3, 129.0, 128.9, 127.5, 126.2, 126.0, 80.1, 51.7, 51.7, 48.0, 44.5, 44.1, 33.9, 33.4, 31.9, 31.5, 28.5, 28.4. IR (neat, ATR): ν$_{max}$ 3056, 2977, 2928, 1736, 1690, 1412, 1366, 1160, 739, 689 cm$^{-1}$. HRMS (ESI-TOF): calc'd for C$_{17}$H$_{25}$NO$_4$SNa [M+Na]$^+$ 362.1309, found 362.1305. R$_f$=0.19 (10% EtOAc/hexanes). Purification: (SiO$_2$, 5→10% EtOAc/hexanes). Note: The ester 5da exists as a mixture of rotamers.

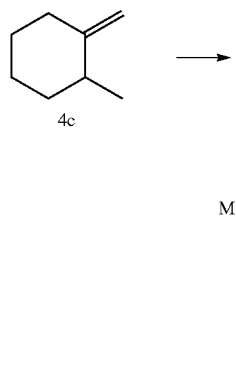

4c

→

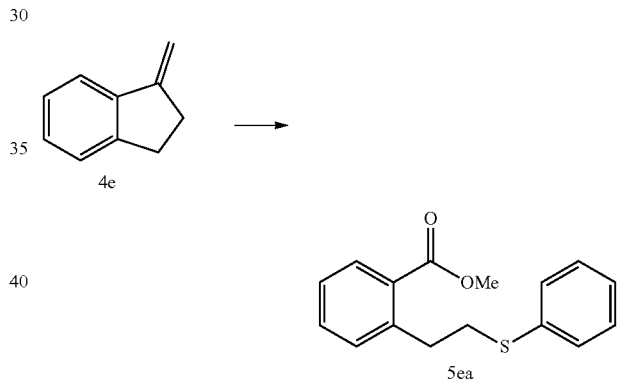

5ca

*1.0 mmol scale reaction

Yield: 75% (190 mg). Physical State: colorless oil. $^1$H NMR (500 MHZ, CDCl$_3$): δ 7.41-7.36 (m, 2H), 7.31-7.26 (m, 2H), 7.25-7.20 (m, 1H), 3.66 (s, 3H), 3.25-3.15 (m, 1H), 2.31 (t, J=7.5 Hz, 2H), 1.68-1.57 (m, 3H), 1.56-1.44 (m, 3H), 1.27 (d, J=6.7 Hz, 3H). $^{13}$C NMR (125 MHZ, CDCl$_3$): δ 173.9, 135.1, 131.9, 128.7, 126.6, 51.4, 43.0, 36.1, 33.8, 26.4, 24.6, 21.0. IR (neat, ATR): ν$_{max}$ 3060, 2935, 2864, 1732, 1435, 1198, 1164, 746, 693 cm$^{-1}$. HRMS (ESI-TOF): calc'd for C$_{14}$H$_{20}$O$_2$SK [M+K]$^+$ 291.0816, found 291.0828. R$_f$=0.41 (10% EtOAc/hexanes). Purification: (SiO$_2$, 2→4% EtOAc/hexanes).

Yield: 51% (139 mg). Physical State: colorless oil. $^1$H NMR (500 MHZ, CDCl$_3$): δ 7.92 (dd, J=7.8, 1.2 Hz, 1H), 7.44 (ddd, J=7.5, 7.5, 1.4 Hz, 1H), 7.42-7.37 (m, 2H), 7.33-7.24 (m, 4H), 7.21-7.16 (m, 1H), 3.86 (s, 3H), 3.32-3.26 (m, 2H), 3.25-3.19 (m, 2H). $^{13}$C NMR (125 MHZ, CDCl$_3$): δ 167.6, 141.7, 136.5, 132.0, 131.4, 130.8, 129.4, 129.0, 128.8, 126.5, 125.7, 51.9, 34.7, 34.5. IR (neat, ATR): ν$_{max}$ 3060, 2992, 2951, 1716, 1431, 1269, 1251, 1119, 1077, 735, 686 cm$^{-1}$. HRMS (ESI-TOF): calc'd for C$_{16}$H$_{16}$O$_2$SK [M+K]$^+$ 311.0503, found 311.0514. R$_f$=0.48 (10% EtOAc/hexanes). Purification: (SiO$_2$, 2→3% EtOAc/hexanes).

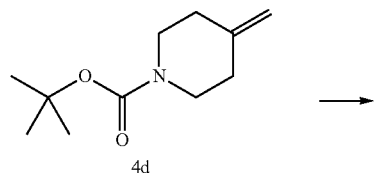

4d

→

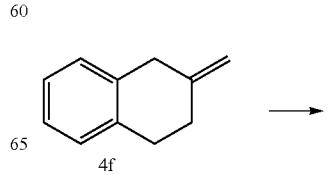

4f

→

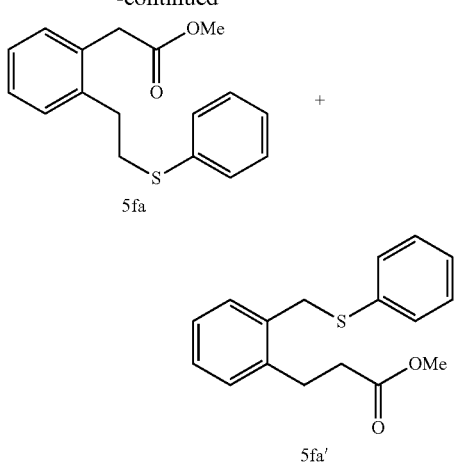

5fa

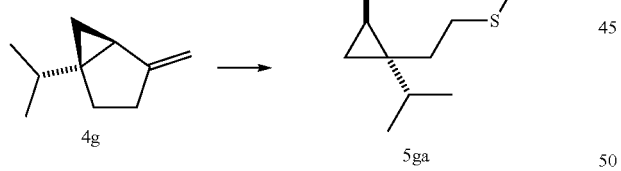

5fa'

*1.0 mmol scale reaction

Combined Yield: 35% (100 mg). Regioisomeric Ratio: 1.6:1 (inseparable mixture). Physical State: colorless oil. $^1$H NMR (500 MHZ, CDCl$_3$) 5fa: δ 7.41-7.09 (m, 9H), 3.65 (s, 3H), 3.61 (s, 2H), 3.15-3.10 (m, 2H), 2.97-2.91 (m, 2H). $^1$H NMR (500 MHZ, CDCl$_3$) 5fa': δ 7.41-7.09 (m, 9H), 4.15 (s, 2H), 3.68 (s, 3H), 3.07-3.02 (m, 2H), 2.70-2.65 (m, 2H). $^{13}$C NMR (125 MHz, CDCl$_3$) 5fa: δ 171.9, 138.8, 136.2, 132.3, 130.7, 129.7, 129.5, 129.0, 127.7, 126.9, 126.2, 52.1, 38.3, 34.5, 32.9. $^{13}$C NMR (125 MHZ, CDCl$_3$) 5fa': δ 173.3, 139.1, 136.4, 134.8, 130.5, 130.3, 129.2, 128.9, 127.8, 126.6, 126.6, 51.7, 37.0, 35.3, 27.5. IR (neat, ATR): ν$_{max}$ 3063, 3026, 2951, 2872, 1736, 1439, 1254, 1152, 743, 693 cm$^{-1}$. HRMS (ESI-TOF): calc'd for C$_{17}$H$_{18}$O$_2$SK [M+K]$^+$ 325.0659, found 326.0665. R$_f$=0.34 (10% EtOAc/hexanes). Purification: (SiO$_2$, 2→5% EtOAc/hexanes).

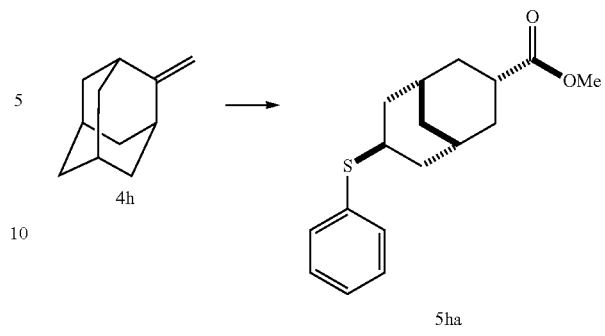

5ha

*1.0 mmol scale reaction

Yield: 51% (149 mg). Physical State: colorless oil. $^1$H NMR (500 MHZ, CDCl$_3$): δ 7.43-7.38 (m, 2H), 7.32-7.27 (m, 2H), 7.24-7.19 (m, 1H), 3.66 (s, 3H), 3.49 (dddd, J=12.5, 12.5, 4.5, 4.5 Hz, 1H), 2.52 (dddd, J=12.2, 12.2, 6.1, 6.1 Hz, 1H), 2.25-2.06 (m, 4H), 1.93-1.85 (m, 2H), 1.67-1.59 (m, 1H), 1.55-1.41 (m, 4H), 1.21-1.13 (m, 1H). $^{13}$C NMR (125 MHz, CDCl$_3$): δ 176.8, 134.5, 131.8, 128.7, 126.6, 51.6, 40.0, 38.0, 35.5, 29.0, 28.4, 25.9. IR (neat, ATR): ν$_{max}$ 3067, 2928, 2872, 1736, 1435, 1198, 1168, 746, 693 cm$^{-1}$. HRMS (ESI-TOF): calc'd for C$_{17}$H$_{22}$O$_2$SK [M+K]$^+$ 329.0972, found 329.0965. R$_f$=0.41 (10% EtOAc/hexanes). Purification: (SiO$_2$, 2→5% EtOAc/hexanes). Note: 2D NMR spectra are consistent with the proposed structure of 5ha.

Example 15: Exemplary General Procedure for Aldehyde Synthesis

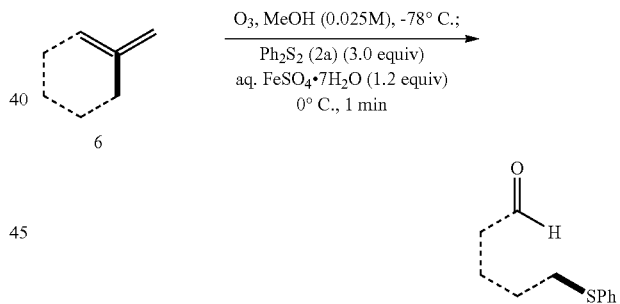

For example, a round-bottom flask equipped with a magnetic stirrer bar was charged with 6a (1.0 equiv) and MeOH (0.025 M), then cooled to −78° C. in a dry-ice/acetone bath while open to the air. Ozone was bubbled through the solution until complete consumption of the starting material (as indicated by TLC and/or a blue color in the reaction mixture). The solution was then sparged with argon for 5 min to expel excess ozone. Diphenyl disulfide (2a, 3.0 equiv) was added, and then the reaction mixture was warmed to 0° C. in an ice-water bath and stirred for 10 min. An aqueous solution (5%, wt/vol) of ferrous sulfate heptahydrate (1.2 equiv) was added over a period of approximately 1 min. Upon completion of the reaction (TLC), the mixture was diluted with water and transferred to a separatory funnel. The MeOH/water layer was extracted with dichloromethane (3×). The combined organic fractions were washed with brine, dried (anhydrous sodium sulfate), fil-

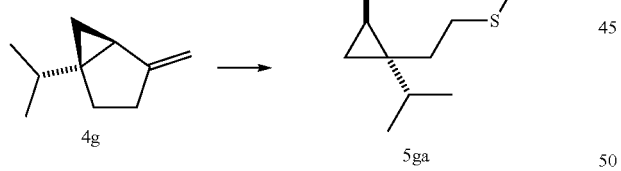

4g → 5ga

*1.0 mmol scale reaction

Yield: 74% (205 mg). Physical State: colorless oil. $^1$H NMR (500 MHZ, CDCl$_3$): δ 7.36-7.31 (m, 2H), 7.30-7.25 (m, 2H), 7.19-7.14 (m, 1H), 3.64 (s, 3H), 2.99 (ddd, J=12.5, 9.6, 7.0 Hz, 1H), 2.85 (ddd, J=12.5, 9.5, 6.9 Hz, 1H), 1.95-1.83 (m, 2H), 1.58 (dd, J=8.2, 5.7 Hz, 1H), 1.46 (sept, J=6.9 Hz, 1H), 1.11 (dd, J=5.3, 5.3 Hz, 1H), 0.94 (dd, J=8.3, 4.8 Hz, 1H), 0.92 (d, J=6.8 Hz, 3H), 0.88 (d, J=6.9 Hz, 3H). $^{13}$C NMR (125 MHZ, CDCl$_3$): δ 172.9, 136.7, 128.9, 128.7, 125.7, 51.6, 35.1, 33.9, 31.6, 28.0, 24.5, 19.4, 19.2, 18.8. IR (neat, ATR): ν$_{max}$ 3067, 2954, 2879, 1724, 1435, 1194, 1168, 739, 689 cm$^{-1}$. HRMS (ESI-TOF): calc'd for C$_{16}$H$_{23}$O$_2$S [M+H]$^+$ 279.1413, found 279.1371. R$_f$=0.48 (10% EtOAc/hexanes). Purification: (SiO$_2$, 0→5% Et$_2$O/pentane).

tered, and concentrated under reduced pressure. Purification through flash column chromatography (SiO$_2$) provided the thiylated aldehyde product 7aa. Any modification of the above procedure is described below with the specific entry. Note: Solid phenyl disulfide was ground to a fine powder prior to use.

6a

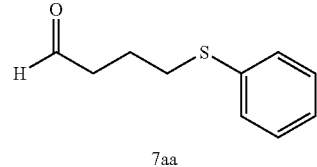

7aa

*1.0 mmol scale reaction

Yield: 67% (121 mg). Physical State: white solid. $^1$H NMR (500 MHZ, CDCl$_3$): δ 9.77 (t, J=1.3 Hz, 1H), 7.36-7.32 (m, 2H), 7.31-7.27 (m, 2H), 7.22-7.17 (m, 1H), 2.96 (t, J=7.1 Hz, 2H), 2.62 (dt, J=7.1, 1.3 Hz, 2H), 1.96 (tt, J=7.1, 7.1 Hz, 2H). $^{13}$C NMR (125 MHZ, CDCl$_3$): δ 201.4, 135.7, 129.3, 128.9, 126.1, 42.4, 32.9, 21.4. R$_f$=0.30 (10% EtOAc/hexanes). Purification: (SiO$_2$, 5→10% Et$_2$O/pentane).

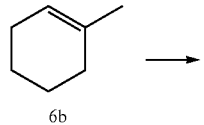

6b

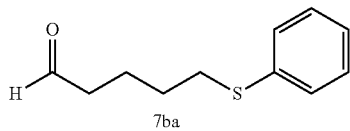

7ba

*1.0 mmol scale reaction

Yield: 63% (122 mg). Physical State: white solid. $^1$H NMR (500 MHZ, CDCl$_3$): δ 9.75 (t, J=1.6 Hz, 1H), 7.35-7.31 (m, 2H), 7.30-7.26 (m, 2H), 7.21-7.16 (m, 1H), 2.93 (t, J=7.1 Hz, 2H), 2.45 (dt, J=7.1, 1.6 Hz, 2H), 1.82-1.73 (m, 2H), 1.72-1.64 (m, 2H). $^{13}$C NMR (125 MHZ, CDCl$_3$): δ 201.9, 136.3, 129.1, 128.8, 125.9, 43.2, 33.3, 28.4, 21.0. R$_f$=0.30 (10% EtOAc/hexanes). Purification: (SiO$_2$, 2→5% EtOAc/hexanes).

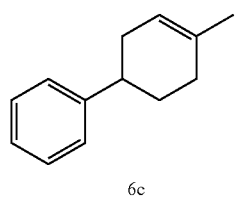

6c

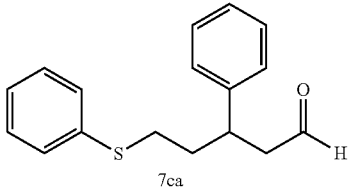

7ca

*1.0 mmol scale reaction

Yield: 75% (203 mg). Physical State: white solid. $^1$H NMR (500 MHZ, CDCl$_3$): δ 9.64 (dd, J=1.9, 1.9 Hz, 1H), 7.35-7.30 (m, 2H), 7.28-7.14 (m, 8H), 3.44-3.35 (m, 1H), 2.84-2.66 (m, 4H), 2.04-1.89 (m, 2H). $^{13}$C NMR (125 MHZ, CDCl$_3$): δ 201.1, 142.3, 136.0, 129.0, 128.8, 128.8, 127.5, 126.9, 125.9, 50.2, 38.8, 35.6, 31.0. MP: 58-59° C. IR (neat, ATR): ν$_{max}$ 3052, 3030, 2931, 2822, 2721, 1724, 743, 697 cm$^{-1}$. HRMS (ESI-TOF): calc'd for C$_{17}$H$_{19}$OS [M+H]$^+$ 271.1151, found 271.1149. R$_f$=0.33 (10% EtOAc/hexanes). Purification: (SiO$_2$, 2→5% EtOAc/hexanes).

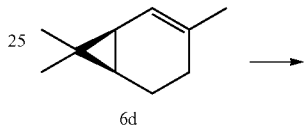

6d

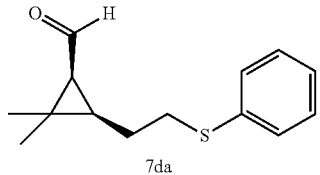

7da

*1.0 mmol scale reaction

Yield: 65% (152 mg). Physical State: colorless oil. $^1$H NMR (500 MHZ, CDCl$_3$): δ 9.51 (d, J=5.6 Hz, 1H), 7.36-7.31 (m, 2H), 7.31-7.27 (m, 2H), 7.21-7.16 (m, 1H), 3.01-2.89 (m, 2H), 2.14-2.00 (m, 2H), 1.66 (dd, J=8.6, 5.6 Hz, 1H), 1.52 (dd, J=15.9, 7.5 Hz, 1H), 1.29 (s, 3H), 1.19 (s, 3H). $^{13}$C NMR (125 MHz, CDCl$_3$): δ 201.4, 136.2, 129.0, 128.8, 125.9, 38.4, 36.5, 33.6, 30.0, 28.8, 24.1, 15.0. IR (neat, ATR): ν$_{max}$ 3063, 2954, 2921, 2872, 2737, 1690, 739, 693 cm$^{-1}$. Optical Rotation: [α]$_D^{23.1}$ 41.8 (c 1.00, CHCl$_3$). HRMS (ESI-TOF): calc'd for C$_{14}$H$_{18}$OSK [M+K]$^+$ 273.0710, found 273.0712. R$_f$=0.39 (10% EtOAc/hexanes). Purification: (SiO$_2$, 5→10% Et$_2$O/pentane).

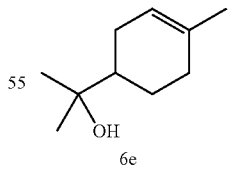

6e

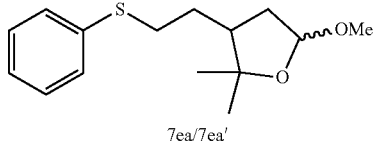

7ea/7ea'

*1.0 mmol scale reaction

Combined Yield: 42% (105 mg, inseparable mixture). Diastereomeric Ratio: 1.2:1. Physical State: colorless oil. $^1$H NMR (500 MHZ, CDCl$_3$) major: δ 7.35-7.27 (m, 4H), 7.22-7.16 (m, 1H), 4.88 (d, J=4.9 Hz, 1H), 3.32 (s, 3H), 3.0-2.92 (m, 1H), 2.91-2.84 (m, 1H), 2.31-2.22 (m, 1H), 2.11 (dd, J=12.5, 6.6 Hz, 1H), 1.77-1.52 (m, 3H), 1.32 (s, 3H), 1.01 (s, 3H). 1H NMR (500 MHz, CDCl$_3$) minor: δ 7.35-7.27 (m, 4H), 7.22-7.16 (m, 1H), 4.97 (dd, J=6.1, 4.5 Hz, 1H), 3.35 (s, 3H), 3.03-2.92 (m, 1H), 2.91-2.78 (m, 1H), 2.50-2.42 (m, 1H), 1.99 (dddd, J=10.7, 10.7, 8.5, 3.9 Hz, 1H), 1.77-1.52 (m, 3H), 1.23 (s, 3H), 1.12 (s, 3H). $^{13}$C NMR (125 MHZ, CDCl$_3$) major: δ 136.2, 129.0, 128.8, 125.9, 102.9, 83.6, 54.1, 44.9, 38.6, 32.8, 29.6, 23.5. $^{13}$C NMR (125 MHz, CDCl$_3$) minor: δ 136.1, 129.2, 128.8, 126.0, 104.2, 82.8, 55.3, 47.2, 38.7, 32.8, 29.7, 27.9, 23.0. IR (neat, ATR): $v_{max}$ 3063, 2973, 2928, 2830, 1096, 1032, 968, 735, 686 cm$^{-1}$ HRMS (ESI-TOF): calc'd for C$_{15}$H$_{22}$O$_2$SK [M+K]$^+$ 305.0972, found 305.0964. R$_f$=0.40 (10% EtOAc/hexanes). Purification: (SiO$_2$, 2→6% EtOAc/hexanes). Note: Solid ferrous sulfate heptahydrate was added at room temperature.

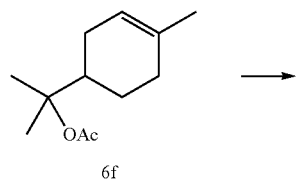

6f

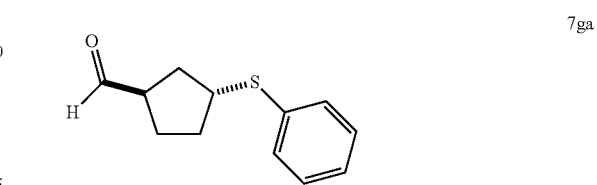

7fa

*1.0 mmol scale reaction

Yield: 61% (179 mg). Physical State: colorless oil. $^1$H NMR (500 MHZ, CDCl$_3$): δ 9.72 (dd, J=2.8, 1.7 Hz, 1H), 7.37-7.27 (m, 4H), 7.22-7.17 (m, 1H), 3.03 (ddd, J=13.1, 9.1, 4.7 Hz, 1H), 2.86 (ddd, J=13.0, 8.8, 7.4 Hz, 1H), 2.69-2.62 (m, 1H), 2.55 (ddd, J=16.8, 6.7, 2.9 Hz, 1H), 2.32 (ddd, J=16.8, 5.3, 1.7 Hz, 1H), 1.91 (s, 3H), 1.85 (dddd, J=13.9, 9.3, 7.3, 2.8 Hz, 1H), 1.54-1.47 (m, 1H), 1.46 (s, 3H), 1.38 (s, 3H). $^{13}$C NMR (125 MHz, CDCl$_3$): δ 201.4, 169.9, 135.6, 129.3, 128.9, 126.2, 84.0, 44.7, 41.7, 32.1, 29.8, 23.9, 22.2, 22.0. IR (neat, ATR): $v_{max}$ 3056, 2939, 2830, 2729, 1724, 1370, 1247, 1134, 1024, 735, 693 cm$^{-1}$. HRMS (ESI-TOF): calc'd for C$_{16}$H$_{22}$O$_3$SNa [M+Na]$^+$ 317.1182, found 317.1166. R$_f$=0.38 (20% EtOAc/hexanes). Purification: (SiO$_2$, 5→15% EtOAc/hexanes).

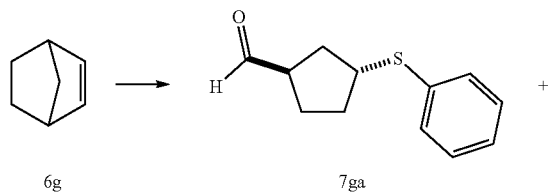

6g  7ga

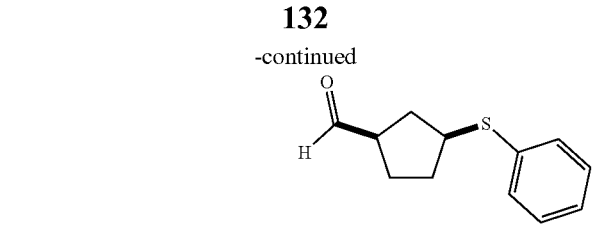

7ga'

*1.0 mmol scale reaction

Combined Yield: 50% (102 mg). Diastereomeric Ratio: 1.2:1 (determined from $^1$H NMR spectrum of the crude products). Note: 2D NMR spectra are consistent with the proposed structures of 7ga/7ga'.

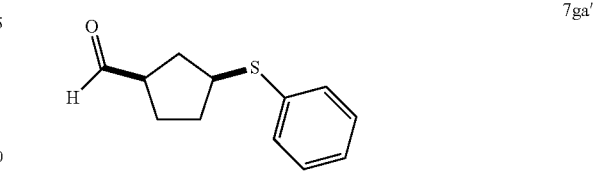

7ga

Yield: 27% (56 mg). Physical State: colorless oil. $^1$H NMR (500 MHZ, CDCl$_3$): δ 9.67 (d, J=1.7 Hz, 1H), 7.39-7.35 (m, 2H), 7.32-7.27 (m, 2H), 7.24-7.19 (m, 1H), 3.69-3.62 (m, 1H), 3.10-3.02 (m, 1H), 2.35 (ddd, J=13.7, 6.8, 6.8 Hz, 1H), 2.15-2.02 (m, 2H), 1.98-1.90 (m, 1H), 1.87 (ddd, J=14.0, 8.7, 5.4 Hz, 1H), 1.77-1.68 (m, 1H). $^{13}$C NMR (125 MHz, CDCl$_3$): δ 202.5, 135.8, 130.1, 128.8, 126.5, 50.3, 45.9, 33.1, 32.6, 24.9. IR (neat, ATR): $v_{max}$ 3056, 2958, 2856, 2717, 1716, 1476, 1435, 739, 689 cm$^{-1}$. HRMS (ESI-TOF): calc'd for C$_{12}$H$_{14}$OSK [M+K]$^+$ 245.0397, found 245.0418. R$_f$=0.39 (10% EtOAc/hexanes). Purification: (SiO$_2$, 2→3% EtOAc/hexanes).

7ga'

Yield: 23% (46 mg). Physical State: colorless oil. $^1$H NMR (500 MHZ, CDCl$_3$): δ 9.66 (d, J=2.2 Hz, 1H), 7.40-7.35 (m, 2H), 7.32-7.27 (m, 2H), 7.25-7.20 (m, 1H), 3.71-3.62 (m, 1H), 2.85-2.76 (m, 1H), 2.30 (ddd, J=13.8, 9.0, 6.9 Hz, 1H), 2.19-2.03 (m, 2H), 2.01-1.88 (m, 2H), 1.77-1.68 (m, 1H). $^{13}$C NMR (125 MHz, CDCl$_3$): δ 202.8, 135.6, 131.0, 128.8, 126.6, 50.6, 46.4, 34.0, 32.8, 25.1. IR (neat, ATR): $v_{max}$ 3060, 2947, 2864, 2713, 1716, 1476, 1439, 1093, 1028, 743, 693 cm$^{-1}$. HRMS (ESI-TOF): calc'd for C$_{12}$H$_{14}$OSK [M+K]$^+$ 245.0397, found 245.0409. R$_f$=0.33 (10% EtOAc/hexanes). Purification: (SiO$_2$, 2→3% EtOAc/hexanes).

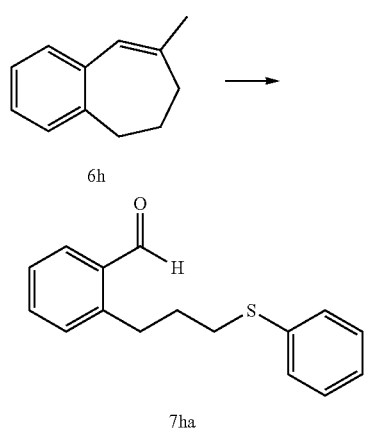

6h

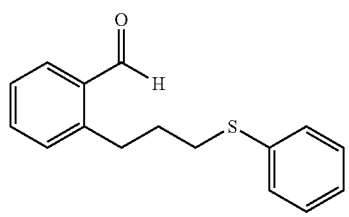

7ha                    7ha'

*1.0 mmol scale reaction

Combined Yield: 95% (144 mg).

7ha

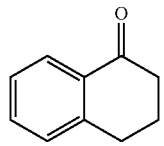

Yield: 5% (12 mg). Physical State: colorless oil. $^1$H NMR (500 MHZ, CDCl$_3$): δ 10.22 (s, 1H), 7.81 (dd, J=7.7, 1.3 Hz, 1H), 7.50 (ddd, J=7.5, 7.5, 1.5 Hz, 1H), 7.38 (ddd, J=7.5, 7.5, 1.0 Hz, 1H), 7.35-7.31 (m, 2H), 7.30-7.26 (m, 3H), 7.20-7.15 (m, 1H), 3.18 (t, J=7.7 Hz, 2H), 2.98 (t, J=7.2 Hz, 2H), 2.00-1.91 (m, 2H). $^{13}$C NMR (125 MHz, CDCl$_3$): δ 192.5, 144.1, 136.3, 133.8, 133.8, 132.8, 131.2, 129.2, 128.9, 126.8, 125.9, 33.1, 31.5, 31.1. IR (neat, ATR): $v_{max}$ 3063, 2928, 2860, 2739, 1694, 739, 693 cm$^{-1}$. HRMS (ESI-TOF): calc'd for C$_{16}$H$_{16}$OSK [M+K]$^+$ 295.0553, found 295.0566. R$_f$=0.51 (10% EtOAc/hexanes). Purification: (SiO$_2$, 2→6% EtOAc/hexanes).

7ha'

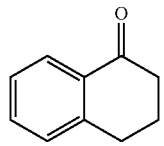

Yield: 90% (132 mg). Physical State: colorless oil. $^1$H NMR (500 MHZ, CDCl$_3$): δ 8.03 (dd, J=7.8, 1.0 Hz, 1H), 7.46 (ddd, J=7.5, 7.5, 1.4 Hz, 1H), 7.33-7.27 (m, 1H), 7.26-7.23 (m, 1H), 2.96 (t, J=6.1 Hz, 2H), 2.65 (t, J=6.6 Hz, 2H), 2.18-2.10 (m, 2H). $^{13}$C NMR (125 MHZ, CDCl$_3$): δ 198.3, 144.4, 133.3, 132.5, 128.7, 127.0, 126.5, 39.1, 29.6, 23.2. R$_f$=0.43 (10% EtOAc/hexanes). Purification: (SiO$_2$, 2→6% EtOAc/hexanes). All characterization data are consistent with that reported in the literature. Note: A proposed mechanism for the formation of 7ha' is provided below.

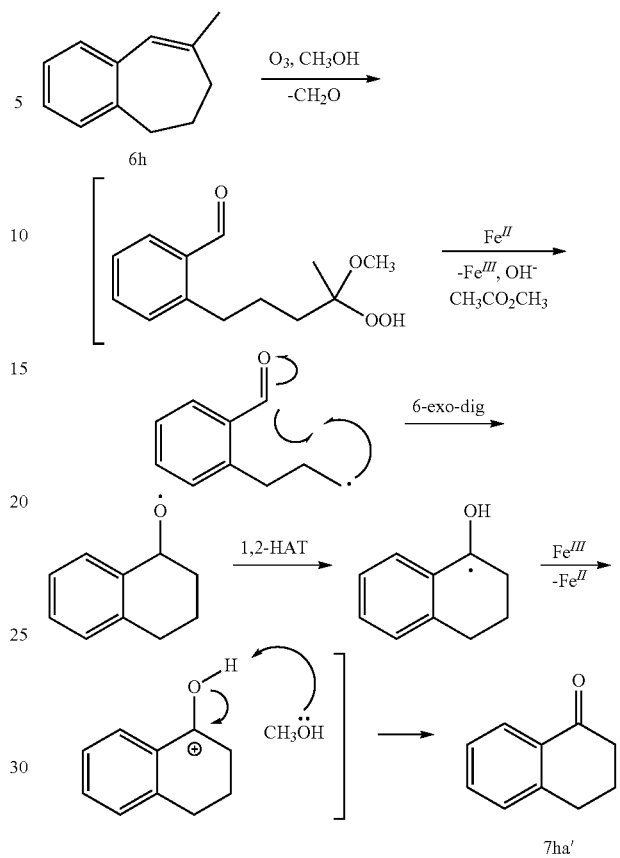

Proposed mechanism for the formation of 7ha'.

Example 16: Exemplary General Procedure for Oxidation to Sulfones

General Procedure A for Oxidation to Sulfones

For example, a round-bottom flask equipped with a magnetic stirrer bar was charged with 3qa (1.0 equiv) and dichloromethane (0.1 M). mCPBA (2.5 equiv) was added in four portions over a period of 10 min at room temperature. The mixture was stirred until complete conversion to the sulfone had occurred (TLC; typically <1 h). Upon its completion, the reaction was quenched through the addition of saturated aqueous sodium thiosulfate. The mixture was poured into saturated aqueous sodium bicarbonate and extracted with dichloromethane (3×). The combined organic fractions were washed with brine, dried, filtered, and concentrated under reduced pressure. The sulfone was purified through flash column chromatography (SiO$_2$) to yield 8.

General Procedure B for Oxidation to Sulfones

For example, a round-bottom flask equipped with a magnetic stirrer bar was charged with the 3ma (1.0 equiv) and MeOH (0.25 M), then cooled to 0° C. in an ice-water bath. A solution of Oxone (3.0 equiv) in water (0.75 M) was added. The cloudy mixture was warmed to room temperature and stirred until complete conversion to the sulfone had occurred (TLC). The mixture was diluted with water and extracted with dichloromethane (3×). The combined organic fractions were washed with water, brine, dried (anhydrous sodium sulfate), filtered, and concentrated under reduced pressure. The sulfone was purified through flash column chromatography (SiO$_2$) to yield SI-XII. Note: Upon addition of Oxone, the thioether was immediately oxidized to the sulfoxides (a mixture of diastereoisomers; the most polar components on TLC). Once the mixture had been warmed to room temperature, both of the sulfoxides had been converted to the sulfone (medium-polarity component on TLC).

Synthesis of Sulfone 8

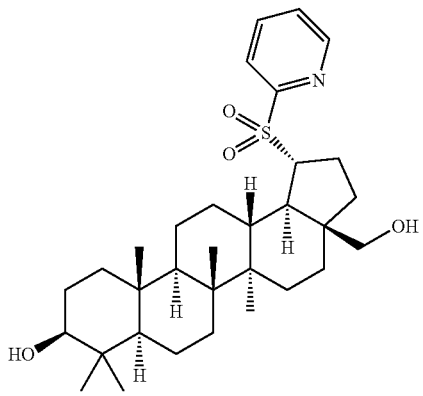

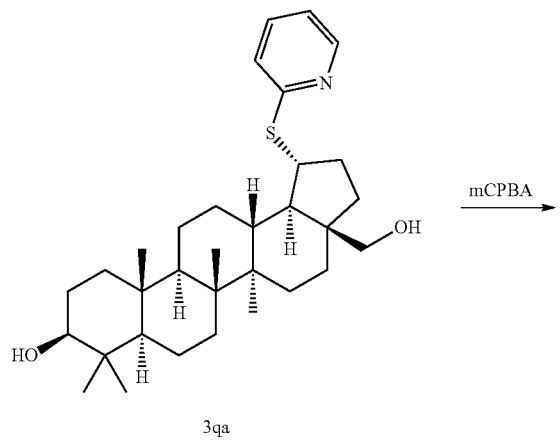

*0.5 mmol scale reaction (from 1q)

Yield: 43% from 1q (116 mg). Physical State: white solid. $^1$H NMR (500 MHZ, CDCl$_3$): δ 8.72 (ddd, J=4.7, 1.6, 0.8 Hz, 1H), 8.07 (ddd, J=7.8, 0.9, 0.9 Hz, 1H), 7.93 (ddd, J=7.7, 7.7, 1.7 Hz, 1H), 7.50 (ddd, J=7.6, 4.7, 1.1 Hz, 1H), 3.92 (ddd, J=10.0, 10.0, 4.1 Hz, 1H), 3.85 (d, J=11.0 Hz, 1H), 3.23 (d, J=10.3 Hz, 1H), 3.20 (dd, J=11.4, 4.7 Hz, 1H), 2.35 (dd, J=11.8, 10.2 Hz, 1H), 1.96-0.86 (m, 24H), 1.05 (s, 3H), 1.04 (s, 3H), 0.97 (s, 3H), 0.83 (s, 3H), 0.76 (s, 3H), 0.73-0.67 (m, 1H). $^{13}$C NMR (125 MHz, CDCl$_3$): δ 158.8, 150.3, 137.9, 126.8, 122.0, 78.9, 61.2, 60.5, 55.1, 50.0, 49.5, 47.8, 43.3, 41.2, 38.9, 38.6, 37.1, 35.4, 34.3, 32.8, 29.3, 28.0, 28.0, 28.0, 27.4, 26.8, 20.9, 18.3, 16.1, 16.0, 15.4, 14.8. MP: 258° C. (decomp). IR (neat, ATR): $v_{max}$ 3410, 3004, 2943, 2872, 1299, 1036, 739 cm$^{-1}$. Optical Rotation: $[α]_D^{23.2}$ −6.4 (c 0.50, CHCl$_3$). HRMS (ESI-TOF): calc'd for C$_{32}$H$_{50}$NO$_4$S [M+H]$^+$ 544.3455, found 544.3455. R$_f$=0.32 (50% EtOAc/hexanes). Purification: (SiO$_2$, 30→60% EtOAc/hexanes).

Synthesis of Sulfone 9

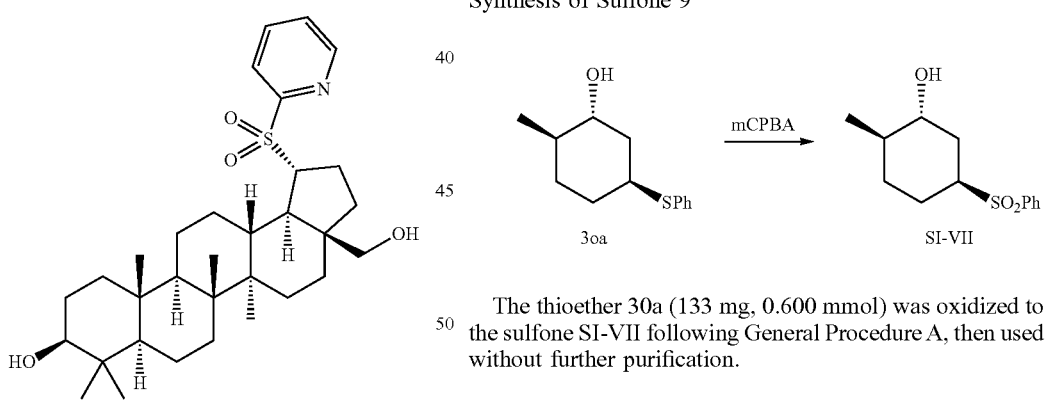

The thioether 30a (133 mg, 0.600 mmol) was oxidized to the sulfone SI-VII following General Procedure A, then used without further purification.

The thioether 3qa was oxidized to the sulfone 8 following General Procedure A. To verify the structure of the product, approximately 5 mg of 8 was placed in a small crystallization tube and dissolved in a minimal amount of dichloromethane. This vial was placed within a larger 4-mL vial containing approximately 1 mL of pentane. The outer vial was capped and sealed with Teflon and Parafilm. After 3 days, single crystals suitable for X-ray diffraction had formed.

SI-VII

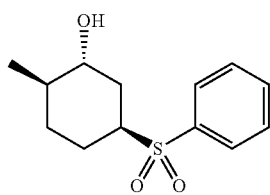

*0.6 mmol scale reaction

Physical State: white solid. $^1$H NMR (500 MHZ, CDCl$_3$): δ 7.91-7.84 (m, 2H), 7.67-7.61 (m, 1H), 7.60-7.52 (m, 2H), 3.92-3.86 (m, 1H), 3.35 (dddd, J=10.0, 10.0, 4.7, 4.7 Hz, 1H), 1.96 (ddd, J=13.7, 10.6, 3.1 Hz, 1H), 1.91-1.68 (m, 6H), 1.54-1.46 (m, 1H), 0.94 (d, J=7.1 Hz, 3H). $^{13}$C NMR (125 MHZ, CDCl$_3$): δ 137.4, 133.5, 129.0, 128.7, 70.4, 58.7, 34.4, 27.7, 25.1, 20.0, 16.3. MP: 122-124° C. IR (neat, ATR): $v_{max}$ 3500, 2949, 2932, 2876, 1444, 1297, 1143, 725, 689, 590 cm$^{-1}$. Optical Rotation: $[α]_D^{23.2}$ −8.6 (c 1.00, CHCl$_3$). HRMS (ESI-TOF): calc'd for C$_{13}$H$_{18}$O$_3$SNa [M+Na]$^+$ 277.0869, found 277.0860. R$_f$=0.45 (50% EtOAc/hexanes).

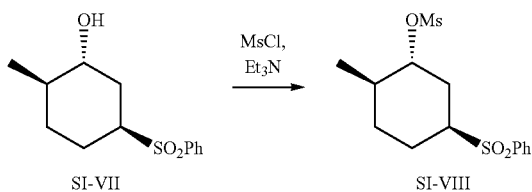

A round-bottom flask equipped with a magnetic stirrer bar was charged with the sulfone SI-VII (153 mg, 0.600 mmol, 1.0 equiv) and anhydrous dichloromethane (0.1 M), then cooled to 0° C. in an ice-water bath. Triethylamine (126 μL, 0.900 mmol, 1.5 equiv) was added, followed by dropwise addition of methanesulfonyl chloride (70.0 μL, 0.900 mmol, 1.5 equiv). The mixture was warmed to room temperature and stirred until complete conversion to the mesylate had occurred (TLC, ca. 30 min). Upon completion of the reaction, the mixture was diluted with water and extracted with dichloromethane (3×). The combined organic fractions were washed with brine, dried (anhydrous sodium sulfate), filtered, and concentrated under reduced pressure. The crude product was filtered through a short silica (SiO$_2$) plug to give the mesylate SI-VIII, which was used without further purification.

SI-VIII

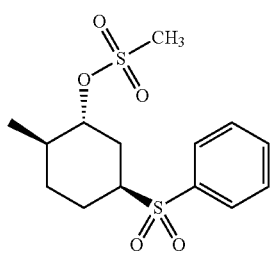

*0.6 mmol scale reaction

Physical State: colorless oil. $^1$H NMR (500 MHZ, CDCl$_3$): δ 7.93-7.86 (m, 2H), 7.72-7.64 (m, 1H), 7.63-7.55 (m, 2H), 4.88-4.81 (m, 1H), 3.31-3.22 (m, 1H), 2.98 (s, 3H), 2.17-2.03 (m, 3H), 1.97-1.87 (m, 1H), 1.87-1.72 (m, 2H), 1.68-1.59 (m, 1H), 1.02 (d, J=7.2 Hz, 3H). $^{13}$C NMR (125 MHZ, CDCl$_3$): δ 136.8, 133.9, 129.2, 128.8, 81.5, 58.5, 38.5, 32.9, 26.6, 25.5, 19.7, 16.1. IR (neat, ATR): $v_{max}$ 2972, 2940, 1345, 1301, 1174, 1147, 928, 901 cm$^{-1}$. Optical Rotation: $[α]_D^{23.4}$ −16.4 (c 1.00, CHCl$_3$). HRMS (ESI-TOF): calc'd for C$_{14}$H$_{20}$OsS2Na [M+Na]$^+$ 355.0644, found 355.0630. R$_f$=0.56 (50% EtOAc/hexanes).

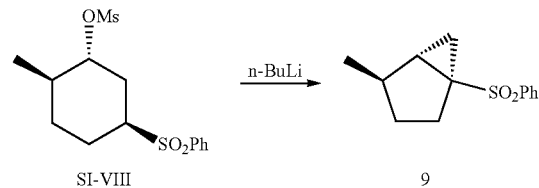

A flame-dried round-bottom flask equipped with a magnetic stirrer bar was charged under argon protection with the mesylate SI-VIII (200 mg, 0.600 mmol, 1.0 equiv) and anhydrous THF (0.1 M), then cooled to −20° C. in a NaCl/ice bath. n-Butyllithium (2.3 M, 391 μL, 0.900 mmol, 1.5 equiv) was added dropwise. Once the starting material had been consumed (TLC), the reaction was quenched through the addition of saturated aqueous ammonium chloride. The aqueous layer was extracted with dichloromethane (3×). The combined organic fractions were washed with brine, dried (anhydrous sodium sulfate), filtered, and concentrated under reduced pressure. Purification through flash column chromatography (SiO$_2$) provided the sulfone 9. Note: The mesylate SI-VIII was azeotroped with benzene three times prior to use.

9

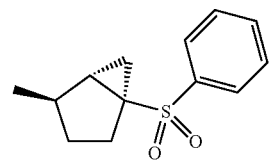

*0.6 mmol scale reaction

Yield: 85% from 30a (121 mg). Physical State: white solid. $^1$H NMR (500 MHZ, CDCl$_3$): δ 7.91-7.85 (m, 2H), 7.65-7.60 (m, 1H), 7.57-7.50 (m, 2H), 2.20-2.10 (m, 2H), 1.95 (dd, J=9.0, 5.1 Hz, 1H), 1.71 (dd, J=12.4, 7.9 Hz, 1H), 1.65 (ddd, J=9.0, 5.6, 1.2 Hz, 1H), 1.46-1.31 (m, 2H), 0.95 (dd, J=5.3, 5.3 Hz, 1H), 0.80 (d, J=7.0 Hz, 3H). $^{13}$C NMR (125 MHZ, CDCl$_3$): δ 139.2, 133.1, 128.8, 128.2, 48.0, 33.5, 33.4, 28.7, 25.0, 20.5, 14.2. MP: 52-53° C. IR (neat, ATR): $v_{max}$ 3067, 2958, 2879, 1299, 1138, 1085, 723, 686, 592, 558 cm$^{-1}$. Optical Rotation: $[α]_D^{23.4}$ −2.5 (c 1.00, CHCl$_3$). HRMS (DART): calc'd for C$_{13}$H$_{17}$O$_2$S [M+H]$^+$ 237.0944, found 237.0930. R$_f$=0.32 (10% EtOAc/hexanes). Purification: (SiO$_2$, 5→10% EtOAc/hexanes). Note: The sulfone 9 was also synthesized in 78% overall yield starting from a mixture of the thioethers 3oa/3oa □(2:1 d.r.) by following the procedures given above.

Synthesis of Sulfone 10

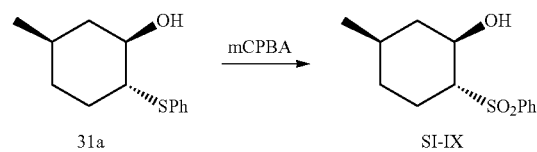

The thioether 3la (111 mg, 0.500 mmol) was oxidized to the sulfone SI-IX following General Procedure A, then used without further purification.

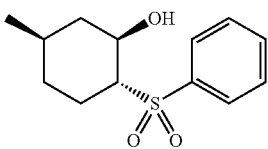

SI-IX

*0.5 mmol scale reaction

Physical State: white solid. $^1$H NMR (500 MHz, CDCl$_3$): δ 7.95-7.87 (m, 2H), 7.73-7.66 (m, 1H), 7.64-7.56 (m, 2H), 4.13 (br s, 1H), 3.96 (ddd, J=10.3, 10.3, 4.8 Hz, 1H), 2.94 (ddd, J=12.9, 9.5, 3.7 Hz, 1H), 2.14-2.04 (m, 1H), 1.88 (dddd, J=13.3, 3.6, 3.6, 3.6 Hz, 1H), 1.71-1.62 (m, 1H), 1.46-1.34 (m, 1H), 1.33 (ddd, J=26.2, 13.2, 3.9 Hz, 1H), 1.07 (q, J=12.1 Hz, 1H), 0.89 (d, J=6.6 Hz, 3H), 0.86 (ddd, J=25.4, 13.6, 3.5 Hz, 1H). $^{13}$C NMR (125 MHZ, CDCl$_3$): δ 136.7, 134.0, 129.1, 128.9, 68.6, 67.8, 42.4, 32.7, 30.1, 25.3, 21.4. MP: 101-102° C. IR (neat, ATR): $\nu_{max}$ 3500, 3067, 2954, 2928, 2864, 1445, 1291, 1134, 1081, 610 cm$^{-1}$. Optical Rotation: $[\alpha]_D^{23.5}$ −15.5 (c 1.00, CHCl$_3$). HRMS (ESI-TOF): calc'd for C$_{13}$H$_{18}$O$_3$SNa [M+Na]$^+$ 277.0869, found 277.0850. R$_f$=0.42 (30% EtOAc/hexanes).

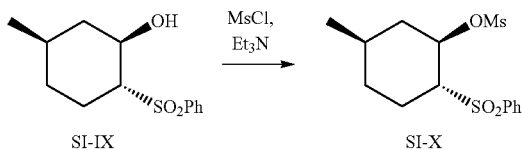

SI-IX      SI-X

A round-bottom flask equipped with a magnetic stirrer bar was charged with the sulfone SI-IX (127 mg, 0.500 mmol, 1.0 equiv) and anhydrous dichloromethane (0.1 M), then cooled to 0° C. in an ice-water bath. Triethylamine (105 μL, 0.750 mmol, 1.5 equiv) was added, followed by dropwise addition of methanesulfonyl chloride (58 μL, 0.750 mmol, 1.5 equiv). The mixture was warmed to room temperature and stirred until complete conversion to the mesylate had occurred (TLC, ca. 30 min). The mixture was diluted with water and extracted with dichloromethane (3×). The combined organic fractions were washed with brine, dried (anhydrous sodium sulfate), filtered, and concentrated under reduced pressure. The crude product was filtered through a short silica (SiO$_2$) plug to give the mesylate SI-X, which was used without further purification.

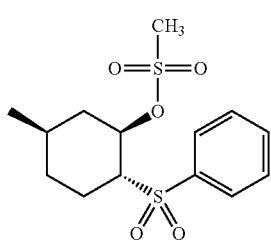

SI-X

*0.5 mmol scale reaction

Physical State: white solid. $^1$H NMR (500 MHZ, CDCl$_3$): δ 7.93-7.86 (m, 2H), 7.71-7.65 (m, 1H), 7.63-7.56 (m, 2H), 4.99 (ddd, J=10.7, 10.7, 4.7 Hz, 1H), 3.24 (ddd, J=12.9, 10.2, 4.1 Hz, 1H), 3.09 (s, 3H), 2.47 (dddd, J=12.7, 4.9, 3.0, 2.0 Hz, 1H), 1.79 (dq, J=13.5, 3.7 Hz, 1H), 1.73-1.65 (m, 1H), 1.58-1.49 (m, 1H), 1.46 (dq, J=13.3, 3.9 Hz, 1H), 1.37 (q, J=12.1 Hz, 1H), 0.92 (d, J=6.5 Hz, 3H), 0.87 (dq, J=11.9, 3.7 Hz, 1H). $^{13}$C NMR (125 MHZ, CDCl$_3$): δ 138.0, 133.9, 129.2, 128.5, 77.7, 65.1, 41.9, 39.1, 32.2, 30.4, 26.2, 21.1. MP: 180-182° C. IR (neat, ATR): $\nu_{max}$ 3028, 2953, 2932, 2873, 1349, 1305, 1178, 1143, 944, 749, 607 cm$^{-1}$. Optical Rotation: $[\alpha]_D^{23.5}$ −42.5 (c 1.00, CHCl$_3$). HRMS (ESI-TOF): calc'd for C$_{14}$H$_{20}$O$_5$S$_2$Na [M+Na]$^+$ 355.0644, found 355.0649. R$_f$=0.30 (30% EtOAc/hexanes).

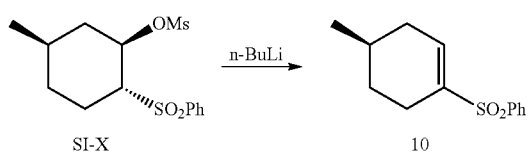

SI-X      10

A flame-dried round-bottom flask equipped with a magnetic stirrer bar under argon protection was charged with the mesylate SI-X (166 mg, 0.500 mmol, 1.0 equiv) and anhydrous THF (0.1 M), then cooled to −78° C. in a dry-ice/acetone bath. n-Butyllithium (2.3 M, 261 μL, 0.600 mmol, 1.2 equiv) was added dropwise. After stirring for 20 min, the mixture was warmed to room temperature and stirred until the starting material had been consumed (TLC). The reaction was quenched through the addition of half-saturated aqueous ammonium chloride. The aqueous phase was extracted with dichloromethane (3×). The combined organic fractions were washed with brine, dried (anhydrous sodium sulfate), filtered, and concentrated under reduced pressure. Purification through flash column chromatography (SiO$_2$) provided the sulfone 10. Note: The mesylate SI-X was azeotroped with benzene three times prior to use.

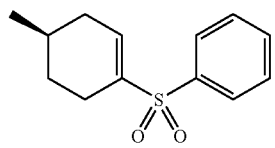

10

*0.5 mmol scale reaction

Yield: 96% from 3la (112 mg). Physical State: colorless oil. $^1$H NMR (500 MHZ, CDCl$_3$): δ 7.90-7.83 (m, 2H), 7.63-7.57 (m, 1H), 7.57-7.49 (m, 2H), 7.07-7.01 (m, 1H), 2.44-2.34 (m, 1H), 2.34-2.24 (m, 1H), 2.19-2.08 (m, 1H), 1.85 (ddddd, J=19.1, 9.5, 3.9, 2.7, 2.7 Hz, 1H), 1.80-1.72 (m, 1H), 1.69-1.60 (m, 1H), 1.28-1.16 (m, 1H), 0.95 (d, J=6.7 Hz, 3H). $^{13}$C NMR (125 MHz, CDCl$_3$): δ 139.4, 139.4, 138.1, 133.0, 128.9, 127.9, 33.6, 29.8, 27.0, 22.8, 20.9. IR (neat, ATR): $\nu_{max}$ 3063, 2954, 2928, 2875, 1307, 1288, 1148, 1081, 915, 735, 719, 686, 618, 569 cm$^{-1}$. Optical Rotation: $[\alpha]_D^{23.5}$ 53.3 (c 1.00, CHCl$_3$). HRMS (ESI-TOF): calc'd for C$_{13}$H$_{16}$O$_2$SNa [M+Na]$^+$ 259.0763, found 259.0774. R$_f$=0.33 (10% EtOAc/hexanes). Purification: (SiO$_2$, 10% EtOAc/hexanes). Note: The silyl ether SI-XI also underwent elimination to provide the sulfone 10 in 95% yield from 3la.

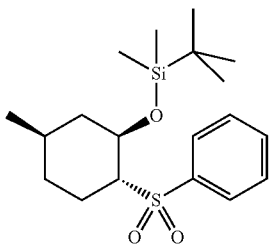

SI-XI

Physical State: white solid. ¹H NMR (500 MHZ, CDCl₃): δ 7.90-7.83 (m, 2H), 7.62-7.56 (m, 1H), 7.55-7.48 (m, 2H), 4.17 (ddd, J=10.7, 9.5, 4.5 Hz, 1H), 3.09 (ddd, J=12.9, 9.3, 3.6 Hz, 1H), 2.04-1.97 (m, 1H), 1.74-1.63 (m, 2H), 1.51-1.38 (m, 1H), 1.10 (dd, J=23.6, 12.4 Hz, 1H), 0.94-0.78 (m, 2H), 0.90 (d, J=6.6 Hz, 3H), 0.86 (s, 9H), 0.12 (s, 3H), 0.04 (s, 3H). ¹³C NMR (125 MHz, CDCl₃): δ 140.2, 132.8, 128.8, 127.9, 70.2, 68.3, 44.6, 32.8, 30.4, 25.8, 21.5, 18.0, −4.1, −4.2. MP: 54-56° C. IR (neat, ATR): $\nu_{max}$ 3063, 2954, 2928, 2852, 1303, 1145, 829, 780, 607 cm⁻¹. Optical Rotation: $[\alpha]_D^{23.5}$ −45.6 (c 1.00, CHCl₃). HRMS (ESI-TOF): calc'd for C₁₉H₃₂O₃SSiNa [M+Na]⁺ 391.1734, found 391.1759. $R_f$=0.42 (10% EtOAc/hexanes).

Synthesis of Ketals 11/11' and the Lactone 12

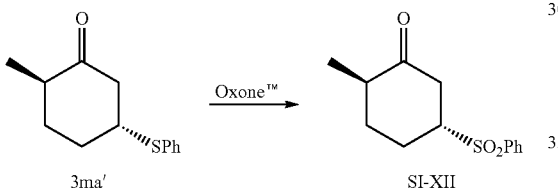

3ma'    SI-XII

The thioether 3ma (528 mg, 2.40 mmol) was oxidized to the sulfone SI-XII following General Procedure B.

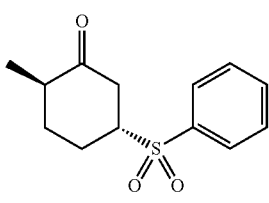

SI-XII

*2.4 mmol scale reaction

Yield: 94% (569 mg). Physical State: white solid. ¹H NMR (500 MHZ, CDCl₃): δ 7.92-7.83 (m, 2H), 7.73-7.65 (m, 1H), 7.64-7.55 (m, 2H), 3.27 (dddd, J=12.5, 8.8, 8.8, 3.7 Hz, 1H), 2.58 (d, J=9.4 Hz, 2H), 2.38 (sept, J=6.4 Hz, 1H), 2.33-2.26 (m, 1H), 2.21 (dddd, J=13.7, 5.8, 3.5, 3.5 Hz, 1H), 2.00 (dddd, J=13.0, 13.0, 13.0, 3.7 Hz, 1H), 1.34 (dddd, J=13.3, 13.3, 13.3, 3.5 Hz, 1H), 1.01 (d, J=6.5 Hz, 3H). ¹³C NMR (125 MHz, CDCl₃): δ 207.8, 136.6, 134.1, 129.3, 128.8, 62.9, 44.3, 40.4, 32.5, 24.0, 13.9. MP: 146-148° C. IR (neat, ATR): $\nu_{max}$ 2977, 2931, 2872, 1709, 1281, 1257, 1141 cm⁻¹. Optical Rotation: $[\alpha]_D^{23.6}$ 66.1 (c 1.00, CHCl₃). HRMS (ESI-TOF): calc'd for C₁₃H₁₆O₃SNa [M+Na]⁺ 275.0712, found 275.0721. $R_f$=0.43 (30% EtOAc/hexanes). Purification: (SiO₂, 20→30% EtOAc/hexanes).

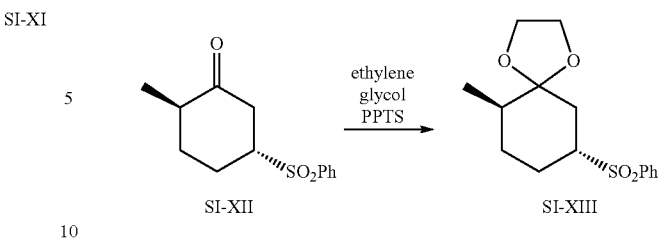

SI-XII    SI-XIII

A round-bottom flask equipped with a magnetic stirrer bar was charged with the sulfone SI-XII (252 mg, 1.00 mmol, 1.0 equiv), pyridinium p-toluenesulfonate (38.0 mg, 0.15 mmol, 0.15 equiv), ethylene glycol (168 μL, 3.00 mmol, 3.0 equiv), and anhydrous benzene (0.1 M). The mixture was heated under reflux for 4 h using a Dean-Stark apparatus. Upon completion of the reaction (TLC), the mixture was cooled, poured into saturated aqueous sodium bicarbonate, and extracted with EtOAc (3×). The combined organic fractions were washed with brine, dried (anhydrous sodium sulfate), filtered, and concentrated under reduced pressure. Purification through flash column chromatography (SiO₂) provided the ketal SI-XIII.

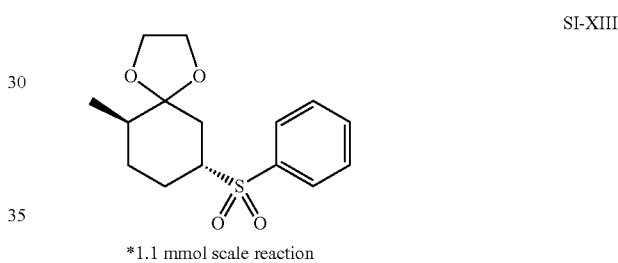

SI-XIII

*1.1 mmol scale reaction

Yield: 91% (301 mg). Physical State: white solid. ¹H NMR (500 MHz, CDCl₃): δ 7.89-7.83 (m, 2H), 7.68-7.62 (m, 1H), 7.59-7.52 (m, 2H), 4.00-3.85 (m, 4H), 3.19 (dddd, J=12.6, 12.6, 3.4, 3.4 Hz, 1H), 2.18 (ddd, J=12.7, 3.2, 2.4 Hz, 1H), 1.97-1.88 (m, 1H), 1.71 (ddd, J=13.1, 7.1, 3.9 Hz, 1H), 1.71-1.59 (m, 1H), 1.51 (dd, J=12.8, 12.8 Hz, 1H), 1.41 (dddd, J=12.9, 12.9, 12.9, 3.8 Hz, 1H), 1.29 (dddd, J=12.9, 12.9, 12.9, 3.6 Hz, 1H), 0.82 (d, J=6.6 Hz, 3H). ¹³C NMR (125 MHZ, CDCl₃): δ 136.9, 133.6, 129.0, 128.9, 109.4, 65.3, 65.1, 61.4, 38.9, 34.0, 30.1, 25.0, 13.3. MP: 104-105° C. IR (neat, ATR): $\nu_{max}$ 3067, 2958, 2935, 2883, 1299, 1148, 1081 cm⁻¹. Optical Rotation: $[\alpha]_D^{23.6}$ 6.5 (c 1.00, CHCl₃). HRMS (ESI-TOF): calc'd for C₁₅H₂₀O₄SNa [M+Na]⁺ 319.0975, found 319.0969. $R_f$=0.50 (30% EtOAc/hexanes). Purification: (SiO₂, 20→30% EtOAc/hexanes).

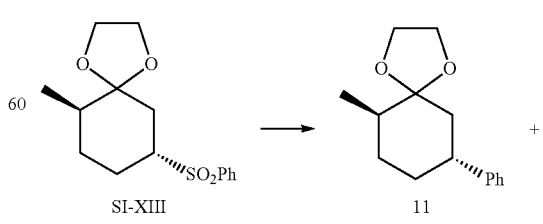

SI-XIII    11

-continued

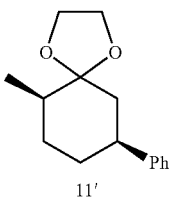

11'

A flame-dried vial was charged with the ketal SI-XIII (148 mg, 0.500 mmol, 1.0 equiv) and Fe(acac)$_3$ (35.4 mg, 0.100 mmol, 0.2 equiv) in a glove box, then sealed with a rubber septum and removed. A flame-dried round-bottom flask equipped with a magnetic stirrer bar was charged under argon protection with tetramethylethylenediamine (598 μL, 4.00 mmol, 8.0 equiv) and stirring was commenced. The first vial was charged with cyclopentyl methyl ether (3.0 mL), then sonicated until the contents became homogeneous. The clear-red solution was transferred via syringe to the reaction flask. The vial was rinsed with another portion of cyclopentyl methyl ether (3.0 mL) and then the contents were also transferred to the reaction flask via syringe. Phenylmagnesium bromide (3.0 M, 0.500 mL, 1.50 mmol, 3.0 equiv) was added over 30 s (the color changed from red to black upon addition of the Grignard reagent). After stirring for 24 h, the reaction was quenched through the addition of water (5.0 mL). The mixture was filtered through a Celite plug and then the filter cake was washed with water (2×) and EtOAc (3×). The mixture was transferred to a separatory funnel. The aqueous phase was extracted with EtOAc (3×). The combined organic fractions were washed with brine, dried (anhydrous sodium sulfate), filtered, and concentrated under reduced pressure. Purification through flash column chromatography (SiO$_2$) provided the arylated products 11/11☐. Note: Ketal SI-XIII was azeotroped with benzene three times prior to use.

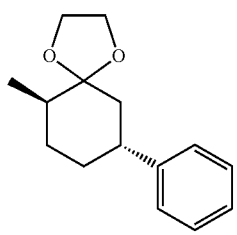

11

*0.5 mmol scale reaction

Yield: 55% (64 mg combined). Diasteromeric Ratio: 4.3:1. Physical State: white solid. $^1$H NMR (500 MHZ, CDCl$_3$) major: δ 7.34-7.27 (m, 2H), 7.26-7.17 (m, 3H), 4.05-3.92 (m, 4H), 2.84 (dddd, J=12.5, 12.5, 3.4, 3.4 Hz, 1H), 1.97 (ddd, J=12.9, 3.4, 2.1 Hz, 1H), 1.91-1.72 (m, 3H), 1.62 (t, J=12.9 Hz, 1H), 1.56-1.42 (m, 2H), 0.94 (d, J=6.5 Hz, 3H). $^1$H NMR (500 MHZ, CDCl$_3$) minor: δ 7.34-7.27 (m, 2H), 7.26-7.17 (m, 3H), 4.05-3.92 (m, 4H), 2.94-2.85 (m, 1H), 2.05-1.39 (m, 7H), 1.12 (d, J=7.3 Hz, 3H). $^{13}$C NMR (125 MHZ, CDCl$_3$) major: δ 146.1, 128.3, 126.7, 126.0, 110.6, 65.3, 64.8, 42.4, 41.8, 39.3, 33.8, 32.3, 13.8. $^{13}$C NMR (125 MHz, CDCl$_3$) minor: δ 146.2, 128.3, 126.7, 126.0, 111.4, 64.2, 64.1, 41.7, 36.7, 35.6, 29.8, 27.3, 14.6. MP: 67-68° C. IR (neat, ATR): ν$_{max}$ 2972, 2925, 2885, 2857, 1170, 1087, 761 cm$^{-1}$. Optical Rotation: [α]$_D^{20.7}$ −6.4 (c 0.50, CHCl$_3$). HRMS (ESI-TOF): calc'd for C$_{15}$H$_{21}$O$_2$ [M+H]$^+$ 233.3305, found 233.3301. R$_f$=0.36 (5% EtOAc/hexanes). Purification: (SiO$_2$, 2→5% EtOAc/hexanes). Note: Approximately 25 mg of the major diastereoisomer 11 was separated from the mixture of 11 and 11☐(the major product is slightly more polar). In contrast, the minor diastereoisomer could not be separated completely from the major product. NMR spectra are provided for both pure 11 and a mixture of 11 and 11☐(2.3:1 d.r.). All presented characterization data (MP, IR, optical rotation, HRMS) are those for pure 11. 2D NMR spectra are consistent with the proposed structure of 11.

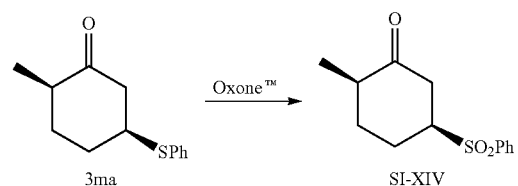

3ma        SI-XIV

Thioether 3ma (682 mg, 3.10 mmol) was oxidized to the sulfone SI-XIV following General Procedure B.

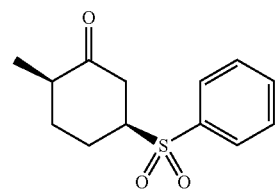

13

*3.1 mmol scale reaction

Yield: 95% (751 mg). Physical State: white solid. $^1$H NMR (500 MHZ, CDCl$_3$): δ 7.92-7.86 (m, 2H), 7.72-7.66 (m, 1H), 7.62-7.56 (m, 2H), 3.40 (dddd, J=8.5, 8.5, 4.9, 4.9 Hz, 1H), 2.71 (dd, J=15.4, 8.7 Hz, 1H), 2.52-2.41 (m, 2H), 2.31 (dddd, J=14.1, 8.4, 8.4, 4.5 Hz, 1H), 2.15-2.06 (m, 1H), 2.05-1.96 (m, 1H), 1.96-1.87 (m, 1H), 1.15 (d, J=7.0 Hz, 3H). $^{13}$C NMR (125 MHZ, CDCl$_3$): δ 208.9, 136.9, 134.0, 129.3, 128.8, 61.8, 43.4, 37.7, 29.5, 20.5, 15.6. MP: 119-120° C. IR (neat, ATR): ν$_{max}$ 3063, 2973, 2939, 2872, 1709, 1291, 1148, 1073, 723 cm$^{-1}$. Optical Rotation: [α]$_D^{23.7}$ −63.3 (c 1.00, CHCl$_3$). HRMS (ESI-TOF): calc'd for C$_{13}$H$_{16}$O$_3$SK [M+K]$^-$ 291.0452, found 291.0492. R$_f$=0.52 (50% EtOAc/hexanes). Purification: (SiO$_2$, 30→50% EtOAc/hexanes).

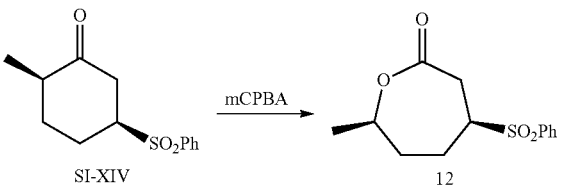

SI-XIV        12 mCPBA (671 mg, 2.80 mmol, 1.4 equiv) was added to a stirred solution of the sulfone SI-XIV (504 mg, 2.00 mmol, 1.0 equiv) in dichloromethane (0.5 M) at room temperature. The mixture was stirred until complete conversion to the lactone had occurred (TLC, ca. 6 h). The mixture was filtered to remove solids and then the filter cake washed with dichloromethane (3×). The organic fractions were washed with aqueous sodium bisulfite (5%, wt/vol), saturated aqueous sodium bicarbonate (3×), and brine (2×), then dried (anhydrous sodium sulfate), filtered, and concentrated under reduced pressure. Purification through flash column chromatography (SiO$_2$) provided the lactone 12.

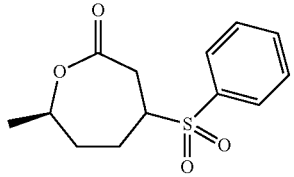

12

*2.0 mmol scale reaction

Yield: 73% (390 mg). Physical State: white solid. $^1$H NMR (500 MHZ, CDCl$_3$): δ 8.02-7.96 (m, 2H), 7.73-7.67 (m, 1H), 7.65-7.58 (m, 2H), 4.45 (ddq, J=10.1, 6.2, 2.4 Hz, 1H), 3.31 (ddd, J=10.9, 5.5, 5.5 Hz, 1H), 3.05 (dd, J=15.7, 5.7 Hz, 1H), 2.92 (ddd, J=15.8, 5.3, 0.7 Hz, 1H), 2.44 (dddd, J=14.8, 6.3, 6.3, 4.2 Hz, 1H), 2.28 (dddd, J=15.1, 9.6, 9.6, 4.1 Hz, 1H), 2.09 (dddd, J=14.6, 9.6, 4.8, 4.8 Hz, 1H), 1.88 (J=15.1, 6.9, 4.9, 2.0 Hz, 1H), 1.42 (d, J=6.4 Hz, 3H). $^{13}$C NMR (125 MHZ, CDCl$_3$): δ 170.0, 136.8, 134.3, 129.4, 129.2, 75.7, 58.1, 34.5, 32.6, 25.1, 21.8. MP: 173-175° C. IR (neat, ATR): $v_{max}$ 3060, 2935, 1720, 1307, 1287, 1263, 1181, 1143, 1081, 735, 693 cm$^{-1}$. Optical Rotation: $[\alpha]_D^{23.7}$ −26.7 (c 1.00, CHCl$_3$). HRMS (ESI-TOF): calc'd for C$_{13}$H$_{16}$O$_4$SNa [M+Na]$^+$ 291.0662, found 291.0661. R$_f$=0.22 (50% EtOAc/hexanes). Purification: (SiO$_2$, 50→75% EtOAc/hexanes). Note: 2D NMR spectra are consistent with the proposed structure of 12.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of making a compound, comprising:
   providing a starting material comprising an sp$^3$-hybridized carbon and an sp$^2$-hybridized carbon, wherein the sp$^3$-hybridized carbon and the sp$^2$-hybridized carbon are connected by a single bond;
   placing the starting material in a reaction vessel, thereby forming a reaction mixture; and
   cleaving the single bond, wherein cleaving the single bond comprises:
   contacting the reaction mixture with an oxidant; and
   contacting the reaction mixture with a transition metal salt;
   wherein the method further comprises quenching the reaction mixture with a radical quencher.

2. The method of claim 1, wherein the method further comprises adjusting the temperature of the reaction mixture to between −50° C. and −110° C. before contacting the reaction mixture with an oxidant.

3. The method of claim 1, wherein quenching the reaction mixture with the radical quencher occurs after cleaving the single bond.

4. The method of claim 1, wherein the radical quencher is a hydrogen atom donor.

5. The method of claim 4, wherein the hydrogen atom donor is an aryl thiol or heteroaryl thiol.

6. The method of claim 4, wherein the hydrogen atom donor is a terpinene or an alkyltinhydride.

7. The method of claim 1, wherein the radical quencher is a radical.

8. The method of claim 7, wherein the radical is an oxygen radical, a sulfur radical, a nitrogen radical, or a nitroxyl radical.

9. The method of claim 1, wherein the radical quencher is a disulfide.

10. The method of claim 1, wherein the method further comprises contacting the reaction mixture with a glycol and an acid.

11. The method of claim 1, wherein the transition metal salt is represented by Formula I:

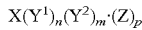

wherein
X is Fe, Fe, Cu, Ce, Ti, Mn, Cr, V, Ag, Co, or Ni;
Y$^1$ and Y$^2$ are each independently selected from SO$_4$, NH$_4$, halo, and BF$_4$;
Z is H$_2$O;
n is an integer from 1-4;
m is an integer from 0-2; and
p is an integer from 0-7.

12. The method of claim 1, wherein the transition metal salt is a ferrous salt.

13. The method of claim 1, wherein the oxidant is ozone.

14. The method of claim 1, wherein the starting material is represented by Formula II:

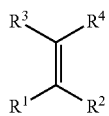

II or a salt thereof, wherein
R$^1$ is alkyl, heterocyclyl, or cycloalkyl;
R$^2$ is H, alkyl, or cycloalkyl; or R$^1$ and R$^2$ combine to form a cycloalkyl or heterocyclyl;
R$^3$ is H, alkyl, or cycloalkyl; or R$^1$ and R$^3$ combine to form a cycloalkyl or heterocyclyl; and
R$^4$ is hydrogen or alkyl.

15. The method of claim 14, wherein R$^1$ is cycloalkyl.

16. The method of claim 14, wherein R$^1$ is a steroid.

17. The method of claim 14, wherein R[1] is further substituted with oxo, alkyl, cycloalkyl, cycloalkenyl, hydroxyl, aryl, heterocyclyl, epoxyl, phophoryl, acyl, or ester.

18. The method of claim 1, wherein the starting material comprises at least one stereocenter and quenching the reaction mixture with the radical quencher results in a product that comprises at least one stereocenter.

19. The method of claim 1, wherein the starting material is

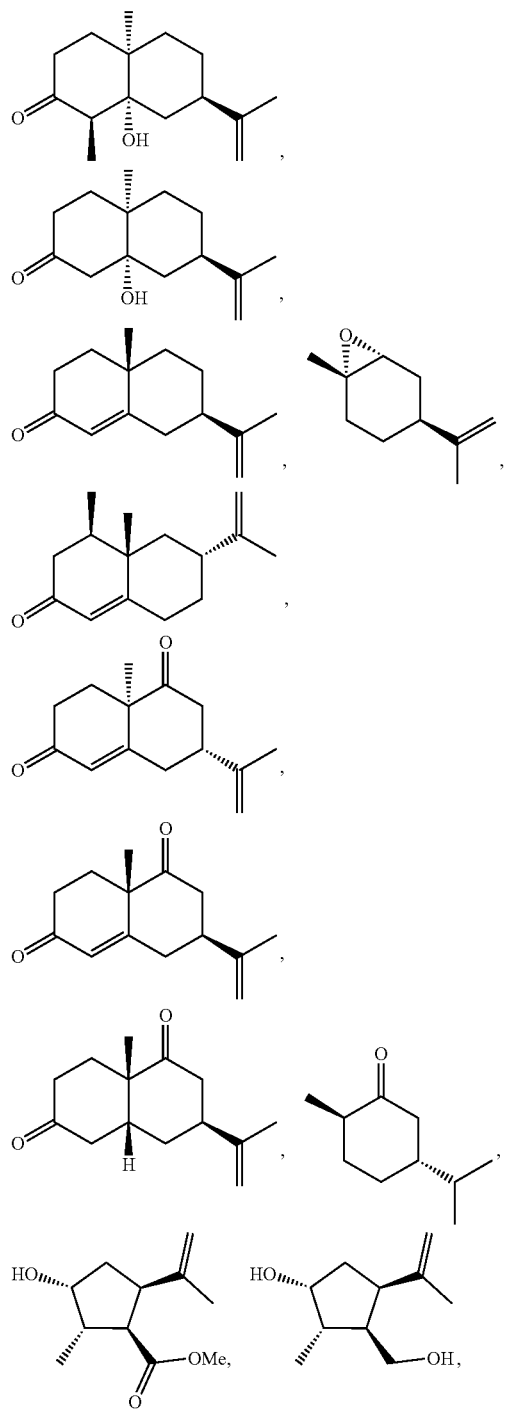

-continued

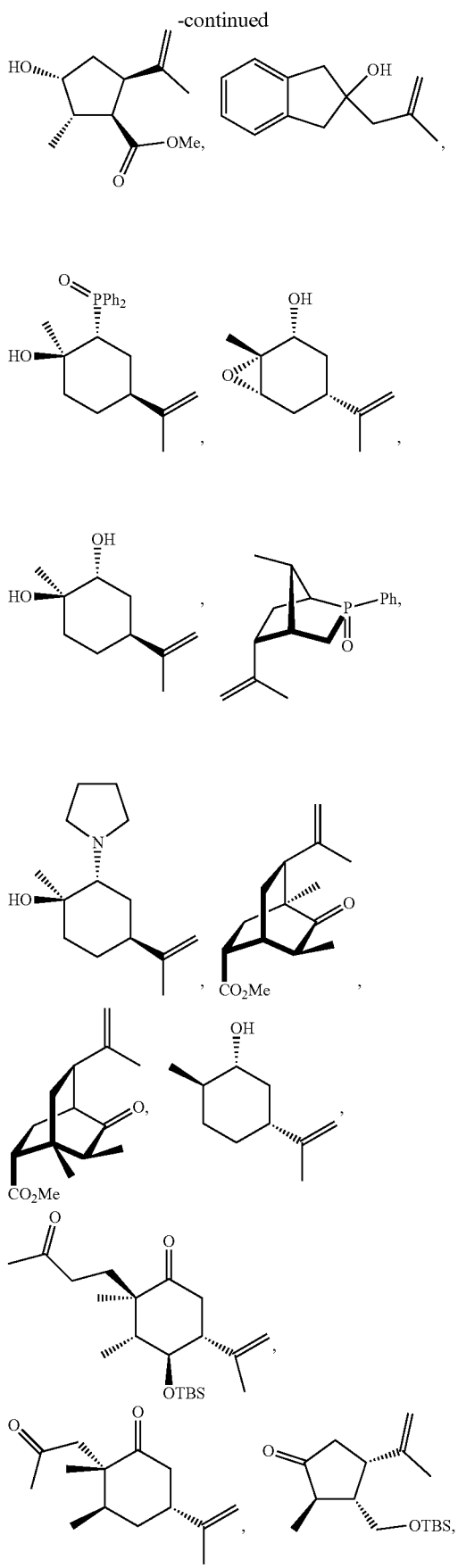

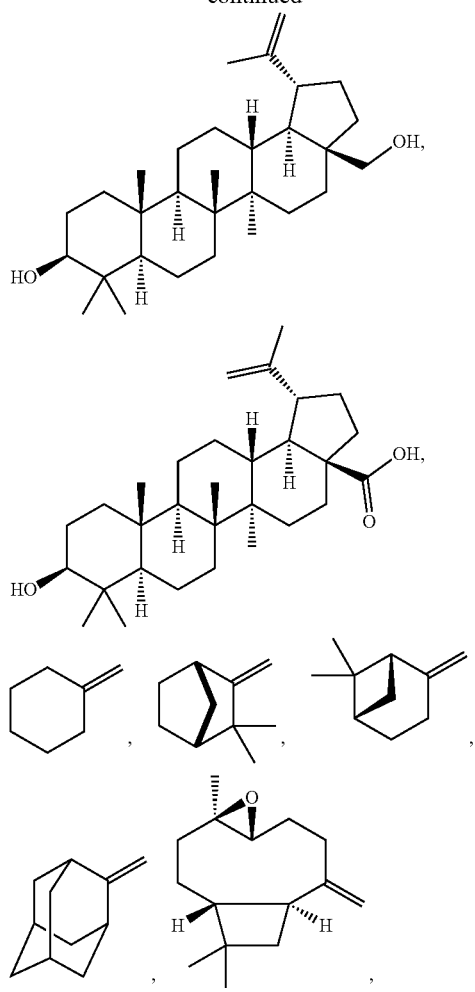
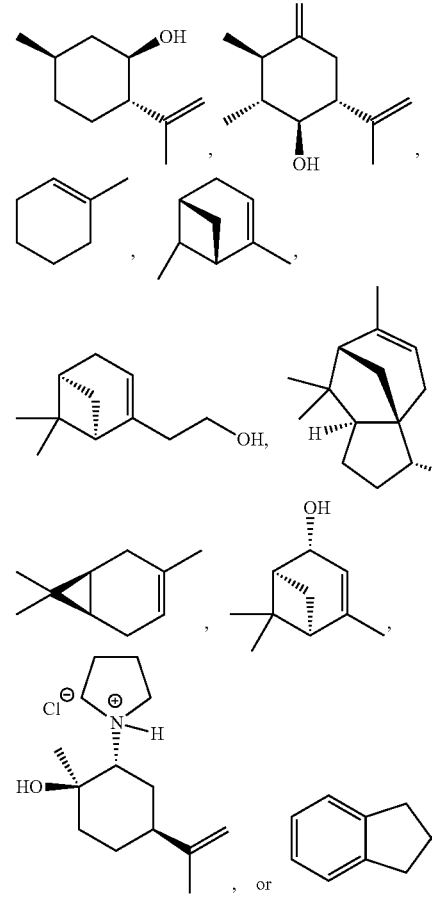
or a salt thereof.
* * * * *